United States Patent
Okada

(10) Patent No.: US 10,874,730 B2
(45) Date of Patent: Dec. 29, 2020

(54) METHODS FOR TREATING BRAIN CANCER USING IL-13R ALPHA 2 PEPTIDE-BASED COMPOSITIONS

(71) Applicant: University of Pittsburgh—Of the Commonwealth System of Higher Education, Pittsburgh, PA (US)

(72) Inventor: Hideho Okada, Pittsburgh, PA (US)

(73) Assignee: University of Pittsburgh—Of the Commonwealth System, Pittsburgh, PA (US)

(*) Notice: Subject to any disclaimer, the term of this patent is extended or adjusted under 35 U.S.C. 154(b) by 0 days.

(21) Appl. No.: 14/724,127

(22) Filed: May 28, 2015

(65) Prior Publication Data

US 2016/0114017 A1    Apr. 28, 2016

Related U.S. Application Data

(63) Continuation of application No. 14/515,939, filed on Oct. 16, 2014, now abandoned, which is a continuation of application No. 13/925,093, filed on Jun. 24, 2013, now abandoned, which is a continuation of application No. 13/215,938, filed on Aug. 23, 2011, now abandoned, which is a continuation-in-part of application No. 12/561,973, filed on Sep. 17, 2009, now Pat. No. 8,859,488, which is a continuation of application No. 11/231,618, filed on Sep. 21, 2005, now Pat. No. 7,612,162.

(60) Provisional application No. 61/376,582, filed on Aug. 24, 2010, provisional application No. 60/611,797, filed on Sep. 21, 2004.

(51) Int. Cl.

| | |
|---|---|
| *A61K 38/00* | (2006.01) |
| *A61K 39/00* | (2006.01) |
| *A61K 38/17* | (2006.01) |
| *C07K 14/715* | (2006.01) |
| *C07K 14/47* | (2006.01) |
| *C07K 14/705* | (2006.01) |
| *A61K 9/00* | (2006.01) |
| *A61K 38/20* | (2006.01) |
| *A61K 39/39* | (2006.01) |

(52) U.S. Cl.
CPC .... *A61K 39/001119* (2018.08); *A61K 9/0019* (2013.01); *A61K 38/17* (2013.01); *A61K 38/177* (2013.01); *A61K 38/1709* (2013.01); *A61K 38/2086* (2013.01); *A61K 39/0011* (2013.01); *A61K 39/00115* (2018.08); *A61K 39/001122* (2018.08); *A61K 39/001153* (2018.08); *A61K 39/001192* (2018.08); *A61K 39/39* (2013.01); *C07K 14/4703* (2013.01); *C07K 14/4705* (2013.01); *C07K 14/705* (2013.01); *C07K 14/7155* (2013.01); *A61K 2039/5154* (2013.01); *A61K 2039/55566* (2013.01); *A61K 2039/55583* (2013.01); *A61K 2039/572* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 5,057,540 | A | 10/1991 | Kensil et al. |
| 6,162,432 | A | 12/2000 | Wallner et al. |
| 7,297,337 | B2 | 11/2007 | Storkus et al. |
| 7,338,929 | B2 | 3/2008 | Debinski et al. |
| 7,354,584 | B2 | 4/2008 | Reed et al. |
| 7,612,162 | B2 | 11/2009 | Okada et al. |
| 7,842,294 | B2 | 11/2010 | Anderson et al. |
| 7,902,143 | B2 | 3/2011 | Okano |
| 7,943,138 | B2 | 5/2011 | Ciesielski et al. |
| 8,097,256 | B2 | 1/2012 | Yu et al. |
| 8,114,407 | B2 | 2/2012 | Storkus et al. |
| 8,574,584 | B2 | 11/2013 | Storkus et al. |
| 8,859,488 | B2 | 10/2014 | Okada et al. |
| 2002/0168360 | A1 | 11/2002 | Dingivan et al. |
| 2002/0182219 | A1 | 12/2002 | Debinski et al. |
| 2005/0002934 | A1 | 1/2005 | Reed |
| 2005/0048550 | A1 | 3/2005 | Storkus et al. |
| 2005/0153923 | A1 | 7/2005 | Kinch |
| 2005/0281783 | A1 | 12/2005 | Kinch et al. |
| 2006/0034856 | A1 | 2/2006 | Kosmatopoulos et al. |
| 2006/0084609 | A1 | 4/2006 | Scheinberg et al. |
| 2006/0099652 | A1 | 5/2006 | Gately et al. |
| 2007/0167375 | A1 | 7/2007 | Okada et al. |
| 2008/0311141 | A1 | 12/2008 | Yu et al. |

(Continued)

FOREIGN PATENT DOCUMENTS

| | | |
|---|---|---|
| EP | 1 835 027 A1 | 9/2007 |
| EP | 2 172 211 A1 | 4/2010 |

(Continued)

OTHER PUBLICATIONS

Clinical Trial NCT00874861 (Apr. 2, 2009).*

(Continued)

*Primary Examiner* — Dong Jiang
(74) *Attorney, Agent, or Firm* — Leydig, Voit & Mayer

(57) ABSTRACT

Provided herein are interleukin-13 receptor α2 peptide-based brain cancer vaccines and methods for treating and vaccinating against brain cancer comprising administering to patients in need thereof interleukin-13 receptor α2 peptide-based brain cancer vaccines. Also provided herein are regimens comprising interleukin-13 receptor α2 peptides and at least one additional peptide and/or immunostimulant.

Figure 1:
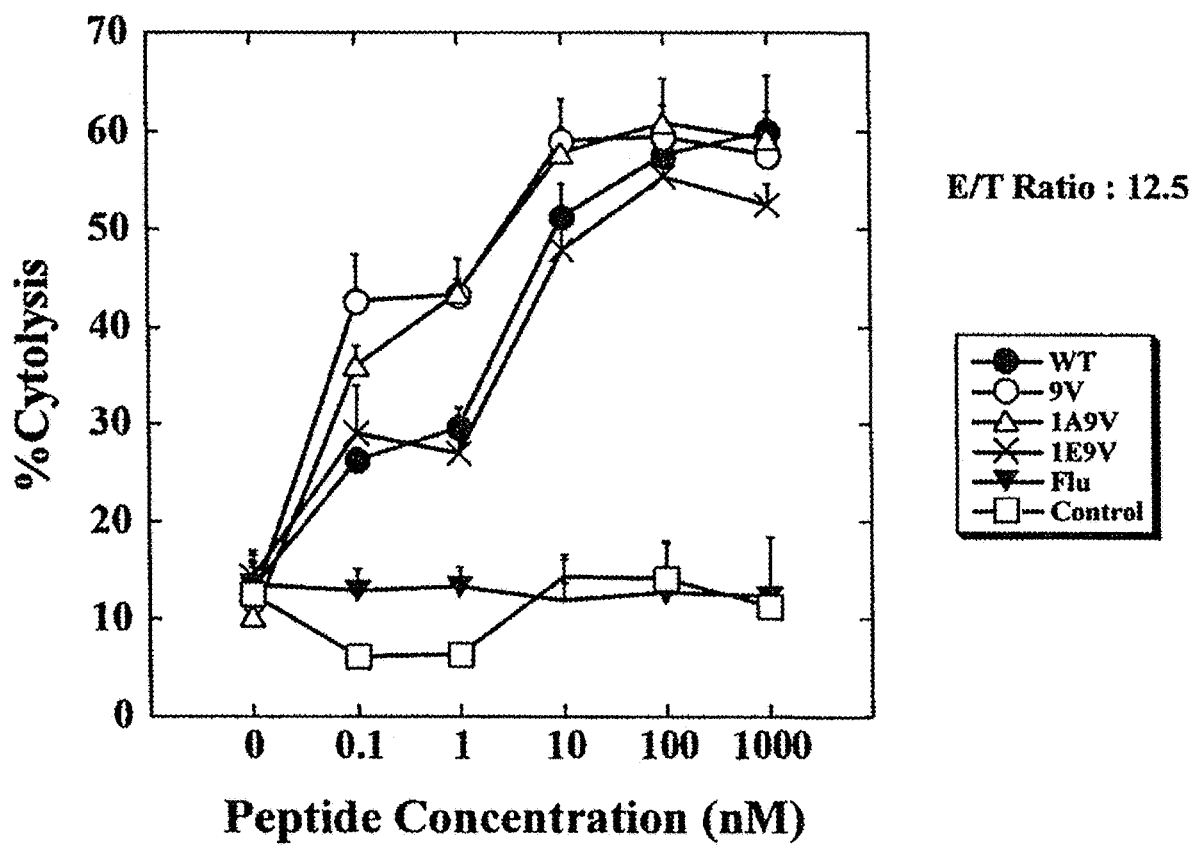

14 Claims, 21 Drawing Sheets
Specification includes a Sequence Listing.

(56) References Cited

U.S. PATENT DOCUMENTS

| | | | |
|---|---|---|---|
| 2009/0041732 | A1 | 2/2009 | Ciesielski et al. |
| 2010/0008940 | A1 | 1/2010 | Okada et al. |
| 2011/0223187 | A1 | 9/2011 | Shahabi et al. |
| 2012/0052080 | A1 | 3/2012 | Okada |

FOREIGN PATENT DOCUMENTS

| | | | |
|---|---|---|---|
| EP | 2 228 072 A1 | 9/2010 | |
| JP | 2004-353820 A1 | 12/2004 | |
| JP | 2009-511637 A | 3/2009 | |
| WO | WO 93/06866 A2 | 4/1993 | |
| WO | WO 95/22317 A1 | 8/1995 | |
| WO | WO 96/18409 A1 | 6/1996 | |
| WO | WO 01/58479 A1 | 8/2001 | |
| WO | WO 01/62979 A2 | 8/2001 | |
| WO | WO 02/098370 A2 | 12/2002 | |
| WO | WO 03/091383 A2 | 11/2003 | |
| WO | WO 2005/012350 A2 | 2/2005 | |
| WO | WO 2005/028505 A2 | 3/2005 | |
| WO | WO 2005/067460 A2 | 7/2005 | |
| WO | WO 2006/034334 A2 | 3/2006 | |
| WO | WO 20061062094 A1 | 6/2006 | |
| WO | WO 2007/109812 A2 | 9/2007 | |
| WO | WO 2007/109813 A1 | 9/2007 | |
| WO | WO 2008/039969 A2 | 4/2008 | |
| WO | WO 2010/037513 A1 | 4/2010 | |
| WO | WO 2010/065876 A2 | 6/2010 | |

OTHER PUBLICATIONS

Otto et al. Lack of toxicity of therapy-induced T cell responses against the universal tumour antigen survivin. Vaccine, 2005, 23:884-889.*

Clinical Trial NCT00345163, A Study to Evaluate Bevacizumab Alone or in Combination With Irinotecan for Treatment of Glioblastoma Multiforme (Brain). Jun. 27, 2006.*

Krug et al. WT1 peptide vaccinations induce CD4 and CD8 T cell immune responses in patients with mesothelioma and non-small cell lung cancer. Cancer Immunol Immunother. Oct. 2010;59(10):1467-79. Epub Jun. 8, 2010.*

Clinical Trial NCT00874861 (Apr. 3, 2009).*

History of Changes for Study: NCT00874861 (Apr. 2, 2009).*

History of Changes for Study: NCT00345163 (Jun. 26, 2006).*

Ahmed et al., "Nonenzymic Reactivation of Reduced Bovine Pancreatic Ribonuclease by Air Oxidation and by Glutathione Oxidoreduction Buffers," *The Journal of Biological Chemistry*, 250(21): 8477-8482 (Nov. 10, 1975).

Albericio et al., "Improved approach for anchoring $N^{\alpha}$-9-fluorenylmethyloxycarbonylamino acids as p-alkoxybenzyl esters in solid-phase peptide synthesis," *International Journal of Peptide and Protein Research*, 26(9): 92-97 (Jul. 1985).

Alexander et al., "Development of High Potency Universal DR-Restricted Helper Epitopes by Modification of High Affinity DR-Blocking Peptides," *Immunity*, 1: 751-761 (Dec. 1994).

Alves et al., "EphA2 as Target of Anticancer Immunotherapy: Identification of HLA-A*0201-Restricted Epitopes," Cancer Research, 63: 8476-8480 (Dec. 1, 2003).

Annex to Form PCT/ISA/206 Communication Relating to the Results of the Partial International Search dated Apr. 3, 2006, in PCT/US2005/033794.

Australian Patent Office, Patent Examination Report No. 1, dated Feb. 10, 2014, in Australian Patent Application No. 2100293522.

Baca et al., "Chemical Ligation of Cysteine-Containing Peptides: Synthesis of a 22 kDa Tethered Dimer of HIV-1 Protease," *J. Am. Chem. Soc.* 117: 1881-1887 (1995).

Bakker et al., "Generation of Antimelanoma Cytotoxic T Lymphocytes from Healthy Donors after Presentation of Melanoma-associated Antigen-derived Epitopes by Dendritic Cells in Vitro," *Cancer Research*, 55: 5330-5334 (Nov. 15, 1995).

Bedrosian et al., "Intranodal Administration of Peptide-Pulsed Mature Dendritic Cell Vaccines Results in Superior CD8+ T-Cell Function in Melanoma Patients," *Journal of Clinical Oncology*, 21(20): 3826-3835 (Oct. 15, 2003).

Berzofsky, "New Strategies for designing and Optimizing Vaccines," *ASM News*, 70(5): 219-223 (2004).

Bigg et al., "The Mammalian Chitinase-like Lectin, YKL-40, Binds Specifically to Type I Collagen and Modulates the Rate of Type I Collagen Fibril Formation," *The Journal of Biological Chemistry*, 281(30): 21081-21095 (Jul. 28, 2006).

Bigner et al., "Induction of lethal experimental allergic encephalomyelitis in nonhuman primates and guinea pigs with human glioblastoma multiforme tissue," *Journal of Neurosurgery*, 55(1): 32-42 (Jul. 1981).

Bitter et al., "Expression and Secretion Vectors for Yeast," *Methods in Enzymology, Recombinant DNA*, 153(Part D): 516-544 (1987).

Blanc-Brude et al., "Inhibitor of apoptosis protein survivin regulates vascular injury," *Nature Medicine*, 8(9): 987-994 (Sep. 2002).

Boon, "Towards a Genetic Analysis of Tumor Rejection Antigens," *Advances in Cancer Research* 58: 177-210 (1992).

Bownds et al., "Induction of Tumor-Reactive Cytotoxic T-Lymphocytes Using a Peptide from NY-ESO-1 Modified at the Carboxy-terminus to Enhance HLA-A2.1 Binding Affinity and Stability in Solution," *Journal of Immunotherapy*, 24(1): 1-9 (Jan./Feb. 2001).

Brantley et al., "Soluble Eph A receptors inhibit tumor angiogenesis and progression in vivo," *Oncogene*, 21(46): 7011-7026 (Oct. 10, 2002).

Buchwald et al., "Long-term, continuous intravenous heparin administration by an implantable infusion pump in ambulatory patients with recurrent venous thrombosis," *Surgery*, 88(4): 507-516 (Oct. 1980).

Butowski et al., "A North American brain tumor consortium phase II study of poly-ICLC for adult patients with recurrent anaplastic gliomas," *J. Neurooncol.*, 91: 183-189 (2009).

Butowski et al., "A phase II clinical trial of poly-ICLC with radiation for adult patients with newly diagnosed supratentorial glioblastoma: a North American Brain Tumor Consortium (NABTC01-05)," *J. Neurooncol.*, 91: 175-182 (2009).

Byers, "What Can Randomized Controlled Trials Tell Us About Nutrition and Cancer Prevention," *CA Journal*, 49(6): 353-361 (Nov./Dec. 1999).

Carmon et al., "Characterization of novel breast carcinoma-associated BA46-derived peptides in HLA-A2.1/$D^b\beta$2m transgenic mice," *The Journal of Clinical Investigation*, 110(4): 453-462 (Aug. 2002).

Celis, "Overlapping Human Leukocyte Antigen Class I/II Binding Peptide Vaccine for the Treatment of Patients With Stage IV Melanoma," *Cancer*, 110(1): 203-214 (Jul. 1, 2007).

Chen et al., "Identification of NY-ESO-1 Peptide Analogues Capable of Improved Stimulation of Tumor-Reactive CTL," *The Journal of Immunology*, 165(2): 948-955 (Jul. 15, 2000).

Chianese-Bullock et al., "MAGE-A1-, MAGE-A10, and gp100-Derived Peptides Are Immunogenic When Combined with Granulocyte-Macrophage Colony-Stimulating Factor and Montanide ISA-51 Adjuvant and Administered as Part of a Multipeptide Vaccine for Melanoma," *The Journal of Immunology*, 174: 3080-3086 (2005).

Ciesielski et al., "Antitumor cytotoxic T-cell response induced by a surviving peptide mimic," *Cancer Immunol. Immunother.*, 59: 1211-1221 (2010).

Cockett et al., "High Level Expression of Tissue Inhibitor or Metalloproteinases in Chinese Hamster Ovary Cells Using Glutamine Synthetase Gene Amplification," *Bio/Technology*, 8(7): 662-667 (Jul. 1990).

Cohen et al., "FDA Drug Approval Summary: Bevacizumab (Avastin®) as Treatment of Recurrent Glioblastoma Multiforme," *The Oncologist*, 14: 1131-1138 (2009).

Colbère-Garapin et al., "A New Dominant Hybrid Selective Marker for Higher Eukaryotic Cells," *J. Mol. Biol.*, 150: 1-14 (1981).

Correction, *Clinical Cancer Research*, 12(11): 3553 (Jun. 1, 2006).

Cotterchio et al., "Ontario Familial Colon Cancer Registry: Methods and First-year Response Rates," *Chronic Diseases in Canada*, 21(2): 1-10 (2000).

(56) References Cited

OTHER PUBLICATIONS

Crouse et al., "Expression and Amplification of Engineered Mouse Dihydrofolate Reductase Minigenes," *Molecular and Cellular Biology*, 3(2): 257-266 (Feb. 1983).
D' Aoust et al., "Influenza virus-like particles produced by transient expression in Nicotiana benthamiana induce a protective immune response against a lethal viral challenge in mice," *Plant Biotechnology Journal*, 6: 930-940 (2008).
De Vleeschouwer et al., "Postoperative Adjuvant Dendritic Cell-Based Immunotherapy in Patients with Relapsed Glioblastoma Multiforme," *Clinical Cancer Research*, 14(10): 3098-3104 (May 15, 2008).
Debinski et al., EphA2 Receptor Represents a New Marker and Therapeutic Target in Glioblastoma Multiforme (GMB), Neuro-Oncology, Abstract GE-02, 6: 336-337 (Oct. 2004).
Debinski et al., "Expression of a restrictive receptor for interleukin 13 is associated with glial transformation," *Journal of Neuro-Oncology*, 48(2): 103-111 (Jun. 2000).
Debinski et al., "Molecular Expression Analysis of Restrictive Receptor for Interleukin 13, a Brain tumor-associated Cancer/Testis Antigen," *Molecular Medicine*, 6(5): 440-449 (May 2000).
Debinski et al., "Receptor for Interleukin 13 Is a Marker and Therapeutic Target for Human High-Grade Gliomas," *Clinical Cancer Research*, 5: 985-990 (May 1999).
Debinski et al., "Receptor for interleukin 13 is abundantly and specifically over-expressed in patients with glioblastoma multiforme," *International Journal of Oncology*, 15(3): 481-486 (Sep. 1999).
Dorland's Illustrated Medical Dictionary, "Vaccine" (2007).
Eguchi et al., "Identification of Interleukin-13 Receptor α2 Peptide Analogues Capable of Inducing Improved Antiglioma CTL Responses," *Cancer Research*, 66(11): 5883-5891 (Jun. 1, 2006).
European Patent Office, International Search Report/Written Opinion, with respect to PCT/US2005/033794 (dated Jun. 29, 2006).
Fallert et al., "Improved detection of simian immunodeficiency virus RNA by in situ hybridization in fixed tissue sections: combined effects of temperatures for tissue fixation and probe hybridization," *Journal of Virological Methods*, 99: 23-32 (2002).
Fichtner-Feigl et al., "IL-13 signaling through the IL-13α$_2$ receptor is involved in induction of TGF-β$_1$ production and fibrosis," *Nature Medicine*, 12(1): 99-106 (Jan. 2006).
Foecking et al., "Powerful and versatile enhancer-promoter unit for mammalian expression vectors," *Gene* 45: 101-105 (1986).
Francini et al., "High-Affinity HLA-A(*)02.01 Peptides from Parathyroid Hormone-Related Protein Generate In Vitro and In Vivo Antitumor CTL Response Without Autoimmune Side Effects," *The Journal of Immunology*, 169(9): 4840-4849 (Nov. 1, 2002).
Fujita et al., "Effective Immunotherapy against Murine Gliomas Using Type 1 Polarizing Dendritic Cells—Significant Roles of CXCL 10," *Cancer Research*, 69(4): 1587-6683 (Feb. 15, 2009).
Gilliet et al., "Intranodal injection of semimature monocyte-derived dendritic cells induces T helper type 1 responses to protein neoantigen," *Blood*, 102(1): 36-42 (Jul. 1, 2003).
Graff-Dubois et al., "Generation of CTL Recognizing an HLA-A*0201-Restricted Epitope Shared by MAGE-A1, -A2, -A3, -A4, -A6, -A10, and -A12 Tumor Antigens: Implication in a Broad-Spectrum Tumor Immunotherapy," *The Journal of Immunology*, 169: 575-580 (2002).
Greenspan et al., "Defining epitopes: It's not as easy as it seems," *Nature Biotechnology*, 17: 936-937 (Oct. 1999).
Greten et al., "Peptide-β2-microglobulin-MHC fusion molecules bind antigen-specific T cells and can be used for multivalent MHC-Ig complexes," *Journal of Immunological Methods*, 271: 125-135 (2002).
Gross et al., "High vaccination efficiency of low-affinity epitopes in antitumor immunotherapy," *The Journal of Clinical Investigation*, 113(3): 425-433 (Feb. 2004).
Gura, "Systems for Identifying New Drugs Are Often Faulty," *Science*, 278: 1041-1042 (Nov. 7, 1997).
Hatano et al., "EphA2 as a Glioma-Associated Antigen: A Novel Target for Glioma Vaccines," *Neoplasia*, 7(8): 717-722 (Aug. 2005).
Hatano et al., "Vaccination with EphA2-derived T cell-epitopes promotes immunity against both EphA2-expressing and EphA2-negative tumors," *Journal of Translational Medicine*, 2(40): 1-9 (2004).
Herrem et al., "Expression of EphA2 is Prognostic of Disease-Free Internal and Overall Survival Treated Patients with Renal Cell Carcinoma," *Clinical Cancer Research*, 11(1): 226-231 (Jan. 1, 2005).
Inouye et al., "Up-promoter mutations in the Ipp gene *Escherichia coli*," *Nucleic Acids Research*, 13(9): 3101-3110 (1985).
International Bureau of WIPO, International Preliminary Report on Patentability, with respect to PCT/US2005/033794 (dated Apr. 5, 2007).
International Bureau of WIPO, International Preliminary Report on Patentability in International Patent Application No. PCT/US2011/048823 (dated Mar. 7, 2013).
Izumoto et al., "Phase II clinical trial of Wilms tumor 1 peptide vaccination for patients with recurrent glioblastoma multiforme," *J. Neurosurg.*, 108: 963-971 (May 2008).
Kaiser, "First Pass at Cancer Genome Reveals Complex Landscape," *Science*, 313: 1370 (Sep. 8, 2006).
Kaliński et al., "Final Maturation of Dendritic Cells Is Associated with Impaired Responsiveness to IFN-γ and to Bacterial IL-12 Inducers: Decreased Ability of Mature Dendritic Cells to Produce IL-12 During the Interaction with Th Cells," *The Journal of Immunology*, 162(6): 3231-3236 (Mar. 15, 1999).
Kaliński et al., "IL-12-Deficient Dendritic Cells, Generated in the Presence of Prostaglandin E$_2$, Promote Type 2 Cytokine Production in Maturing Human Naïve T Helper Cells," *The Journal of Immunology*, 159(1): 28-35 (Jul. 1, 1997).
Kaliński et al., "Polarized Dendritic Cells as Cancer Vaccines: Directing Effector-type T Cells to Tumors," *Semin. Immunol.*, 22(3): 173-182 (Jun. 2010).
Kamber et al., "The Synthesis of Cystine Peptides by Iodine Oxidation of S-Trityl-cysteine and S-Acetamidomethyl-cysteine Peptides," *Helvetica Chimica Acta*, 63(4): 899-915 (1980).
Kikuchi et al., "Vaccination of Glioma Patients with Fusions of Dendritic and Glioma Cells and Recombinant Human Interleukin 12," *J. Immunother*, 27(6): 452-459 (Nov./Dec. 2004).
Kinch et al., "Overexpression and functional alterations of the EphA2 tyrosine kinase in cancer," *Clinical & Experimental Metastasis*, 20: 59-68 (2003).
Kirkin et al., "Melanoma-associated antigens recognized by cytotoxic T lymphocytes," *APMIS*, 106: 665-679 (1998).
Kirkwood et al., "Immunogenicity and Antitumor Effects of Vaccination with Peptide Vaccine +/- Granulocyte-Monocyte Colony-Stimulating Factor and/or IFN-α2b in Advanced Metastatic Melanoma: Eastern Cooperative Oncology Group Phase II Trial E1696," *Clinical Cancer Research*, 15(4): 1443-1451 (Feb. 15, 2009).
Koch et al., "An abundant ubiquitous glycoprotein (GP$_{100}$) in nucleated mammalian cells," *FEBS Letters*, 179(2): 294-298 (Jan. 1985).
Korean Intellectual Property Office, International Search Report-Written Opinion dated Apr. 27, 2012, in PCT/US2011/048823.
Kouklis et al., "In vitro assembly properties of vimentin mutagenized at the β-site tail motif," *Journal of Cell Science*, 106(Pt.3): 919-928 (1993).
Liau et al., "Dendritic Cell Vaccination in Glioblastoma Patients Induces Systemic and Intracranial T-cell Responses Modulated by the Local Central Nervous System Tumor Microenvironment," *Clinical Cancer Research*, 11(15): 5515-5525 (Aug. 1, 2005).
Liu et al., "A Genome-Wide Screen Reveals Functional Gene Clusters in the Cancer Genome and Identified EphA2 as a Mitogen in Glioblastoma," *Cancer Research*, 66: 10815-10823 (2006).
Liu et al., "Acyl Disulfide-Mediated Intramolecular Acylation for Orthogonal Coupling Between Unprotected Peptide Segments, Mechanism and Application," *Tetrahedron Letters*, 37(7): 933-936 (1996).
Liu et al., Chemical Ligation Approach to Form a Peptide Bond between Unprotected Peptide Segments. Concept and Model Study, *Journal of the American Chemical Society*, 116(10): 4149-4153 (May 18, 1994).

(56) References Cited

OTHER PUBLICATIONS

Liu et al., "HER-2, gp100, and MAGE-1 Are Expressed in Human Glioblastoma and Recognized by Cytotoxic T Cells," *Cancer Research*, 64: 4980-4986 (Jul. 15, 2004).

Liu et al., "Peptide segment ligation strategy without use of protecting groups," *Proc. Natl. Acad. Sci. USA*, 91: 6584-6588 (Jul. 1994).

Livak et al., "Analysis of Relative Gene Expression Data Using Real-Time Quantitative PCR and the $2^{-\Delta\Delta C_T}$ Method," *Methods*, 25: 402-408 (2001).

Logan et al., "Adenovirus tripartite leader sequence enhances translation of mRNAs late after infection," *Proc. Natl. Acad. Sci. USA*, 81: 3655-3659 (Jun. 1984).

Lupetti et al., "Translation of a Retained Intron in Tyrosinase-related Protein (TRP) 2 mRNA Generates a New Cytotoxic T Lymphocyte (CTL)-defined and Shared Human Melanoma Antigen Not Expressed in Normal Cells of the Melanocytic Lineage," *The Journal of Experimental Medicine*, 188(6): 1005-1016 (Sep. 21, 1998).

Mailliard et al., "α-Type-1 Polarized Dendritic Cells: A Novel Immunization Tool with Optimized CTL-inducing Activity," *Cancer Research*, 64(17): 5934-5937 (Sep. 1, 2004).

Marincola et al., "Tumors as elusive targets of T-cell-based active immunotherapy," *Trends in Immunology*, 24(6): 334-341 (Jun. 2003).

Monsurrò et al., Functional Heterogeneity of Vaccine-Induced CD8$^+$ T Cells, *The Journal of Immunology*, 168: 5933-5942 (2002).

Muthuswamy et al., "Ability of Mature Dendritic Cells to Interact with Regulatory T Cells Is Imprinted during Maturation," *Cancer Research*, 68(14): 5972-5978 (Jul. 15, 2008).

Nakagawa et al., "The Use of Polymer-Bound Oximes for the Synthesis of Large Peptides Usable in Segment Condensation: Synthesis of a 44 Amino Acid Amphiphilic Peptide Model of Apolipoprotein A-1," *J. Am. Chem. Soc.*, 107(24): 7087-7092 (1985).

Naruse-Nakajima et al., "Involvement of EphA2 in the formation of the tail notochord via interaction with ephrinA1," *Mechanisms of Development*, 102: 95-105 (2001).

Neeson et al., "Effects of the Tumor Microenvironment on the Efficacy of Tumor Immunotherapy," *Immunological Investigations*, 35: 359-394 (2006).

Nishimura et al., "Adoptive Transfer of Type 1 CTL Mediates Effective Anti-Central Nervous System Tumor Response: Critical Roles of IFN-Inducible Protein-10," *Cancer Research*, 66(8): 4478-4487 (Apr. 15, 2006).

Nutt et al., "YKL-40 Is a Differential Diagnostic Marker for Histologic Subtypes of High-Grade Gliomas," *Clinical Cancer Research*, 11: 2258-2264 (Mar. 14, 2005).

O'Connell et al., "Elucidating the elite: mechanisms of control in HIV-1 infection," *Trends in Pharmacological Sciences*, 30(12): 631-637 (2009).

Ogawa et al., "The ephrine-A1 ligand and its receptor, EphA2, are expressed during tumor neovascularization," *Oncogene*, 19(52): 6043-6052 (Dec. 7, 2000).

Ogden et al., "Defective Receptor Expression and Dendritic Cell Differentiation of Monocytes in Glioblastomas," *Neurosurgery*, 59(4): 902-910 (Oct. 2006).

Okada et al., "Autologous glioma cell vaccine admixed with interleukin-4 gene transfected fibroblasts in the treatment of recurrent glioblastoma: preliminary observations in a patient with a favorable response to therapy," *Journal of Neuro-Oncology*, 64(1-2): 13-20 (Aug./Sep. 2003).

Okada et al., "Autologous glioma cell vaccine admixed with interleukin-4 gene transfected fibroblasts in the treatment of patients with malignant gliomas," *Journal of Translational Medicine*, 5(67): 1-10 (2007).

Okada et al., "Bone Marrow-Derived Dendritic Cells Pulsed with a Tumor-Specific Peptide Elicit Effective Anti-Tumor Immunity Against Intracranial Neoplasms," *International Journal of Cancer*, 78(1): 196-201 (Sep. 25, 1998).

Okada et al., "Cytokine gene therapy of gliomas: effective induction of therapeutic immunity to intracranial tumors by peripheral immunization with interleukin-4 transduced glioma cells," *Gene Therapy*, 8(15): 1157-1166 (Aug. 2001).

Okada et al., "Expression of glioma-associated antigens in pediatric brain stem and non-brain stem gliomas," *J. Neurooncol.*, 88(3): 245-250 (Jul. 2008).

Okada et al., "Gene Therapy of Malignant Gliomas: A Pilot Study of Vaccination with Irradiated Autologous Glioma and Dendritic Cells Admixed with IL-4 Transduced Fibroblasts to Elicit and Immune Response," *Human Gene Therapy*, 12(5): 575-595 (Mar. 20, 2001).

Okada et al., "Immunotherapeutic Approaches for Glioma," *Crit. Rev. Immunol.*, 29(1): 1-42 (2009).

Okano et al., "Identification of a Novel HLA-A*0201-restricted, Cytotoxic T Lymphocyte Epitope in a Human Glioma-associated Antigen, Interleukin 13 Receptor α2 Chain," *Clinical Cancer Research*, 8(9): 2851-2855 (Sep. 2002).

Pascolo et al., "HLA-A2.1-restricted Education and Cytolytic Activity of CD8+ T Lymphocytes from β2 Microglobulin (β2m) HLA-A2.1 Monochain Transgenic H-2D$^b$ β2m Double Knockout Mice," *The Journal of Experimental Medicine*, 185(12): 2043-2051 (Jun. 16, 1997).

Pelloski et al., "YKL-40 Expression is Associated with Poorer Response to Radiation and Shorter Overall Survival in Glioblastoma," *Clinical Cancer Research*, 11(9): 3326-3334 (May 1, 2005).

Pennington et al., "Comparison of folding procedures on synthetic ω-conotoxin," *Peptides 1990, Proceedings of the Twenty-First European Peptide Symposium*, (Giralt et al., eds) (Platja d' Aro, Spain) (Sep. 2-8, 1990) (164-166).

Pollack et al., Expression of p53 and Prognosis in Children with Malignant Gliomas,: *The New England Journal of Medicine*, 346(6): 420-427 (Feb. 7, 2002).

Prosecution history of U.S. Appl. No. 11/231,618, filed Sep. 21, 2005, current from Sep. 21, 2005 to Jun. 4, 2014.

Prosecution history of U.S. Appl. No. 12/561,973, filed Sep. 17, 2009, current from Sep. 17, 2009 to Sep. 25, 2014.

Prosecution history of U.S. Appl. No. 13/215,938, filed Aug. 23, 2011, current from Aug. 23, 2011 to Nov. 22, 2013.

Prosecution history of U.S. Appl. No. 13/925,093, filed Jun. 24, 2013, current from Jun. 24, 2013 to May 19, 2014.

Rasala et al., "Production of therapeutic proteins in algae, analysis of expression of seven human proteins in the chloroplast of Chlamydomonas reinhardtii," *Plant Biotechnology Journal*, 8: 719-733 (2010).

Riker et al., "Immune selection after antigen-specific immunotherapy of melanoma," *Surgery*, 126(2): 112-120 (Aug. 1999).

Rodrigues et al., "Normal human monocytes exposed to glioma cells acquire myeloid-derived suppressor cell-like properties," *Neuro-Oncology*, 12(4): 351-365 (Apr. 2010).

Saikali et al., "Expression of nine tumour antigens in a series of human glioblastoma multiforme: interest of EGFRvIII, II-13Rα2, gp100 and TRP-2 for immunotherapy," *J. Neurooncol.* 81: 139-148 (2007).

Sainio et al., "Differential regulation of two sets of mesonephric tubules by WT-1," *Development*, 124: 1293-1299 (1997).

Salazar et al., "Long-term Treatment of Malignant Gliomas with Intramuscularly Administered Polyinosinic-Polycytidylic Acid Stabilized with Polylysine and Carboxymethylcellulose: An Open Pilot Study," *Neurosurgery*, 38(6): 1096-1104 (Jun. 1996).

Salgaller et al., "Immunization against Epitopes in the Human Melanoma Antigen gp100 following Patient Immunization with Synthetic Peptides," *Cancer Research*, 56: 4749-4757 (Oct. 15, 1996).

Sampson et al, "An epidermal growth factor receptor variant III-targeted vaccine is safe and immunogenic in patients with glioblastoma multiforme," *Molecular Cancer Therapeutics*, 8(10): 2773-2779 (Oct. 2009).

Sasaki et al., "Preferential Expression of Very Late Antigen-4 on Type 1 CTL Cells Plays a Critical Role in Trafficking into Central Nervous System Tumors," *Cancer Research*, 67(13): 6451-6458 (Jul. 1, 2007).

(56) References Cited

OTHER PUBLICATIONS

Saudek et al., "A Preliminary Trial of the Programmable Implantable Medication System for Insulin Delivery," *New England Journal of Medicine*, 321(9): 574-579 (Aug. 31, 1989).
Scardino et al., "HER-2/neu and hTERT Cryptic Epitopes as Novel Targets for Broad Spectrum Tumor Immunotherapy," *The Journal of Immunology*, 169: 5900-5906 (2002).
Schnölzer et al., "Constructing Proteins by Dovetailing Unprotected Synthetic Peptides: Backbone-Engineered HIV Protease," *Science*, 256(5054): 221-225 (Apr. 10, 1992).
Schreier et al., "Allotypic differences in murine μ genes," *Nucleic Acids Research*, 14(5): 2381-2389 (1986).
Sefton et al., "Implantable Pumps," *CRC Critical Reviews in Biomedical Engineering*, 14(3): 201-240 (1987).
Sherman et al., "Strategies for Tumor Elimination by Cytotoxic T Lymphocytes," *Critical Reviews in Immunology* 18: 47-54 (1998).
Shoji et al., "Plant-expressed HA as a seasonal influenza vaccine candidate," *Vaccine*, 26: 2930-2934 (2008).
Slingluff et al., "Helper T-Cell Responses and Clinical Activity of a Melanoma Vaccine With Multiple Peptides From MAGE and Melanocytic Differentiation Antigens," *Journal of Clinical Oncology*, 26(30): 4973-4980 (Oct. 20, 2008).
Smith et al., "PTEN Mutation, EGFR Amplification, and Outcome in Patients With Anaplastic Astrocytoma and Glioblastoma Multiforme," *Journal of the National Cancer Institute*, 93(16): 1246-1256 (Aug. 15, 2001).
Smith, "Cancer and the Immune System," *Clinical Immunology*, 41(4): 841-849 (Aug. 1994).
Stoute et al., "A Preliminary Evaluation of a Recombinant Circumsporozoite Protein Vaccine Against Plasmodium Falciparum Malaria," *The New England Journal of Medicine*, 336(2): 86-91 (Jan. 9, 1997).
Szczepanski et al., "Triggering of Toll-like Receptor 4 Expressed on Human Head and Neck Squamous Cell Carcinoma Promotes Tumor Development and Protects the Tumor from Immune Attack," *Cancer Research*, 69(7): 3105-3113 (Apr. 1, 2009).
Tam et al., "Improved Synthesis of 4-(Boc-aminoacyloxymethyl)-phenylacetic Acids for use in Solid Phase Peptide Synthesis," *Synthesis*, 955-957 (Dec. 1979).
Tam et al., "Specificity and formation of unusual amino acids of an amide ligation strategy for unprotected peptides," *International Journal of Peptide & Protein Research*, 45(3): 209-216 (Mar. 1995).
Tatsumi et al., "Disease Stage Variation in CD4+ and CD8 T-Cell Reactivity to the Receptor Tyrosine Kinase EphA2 in Patients with Renal Cell Carcinoma," *Cancer Research*, 63: 4481-4489 (Aug. 1, 2003).
Van Heeke et al., "Expression of Human Asparagine Synthetase in *Escherichia coli*," *The Journal of Biological Chemistry*, 264(10): 5503-5509 (Apr. 5, 1989).
Vredenburgh et al., "Bevacizumab Plus Irinotecan in Recurrent Glioblastoma Multiforme," *Journal of Clinical Oncology*, 25(30): 4722-4729 (Oct. 20, 2007).
Vredenburgh et al., "Phase II Trial of Bevacizumab and Irinotecan in Recurrent Malignant Glioma," *Clinical Cancer Research*, 13(4): 1253-1259 (Feb. 15, 2007).
Watchmaker et al., "Independent Regulation of Chemokine Responsiveness and Cytolytic Function versus $CD8^+$ T Cell Expansion by Dendritic Cells," *The Journal of Immunology*, 184: 591-597 (2010).
Weber et al., "Phase 1 Trial of Intranodal Injection of a Melan-A/MART-1 DNA Plasmid Vaccine in Patients With Stage IV Melanoma," *J. Immunother*, 31(2): 215-223 (Feb./Mar. 2008).
Wen et al., "Malignant Gliomas," *Neurology and Neuroscience Reports*, 4(3): 218-227 (May 2004).
Wheeler et al., "Vaccination Elicits Correlated Immune and Clinical Responses in Glioblastoma Multiforme Patients," *Cancer Research*, 68(14): 5955-5964 (Jul. 15, 2008).
Yamanaka et al., "Clinical Evaluation of Dendritic Cell Vaccination for Patients with Recurrent Glioma: Results of a Clinical Phase I/II Trial," *Clinical Cancer Research*, 11(11): 4160-4167 (Jun. 1, 2005).
Yamanaka et al., "Peptide-based immunotherapeutic approaches to glioma: a review," *Expert Opinion Bio. Ther.*, 7(5): 645-649 (2007).
Yamashiro et al., "New segment synthesis of α-inhibin-92 by the acyl disulfide method," *Int. J. Peptide Protein Res.*, 31(3): 322-334 (Mar. 1988).
Yu et al., "Vaccination with Tumor Lysate-Pulsed Dendritic Cells Elicits Antigen-Specific, Cytotoxic T-Cells in Patients with Malignant Glioma," *Cancer Research*, 64(14): 4973-4979 (Jul. 15, 2004).
Zelinski et al., "EphA2 Overexpression Causes Tumorigenesis of Mammary Epithelial Cells," *Cancer Research*, 61: 2301-2306 (Mar. 1, 2001).
Zhang et al., "Antigenic Profiling of Glioma Cells to Generate Allogeneic Vaccines or Dendritic Cell-Based Therapeutics," *Clin. Cancer Res.* 13(2): 566-575 (Jan. 15, 2007).
Zhu et al., "Poly-ICLC promotes the infiltration of effector T cells into intracranial gliomas via induction of CXCL10 in IFN-α and IFN-γ dependent manners," *Cancer Immunol. Immunother.* 59: 1401-1409 (2010).
Zhu et al., "Toll like receptor-3 ligand poly-ICLC promotes the efficacy of peripheral vaccinations with tumor antigen-derived peptide epitopes in murine CNS tumor models," *Journal of Translational Medicine*, 5(10): 1-15 (Feb. 12, 2007).
Japanese Patent Office, Decision of Refusal, in Japanese Patent Application No. 526099/2013 (dated Mar. 15, 2016).
Izumoto, "Immunotherapy of Glioma—focusing on WT1 peptide vaccine therapy," *No Shinkei Geka Sokuho*, 19(2): 170-177 (2009).
Japanese Patent Office, Notice of Reasons for Refusal, dated Jul. 7, 2015, in Japanese Patent Application No. 526099/2013.
Okada et al., "Type 1 Dendritic Cell (DC) Vaccines in Combination with Poly-ICLC in Participants with Recurrent Malignant Glioma," *Neuro-Oncology*, 11(2), Abstract No. New 14: 224 (Apr. 2009).
Okada et al., "Type-1 Dendritic Cell Vaccines in Combination with Poly-ICLC-Association Between Positive Tetramer Response and 6-Month Progression-Free Survival," *Neuro-Oncology*, 11(5) Abstract No. 207: 611 (Oct. 2009).
Okada et al., "Type 1 Dendritic Cell Vaccines in Combination with Poly-ICLC-Association Between Positive Tetramer Response and 6-Month Progression-Free Survival," *Neuro-Oncology*, 11(6) Abstract No. O29: 883 (Dec. 2009).
Okada et al., "Type-1 dendritic cell vaccines in combination with poly-ICLC-association between positive tetramer response and 6-month progression-free survival in patients with recurrent malignant glioma," *Cancer Research*, 70(8) Abstract No. 4754: (Apr. 15, 2010).
Okada et al., "Induction of Robust Type-I $CD8^+$ T-cell Responses in WHO Grade 2 Low-Grade Glioma Patients Receiving Peptide-Based Vaccines in Combination with Poly-ICLC," *Clinical Cancer Research*, 21(2): 286-294 (Jan. 15, 2015).
Pollack et al., "Antigen-Specific Immune Responses and Clinical Outcome After Vaccination With Glioma-Associated Antigen Peptides and Polyinosinic-Polycytidylic Acid Stabilized by Lysine and Carboxymethylcellulose in Children With Newly Diagnosed Malignant Brainstem and Nonbrainstem Gliomas," *Journal of Clinical Oncology*, 32(19): 2050-2058 (Jul. 1, 2014).
European Patent Office, Extended European Search Report, in European Patent Application No. 11820530.1 (dated Jan. 12, 2015).
Gustafson et al., "Therapeutic vaccines for malignant brain tumors," *Biologics: Targets & Therapy*, 2(4): 753-761 (2008).
Japanese Patent Office, Notice of Reasons for Refusal in Japanese Application No. 139885/2016 dated Jun. 12, 2018.
Yajima et al., "Immunologic Evaluation of Personalized Peptide Vaccination for Patients with Advanced Malignant Glioma," *Clin. Cancer Res.*, 11(16): 5900-5911 (2005).
Japanese Patent Office, Notification of Reasons for Refusal in Japanese Application No. 139885/2016 dated Jun. 6, 2017.
Pollack et al., "Antigen-specific immunoreactivity and clinical outcome following vaccination with glioma-associated antigen peptides in children with recurrent high-grade gliomas: results of a pilot study," *J Neurooncol.*, 130: 517-527 (2016).
Pollack et al., "Immune responses and outcome after vaccination with glioma-associated antigen peptides and poly-ICLC in a pilot study for pediatric recurrent low-grade gliomas," *Neuro-Oncol.*, pp. 1157-1168 (2016).

(56) References Cited

OTHER PUBLICATIONS

Takahashi, T., "Introduction of T Cell-Based Cancer Immunotherapy, Cancer Vaccine and Adoptive T Cell Transfer," *Biotherapy, Aichi Cancer Center Research Institute* 19(1): 15-27 (2005).

European Patent Office, Extended European Search Report in European Patent Application No. 18211075.9, 13 pp. (dated Apr. 8, 2019).

Gura, "Cancer Models, Systems for Identifying New Drugs Are Often Faulty," *Science*, 278: 1041-1042 (Nov. 7, 1997).

Okada, et al., "Induction of CD8+ T-cell responses against novel glioma-associated antigen peptides and clinical activity by vaccinations with {alpha}-type 1 polarized dendritic cells and polyinosinic-polycytidylic acid stabilized by lysine and carboxymethylcellulose in patients with recurrent malignant glioma," *J. Clin. Oncol.*, 29(3): 330-336 (2011).

Okano et al., "Correction, Identification of a Novel HLA-A*2010-restricted, Cytotoxic T Lymphocyte Epitope in a Human Glioma-associated Antigen, Interleukin 13 Receptor α2 Chain," *Clinical Cancer Research*, 12(11): 3552 (Jun. 1, 2006).

Pollack, "HLA-A2-Restricted Glioma Antigen-Peptides Vaccinations With Poly-ICLC for Recurrent WHO Grade II Gliomas," Clinical Trials NCT00874861 from ClinicalTrials.gov (last updated Dec. 8, 2015).

Rüther et al., "Easy identification of cDNA clones," *The EMBO Journal*, 2(10): 1791-1794 (1983).

Sugiyama, H., "WT1 (Wilms' Tumor Gene 1): Biology and Cancer Immunotherapy," *Jpn. J. Clin. Oncol.*, 40(5): 377-387 (2010).

\* cited by examiner

METHODS FOR TREATING BRAIN CANCER USING IL-13R ALPHA 2 PEPTIDE-BASED COMPOSITIONS

CROSS-REFERENCE TO RELATED APPLICATIONS

This patent application is a continuation of copending U.S. patent application Ser. No. 14/515,939, filed Oct. 16, 2014, which is a continuation of U.S. patent application Ser. No. 13/925,093, filed Jun. 24, 2013, which is a continuation of U.S. patent application Ser. No. 13/215,938, filed Aug. 23, 2011, which claims the benefit of U.S. Provisional Patent Application No. 61/376,582, filed Aug. 24, 2010 and which is a continuation-in-part of U.S. patent application Ser. No. 12/561,973, filed Sep. 17, 2009, which issued as U.S. Pat. No. 8,859,488 and which is a continuation of U.S. patent application Ser. No. 11/231,618, filed Sep. 21, 2005, which issued as U.S. Pat. No. 7,612,162 and which claims the benefit of U.S. Provisional Patent Application No. 60/611,797, filed Sep. 21, 2004. Each of these applications is incorporated herein by reference in its entirety.

STATEMENT REGARDING FEDERALLY SPONSORED RESEARCH AND DEVELOPMENT

This invention was made with Government support under Grant Numbers NS040923, CA133859 and CA117152 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3.23 Kilobyte ASCII (Text) file named "720917_ST25.TXT," dated May 26, 2015.

1. INTRODUCTION

Provided herein are interleukin-13 receptor α2 peptide-based brain cancer vaccines and methods for treating and vaccinating against brain cancer comprising administering to patients in need thereof interleukin-13 receptor α2 peptide-based brain cancer vaccines. Also provided herein are vaccine regimens comprising interleukin-13 receptor α2 peptides and at least one additional peptide and/or immunostimulant.

2. BACKGROUND

Brain tumors are particularly difficult to treat using conventional methods such as surgery, radiotherapy, or chemotherapy. Factors such as invasive growth patterns and the blood-brain barrier make the treatment of malignant gliomas more problematic than other tumors. The lack of effective treatment options for patients has led to the development of alternative therapies, such as immunotherapy.

Immunotherapy is a promising new approach in the treatment of malignant gliomas. The efficacy of peripheral immunizations with autologous glioma cells or dendritic cells (DC) pulsed with synthetic peptides for tumor-antigen-specific T cell epitopes has been demonstrated in preclinical mouse models (Okada et al., 2001; Okada et al., 1998). Specific T cell epitope-based vaccines are likely safer than whole glioma cell-based vaccines due to the lack of theoretical autoimmune responses against normal brain components. Such antigen-specific approaches may also be more effective than the bulk tumor-antigen approaches because presentation of immunogenic T cell-epitopes and stimulation of antigen-specific T cell precursors can take place more efficiently with the use of specific antigen-peptides than bulk tumor antigens.

The identification of T cell immuno-epitopes in human glioma associated antigens is required for the development of such vaccines against human gliomas. Few cytotoxic T lymphocyte (CTL) immuno-epitopes have been identified for human malignant gliomas. However, an HLA (human leukocyte antigen)-A2-restricted cytotoxic T lymphocyte (CTL) epitope derived from the interleukin (IL)-13 receptor (R) α2 was recently identified (Okano et al., 2002). IL-13Rα2 is known to be expressed in the majority of human malignant gliomas but not in normal tissues (Debinski et al., 2000), thus making the identified epitope (IL-13Rα2$_{345-353}$) an attractive component of peptide-based vaccines for gliomas. By generating unique CTL lines by stimulation of CD8+ cells with the peptide IL-13Rα2$_{345-353}$, it was demonstrated that IL-13Rα2 positive, HLA-A2 positive glioma cells were efficiently lysed in an antigen-specific manner. However, it remains unclear how efficiently such peptide-based vaccines can induce specific CTLs and whether peptide-analogues can be used for optimal expansion and activation of IL-13Rα2 specific HLA-A2-restricted CTL.

It has been demonstrated that certain amino acid substitutions in peptides identified as CTL epitopes could greatly enhance the binding affinity of such peptides to the HLA (human leukocyte antigen) complex and thus would augment the immunogenicity of the peptide (Bownds et al., 2001; Chen et al., 2000). The enhancement of the immunogenicity of IL-13Rα2$_{345-353}$, and other such epitopes could lead to the development of powerful, tumor-specific peptide-based vaccines, which would be a significant improvement in the current treatment regime for malignant gliomas. However, there remains a need for an improved polypeptide HLA-A2-restricted cytotoxic T lymphocyte (CTL) epitope.

As discussed above, few cytotoxic T lymphocyte (CTL) immuno-epitopes have been identified for human malignant gliomas. Given the marked antigenic heterogeneity of gliomas, however, immunotherapy with a single tumor-specific T-cell epitope might merely promote transient stabilization of disease, prior to the progression of antigen loss variants. EphA2 is a member of the Eph family of receptor tyrosine kinases, comprised of two major classes (EphA2 and EphB), which are distinguished by their specificities for ligands (ephrin-A and ephrin-B, respectively). EphA2 is frequently overexpressed and often functionally dysregulated in advanced cancers, such as metastatic lesions (Kinch et al., 2003). Due to the aggressive and invasive nature of malignant gliomas, EphA2 might be expressed in this tumor entity and could be a potential target for glioma vaccines. T-cell immunoepitopes in EphA2 have been identified and characterized as potential targets and surrogate markers for other forms of cancer immunotherapy (Alves et al., 2003, and Tatsumi et al., 2003). The identification of additional CTL epitopes is a necessary step in the development of multi-epitope-based vaccines for glioma which would be a significant improvement in the current treatment regime for malignant gliomas.

3. SUMMARY

In one aspect, provided herein is a peptide derived from IL-13Rα2, which serves as a HLA-A2-restricted cytotoxic T lymphocyte (CTL) epitope. The IL-13Rα2 peptide can comprise, consist of, or consist essentially of a substitution mutant variant of WLPFGFILI (SEQ ID NO:1), wherein at least one of the amino acid residues can be substituted for an amino acid other than the indicated residue. In addition, the IL-13Rα2 peptide can comprise, consist of, or consist essentially of any of the following sequences: WLPFGFILV (SEQ ID NO:2), ALPFGFILV (SEQ ID NO:3), or ELPFGFILV (SEQ ID NO:4).

Also provided herein is a use of any of the above IL-13Rα2 peptides as a vaccine for glioma. In addition, the invention provides a method of vaccinating a patient against glioma, where the peptide is introduced into a patient under conditions sufficient for the patient to develop a CTL response. Further, provided herein is a use of an EphA2 peptide having the sequence TLADFDPRV (SEQ ID NO:6) or a composition comprising said peptide and a physiologically acceptable carrier, as a vaccine for glioma. Also provided herein is a method of vaccinating a patient against glioma, wherein an EphA2 peptide having the sequence TLADFDPRV (SEQ ID NO:6) or a composition comprising said peptide and a physiologically acceptable carrier, is introduced into a patient under conditions sufficient for the patient to develop a CTL response.

In another aspect, presented herein are IL-13Rα2 peptide-based vaccines comprising an IL-13Rα2 peptide and one, two, three, or more additional brain cancer-associated peptides. In certain embodiments, the IL-13Rα2 peptide-based vaccines described herein are administered concurrently with one or more helper T cell epitopes and/or one or more immune response modifiers. In accordance with such embodiments, the one or more helper T cell epitopes and/or one or more immune response modifiers may be administered as part of the vaccine (e.g., in solution with the IL-13Rα2 peptide and the one, two, three, or more additional brain cancer-associated peptides) or separate from the vaccine (i.e., the helper T cell epitopes and/or immune response modifiers may be administered as a formulation that is not a part of the vaccine formulation). In some embodiments, the IL-13Rα2 peptide-based vaccines described herein are administered as cell-free vaccines. In another embodiment, the IL-13Rα2 peptide-based vaccine is administered with an adjuvant. In a preferred embodiment, the IL-13Rα2 peptide-based vaccine is administered in combination with additional peptides. In another embodiment, the IL-13Rα2 peptide-based vaccine is administered with an immunomodulatory agent. In another embodiment, the IL-13Rα2 peptide-based vaccine is administered as an emulsion in Montanide ISA 51, as a component of a regimen that includes injections with an immunostimulatory agent. In a preferred embodiment, the immunostimulatory agent is poly ICLC. In other embodiments, the IL-13Rα2 peptide-based vaccines described herein are administered as dendritic cell vaccines.

In one embodiment, an IL-13Rα2 peptide-based vaccine comprises an IL-13Rα2 peptide, an EphA2 peptide, a YKL-40 peptide, and a GP100 peptide. In a specific embodiment, an IL-13Rα2 peptide-based vaccine comprises the IL-13Rα2 peptide corresponding to any one of SEQ ID NOs:1-4, the EphA2 peptide corresponding to SEQ ID NO:6, the YKL-40 peptide corresponding to SEQ ID NO:10, and the GP100 peptide corresponding to SEQ ID NO:11. In another specific embodiment, an IL-13Rα2 peptide-based vaccine comprises the IL-13Rα2 peptide corresponding to SEQ ID NO:3, the EphA2 peptide corresponding to SEQ ID NO:6, the YKL-40 peptide corresponding to SEQ ID NO:10, and the GP100 peptide corresponding to SEQ ID NO:11. In some embodiments, the IL-13Rα2 peptide-based vaccine is administered concurrently with one or more helper T cell epitopes. In a specific embodiment, the IL-13Rα2 peptide-based vaccine is administered concurrently with a helper T cell epitope, wherein the helper T cell epitope is the PADRE peptide. In some embodiments, the IL-13Rα2 peptide-based vaccine is administered concurrently with one or more immune response modifiers. In some embodiments, the IL-13Rα2 peptide-based vaccine is a cell-free vaccine. In other embodiments, the IL-13Rα2 peptide-based vaccine is a dendritic cell vaccine.

In another embodiment, an IL-13Rα2 peptide-based vaccine comprises an IL-13Rα2 peptide, an EphA2 peptide, a survivin peptide, and a WT1 peptide. In a specific embodiment, an IL-13Rα2 peptide-based vaccine comprises the IL-13Rα2 peptide corresponding to any one of SEQ ID NOs:1-4, the EphA2 peptide corresponding to SEQ ID NO:6, the survivin peptide corresponding to SEQ ID NO:7, and the WT1 peptide corresponding to SEQ ID NO:8. In another specific embodiment, an IL-13Rα2 peptide-based vaccine comprises the IL-13Rα2 peptide corresponding to SEQ ID NO:3, the EphA2 peptide corresponding to SEQ ID NO:6, the survivin peptide corresponding to SEQ ID NO:7, and the WT1 peptide corresponding to SEQ ID NO:8. In some embodiments, the IL-13Rα2 peptide-based vaccine is administered concurrently with one or more helper T cell epitopes. In a specific embodiment, the IL-13Rα2 peptide-based vaccine is administered concurrently with a helper T cell epitope, wherein the helper T cell epitope is the Tetanus toxoid. In some embodiments, the IL-13Rα2 peptide-based vaccine is administered concurrently with one or more immune response modifiers. In a specific embodiment, the IL-13Rα2 peptide-based vaccine is administered concurrently with an immune response modifier, wherein the immune response modifier is poly-ICLC. In a specific embodiment, the IL-13Rα2 peptide-based vaccine is administered concurrently with an immune response modifier, wherein the immune response modifier is Montanide ISA-51. In some embodiments, the IL-13Rα2 peptide-based vaccine is a cell-free vaccine. In other embodiments, the IL-13Rα2 peptide-based vaccine is a dendritic cell vaccine.

In another embodiment, an IL-13Rα2 peptide-based vaccine comprises an IL-13Rα2 peptide, an EphA2 peptide, and a survivin peptide. In a specific embodiment, an IL-13Rα2 peptide-based vaccine comprises the IL-13Rα2 peptide corresponding to any one of SEQ ID NOs:1-4, the EphA2 peptide corresponding to SEQ ID NO:6, and the survivin peptide corresponding to SEQ ID NO:7. In another specific embodiment, an IL-13Rα2 peptide-based vaccine comprises the IL-13Rα2 peptide corresponding to SEQ ID NO:3, the EphA2 peptide corresponding to SEQ ID NO:6, and the survivin peptide corresponding to SEQ ID NO:7. In some embodiments, the IL-13Rα2 peptide-based vaccine is administered concurrently with one or more helper T cell epitopes. In a specific embodiment, the IL-13Rα2 peptide-based vaccine is administered concurrently with a helper T cell epitope, wherein the helper T cell epitope is the Tetanus toxoid. In some embodiments, the IL-13Rα2 peptide-based vaccine is administered concurrently with one or more immune response modifiers. In a specific embodiment, the IL-13Rα2 peptide-based vaccine is administered concurrently with an immune response modifier, wherein the immune response modifier is poly-ICLC. In a specific embodiment, the IL-13Rα2 peptide-based vaccine is administered concurrently with an immune response modifier, wherein the immune response modifier is Montanide ISA-51. In some embodiments, the IL-13Rα2 peptide-based vaccine is a cell-free vaccine. In other embodiments, the IL-13Rα2 peptide-based vaccine is a dendritic cell vaccine.

4. DEFINITIONS

As used herein, the terms "about" or "approximately" when used in conjunction with a number refers to any number within 1, 5 or 10% of the referenced number.

As used herein, the term "agent" refers to any molecule, compound, and/or substance that can be used in or in combination with an interleukin-13 receptor α2 peptide-based brain cancer vaccines described herein. The term agent includes, without limitation, proteins, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents, anti-angiogenic agents, and small molecule drugs.

As used herein, the term "amino acid sequence identity" refers to the degree of identity or similarity between a pair of aligned amino acid sequences, usually expressed as a percentage. As used herein, the terms "percent identity," "percent identical," "% identity," and "% identical" with respect to amino acid sequence refer to the percentage of amino acid residues in a candidate sequence that are identical (i.e., the amino acid residues at a given position in the alignment are the same residue) to the corresponding amino acid residue in the peptide after aligning the sequences and introducing gaps, if necessary, to achieve the maximum percent sequence homology. As used herein, the terms "percent similarity," "percent similar," "% similarity," and "% similar" with respect to amino acid sequence refer to the percentage of amino acid residues in a candidate sequence that are similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, are determined using sequence alignment techniques well-known in the art, including computer algorithms designed for this purpose, using the default parameters of said computer algorithms or the software packages containing them.

As used herein, the term "conservative substitution" refers to replacement of an amino acid of one class with another amino acid of the same class. In particular embodiments, a conservative substitution does not alter the structure or function, or both, of a peptide. Classes of amino acids for the purposes of conservative substitution include hydrophobic (Met, Ala, Val, Leu, Ile), neutral hydrophilic (Cys, Ser, Thr), acidic (Asp, Glu), basic (Asn, Gln, His, Lys, Arg), conformation disrupters (Gly, Pro) and aromatic (Trp, Tyr, Phe).

As used herein, the term "peptide" refers to a polymer of amino acids linked by amide bonds as is known to those of skill in the art. A peptide can be a polymer of 4, 5, 6, 7, 8, 9, 10, 15, 20, 25, 30, 35, 40, 45, 50, 55, 60, 65, 70, 75, 80, 85, 90, 95, 100 or more amino acids linked by covalent amide bonds. In some embodiments, the peptide is a polymer of 6 to 8, 8 to 10, 10 to 15, 10 to 20, 10 to 25, 10 to 30, 10 to 40, 10 to 50, or 25 to 25 amino acids linked by covalent amide bonds. In certain embodiments, the peptide is a polymer of 50 to 65, 50 to 75, 50 to 85, 50 to 95, 50 to 100, 75 to 100 amino acids linked by covalent amide bonds. As used herein, the term can refer to a single peptide chain linked by covalent amide bonds. The term can also refer to multiple peptide chains associated by non-covalent interactions such as ionic contacts, hydrogen bonds, Van der Waals contacts and hydrophobic contacts. Those of skill in the art will recognize that the term includes peptides that have been modified, for example by post-translational processing such as signal peptide cleavage, disulfide bond formation, glycosylation (e.g., N-linked glycosylation), protease cleavage and lipid modification (e.g. S-palmitoylation).

As used herein, the terms "purified" and "isolated" when used in the context of a peptide that is obtained from a natural source, e.g., cells, refers to a peptide which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a peptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a peptide that is chemically synthesized refers to a peptide which is substantially free of chemical precursors or other chemicals which are involved in the syntheses of the polypeptide.

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded.

As used herein, the phrase "prophylactic vaccine" refers to a vaccine described herein that is used for the purpose of preventing cancer.

As used herein, the term "prophylactically effective regimen" refers to an effective regimen for dosing, timing, frequency and duration of the administration of one or more therapies for the prevention of brain cancer or a symptom thereof.

As used herein, the term "therapeutic vaccine" refers to a vaccine described herein that is used for the purpose of treating and/or managing brain cancer.

As used herein, the term "therapeutically effective regimen" refers to a regimen for dosing, timing, frequency, and duration of the administration of one or more therapies for the treatment and/or management of brain cancer or a symptom thereof.

As used herein, the terms "subject" or "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, clog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human toddler. In another embodiment, a subject is a human child. In another embodiment, a subject is a human adult. In another embodiment, a subject is an elderly human.

As used herein, the term "human infant" refers to a newborn to 1 year old human.

As used herein, the term "human toddler" refers to a human that is 1 years to 3 years old.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the term "brain cancer" refers to a tumor located inside the cranium or in the central spinal canal. Brain cancer refers to both primary tumors (i.e., tumors that originate in the intracranial sphere or the central spinal canal) and secondary tumors (i.e., tumors that invaded the intracranial sphere or the central spinal canal after originating from tumors primarily located in other organs).

As used herein, the terms "therapies" and "therapy" can refer to any protocol(s), method(s), composition(s), formulation(s), and/or agent(s) that can be used in the prevention or treatment of brain cancer or a disease or symptom associated therewith. In certain embodiments, the terms "therapies" and "therapy" refer to biological therapy, supportive therapy, and/or other therapies useful in treatment or prevention of brain cancer or a disease or symptom associated therewith known to one of skill in the art.

As used herein, the term "effective amount" refers to the amount of a therapy that is sufficient to result in the prevention of the development, recurrence, or onset of brain cancer and/or one or more symptoms thereof, to enhance or improve the prophylactic effect(s) of another therapy, reduce the severity, the duration of brain cancer, ameliorate one or more symptoms of brain cancer, prevent the advancement of brain cancer, cause regression of brain cancer, and/or enhance or improve the therapeutic effect(s) of another therapy.

As used herein, the term "in combination" in the context of the administration of a therapy to a subject refers to the use of more than one therapy (e.g., prophylactic and/or therapeutic). The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to brain cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

As used herein, the terms "manage," "managing," and "management" in the context of the administration of a therapy to a subject refer to the beneficial effects that a subject derives from a therapy (e.g., a prophylactic or therapeutic vaccine) or a combination of therapies, while not resulting in a cure of brain cancer. In certain embodiments, a subject is administered one or more therapies (e.g., one or more prophylactic or therapeutic vaccines) to "manage" brain cancer so as to prevent the progression or worsening of the condition.

As used herein, the terms "prevent," "preventing" and "prevention" in the context of the administration of a therapy to a subject refer to the prevention or inhibition of the recurrence, onset, and/or development of brain cancer or a symptom thereof in a subject resulting from the administration of a therapy (e.g., a prophylactic or therapeutic agent), or a combination of therapies (e.g., a combination of prophylactic or therapeutic agents).

As used herein, the term "concurrently" means sufficiently close in time to produce a combined effect (that is, concurrently may be simultaneously, or it may be two or more events occurring within a time period before or after each other). When administered with other agents, the IL-13Rα2 peptide-based vaccines provided herein may be administered concurrently with the other active agent. In some embodiments an IL-13Rα2 peptide-based vaccine provided herein and one or more other agents (e.g., a helper T cell epitope, an adjuvant, and/or an immune response modifier) are administered to a subject concurrently, wherein the administration IL-13Rα2 peptide-based vaccine provided herein and one or more other agents are in the same composition. In other embodiments an IL-13Rα2 peptide-based vaccine provided herein and one or more other agents (e.g., a helper T cell epitope, an adjuvant, and/or an immune response modifier) are administered to a subject concurrently, wherein the administration IL-13Rα2 peptide-based vaccine provided herein and one or more other agents are not in the same composition. In one embodiment, the agent that is administered concurrently with the IL13Rα2 peptide-based vaccine is administered as a separate injection. In certain embodiments, an IL-13Rα2 peptide-based vaccine provided herein and one or more other agents e.g., a helper T cell epitope, an adjuvant, and/or an immune response modifier) are administered to a subject concurrently, wherein the concurrent administration is separated by at least 1 hour, 2 hours, 3 hours, 4 hours, 5 hours, 10 hours, 12 hours, 1 day, 2 days, 3 days, 4 days, 5 days, 6 days, 1 week, or 2 weeks.

As used herein, the term "brain cancer-associated peptide" refers to a peptide found to be associated with one or more brain cancers and which serves as an HLA-A2 restricted cytotoxic T lymphocyte (CTL) epitope. In some embodiments, a brain cancer-associated peptide is a glioma-associated peptide, i.e., the brain cancer that the peptide is associated with is glioma. In a preferred embodiment, the brain cancer-associated peptide is expressed by glioma cells. Exemplary brain cancer-associated peptides include, without limitation, IL-13Rα2 peptides, EphA2 peptides, YKL-40 peptides, GP100 peptides, survivin peptides, and WT1 peptides.

As used herein, the term "IL-13Rα2 peptide" refers to a peptide derived from the IL-13Rα2 protein and which serves as an HLA-A2 restricted cytotoxic T lymphocyte (CTL) epitope. In a specific embodiment the IL-13Rα2 protein from which an IL-13Rα2 peptide is derived is the human IL-13Rα2 protein. In another specific embodiment, an IL-13Rα2 peptide comprises any one of SEQ ID NOs:1-4. In some embodiments, an IL-13Rα2 peptide comprises one, two, three, or more amino acid mutations (e.g., additions, substitutions, or deletions) relative to the IL-13Rα2 peptide as it exists in the native (e.g., wild-type) form of the IL-13Rα2 protein.

As used herein, the term "EphA2 peptide" refers to a peptide derived from the EphA2 protein and which serves as an HLA-A2 restricted cytotoxic T lymphocyte (CTL) epitope. In a specific embodiment the EphA2 protein from which an EphA2 peptide is derived is the human EphA2 protein. In another specific embodiment, an EphA2 peptide comprises SEQ ID NO:6. In some embodiments, an EphA2 peptide comprises one, two, three, or more amino acid mutations (e.g., additions, substitutions, or deletions) relative to the EphA2 peptide as it exists in the native (e.g., wild-type) form of the EphA2 protein.

As used herein, the term "YKL-40 peptide" refers to a peptide derived from the YKL-40 protein and which serves as an HLA-A2 restricted cytotoxic T lymphocyte (CTL) epitope. In a specific embodiment the YKL-40 protein from which a YKL-40 peptide is derived is the human YKL-40 protein. In another specific embodiment, a YKL-40 peptide comprises SEQ ID NO:10. In some embodiments, a YKL-40 peptide comprises one, two, three, or more amino acid mutations (e.g., additions, substitutions, or deletions) relative to the YKL-40 peptide as it exists in the native (e.g., wild-type) form of the YKL-40 protein.

As used herein, the term "GP100 peptide" refers to a peptide derived from the GP100 protein and which serves as an HLA-A2 restricted cytotoxic T lymphocyte (CTL) epitope. In a specific embodiment the GP100 protein from which a GP100 peptide is derived is the human GP100 protein. In another specific embodiment, a GP100 peptide comprises SEQ ID NO:11. In some embodiments, a GP100 peptide comprises one, two, three, or more amino acid mutations (e.g., additions, substitutions, or deletions) relative to the GP100 peptide as it exists in the native (e.g., wild-type) form of the GP100 protein.

As used herein, the term "survivin peptide" refers to a peptide derived from the survivin protein and which serves as an HLA-A2 restricted cytotoxic T lymphocyte (CTL) epitope. In a specific embodiment the survivin protein from which a survivin peptide is derived is the human survivin protein. In another specific embodiment, a survivin peptide comprises SEQ ID NO:7. In some embodiments, a survivin peptide comprises one, two, three, or more amino acid mutations (e.g., additions, substitutions, or deletions) relative to the survivin peptide as it exists in the native (e.g., wild-type) form of the survivin protein.

As used herein, the term "WT1 peptide" refers to a peptide derived from the WT1 protein and which serves as an HLA-A2 restricted cytotoxic T lymphocyte (CTL) epitope. In a specific embodiment the WT1 protein from which a WT1 peptide is derived is the human WT1 protein. In another specific embodiment, a WT1 peptide comprises SEQ ID NO:8. In some embodiments, a WT1 peptide comprises one, two, three, or more amino acid mutations (e.g., additions, substitutions, or deletions) relative to the WT1 peptide as it exists in the native (e.g., wild-type) form of the WT1 protein.

As used herein, the term "cell-free vaccine" refers to a vaccine comprising an IL-13Rα2 peptide, wherein the IL-13Rα2 peptide is not loaded on a cell (e.g., a dendritic cell) in the vaccine (e.g., the peptide derived from IL-13Rα2 is in solution). In a preferred embodiment, the peptides are emulsified in adjuvant. In another preferred embodiment, the adjuvant is Montanide ISA 51.

As used herein, the term "dendritic cell vaccine" refers to a vaccine comprising an IL-13Rα2 peptide, wherein the IL-13Rα2 peptide is loaded on dendritic cells in the vaccine.

5. BRIEF DESCRIPTION OF THE DRAWINGS

FIG. 1 graphically presents data demonstrating that IL-13Rα2-V9 and IL-13Rα2-A1V9 induced a higher magnitude of CTL reactivity than the native IL-13Rα2$_{345-353}$ or IL-13Rα2-E 1V9 against T2 cells loaded with various concentrations of native IL-13Rα2$_{345-353}$. CD8+ T cells from an HLA-A2+ glioma patient were stimulated with DCs loaded with either native IL-13Rα2$_{345-353}$ (●), IL-13Rα2-V9 (○), IL-13Rα2-A1V9 (Δ), IL-13Rα2-E1V9 (X), Influenza M1$_{58-66}$ peptide (▼), or no peptide (□) for 10 days. Then, the T cells were tested for lytic activity against T2 cells loaded with indicated concentrations of IL-13Rα2$_{345-353}$ or no peptide by 4-hr $^{51}$Cr-release assay. The E/T ratio was 12.5. P<0.01 for IL-13Rα2-V9 vs. native as well as IL-13Rα2-A 1V9 vs. native at 0.1 and 1 nM by two-tailed Student-t test. These data demonstrate results from one of three separate experiments with similar results.

Figure 2:
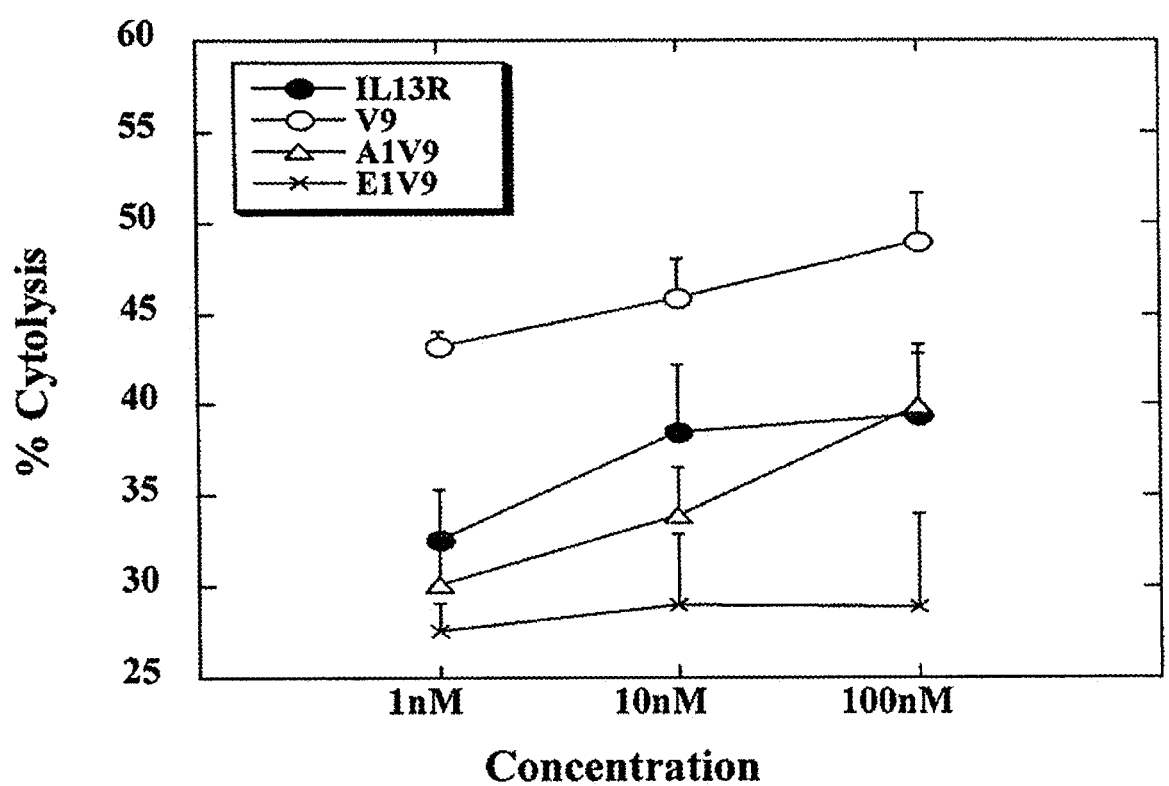

FIG. 2 graphically presents data demonstrating that the CTL line induced by the V9 peptide (open circles) had increased lytic activity against T2 cells loaded with various concentrations of the wild type IL-13Rα2$_{345-353}$ peptide. The CTL lines induced by each of the 3 agonist analogues (V9 (open circles), A1V9 (triangles); E1V9 (X)) or the wild type peptide (closed circles) were examined for CTL activities against lower concentrations of target IL-13Rα2$_{345-353}$ peptide with T2 cells loaded with various concentrations (1-100 nM) of IL-13Rα2$_{345-353}$ by 4-Hr $^{51}$Cr-release assay (E/T ratio=50).

Figure 3:
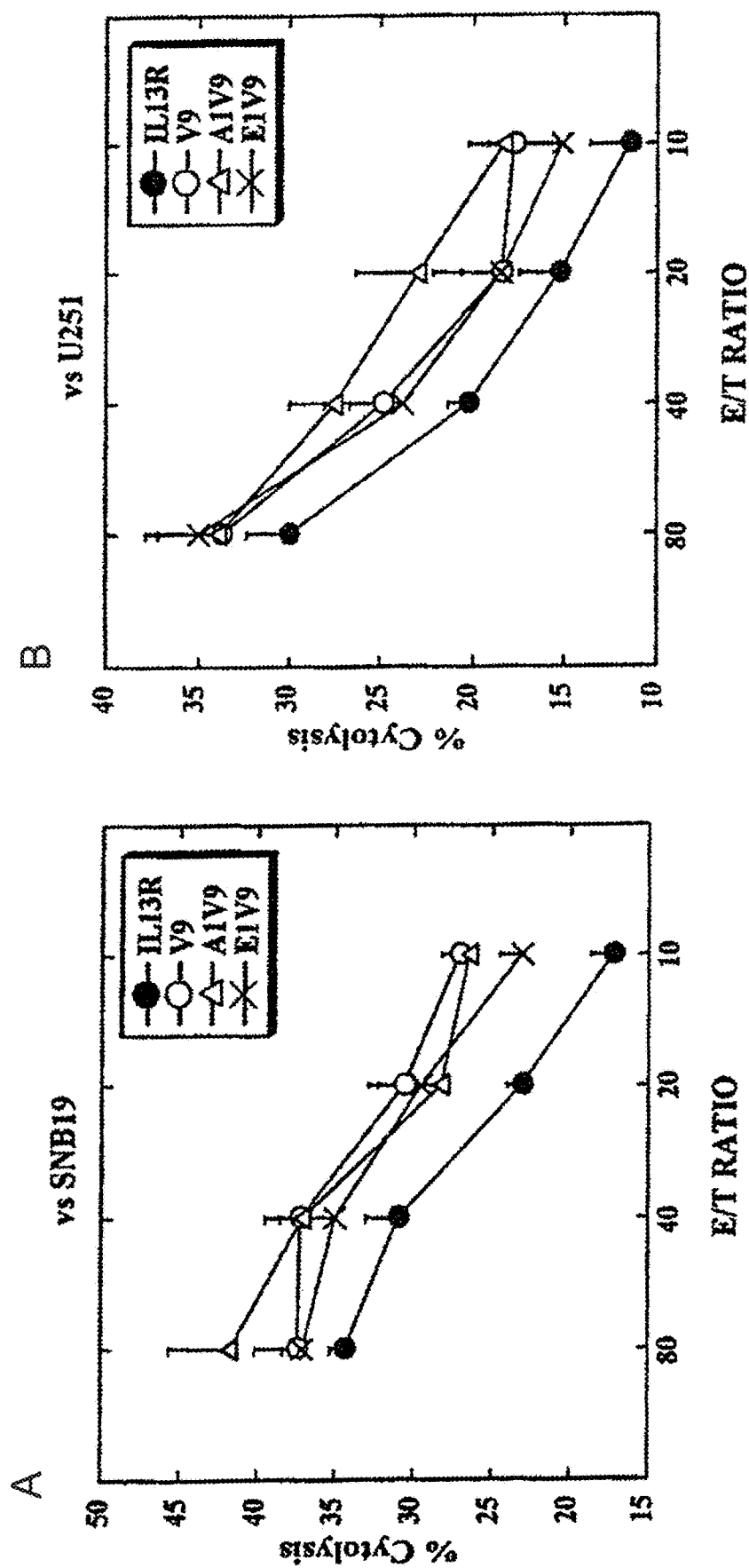

FIG. 3 graphically presents data demonstrating that the modified peptides induced a higher magnitude of CTL reactivity than the native IL-13Rα2$_{345-353}$ against human glioma cell lines. CD8+ cells derived from an HLA-A2+ glioma patient were stimulated with native IL-13Rα2$_{345-353}$ (●), IL-13Rα2-V9 (○), IL-13Rα2-A1V9 (Δ), or IL-13Rα2-E1V9 (X). On day 10, the cells were tested for lytic ability against human glioma cells SNB19 (A) and U-251 (B) (both are IL-13Rα+/HLA-A2+) using 4-Hr $^{51}$Cr-release assay. Against SNB19 glioma cells, p<0.05 at all E/T ratios for IL-13Rα2-V9 vs. native IL-13Rα2$_{345-353}$ as well as IL-13Rα2-A1V9 vs. native IL-13Rα2$_{345-353}$ by two-tailed Student-t tests. Against U251 glioma cells, p<0.05 at E/T ratio of 10 and 40 for IL-13Rα2-V9 vs. native IL-13Rα2$_{345-353}$ as well as IL-13Rα2-A1V9 vs. native IL-13Rα2$_{345-353}$ by two-tailed Student-t tests. IL-13Rα2-E1V9 did not improve the CTL reactivity for a statistically significant level in comparison to the native. The data presented represent one of three experiments with different donors with similar results.

Figure 4:
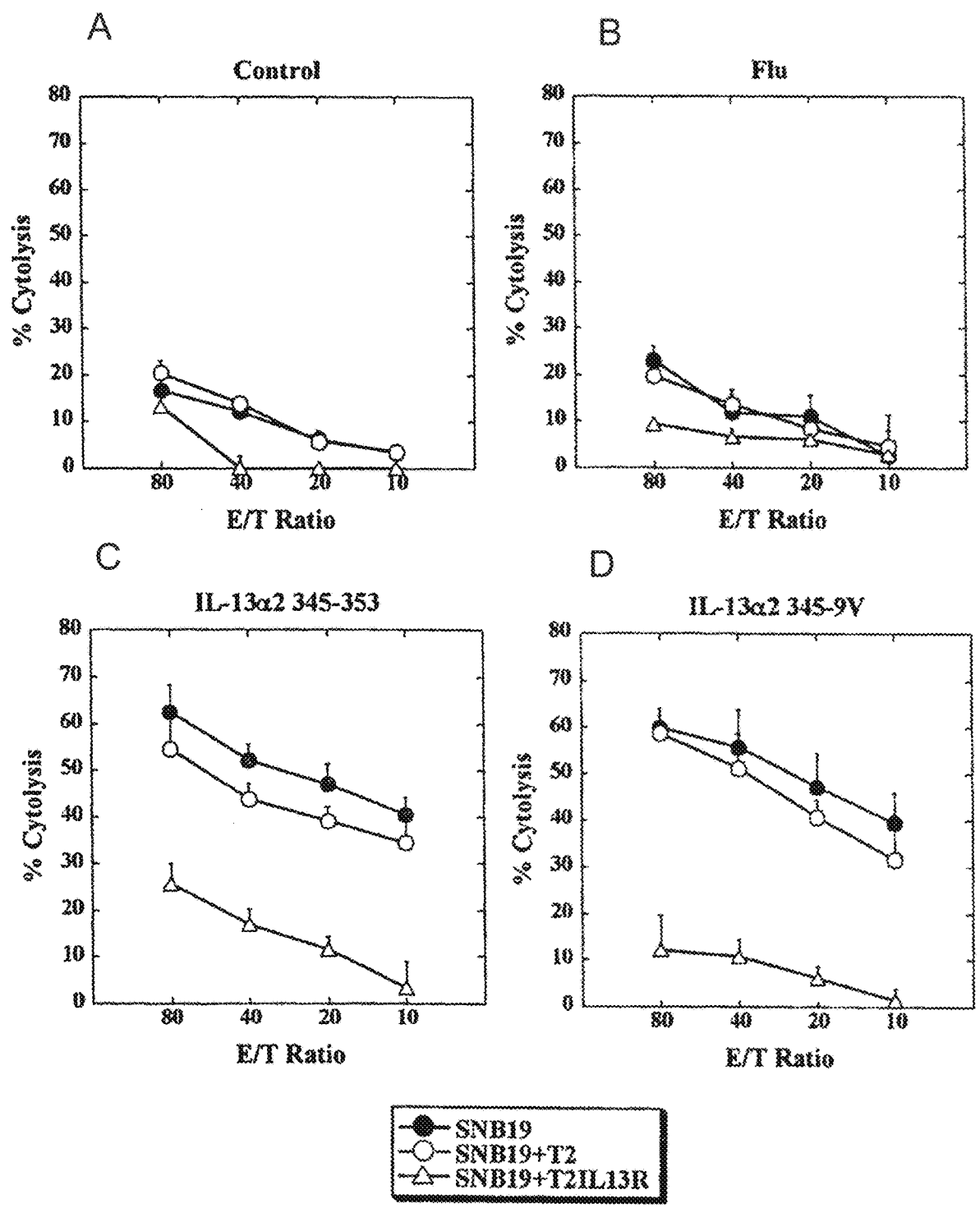

FIG. 4 graphically presents data demonstrating that the addition of "cold" T2 cells pulsed with IL-13Rα2$_{345-353}$ inhibited the CTL activities indicating the antigen-specificity of the CTL lines. The CTL lines induced with each peptide (control (A); Flu (B); IL-13Rα2$_{345-353}$ (C); IL-13Rα2$_{345-9V}$ (D)) were incubated for 4 h with $^{51}$Cr-labeled human glioma cell lines SNB19 at the indicated E:T ratios for evaluation of specific lytic ability (●). For the cold target inhibition assay, $^{51}$Cr-labeled target SNB19 cells (1×10$^3$ cells/well) and cold T2 cells (1×10$^4$ cells/well) pulsed with (Δ) or without (○) peptide IL-13Rα2$_{345-353}$ were incubated with the CTLs.

Figure 5:
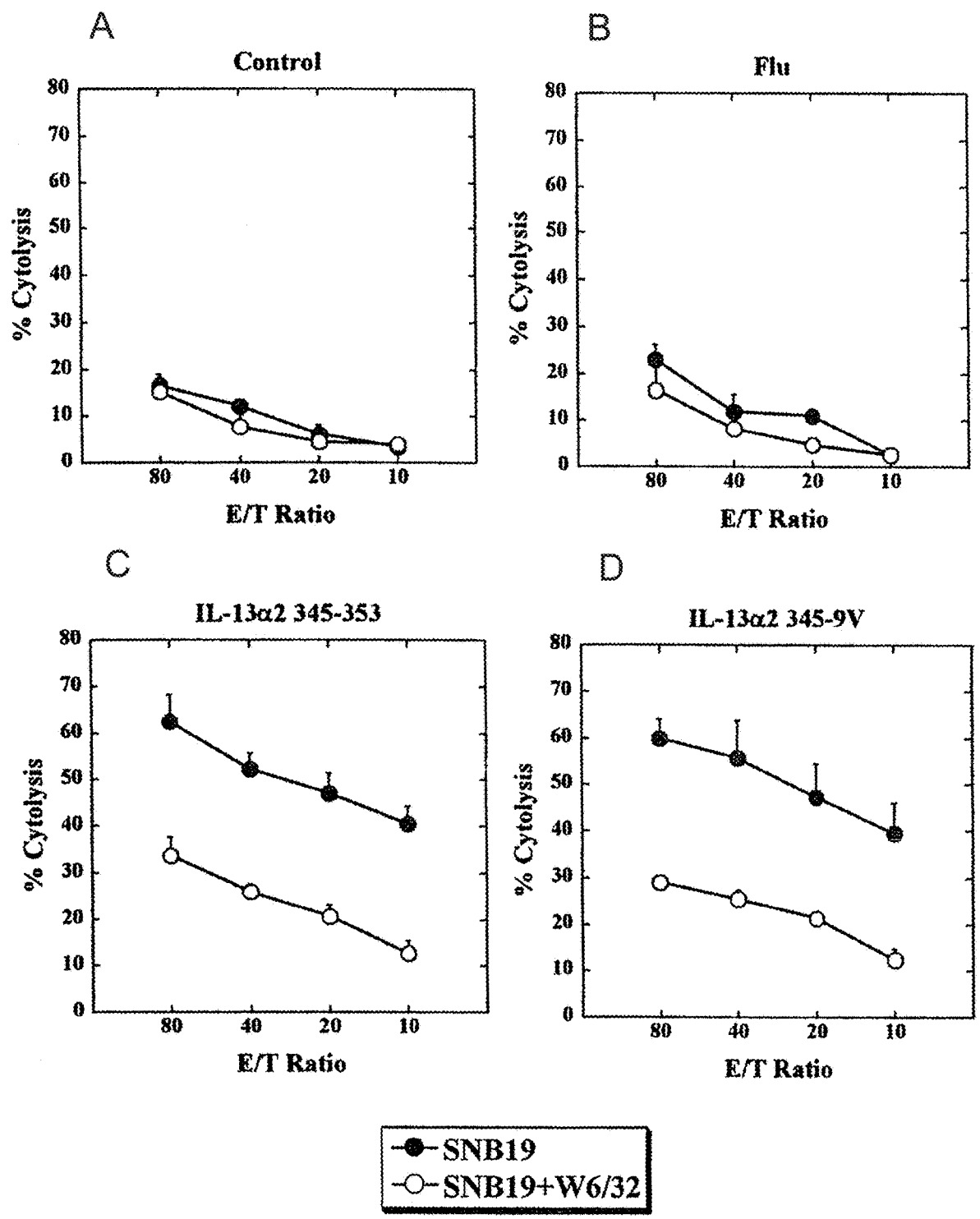

FIG. 5 graphically presents data demonstrating that the addition of anti-HLA-A2 antibody inhibited the CTL activities indicating HLA-A2-restricted recognition of the CTL lines. The CTL lines induced with each peptide (control (A); Flu (B); IL-13Rα2$_{345-353}$ (C); IL-13Rα2$_{345-9V}$ (D)) were incubated for 4 h with $^{51}$Cr-labeled human glioma cell line SNB19 at the indicated E:T ratios for evaluation of specific lytic ability (●). Anti-HLA-A2 antibody (W6/32; 10 μg/ml) was added to block the function of HLA-A2 mediated recognition by the T cells (a).

Figure 6:
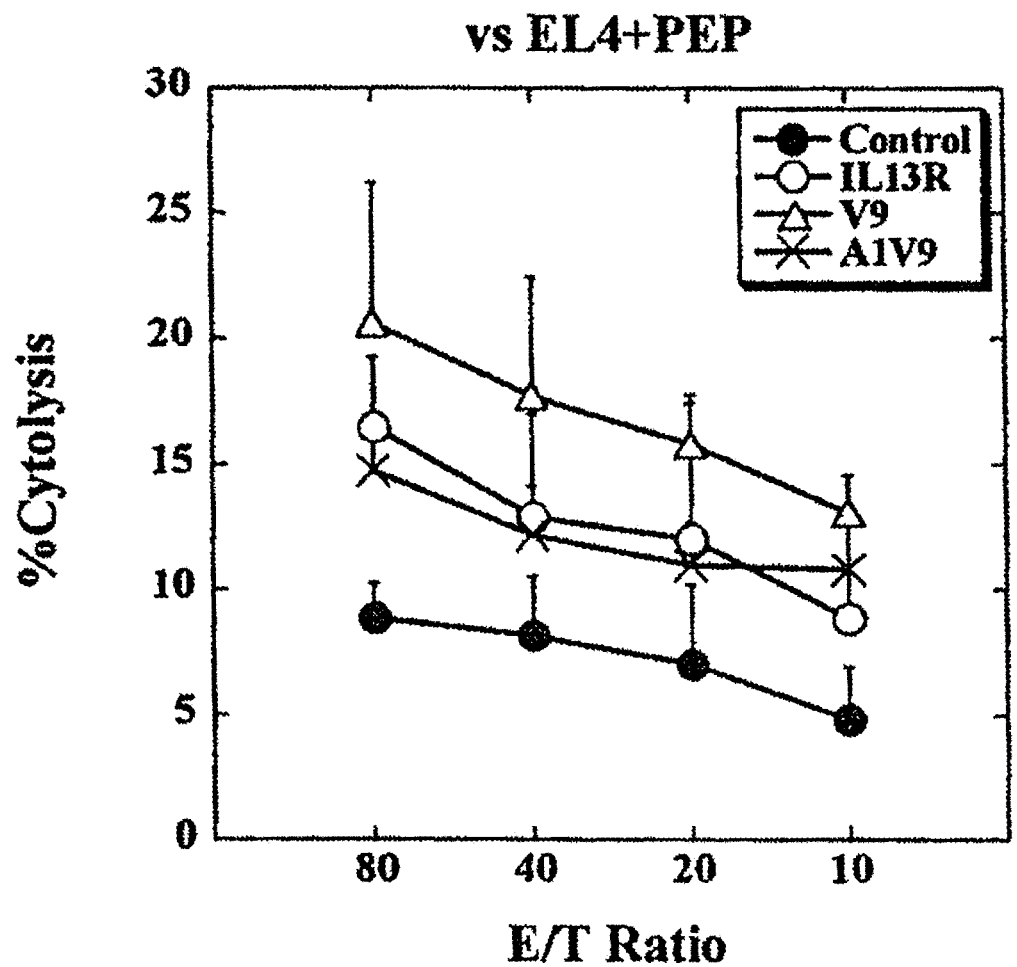

FIG. 6 graphically presents data demonstrating that the modified peptides induced higher magnitude of CTL reactivity than the native IL-13Rα2$_{345-353}$ against EL4-HHD loaded with the native IL-13Rα2$_{345-353}$. SPCs obtained from HHD mice that had been immunized with either control MART-1$_{27-35}$ (●), native IL-13Rα2$_{345-353}$ (○), IL-13Rα2-V9 (Δ) or IL-13Rα2-A1V9 (X) were tested for their specific lytic activity against EL4-HHD cells pulsed with the native IL-13Rα2$_{345-353}$ by standard 4 hr $^{51}$Cr-release assays.

Figure 7:
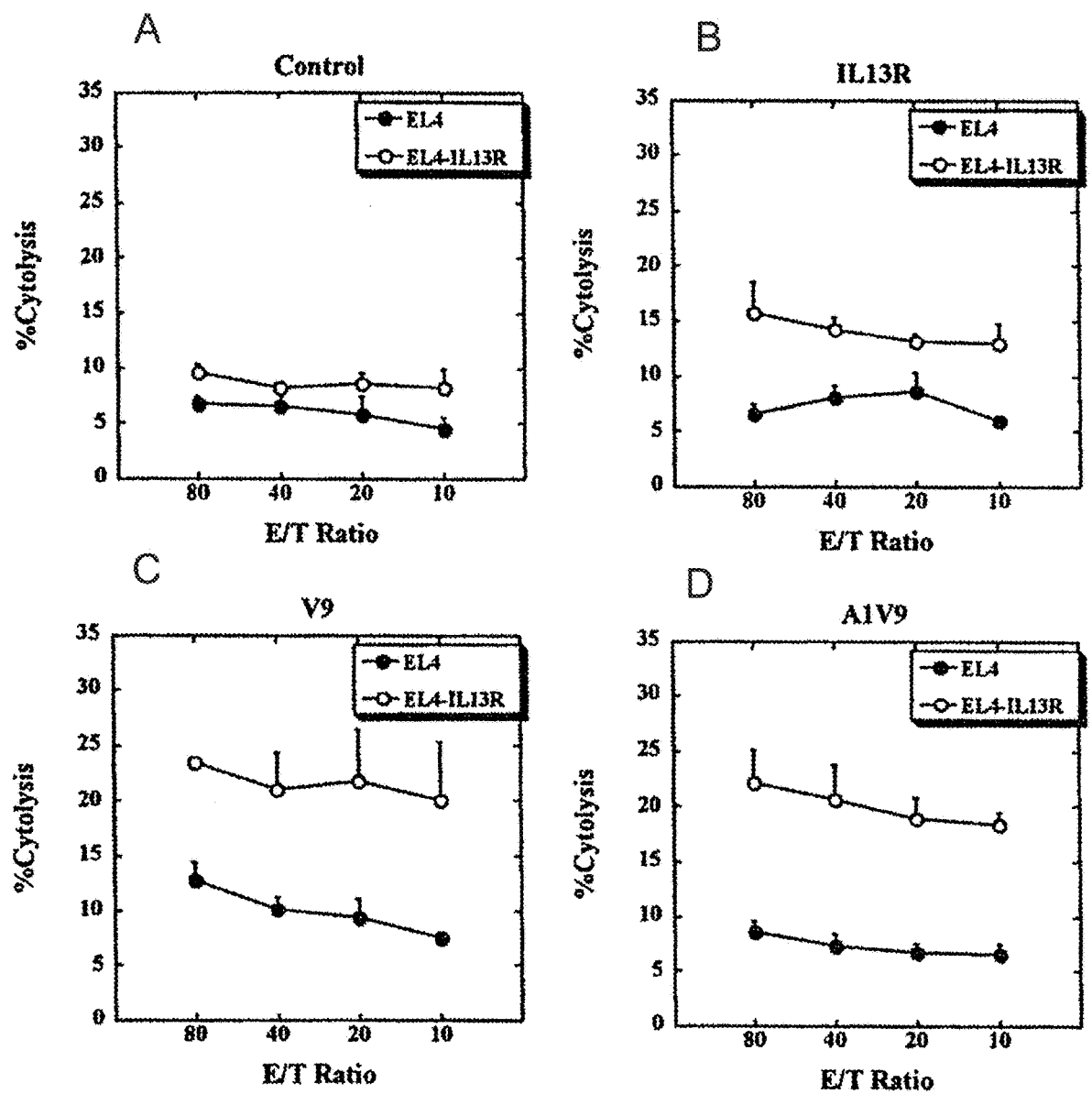

FIG. 7 graphically presents data demonstrating that the modified peptides induced a higher magnitude of CTL reactivity than the native IL-13Rα2$_{345-353}$ against EL4-HHD-IL-13Rα2. SPCs obtained from HHD mice that had been immunized with either control MART-1$_{27-35}$ (A), native IL-13Rα2$_{345-353}$ (B), IL-13Rα2-V9 (C), or IL-13Rα2-A1V9 (D) were tested for their specific lytic activity against EL4-HHD-IL-13Rα2 (○) or control EL4-HHD (●) by standard 4 hr $^{51}$Cr-release assays.

Figure 8:
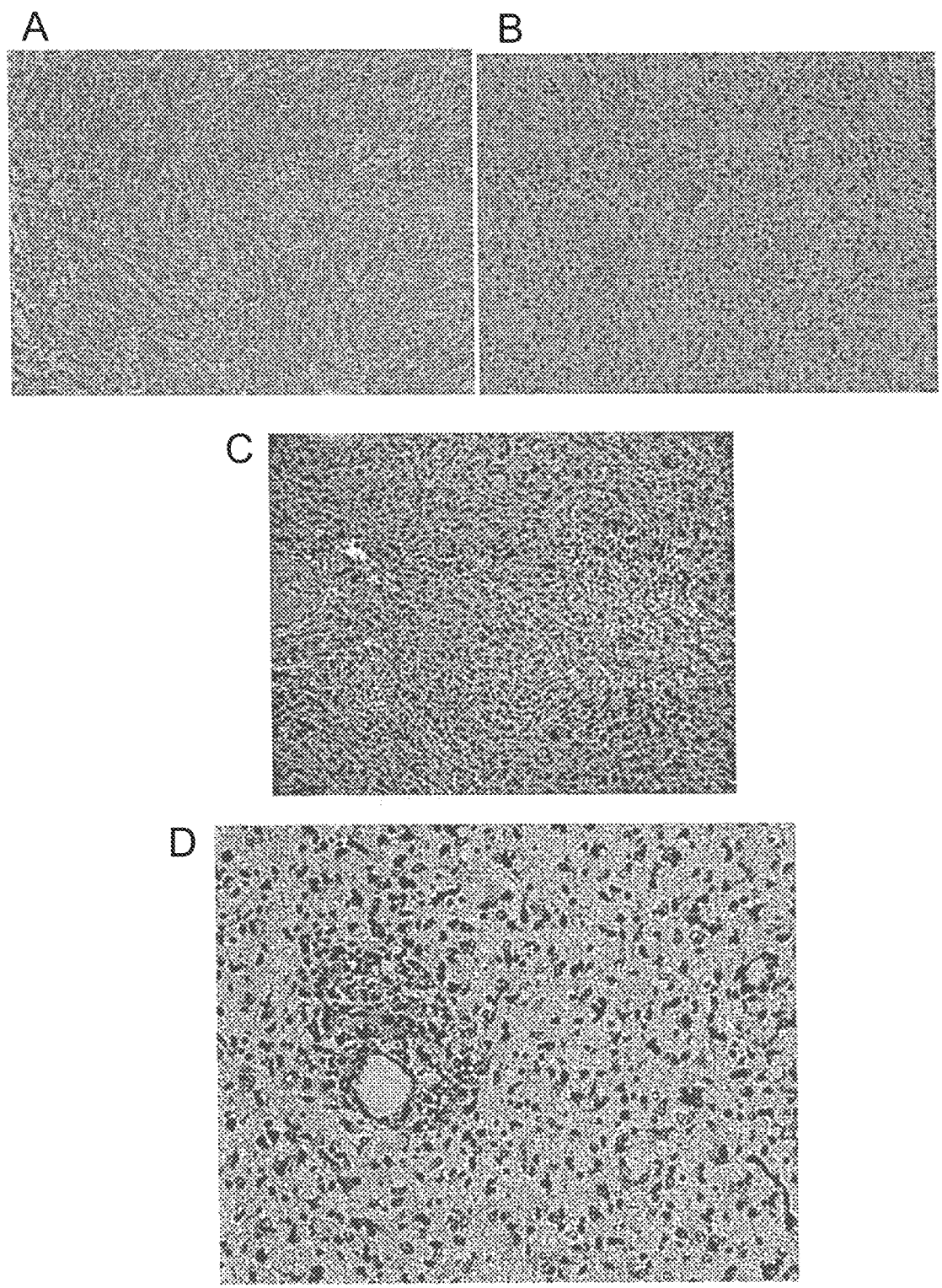

FIG. 8 depicts the expression of EphA2 protein in glioblastoma multiforme (GBM) and anaplastic astrocytoma (AA). Paraffin embedded sections of surgical specimens obtained from patients with GBM (A-C) or AA (D) were deparaffinized and stained with anti-EphA2 polyclonal antibody (C-20: Santa Cruz Biotechnology, Inc., Santa Cruz, Calif.), or control rabbit IgG (upper right corner window for each sample). Relatively dense staining on endothelia and tumor cells surrounding the vessel was observed (D). Nine of fourteen GBM and six of nine AA cases examined were positive for EphA2 (not shown). Original magnification; ×20.

Figure 9:
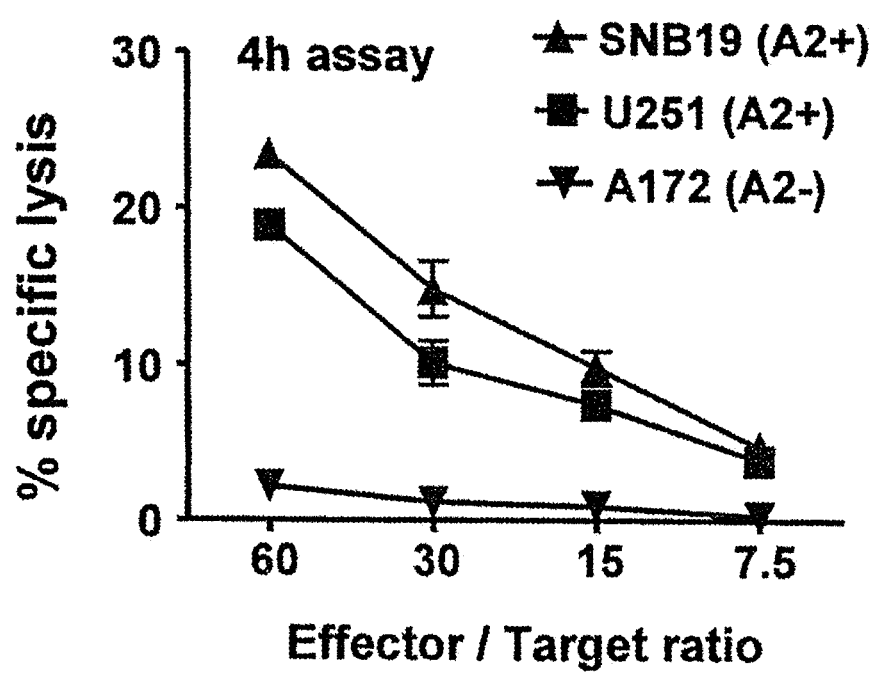

FIG. 9 graphically presents data demonstrating that the CD8+ cells stimulated with EphA2$_{883-891}$ elicited CTL responses against human glioma cells expressing HLA-A2 and EphA2 protein. CD8+ T cells from an HLA-A2+ glioma patients were stimulated with DCs loaded with EphA2$_{883-891}$ for 10 days. These T cells were then tested for their lytic activity against human glioma cells SNB19 (HLA-A2+, EphA2+) (▲), U251 (HLA-A2+, EphA2+) (■) and A172 (HLA-A2−, EphA2+) (▼) by 4-hr $^{51}$Cr-release assay.

Figure 10:
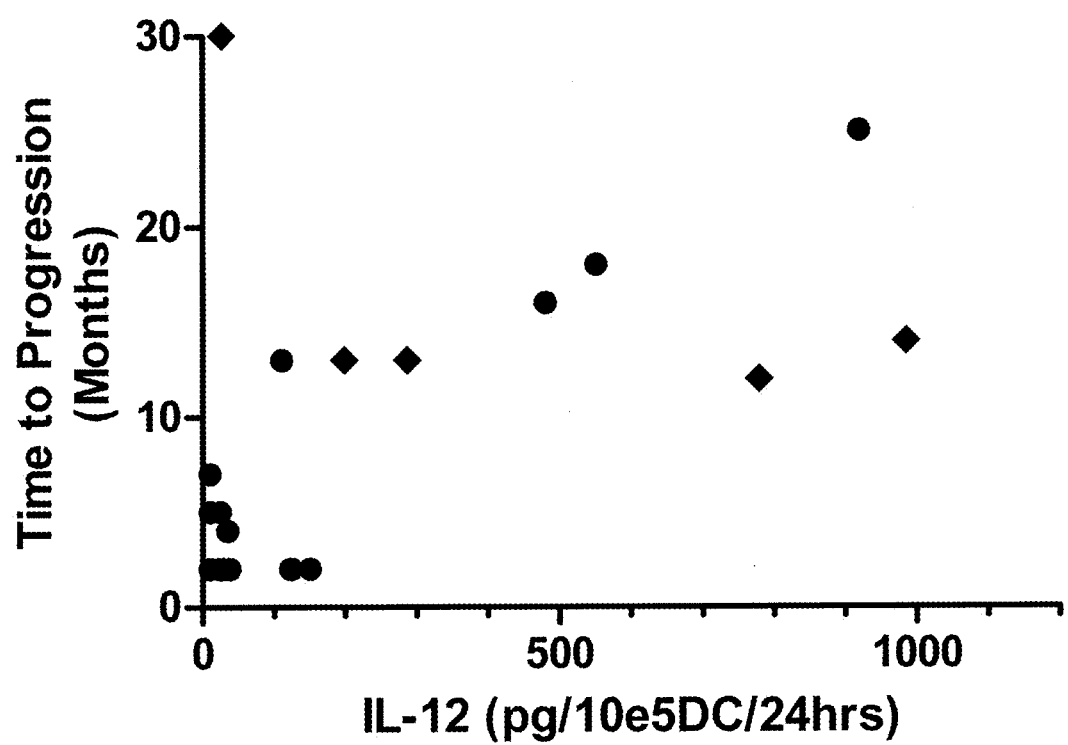

FIG. 10: IL-12 production levels positively correlated with TTP. P=0.0255 based on Cox regression followed by likelihood-ratio test. Closed circles indicate patients who have already progressed, whereas closed diamonds represent patients who have not recurred to date.

Figure 11:
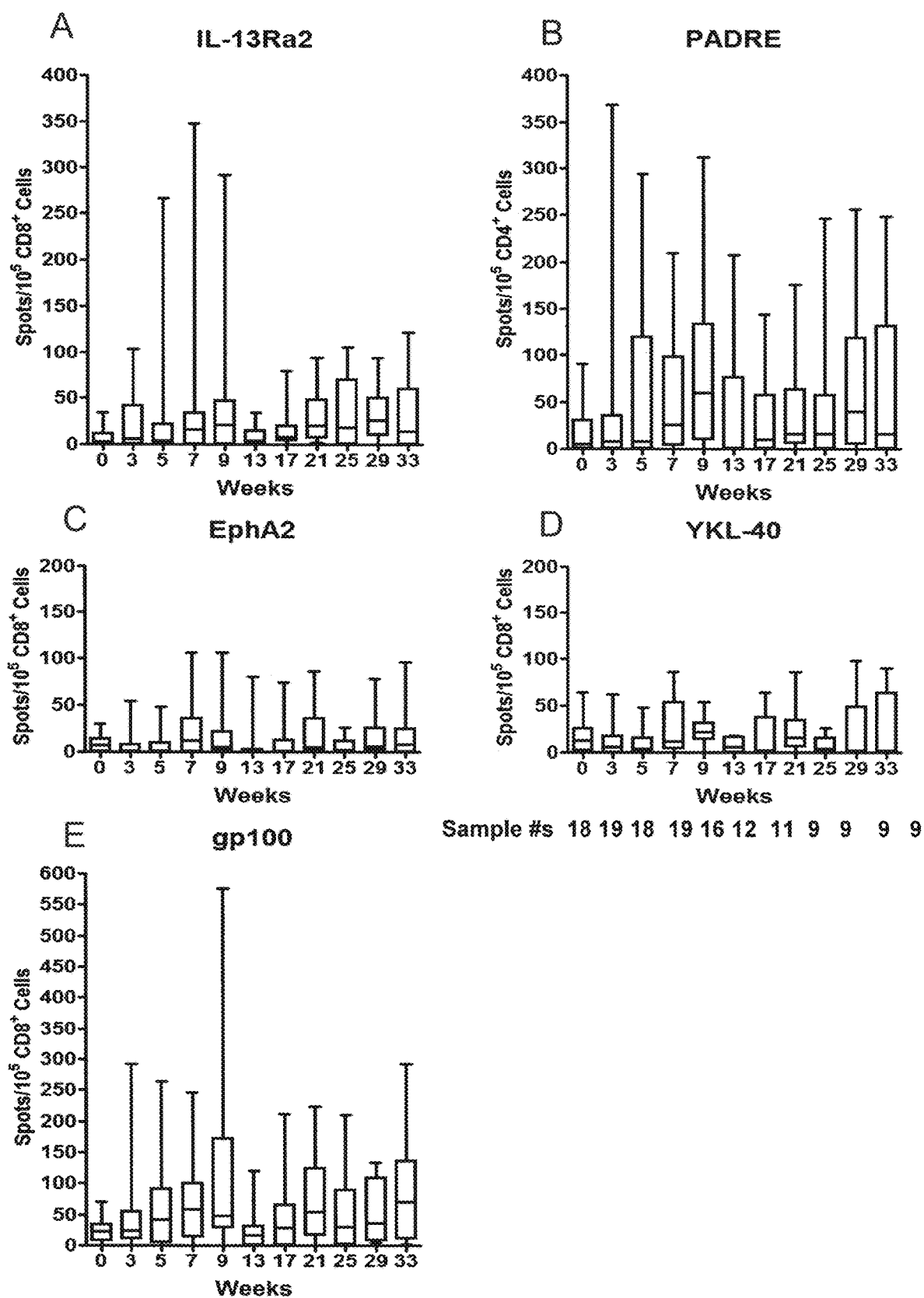

FIG. 11: T-cell responses to IL-13Rα2 (A), PADRE (B), EphA2 (C), YKL-40 (D), or gp100 (E) evaluated by IFN-γ ELISPOT. Time course for IFN-γ ESLIPOT assays for all evaluated patients with box plots (boxes=25th to 75th percentiles; vertical lines=minimum to maximum). Numbers at the bottom of each time point in the panel for YKL-40 (D) are the number of assessable patients at the time shown. These numbers also pertain to the other GAAs and PADRE.

Figure 12:
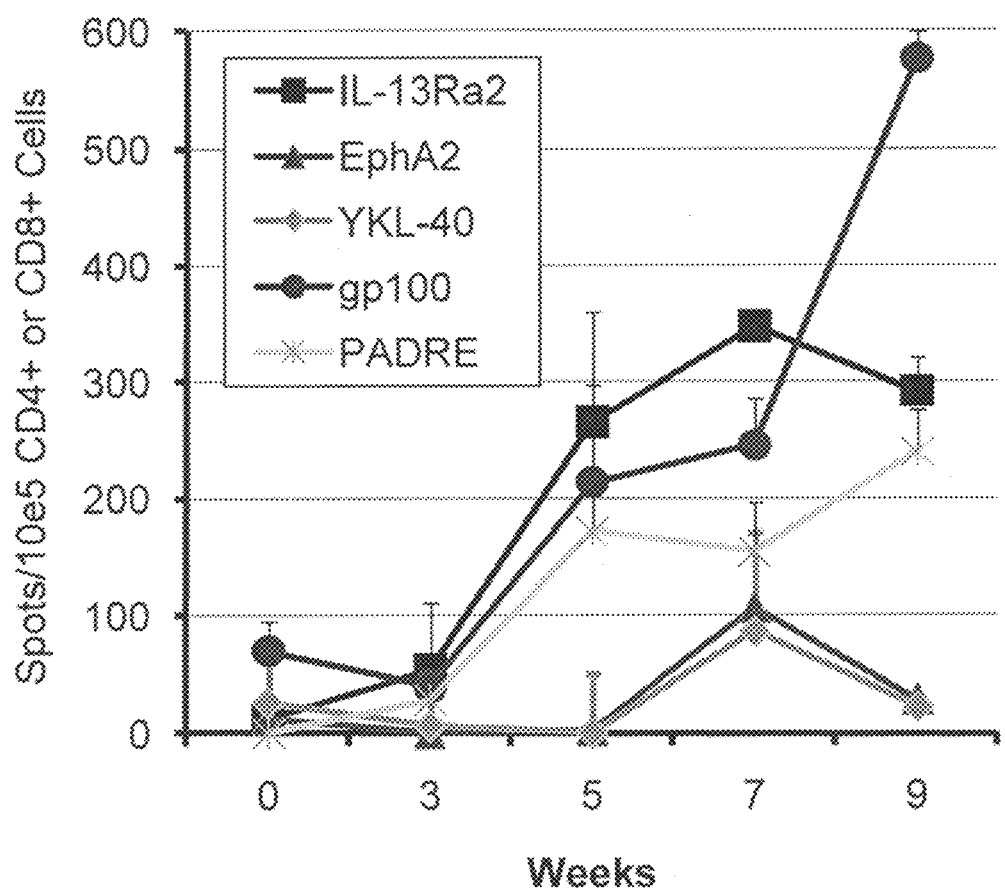

FIG. 12: T-cell responses to IL-13Rα2 (a), PADRE (*), EphA2 (Δ), YKL-40 (i), or gp100 (●) evaluated by IFN-γ ESLIPOT analyses for Patient 10.

Figure 13:
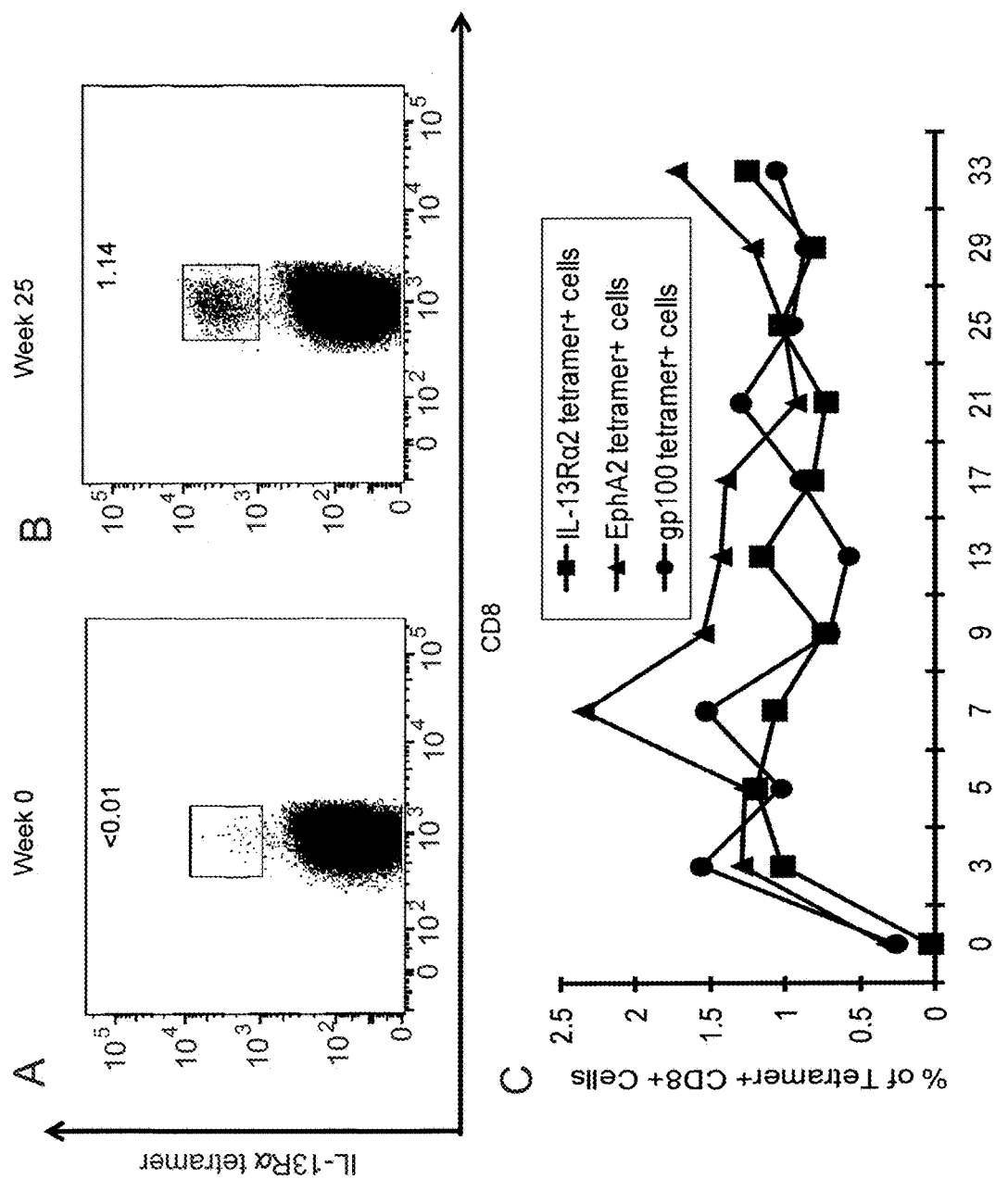

FIG. 13: Patient 6 showed durable tetramer responses, which were analyzed for up to 33 weeks (IL-13Rα2 tetramer+cells (■); EphA2 tetramer+cells (▲); gp100 tetramer+cells (●)) (C). Examples of dot plots for positive tetramer responses against the IL-13Rα2-epitope are shown (A-B).

Figure 14:
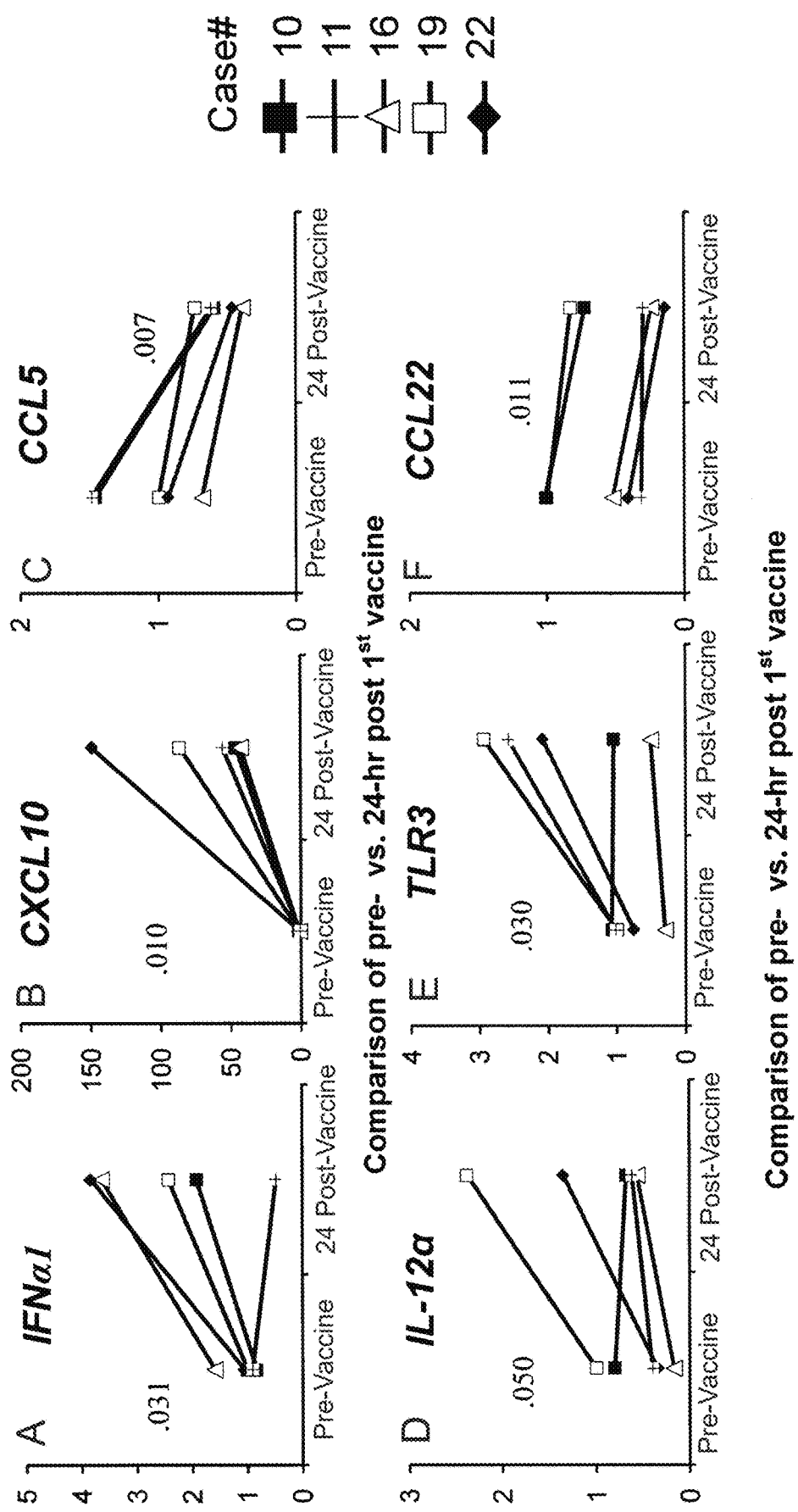

FIG. 14: Induction of type-1 cytokine and chemokine responses. Line graphs represent paired relative gene expression of IFNα1 (A), CXCL10 (B), CCL5 (C), IL-12α (D), TLR3 (E), or CCL22 (F) by RT-PCR on one day prior to the 1$^{st}$ vaccination compared to 24 hours post 1$^{st}$ vaccine for case number 10 (■), 11 (|), 16 (Δ), 19 (□), or 22 (♦). Y axes indicate concentrations of cytokine/chemokines by pg/ml. Numbers in the panels of each of (A)-(F) indicate p-values based on paired student t test using the means of each patient's ΔΔC$_T$ value.

Figure 15:
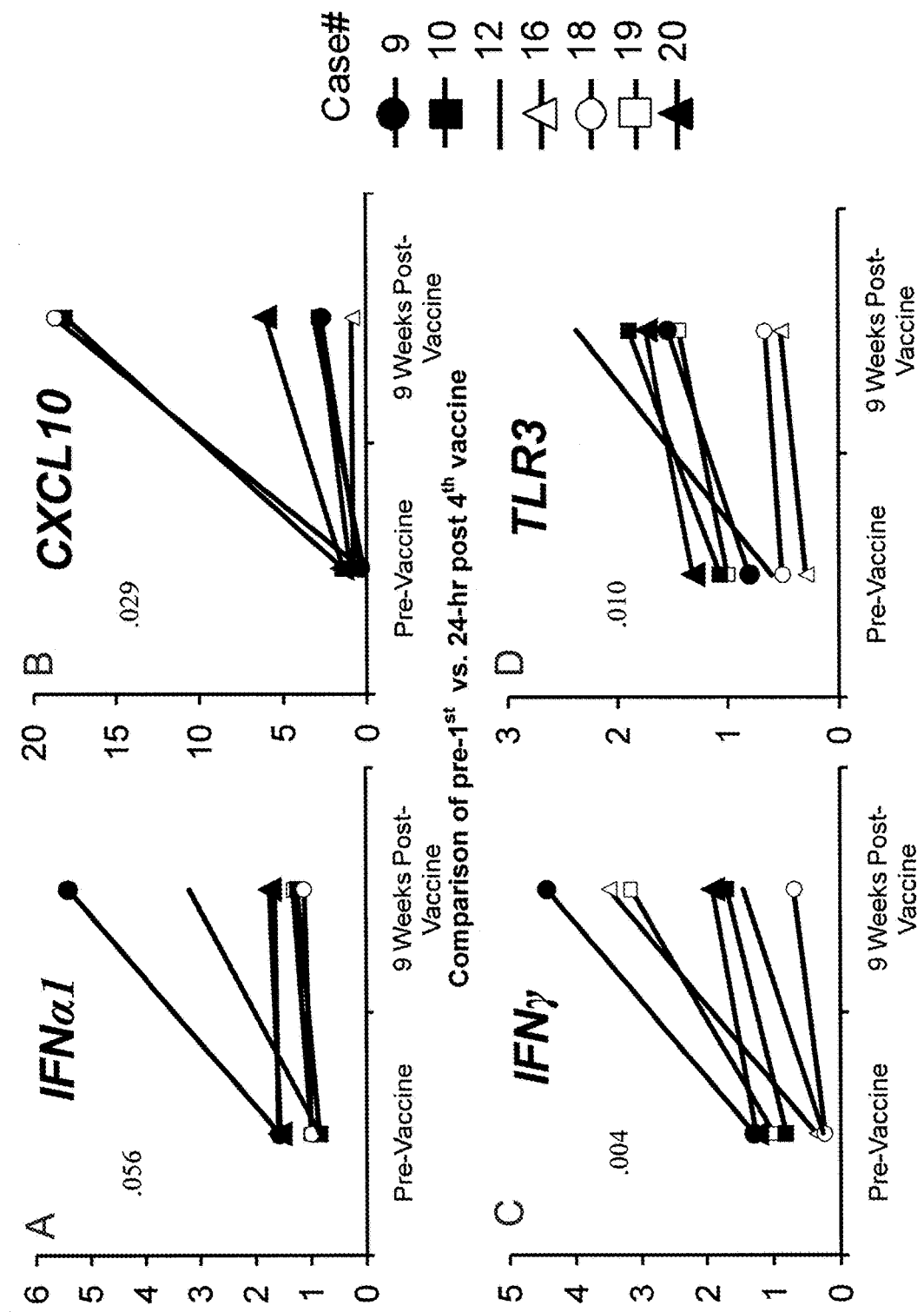

FIG. 15: Induction of type-1 cytokine and chemokine responses. Line graphs represent paired relative gene expression of IFNα1 (A), CXCL10 (B), IFNγ (C), TLR3 (D) by RT-PCR on one day prior to the 1st vaccination compared to 9 weeks post 1$^{st}$ vaccine for case number 9 (●), 10 (■), 12 (no symbol), 16 (Δ), 18 (○), 19 (□), or 20 (▼). Y axes indicate concentrations of cytokine/chemokines by pg/ml. Numbers in the panels of each of (A)-(D) indicate p-values based on paired student t test using the means of each patient's ΔΔC$_T$ value.

Figure 16:
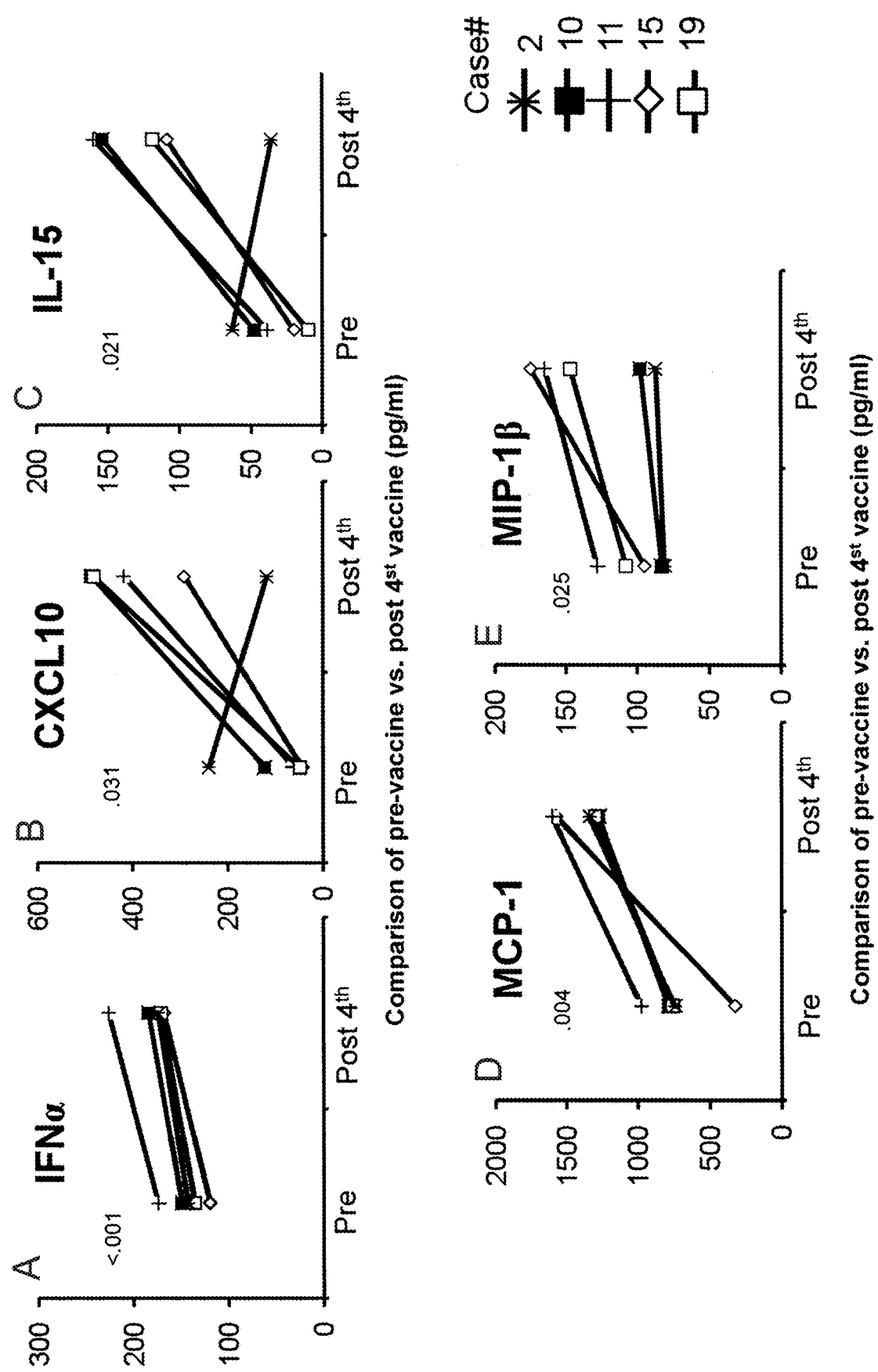

FIG. 16: Luminex analyses were performed in pre-1$^{st}$ and post-4$^{th}$ vaccine serum samples. Y axes indicate concentrations of cytokine/chemokines by pg/ml. Numbers in the panels of each of (A)-(E) indicate p-values based on paired student t test using the means of the concentrations.

Figure 17:
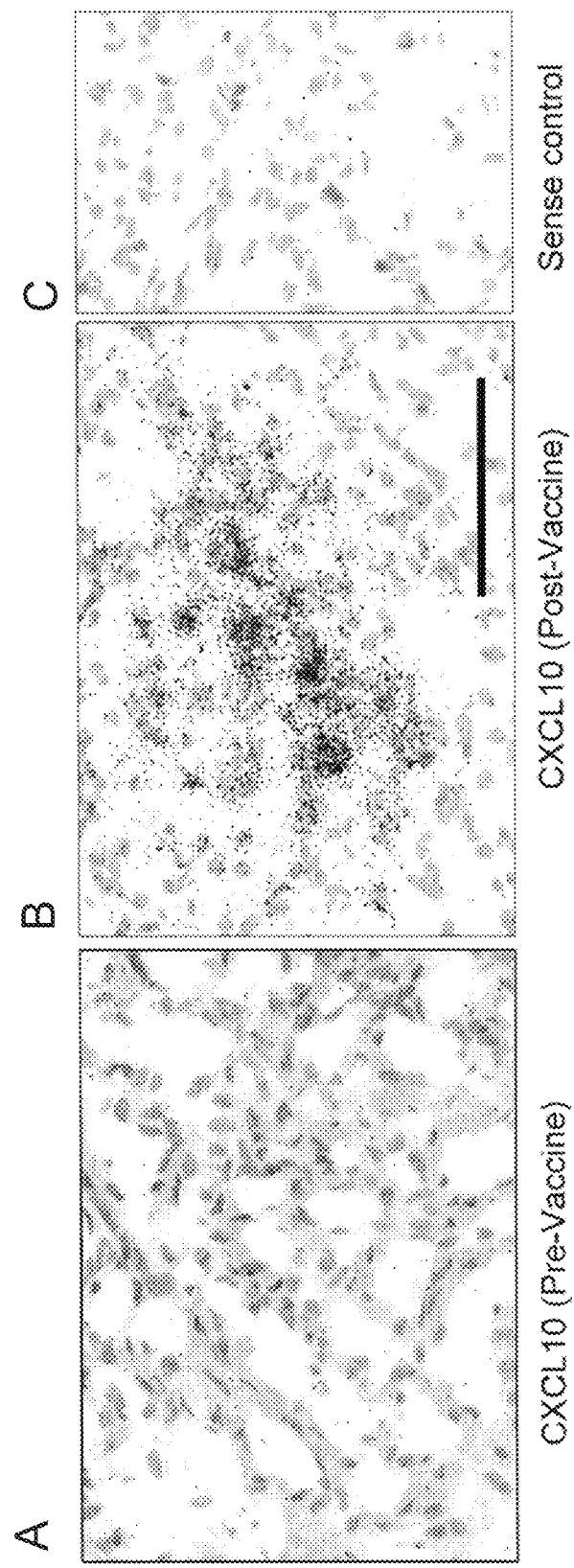

FIG. 17: Patient 1 demonstrated increase in the size of Gd-enhanced lesion following two booster vaccines and underwent surgical resection of the lesion. In situ hybridization detected mRNA for CXCL10 (dark spots) in the post-vaccine tissue (B) but not in the initially resected tumor (pre-vaccine) (A). Control, (C). None of two other pre-vaccine tissues demonstrated positive CXCL10 messages. The scale bar equals to 100 μm. Hematoxylin and eosin staining was performed for background.

Figure 18:
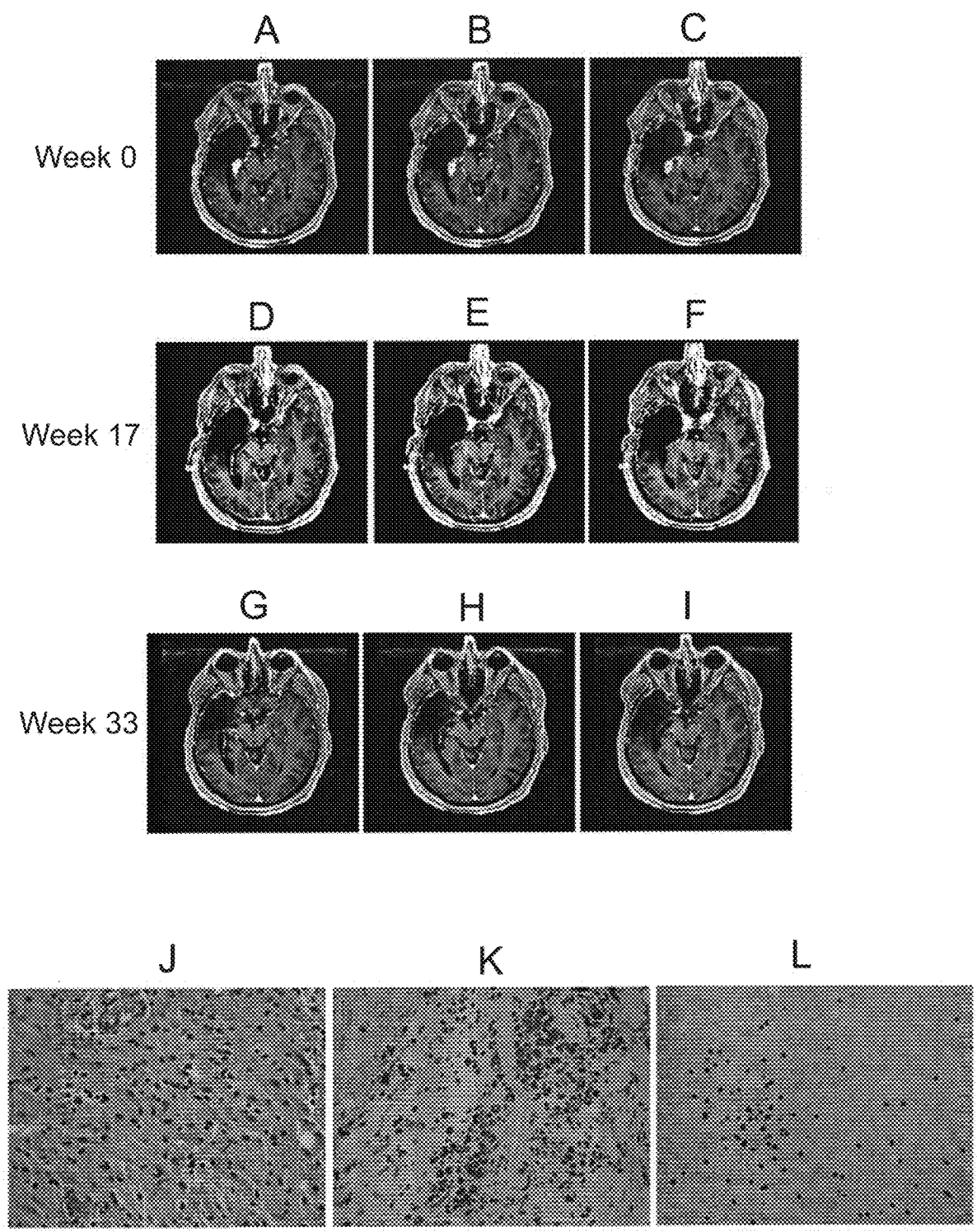

FIG. 18: Patients with clinical response. Patient 20 demonstrated complete radiological response of Gd-enhancing tumor on MRI on Weeks 17 and 33 (three consecutive slices shown for Week 0 (A-C), Week 17 (D-F), and Week 33 (G-I)). Following two booster vaccines, Patient 1 demonstrated enlargement of Gd-enhanced lesion. Resected tissue revealed no evidence of mitotically active tumor (J), but remarkable infiltration of CD68$^+$ macrophages (K) and CD8$^+$ T-cells (L). Original magnifications×20 for J-L.

Figure 19:
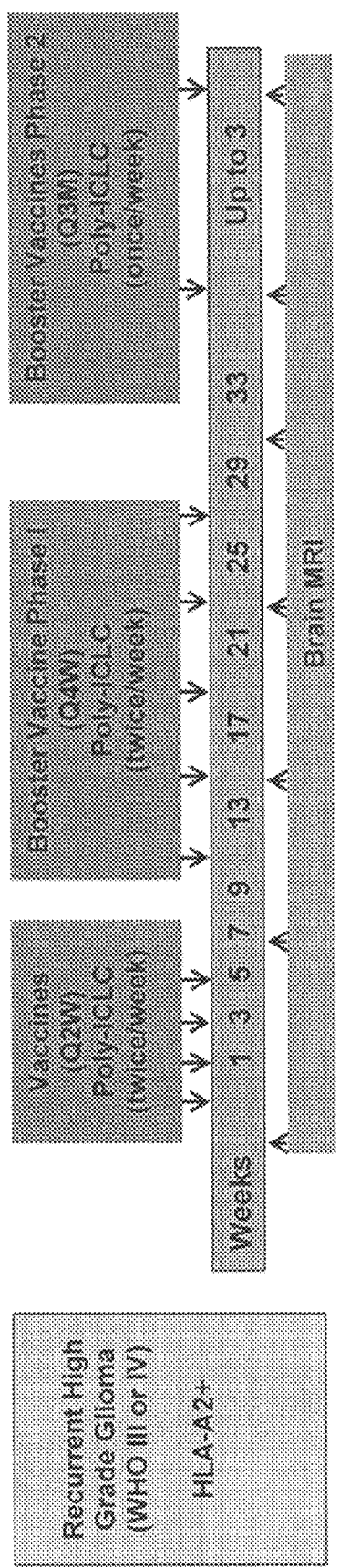

FIG. 19: Flow diagram for the trial. See Section 7.7 for details of treatment. The second phase of booster vaccines could start any time after Week 37 and administered every 3 months up to 3 years from the first vaccine, unless patients demonstrated major AE or disease progression. The αDC1 vaccines were administered using ultrasound to inguinal lymph nodes (right and left for the first and second vaccines, respectively) and axillary lymph nodes (right and left for the third and forth vaccines, respectively). The site was rotated in the same order for booster vaccines to minimize the potential effects of injection-induced trauma in the microenvironment of the lymph nodes by repeating injections in short periods of time.

Figure 20:
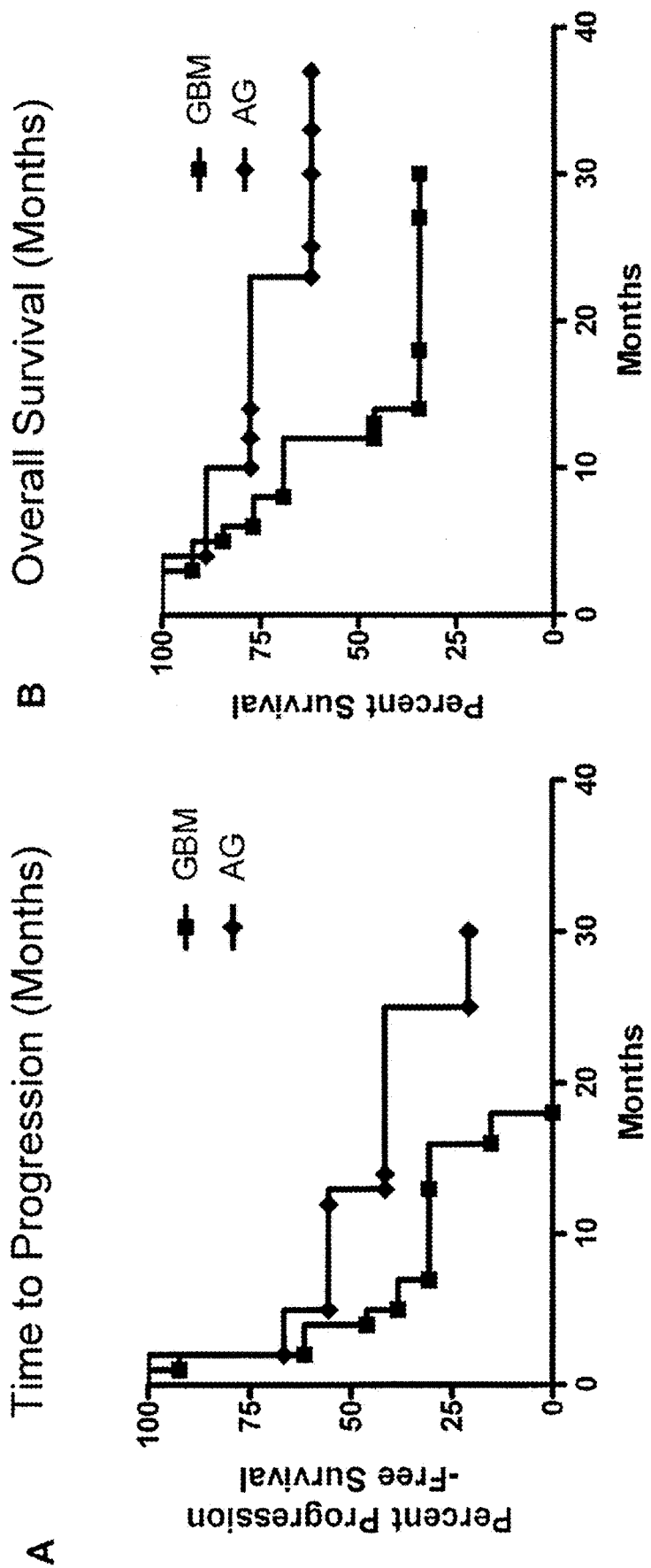

FIG. 20: Time to progression (A) and overall survival (B) for GBM (■) and AG (♦). Median TTP are 4 and 13 months for GBM and AG, respectively.

Figure 21:
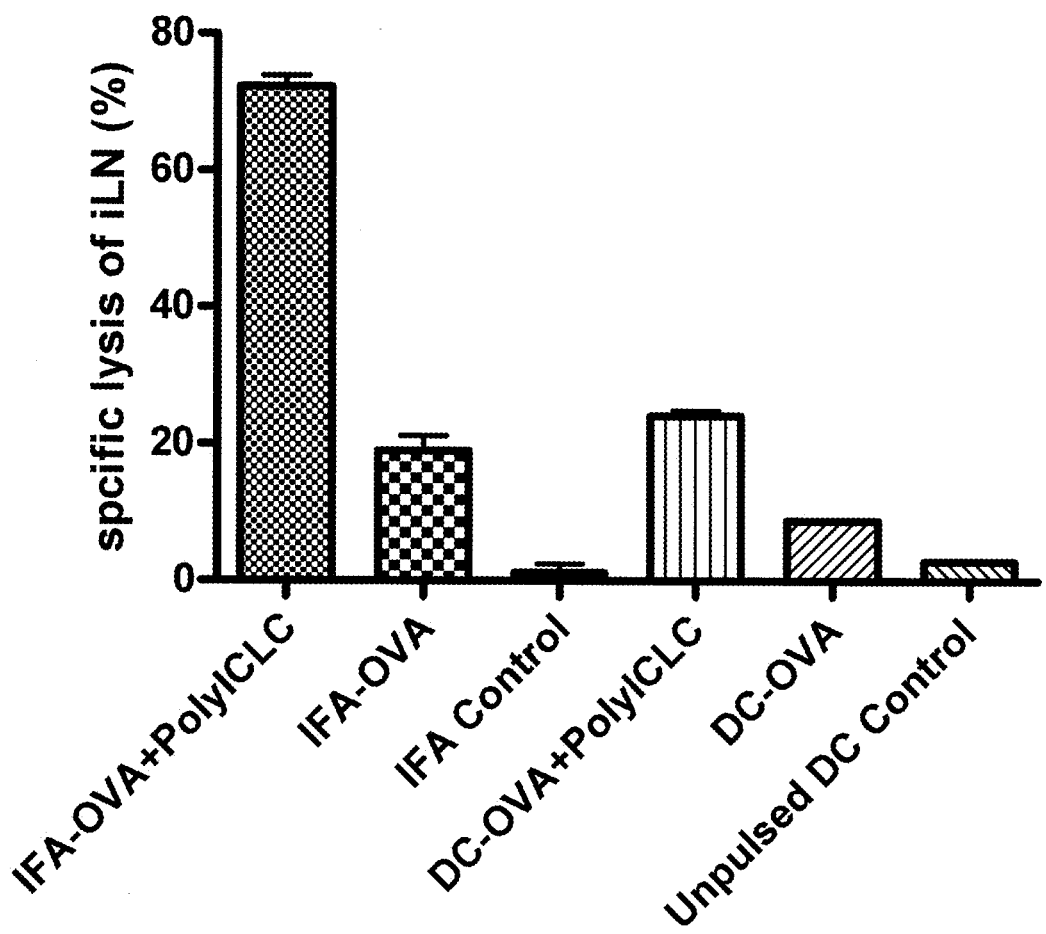

FIG. 21: IFA-based peptide vaccines induce superior CTL activities to DC-based vaccines combined with intramuscular (i.m.) injections of poly-ICLC. C57BL/6 mice received two injections (on Days 0 and 7) of either: 1) subcutaneous (s.c.) ovalbumin$_{257-264}$ peptide emulsified in IFA (IFA-OVA) plus concurrent i.m. injection of poly-ICLC (50 μg/injection); 2) s.c. IFA-OVA plus i.m. saline; 3) bone marrow-derived DC loaded with ovalbumin$_{257-264}$ peptide (DC-OVA) plus i.m. poly-ICLC; or 4) DC-OVA plus i.m. saline. Other control groups included mice receiving IFA or DC alone without the OVA-peptide. IFA-OVA vaccines combined with poly-ICLC demonstrated the highest level of OVA-specific CTL in vivo. Use of non-mutated self GAA-peptides emulsified in IFA with poly-ICLC improved survival of mice without inducing autoimmunity. These data demonstrate that poly-ICLC assisted IFA-peptide vaccines represent an effective and safe vaccination strategy.

6. DETAILED DESCRIPTION

Provided herein are interleukin-13 receptor α2 (IL-13Rα2) peptide-based vaccines comprising an IL-13Rα2 peptide. The IL-13Rα2 peptide-based vaccines provided herein comprise an IL-13Rα2 peptide and at least one additional brain cancer-associated peptide.

In one aspect, presented herein are IL-13Rα2 peptide-based vaccines comprising an IL-13Rα2 peptide and one, two, three, or more additional brain cancer-associated peptides. In certain embodiments, the IL-13Rα2 peptide-based vaccines described herein are administered concurrently with one or more helper T cell epitopes and/or one or more immune response modifiers. In accordance with such embodiments, the one or more helper T cell epitopes and/or one or more immune response modifiers may be administered as part of the vaccine (e.g., in solution with the IL-13Rα2 peptide and the one, two, three, or more additional brain cancer-associated peptides) or separate from the vaccine (i.e., the helper T cell epitopes and/or immune response modifiers may be administered as a formulation that is not a part of the vaccine formulation). In some embodiments, the IL-13Rα2 peptide-based vaccines described herein are administered as cell-free vaccines. In other embodiments, the IL-13Rα2 peptide-based vaccines described herein are administered as dendritic cell vaccines.

In one embodiment, an IL-13Rα2 peptide-based vaccine comprises an IL-13Rα2 peptide, an EphA2 peptide, a YKL-40 peptide, and a GP100 peptide. In a specific embodiment, an IL-13Rα2 peptide-based vaccine comprises the IL-13Rα2 peptide corresponding to any one of SEQ ID NOs:1-4, the EphA2 peptide corresponding to SEQ ID NO:6, the YKL-40 peptide corresponding to SEQ ID NO:10, and the GP100 peptide corresponding to SEQ ID NO:11. In another specific embodiment, an IL-13Rα2 peptide-based vaccine comprises the IL-13Rα2 peptide corresponding to SEQ ID NO:3, the EphA2 peptide corresponding to SEQ ID NO:6, the YKL-40 peptide corresponding to SEQ ID NO:10, and the GP100 peptide corresponding to SEQ ID NO:11. In some embodiments, the IL-13Rα2 peptide-based vaccine is administered concurrently with one or more helper T cell epitopes. In a specific embodiment, the IL-13Rα2 peptide-based vaccine is administered concurrently with a helper T cell epitope, wherein the helper T cell epitope is the PADRE peptide. In some embodiments, the IL-13Rα2 peptide-based vaccine is administered concurrently with one or more immune response modifiers. In some embodiments, the IL-13Rα2 peptide-based vaccine is a cell-free vaccine. In other embodiments, the IL-13Rα2 peptide-based vaccine is a dendritic cell vaccine.

In another embodiment, an IL-13Rα2 peptide-based vaccine comprises an IL-13Rα2 peptide, an EphA2 peptide, a survivin peptide, and a WT1 peptide. In a specific embodiment, an IL-13Rα2 peptide-based vaccine comprises the IL-13Rα2 peptide corresponding to any one of SEQ ID NOs:1-4, the EphA2 peptide corresponding to SEQ ID NO:6, the survivin peptide corresponding to SEQ ID NO:7, and the WT1 peptide corresponding to SEQ ID NO:8. In another specific embodiment, an IL-13Rα2 peptide-based vaccine comprises the IL-13Rα2 peptide corresponding to SEQ ID NO:3, the EphA2 peptide corresponding to SEQ ID NO:6, the survivin peptide corresponding to SEQ ID NO:7, and the WT1 peptide corresponding to SEQ ID NO:8. In some embodiments, the IL-13Rα2 peptide-based vaccine is administered concurrently with one or more helper T cell epitopes. In a specific embodiment, the IL-13Rα2 peptide-based vaccine is administered concurrently with a helper T cell epitope, wherein the helper T cell epitope is the Tetanus toxoid. In some embodiments, the IL-13Rα2 peptide-based vaccine is administered concurrently with one or more immune response modifiers. In a specific embodiment, the IL-13Rα2 peptide-based vaccine is administered concurrently with an immune response modifier, wherein the immune response modifier is poly-ICLC. In a specific embodiment, the IL-13Rα2 peptide-based vaccine is administered concurrently with an immune response modifier, wherein the immune response modifier is Montanide ISA-51. In some embodiments, the IL-13Rα2 peptide-based vaccine is a cell-free vaccine. In other embodiments, the IL-13Rα2 peptide-based vaccine is a dendritic cell vaccine.

In another embodiment, an IL-13Rα2 peptide-based vaccine comprises an IL-13Rα2 peptide, an EphA2 peptide, and a survivin peptide. In a specific embodiment, an IL-13Rα2 peptide-based vaccine comprises the IL-13Rα2 peptide corresponding to any one of SEQ ID NOs:1-4, the EphA2 peptide corresponding to SEQ ID NO:6, and the survivin peptide corresponding to SEQ ID NO:7. In another specific embodiment, an IL-13Rα2 peptide-based vaccine comprises the IL-13Rα2 peptide corresponding to SEQ ID NO:3, the EphA2 peptide corresponding to SEQ ID NO:6, and the survivin peptide corresponding to SEQ ID NO:7. In some embodiments, the IL-13Rα2 peptide-based vaccine is administered concurrently with one or more helper T cell epitopes. In a specific embodiment, the IL-13Rα2 peptide-based vaccine is administered concurrently with a helper T cell epitope, wherein the helper T cell epitope is the Tetanus toxoid. In some embodiments, the IL-13Rα2 peptide-based vaccine is administered concurrently with one or more immune response modifiers. In a specific embodiment, the IL-13R≠2 peptide-based vaccine is administered concurrently with an immune response modifier, wherein the immune response modifier is poly-ICLC. In a specific embodiment, the IL-13Rα2 peptide-based vaccine is administered concurrently with an immune response modifier, wherein the immune response modifier is Montanide ISA-51. In some embodiments, the IL-13Rα2 peptide-based vaccine is a cell-free vaccine. In other embodiments, the IL-13Rα2 peptide-based vaccine is a dendritic cell vaccine.

6.1 Peptides

6.1.1 IL-13Rα2 Peptide

IL-13Rα2 a membrane glycoprotein that binds as a component of a heterodimer to the Th2 cytokine, IL-13, which induces monocytes and macrophages to produce TGFβ (see, e.g., Fichtner-Feigl et al., Nat. Med., 12: 99-106, 2006).

The IL-13Rα2 peptide-based vaccines provided herein comprise an IL-13Rα2 peptide. Any IL-13Rα2 peptide capable of serving as an HLA-A2 restricted cytotoxic T lymphocyte (CTL) epitope may be used in a vaccine described herein. In some embodiments, the IL-13Rα2 peptide used in a vaccine described herein comprises any one of SEQ ID NOs:1-4. In a specific embodiment, the IL-13Rα2 peptide used in a vaccine described herein comprises SEQ ID NO:3.

In some embodiments, the IL-13Rα2 peptide used in a vaccine described herein comprises a mutated version of SEQ ID NO:1, wherein the mutated version of SEQ ID NO:1 comprises at least 1, at least 2, or at least 3 amino acid substitutions (e.g., conservative substitutions), additions, or deletions.

In some embodiments, the IL-13Rα2 peptide used in a vaccine described herein comprises an amino acid sequence with at least 50%, 60%, 70%, 80%, or 90% identity to SEQ ID NO:1. In other embodiments, the IL-13Rα2 peptide used in a vaccine described herein comprises an amino acid sequence with at least 50% to 60%, 50% to 70%, 60% to 70%, 70% to 80%, 70% to 90%, or 80% to 90% identity to SEQ ID NO:1. In some embodiments, the IL-13Rα2 peptide used in a vaccine described herein comprises an amino acid sequence with at least 50%, 60%, 70%, 80%, or 90% similarity to SEQ ID NO:1. In other embodiments, the IL-13Rα2 peptide used in a vaccine described herein comprises an amino acid sequence with at least 50% to 60%, 50% to 70%, 60% to 70%, 70% to 80%, 70% to 90%, or 80% to 90% similarity to SEQ ID NO:1.

6.1.2 EphA2 Peptide

EphA2 is a tyrosine kinase receptor that is involved in the formation of the notochord via interaction with ephrinA1. (see, e.g., Naruse-Nakajima et al., Mech. Dev., 102: 95-105, 2001).

In some embodiments, the IL-13Rα2 peptide-based vaccines provided herein comprise an EphA2 peptide. Any EphA2 peptide capable of serving as an HLA-A2 restricted cytotoxic T lymphocyte (CTL) epitope may be used in a vaccine described herein. In some embodiments, the EphA2 peptide used in a vaccine described herein comprises SEQ ID NO:6. In other embodiments, the EphA2 peptide used in a vaccine described herein is an EphA2 peptide described in U.S. Pat. No. 7,297,337.

In some embodiments, the EphA2 peptide used in a vaccine described herein comprises a mutated version of SEQ ID NO:6, wherein the mutated version of SEQ ID NO:6 comprises at least 1, at least 2, or at least 3 amino acid substitutions (e.g., conservative substitutions), additions, or deletions.

In some embodiments, the EphA2 peptide used in a vaccine described herein comprises an amino acid sequence with at least 50%, 60%, 70%, 80%, or 90% identity to SEQ ID NO:6. In other embodiments, the EphA2 peptide used in a vaccine described herein comprises an amino acid sequence with at least 50% to 60%, 50% to 70%, 60% to 70%, 70% to 80%, 70% to 90%, or 80% to 90% identity to SEQ ID NO:6. In some embodiments, the EphA2 peptide used in a vaccine described herein comprises an amino acid sequence with at least 50%, 60%, 70%, 80%, or 90% similarity to SEQ ID NO:6. In other embodiments, the EphA2 peptide used in a vaccine described herein comprises an amino acid sequence with at least 50% to 60%, 50% to 70%, 60% to 70%, 70% to 80%, 70% to 90%, or 80% to 90% similarity to SEQ ID NO:6.

6.1.3 Survivin Peptide

Survivin is an apoptosis inhibitor protein that is overexpressed in most human cancers, and inhibition of its function results in increased apoptosis (see, e.g., Blanc-Brude et al., Nat. Med., 8: 987-994, 2002).

In some embodiments, the IL-13Rα2 peptide-based vaccines provided herein comprise a survivin peptide. Any survivin peptide capable of serving as an HLA-A2 restricted cytotoxic T lymphocyte (CTL) epitope may be used in a vaccine described herein. In some embodiments, the survivin peptide used in a vaccine described herein comprises SEQ ID NO:7. In a specific embodiment, the IL-13Rα2 peptide used in a vaccine described herein comprises SEQ ID NO:7. In other embodiments, the survivin peptide used in a vaccine described herein is a survivin peptide described in U.S. Application Publication No. 2009/0041732 or by Ciesielski et al., Cancer Immunol. Immunother., 59:1211-1221, 2010.

In some embodiments, the survivin peptide used in a vaccine described herein comprises a mutated version of SEQ ID NO:7, wherein the mutated version of SEQ ID NO:7 comprises at least 1, at least 2, or at least 3 amino acid substitutions (e.g., conservative substitutions), additions, or deletions.

In some embodiments, the survivin peptide used in a vaccine described herein comprises an amino acid sequence with at least 50%, 60%, 70%, 80%, or 90% identity to SEQ ID NO:7. In other embodiments, the survivin peptide used in a vaccine described herein comprises an amino acid sequence with at least 50% to 60%, 50% to 70%, 60% to 70%, 70% to 80%, 70% to 90%, or 80% to 90% identity to SEQ ID NO:7. In some embodiments, the survivin peptide used in a vaccine described herein comprises an amino acid sequence with at least 50%, 60%, 70%, 80%, or 90% similarity to SEQ ID NO:7. In other embodiments, the survivin peptide used in a vaccine described herein comprises an amino acid sequence with at least 50% to 60%, 50% to 70%, 60% to 70%, 70% to 80%, 70% to 90%, or 80% to 90% similarity to SEQ ID NO:7.

6.1.4 WT1 Peptide

WT1, is a transcription factor, that is expressed during renal development and regulates development of the caudal mesonephric tubules (see, e.g., Sainio, Development, 124: 1293-1299, 1997).

In some embodiments, the IL-13Rα2 peptide-based vaccines provided herein comprise a WT1 peptide. Any WT1 peptide capable of serving as an HLA-A2 restricted cytotoxic T lymphocyte (CTL) epitope may be used in a vaccine described herein. In some embodiments, the WT1 peptide used in a vaccine described herein comprises SEQ ID NO:8.

In some embodiments, the WT1 peptide used in a vaccine described herein comprises a mutated version of SEQ ID NO:8, wherein the mutated version of SEQ ID NO:8 comprises at least 1, at least 2, or at least 3 amino acid substitutions (e.g., conservative substitutions), additions, or deletions.

In some embodiments, the WT1 peptide used in a vaccine described herein comprises an amino acid sequence with at least 50%, 60%, 70%, 80%, or 90% identity to SEQ ID NO:8. In other embodiments, the WT1 peptide used in a vaccine described herein comprises an amino acid sequence with at least 50% to 60%, 50% to 70%, 60% to 70%, 70% to 80%, 70% to 90%, or 80% to 90% identity to SEQ ID NO:8. In some embodiments, the WT1 peptide used in a vaccine described herein comprises an amino acid sequence with at least 50%, 60%, 70%, 80%, or 90% similarity to SEQ ID NO:8. In other embodiments, the WT1 peptide used in a vaccine described herein comprises an amino acid sequence with at least 50% to 60%, 50% to 70%, 60% to 70%, 70% to 80%, 70% to 90%, or 80% to 90% similarity to SEQ ID NO:8.

6.1.5 GP100 Peptide

Human melanoma-associated antigen, GP100, is a melanocyte differentiation antigen that is expressed in nucleated mammalian cells. (see, e.g., Koch et al., FEBS Lett., 179: 294-298, 1985).

In some embodiments, the IL-13Rα2 peptide-based vaccines provided herein comprise a GP100 peptide. Any GP100 peptide capable of serving as an HLA-A2 restricted cytotoxic T lymphocyte (CTL) epitope may be used in a vaccine described herein. In some embodiments, the GP100 peptide used in a vaccine described herein comprises SEQ ID NO:11.

In some embodiments, the GP100 peptide used in a vaccine described herein comprises a mutated version of SEQ ID NO:11, wherein the mutated version of SEQ ID NO:11 comprises at least 1, at least 2, or at least 3 amino acid substitutions (e.g., conservative substitutions), additions, or deletions.

In some embodiments, the GP100 peptide used in a vaccine described herein comprises an amino acid sequence with at least 50%, 60%, 70%, 80%, or 90% identity to SEQ ID NO:11. In other embodiments, the GP100 peptide used in a vaccine described herein comprises an amino acid sequence with at least 50% to 60%, 50% to 70%, 60% to 70%, 70% to 80%, 70% to 90%, or 80% to 90% identity to SEQ ID NO:11. In some embodiments, the GP100 peptide used in a vaccine described herein comprises an amino acid sequence with at least 50%, 60%, 70%, 80%, or 90% similarity to SEQ ID NO:11. In other embodiments, the GP100 peptide used in a vaccine described herein comprises an amino acid sequence with at least 50% to 60%, 50% to 70%, 60% to 70%, 70% to 80%, 70% to 90%, or 80% to 90% similarity to SEQ ID NO:11.

6.1.6 YKL-40 Peptide

YKL-40, a secreted glycoprotein, has been known to be involved in extracellular matrix degradation and/or angiogenesis, such as hepatic fibrosis, rheumatoid arthritis and severe osteoarthritis, (see, e.g., Bigg et al., (2006), J Biol Chem. 281, 21082-95).

In some embodiments, the IL-13Rα2 peptide-based vaccines provided herein comprise a YKL-40 peptide. Any YKL-40 peptide capable of serving as an HLA-A2 restricted cytotoxic T lymphocyte (CTL) epitope may be used in a vaccine described herein. In some embodiments, the YKL-40 peptide used in a vaccine described herein comprises SEQ ID NO:10.

In some embodiments, the YKL-40 peptide used in a vaccine described herein comprises a mutated version of SEQ ID NO:10, wherein the mutated version of SEQ ID NO:10 comprises at least 1, at least 2, or at least 3 amino acid substitutions (e.g., conservative substitutions), additions, or deletions.

In some embodiments, the YKL-40 peptide used in a vaccine described herein comprises an amino acid sequence with at least 50%, 60%, 70%, 80%, or 90% identity to SEQ ID NO:10. In other embodiments, the YKL-40 peptide used in a vaccine described herein comprises an amino acid sequence with at least 50% to 60%, 50% to 70%, 60% to 70%, 70% to 80%, 70% to 90%, or 80% to 90% identity to SEQ ID NO:10. In some embodiments, the YKL-40 peptide used in a vaccine described herein comprises an amino acid sequence with at least 50%, 60%, 70%, 80%, or 90% similarity to SEQ ID NO:10. In other embodiments, the YKL-40 peptide used in a vaccine described herein comprises an amino acid sequence with at least 50% to 60%, 50% to 70%, 60% to 70%, 70% to 80%, 70% to 90%, or 80% to 90% similarity to SEQ ID NO:10.

6.2 Immune Response Modifiers

In some embodiments, the IL-13Rα2 peptide-based vaccines provided herein are administered concurrently with an immune response modifier. Immune response modifiers include agents capable of modifying the immune response of a subject. In some embodiments, an immune response modifier polarizes the immune response of a subject toward a Th1 response. In other embodiments, an immune response modifier polarizes the immune response of a subject toward a Th2 response. In a preferred embodiment, the immune response modifed binds to a toll-like receptor, also known as a TLR, such as TLR3. Exemplary immune response modifiers that can be administered concurrently with the IL-13Rα2 peptide-based vaccines provided herein include, without limitation, poly-ICLC, imiquimod (Aldara®; Beselna®), and MIS-416 (Innate Therapeutics).

6.2.1 Poly-ICLC

Polyinosinic-Polycytidylic acid stabilized with polylysine and carboxymethylcellulose (poly-ICLC) is a synthetic nucleic acid, and functions as a Toll-like receptor-3 (TLR3) ligand. Poly-ICLC is also known as Hiltonol.

6.3 Adjuvants

In some embodiments, the IL-13Rα2 peptide-based vaccines provided herein are administered concurrently with an adjuvant. In some embodiments, the term "adjuvant" refers to an agent that when administered concurrently with or in the same composition as IL-13Rα2 peptide-based vaccine described herein augments, accelerates, prolongs, enhances and/or boosts the immune response to the IL-13Rα2 peptide-based vaccine. In some embodiments, the adjuvant generates an immune response to the IL-13Rα2 peptide-based vaccine and does not produce an allergy or other adverse reaction. Adjuvants can enhance an immune response by several mechanisms including, e.g., lymphocyte recruitment, stimulation of B and/or T cells, stimulation of dendritic cells and stimulation of macrophages.

Specific examples of adjuvants include, but are not limited to, Montanide ISA-51, Montanide ISA 50V, Montanide, ISA 206, Montanide IMS 1312, VaxImmune® (CpG7909; Coley Pharmaceuticals), aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057, 540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine, or other immunopotentiating agents. It should be understood that different formulations of IL-13Rα2 peptide-based vaccines may comprise different adjuvants or may comprise the same adjuvant.

6.4 Helper T Cell Epitopes

In some embodiments, the IL-13Rα2 peptide-based vaccines provided herein are administered concurrently with a helper T cell epitope. Helper T cell epitopes include agents that are capable of inducing a helper T cell response by the immune system. Helper T cells are CD4+ T cells. In some embodiments, helper T cell epitopes are presented by Class II MHC molecules, and may be recognized by the T cell receptor (TCR) of helper T cells (CD4+ T cells), thereby activating the CD4+ T cells, causing them to proliferate, secrete cytokines such as IL2, and activate professional antigen presenting cells. Through a variety of mechanisms, activated helper T cells also stimulate killer T cells (also known as CD8+ T cells), thereby prolonging and increasing the CD8+ T cell response. Exemplary helper T cell epitopes that can be administered concurrently with the IL-13Rα2 peptide-based vaccines provided herein include, without limitation, PADRE, HBVcore$_{128\text{-}140}$, and tetanus toxoid.

6.4.1 PADRE Peptide

PADRE is a non-natural epitope optimized for both HLA-DR binding and T-cell receptor stimulation (see, e.g., Alexander et al, Immunity, 1:751-761, 1994).

6.4.2 Tetanus Toxoid

A well characterized Th epitope (SEQ ID NO:9) from the Tetanus Toxoid (TT) protein, to which the vast majority of the population has been sensitized, is known to act as a helper T cell epitope.

6.4.2.1 HBV Core$_{128\text{-}140}$

A well characterized Th epitope (SEQ ID NO:5) from the HBV protein is known to act as a helper T cell epitope.

6.5 Production and Purification of Peptides

The peptides described herein can be produced by any method known in the art for the synthesis of peptides, in particular, by chemical synthesis or by recombinant expression techniques. The methods provided herein encompass, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al. (eds.) (1999) Genome Analysis: A Laboratory Manual, Cold Spring Harbor Laboratory Press.

6.5.1.1 Synthetic Production of Peptides

The peptides described herein may be prepared using conventional step-wise solution or solid phase synthesis (see, e.g., Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein).

Alternatively, the peptides described herein may be prepared by way of segment condensation, as described, for example, in Liu et al., 1996, Tetrahedron Lett. 37(7):933-936; Baca, et al., 1995, J. Am. Chem. Soc. 117:1881-1887; Tam et al., 1995, Int. J. Peptide Protein Res. 45:209-216; Schnolzer and Kent, 1992, Science 256:221-225; Liu and Tam, 1994, J. Am. Chem. Soc. 116(10):4149-4153; Liu and Tam, 1994, Proc. Natl. Acad. Sci. USA 91:6584-6588; Yamashiro and Li, 1988, Int. J. Peptide Protein Res. 31:322-334. Other methods useful for synthesizing the peptides described herein are described in Nakagawa et al., 1985, J. Am. Chem. Soc. 107:7087-7092.

Formation of disulfide linkages, if desired, is generally conducted in the presence of mild oxidizing agents. Chemical oxidizing agents may be used, or the compounds may simply be exposed to atmospheric oxygen to effect these linkages. Various methods are known in the art, including those described, for example, by Tam et al., 1979, Synthesis 955-957; Stewart et al., 1984, Solid Phase Peptide Synthesis, 2d Ed., Pierce Chemical Company Rockford, Ill.; Ahmed et al., 1975, J. Biol. Chem. 250:8477-8482; and Pennington et al., 1991 Peptides 1990 164-166, Giralt and Andreu, Eds., ESCOM Leiden, The Netherlands. An additional alternative is described by Kamber et al., 1980, Helv. Chim. Acta 63:899-915. A method conducted on solid supports is described by Albericio, 1985, Int. J. Peptide Protein Res. 26:92-97, each of which is incorporated by reference herein in its entirety.

6.5.1.2 Recombinant Expression of Peptides

Recombinant expression of a peptide requires construction of an expression vector containing a polynucleotide that encodes the peptide. Once a polynucleotide encoding a peptide has been obtained, the vector for the production of the peptide may be produced by recombinant DNA technology using techniques well-known in the art. Thus, methods for preparing a peptide by expressing a polynucleotide containing a peptide-encoding nucleotide sequence are described herein. Methods which are well known to those skilled in the art can be used to construct expression vectors containing peptide coding sequences and appropriate transcriptional and translational control signals. These methods include, for example, in vitro recombinant DNA techniques, synthetic techniques, and in vivo genetic recombination. Thus, provided herein are replicable expression vectors comprising a nucleotide sequence encoding a peptide operably linked to a promoter.

An expression vector comprises a nucleic acid encoding a peptide in a form suitable for expression of the nucleic acid in a host cell. In specific embodiments, the host cell is an isolated host cell. In a specific embodiment, an expression vector includes one or more regulatory sequences, selected on the basis of the host cells to be used for expression, which is operably linked to the nucleic acid to be expressed. Within an expression vector, "operably linked" is intended to mean that a nucleic acid of interest is linked to the regulatory sequence(s) in a manner which allows for expression of the nucleic acid (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid in many types of host cells, those which direct expression of the nucleic acid only in certain host cells (e.g., tissue-specific regulatory sequences), and those which direct the expression of the nucleic acid upon stimulation with a particular agent (e.g., inducible regulatory sequences). It will be appreciated by those skilled in the art that the design of the expression vector can depend on such factors as the choice of the host cell to be transformed, the level of expression of protein desired, etc. The term "host cell" is intended to include a particular subject cell transformed or transfected with a nucleic acid and the progeny or potential progeny of such a cell. Progeny of such a cell may not be identical to the parent cell transformed or transfected with the nucleic acid due to mutations or environmental influences that may occur in succeeding generations or integration of the nucleic acid into the host cell genome. In specific embodiments, the host cell is isolated.

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning—A Laboratory Manual, 2nd Edition, Cold Spring Harbor Press, New York, and other laboratory manuals. In certain embodiments, a host cell is transiently transfected with an expression vector containing a nucleic acid encoding a peptide. In other embodiments, a host cell is stably transfected with an expression vector containing a nucleic acid encoding a peptide. Thus, provided herein are host cells containing a polynucleotide encoding a peptide described herein or generated in accordance with the methods provided herein.

A variety of host-expression vector systems may be utilized to express a peptide. Such host-expression systems represent vehicles by which the coding sequences of interest may be produced and subsequently purified, but also represent cells which may, when transformed or transfected with the appropriate nucleotide coding sequences, express a peptide in situ. These include but are not limited to microorganisms such as bacteria (e.g., *E. coli* and *B. subtilis*) transformed with recombinant bacteriophage DNA, plasmid DNA or cosmid DNA expression vectors containing peptide coding sequences; yeast (e.g., *Saccharomyces Pichia*) transformed with recombinant yeast expression vectors containing peptide coding sequences; insect cell systems infected with recombinant virus expression vectors (e.g., baculovirus) containing peptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing peptide coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells are used for the expression of a peptide. For example, mammalian cells such as Chinese hamster ovary cells (CHO), in conjunction with a vector such as the major intermediate early gene promoter element from human cytomegalovirus is an effective expression system for peptides (Foecking et al., 1986, Gene 45:101; and Cockett et al., 1990, Bio/Technology 8:2). In a specific embodiment, the expression of nucleotide sequences encoding the peptides described herein or generated in accordance with the methods provided herein is regulated by a constitutive promoter, inducible promoter or tissue specific promoter.

In bacterial systems, a number of expression vectors may be advantageously selected depending upon the use intended for the peptide being expressed. For example, when a large quantity of peptide is to be produced, for the generation of pharmaceutical compositions of a peptide, vectors which direct the expression of high levels of fusion protein products that are readily purified may be desirable. Such vectors include, but are not limited to, the *E. coli* expression vector pUR278 (Ruther et al., 1983, EMBO 12:1791), in which the peptide coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The peptide coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the peptide coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the peptide in infected hosts (e.g., see Logan & Shenk, 1984, Proc. Natl. Acad. Sci. USA 8 1:355-359). Specific initiation signals may also be required for efficient translation of inserted peptide coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the peptide. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, Vero, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant peptides, stable expression is preferred. For example, cell lines which stably express the peptide molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the peptide. Such engineered cell lines may be particularly useful in screening and evaluation of compositions that interact directly or indirectly with the peptide. Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds.), Current Protocols in Human Genetics, John Wiley & Sons, NY (1994); Colberre-Garapin et al., 1981, J. Mol. Biol. 150:1, which are incorporated by reference herein in their entireties.

The expression levels of a peptide can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing the peptide is amplifiable, increase in the level of inhibitor present in culture of host cell will increase the number of copies of the marker gene. Since the amplified region is associated with the peptide, production of the peptide will also increase (Crouse et al., 1983, Mol. Cell. Biol. 3:257).

As an alternative to recombinant expression of a peptide using a host cell, an expression vector containing a nucleic acid encoding a peptide can be transcribed and translated in vitro using, e.g., T7 promoter regulatory sequences and T7 polymerase. In a specific embodiment, a coupled transcription/translation system, such as Promega TNT®, or a cell lysate or cell extract comprising the components necessary for transcription and translation may be used to produce a peptide.

Accordingly, provided herein are methods for producing a peptide. In one embodiment, the method comprises culturing a host cell containing a nucleic acid encoding the peptide in a suitable medium such that the peptide is produced. In some embodiments, the method further comprises isolating the peptide from the medium or the host cell.

In certain embodiments, plants (e.g., plants of the genus Nicotiana) may be engineered to express a peptide described herein. In specific embodiments, plants are engineered to express a peptide described herein via an agroinfiltration procedure using methods known in the art. For example, nucleic acids encoding a gene of interest, e.g., a gene encoding a peptide described herein, are introduced into a strain of Agrobacterium. Subsequently the strain is grown in a liquid culture and the resulting bacteria are washed and suspended into a buffer solution. The plants are then exposed (e.g., via injection or submersion) to the Agrobacterium that comprises the nucleic acids encoding a peptide described herein such that the Agrobacterium transforms the gene of interest to a portion of the plant cells. The peptide is then transiently expressed by the plant and can be isolated using methods known in the art and described herein. (For specific examples see Shoji et al., 2008, Vaccine, 26(23):2930-2934; and D'Aoust et al., 2008, 0.1. Plant Biotechnology, 6(9): 930-940). In a specific embodiment, the plant is a tobacco plant (i.e., Nicotiana tabacum). In another specific embodiment, the plant is a relative of the tobacco plant (e.g., Nicotiana benthamiana).

In other embodiments, algae (e.g., Chlamydomonas reinhardtii) may be engineered to express a peptide described herein (see, e.g., Rasala et al., 2010, Plant Biotechnology Journal (Published online Mar. 7, 2010)).

6.5.1.3 Purification of Peptides

The peptides described herein and generated using the approaches described in may be purified by any method known in the art for purification of a peptide, for example, by chromatography (e.g., ion exchange, affinity, particularly by affinity for the specific antigen after Protein A, and sizing column chromatography), centrifugation, differential solubility, or by any other standard technique for the purification of proteins. Further, the peptides may be fused to heterologous peptide sequences described herein or otherwise known in the art to facilitate purification. The actual conditions used to purify a particular peptide will depend, in part, on the synthesis strategy (e.g., synthetic production vs. recombinant production) and on factors such as net charge, hydrophobicity, and/or hydrophilicity of the peptide, and will be apparent to those having skill in the art.

6.6 Pharmaceutical Compositions and Routes of Administration

Provided herein are pharmaceutical compositions comprising. In some embodiments, a composition provided herein comprises an interleukin-13 receptor α2 peptide-based brain cancer vaccine. In other embodiments, a composition provided herein comprises an IL-13Rα2 peptide-based vaccine and a helper T cell epitope, an adjuvant, and/or an immune response modifier. In other embodiments, a composition provided herein comprises an immune response modifier. The pharmaceutical compositions provided herein are suitable for veterinary and/or human administration.

The pharmaceutical compositions provided herein (e.g., a composition comprising an IL-13Rα2 peptide-based vaccine, a composition comprising an IL-13Rα2 peptide-based vaccine and a helper T cell epitope, an adjuvant, and/or an immune response modifier, or a composition comprising an immune response modifier) can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

In specific embodiments, the compositions provided herein (e.g., a composition comprising an IL-13Rα2 peptide-based vaccine, a composition comprising an IL-13Rα2 peptide-based vaccine and a helper T cell epitope, an adjuvant, and/or an immune response modifier, or a composition comprising an immune response modifier) are in the form of a liquid (e.g., an elixir, syrup, solution, emulsion, or suspension). Typical routes of administration of the liquid compositions provided herein may include, without limitation, parenteral, intradermal, intratumoral, intracerebral, and intrathecal. Parenteral administration includes, without limitation, subcutaneous, intranodal, intravenous, intramuscular, intraperitoneal, and intrapleural administration techniques. In a specific embodiment, the compositions are administered parenterally. In a composition for administration by injection, one or more of a surfactant, preservative, wetting agent, dispersing agent, suspending agent, buffer, stabilizer, and isotonic agent may be included. In a specific embodiment, a pump may be used to deliver the vaccines (see, e.g., Sefton, CRC Crit. Ref. Biomed. Eng. 1987, 14, 201; Buchwald et al., Surgery 1980, 88: 507; Saudek et al., N. Engl. J. Med. 1989, 321: 574). In a specific embodiment, the pump may be, but is not limited to, an insulin-like pump.

Materials used in preparing the pharmaceutical compositions provided herein (e.g., a composition comprising an IL-13Rα2 peptide-based vaccine, a composition comprising an IL-13Rα2 peptide-based vaccine and a helper T cell epitope, an adjuvant, and/or an immune response modifier, or a composition comprising an immune response modifier) can be non-toxic in the amounts used. It may be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of brain cancer the subject is in need of treatment of the use of the composition as part of a multi-drug regimen, the particular form of the vaccine being administered, the manner of administration, and the composition employed.

The liquid compositions of the invention, whether they are solutions, suspensions, or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol, or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, or phosphates; and agents for the adjustment of tonicity such as sodium chloride or dextrose. A parenteral composition can be enclosed in an ampoule, a disposable syringe, or a multiple-dose vial made of glass, plastic or other material. An injectable composition is preferably sterile.

The compositions provided herein (e.g., a composition comprising an IL-13Rα2 peptide-based vaccine, a composition comprising an IL-13Rα2 peptide-based vaccine and a helper T cell epitope, an adjuvant, and/or an immune response modifier, or a composition comprising an immune response modifier) may comprise a pharmaceutically acceptable carrier or vehicle. As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In one embodiment, the compositions provided herein (e.g., a composition comprising an IL-13Rα2 peptide-based vaccine, a composition comprising an IL-13Rα2 peptide-based vaccine and a helper T cell epitope, an adjuvant, and/or an immune response modifier, or a composition comprising an immune response modifier) are formulated in accordance with routine procedures as a pharmaceutical composition adapted for parenteral administration to animals, particularly human beings. Generally, the ingredients in the compositions are supplied either separately or mixed together in unit dosage form, for example, as a dry lyophilized powder or water free concentrate in a hermetically sealed container such as an ampoule or sachet indicating the quantity of active agent. Where a composition described herein is administered by injection, an ampoule of sterile water for injection or saline can be provided so that the ingredients can be mixed prior to administration, if necessary.

The compositions provided herein (e.g., a composition comprising an IL-13Rα2 peptide-based vaccine, a composition comprising an IL-13Rα2 peptide-based vaccine and a helper T cell epitope, an adjuvant, and/or an immune response modifier, or a composition comprising an immune response modifier) described herein can comprise an additional active agent selected from among those including, but not limited to, an additional prophylactic agent, an additional therapeutic agent, an antiemetic agent, a hematopoietic colony stimulating factor, an adjuvant therapy, an antibody/antibody fragment-based agent, an anti-depressant and an analgesic agent.

The pharmaceutical compositions provided herein (e.g., a composition comprising an IL-13Rα2 peptide-based vaccine, a composition comprising an IL-13Rα2 peptide-based vaccine and a helper T cell epitope, an adjuvant, and/or an immune response modifier, or a composition comprising an immune response modifier) can be prepared using methodology well known in the pharmaceutical art. For example, a composition intended to be administered by injection can be prepared by combining the peptides of a vaccine described herein with water and/or other liquid components so as to form a solution. A surfactant can be added to facilitate the formation of a homogeneous solution or suspension.

The pharmaceutical compositions described herein can be included in a container, pack, or dispenser together with instructions for administration.

6.7 Prophylactic and Therapeutic Uses

In one aspect, provided herein are methods for preventing, treating, and/or managing brain cancer in a subject in need thereof by administering an effective amount of an IL-13Rα2 peptide-based vaccine described herein.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient an IL-13Rα2 peptide-based vaccine described herein or a pharmaceutical composition described herein, wherein the patient has been diagnosed with brain cancer.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient an IL-13Rα2 peptide-based vaccine described herein or a pharmaceutical composition described herein, wherein the patient has relapsed from brain cancer.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient an IL-13Rα2 peptide-based vaccine described herein or a pharmaceutical composition described herein, wherein the patient has failed or is failing brain cancer therapy that does not comprise a vaccine described herein.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient an IL-13Rα2 peptide-based vaccine described herein or a pharmaceutical composition described herein, wherein the patient is in remission from brain cancer.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient an IL-13Rα2 peptide-based vaccine described herein or a pharmaceutical composition described herein, wherein the patient is refractory to brain cancer therapy that does not comprise a vaccine described herein. In one embodiment of this aspect, the patient has received or is receiving brain cancer therapy that does not comprise a vaccine described herein. In another embodiment of this aspect, the patient has not previously received a brain cancer therapy that does not comprise a vaccine described herein for the prevention, treatment, and/or management of the brain cancer.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient an IL-13Rα2 peptide-based vaccine described herein or a pharmaceutical composition described herein, wherein the patient has received another brain cancer therapy. In some embodiments, the prior brain cancer therapy is, for example, chemotherapy, radiation therapy, surgical therapy, small molecule therapy, biologic therapy, antibody therapy, hormone therapy, immunotherapy, anti-angiogenic therapy or any combination thereof. In some embodiments, the prior therapy has failed in the patient. In some embodiments, the therapeutically effective regimen comprising administration of an IL-13Rα2 peptide-based vaccine described herein is administered to the patient immediately after the patient has undergone the prior therapy. For instance; in certain embodiments, the outcome of the prior therapy may be unknown before the patient is administered the IL-13Rα2 peptide-based vaccine. In one embodiment, the prior chemotherapy is temolozimide. In embodiment, the prior therapy is radiation therapy. In another embodiment, the prior therapy is a combination of temozolomide and radiation therapy. In a preferred embodiment, the combination of temozolomide and radiation are administered using the Stupp regimen. In another embodiment, the prior therapy is surgery. In some embodiments, the patient undergoes surgery before the initiation of combination therapy. In some embodiments, the patient undergoes surgery before treatment with temozolomide. In some embodiments, the patient undergoes surgery before the initiation of radiation therapy. In each of these embodiments that describe the use of combination therapy, the IL-13Rα2 peptide-based vaccine may be administered before, during, or after the treatment of the patient with the therapy that is being combined.

In some embodiments, the IL-13Rα2 peptide-based vaccines described herein are administered as monotherapy for the prevention, treatment, and/or management of brain cancer. In other embodiments, provided herein are methods comprising administering to a subject in need thereof an IL-13Rα2 peptide-based vaccine described herein and one or more agents other than the IL-13Rα2 peptide-based vaccine described herein that are currently being used, have been used, are known to be useful, or may be useful in the prevention, treatment, and/or management of brain cancer or one or more symptoms thereof. The agents of the combination therapies can be administered sequentially or concurrently. In certain embodiments, the combination therapies improve the prophylactic or therapeutic effect of an IL-13Rα2 peptide-based vaccine described herein functioning together with the IL-13Rα2 peptide-based vaccine described herein to have an additive or synergistic effect. In some embodiments, the combination therapies are administered prior to, during, or after the administration of the compositions described herein.

In another aspect, provided herein are methods for inducing an immune response in a subject with brain cancer comprising administering an effective amount of an IL-13Rα2 peptide-based vaccine described herein. In some embodiments, the immune response induced in a subject by an IL-13Rα2 peptide-based vaccine described herein or a composition described herein is effective to prevent, treat, and/or manage brain cancer in the subject. In some embodiments, the immune response induced in a subject by an IL-13Rα2 peptide-based vaccine described herein or a composition described herein is effective to reduce symptoms of brain cancer in the subject.

The medical practitioner can diagnose the patient using any of the conventional brain cancer screening methods including, but not limited to neurological examination; imaging methods (e.g., computed tomography (CT), magnetic resonance imaging (MRI), ultrasound, X-ray imaging, and positron emission tomography (PET) scans); and biopsy (e.g., sterotactic biopsy).

6.7.1 Dosage and Frequency of Administration

The amount of a composition described herein (e.g., a composition comprising an IL-13Rα2 peptide-based vaccine, a composition comprising an IL-13Rα2 peptide-based vaccine and a helper T cell epitope, an adjuvant, and/or an immune response modifier, or a composition comprising an immune response modifier) which will be effective in the treatment, prevention, and or management of brain cancer may depend on the status of the brain cancer, the patient to whom the composition(s) is to be administered, the route of administration, and/or the type of brain cancer. Such doses can be determined by standard clinical techniques and may be decided according to the judgment of the practitioner.

For example, effective doses may vary depending upon means of administration, target site, physiological state of the patient (including age, body weight, health), whether the patient is human or an animal, other medications administered, and whether treatment is prophylactic or therapeutic. Usually, the patient is a human but nonhuman mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

In certain embodiments, the IL-13Rα2 peptide-based vaccine is a cell-free vaccine, wherein the cell-free vaccine comprises an IL-13Rα2 peptide and one, two, three, or more additional brain cancer-associated peptides. In some embodiments, exemplary cell-free IL-13Rα2 peptide-based vaccines comprise about 25, 50, 75, 100, 125, 150, 175, 200, 225, 250, 275, 300, 325, 350, 375, 400, 425, 450, 475, 500, 550, 600, 650, 700, 750, or 800 µg of each brain cancer-associated peptide per dose. In other embodiments, exemplary cell-free IL-13Rα2 peptide-based vaccines comprise about 25 to 50, 25 to 75, 25 to 100, 50 to 100, 50 to 150, 50 to 200, 100 to 150, 100 to 200, 100 to 250, 100 to 300, 150 to 200, 150 to 250, 150 to 300, 200 to 250, 250 to 300, 250 to 350, 250 to 400, 300 to 350, 300 to 400, 300 to 450, 300 to 500, 350 to 400, 350 to 450, 400 to 500, 400 to 600, 500 to 600, 500 to 700, 600 to 700, 600 to 800, or 700 to 800 µg of each brain cancer-associated peptide per dose. In other embodiments, exemplary cell-free IL-13Rα2 peptide-based vaccines comprise about 5 µg to 100 mg, 15 µg to 50 mg, 15 µg to 25 mg, 15 µg to 10 mg, 15 µg to 5 mg, 15 µg to 1 mg, 15 µg to 100 µg, 15 µg to 75 µg, 5 µg to 50 µg, 10 µg to 50 µg, 15 µg to 45 µg, 20 µg to 40 µg, or 25 to 35 µg of each brain cancer-associated peptide per kilogram of the patient.

In certain embodiments, the cell-free IL-13Rα2 peptide-based vaccines are administered concurrently with a helper T cell epitope. In some embodiments, exemplary cell-free IL-13Rα2 peptide-based vaccines are administered concurrently with about 25, 50, 75, 100, 125, 150, 175, 200, 225, 250, 275, 300, 325, 350, 375, 400, 425, 450, 475, 500, 550, or 600 µg of a helper T cell epitope. In other embodiments, exemplary cell-free IL-13Rα2 peptide-based vaccines are administered concurrently with about 25 to 50, 25 to 75, 25 to 100, 50 to 100, 50 to 150, 50 to 200, 100 to 150, 100 to 200, 100 to 250, 100 to 300, 150 to 200, 150 to 250, 150 to 300, 200 to 250, 250 to 300, 250 to 350, 250 to 400, 300 to 350, 300 to 400, 300 to 450, 300 to 500, 350 to 400, 350 to 450, 400 to 500, 400 to 600, or 500 to 600 µg of a helper T cell epitope.

In certain embodiments, the cell-free IL-13Rα2 peptide-based vaccines are administered concurrently with an immune response modifier. In some embodiments, exemplary cell-free IL-13Rα2 peptide-based vaccines are administered concurrently with about 100, 200, 300, 400, 500, 600, 700, 800, 900, 1000, 1100, 1200, 1300, 1400, 1500, 1600, 1700, or 1800 µg of an immune response modifier. In other embodiments, exemplary cell-free IL-13Rα2 peptide-based vaccines are administered concurrently with about 100 to 300, 200 to 400, 400 to 800, 600 to 800, 800 to 1000, 800 to 1200, 1000 to 1200, 1000 to 1400, 1200 to 1400, 1200 to 1600, 1400 to 1600, 1400 to 1800, or 1600 to 1800 µg of an immune response modifier. In other embodiments, exemplary cell-free IL-13Rα2 peptide-based vaccines are administered concurrently with about 1, 5, 10, 15, 20, 25, 30, 35, 40, 45, 50, 55, of 60 µg of an immune response modifier per kilogram of the patient. In other embodiments, exemplary cell-free IL-13Rα2 peptide-based vaccines are administered concurrently with about 1 to 5, 1 to 10, 5 to 10, 5 to 15, 10 to 15, 10 to 20, 15 to 20, 15 to 25, 15 to 30, 20 to 25, 20 to 30, 20 to 35, 25 to 30, 25 to 35, 25 to 40, 30 to 35, 30 to 40, 35 to 40, 35 to 45, 40 to 45, 40 to 50, 45 to 50, 50 to 55, or 50 to 60 µg of an immune response modifier per kilogram of the patient.

In certain embodiments, the cell-free IL-13Rα2 peptide-based vaccines are administered concurrently with an adjuvant. In some embodiments, a composition comprising a cell-free IL-13Rα2 peptide-based vaccine is mixed 0.5 to 1, 1 to 0.5, 1 to 1, 1 to 2, 1 to 3, 2 to 1, or 3 to 1 with an adjuvant.

In certain embodiments, the IL-13Rα2 peptide-based vaccine is a dendritic cell-based vaccine, wherein the dendritic cell-based vaccine comprises dendritic cells loaded with an IL-13Rα2 peptide and dendritic cells loaded with one, two, three, or more additional brain cancer-associated peptides. In some embodiments, exemplary dendritic cell-based IL-13Rα2 peptide-based vaccines comprise about $10^3$, $5\times10^3$, $10^4$, $5\times10^4$, $10^5$, $5\times10^5$, $10^6$, $5\times10^6$, $10^7$, $3\times10^7$ $5\times10^7$, $7\times10^7$, $10^8$, $5\times10^8$, $1\times10^9$ $5\times10^9$, $1\times10^{10}$, $5\times10^{10}$, $1\times10^{11}$, $5\times10^{11}$ or $10^{12}$ dendritic cells loaded with brain cancer-associated peptide(s) per dose. In other embodiments, exemplary dendritic cell-based IL-13Rα2 peptide-based vaccines comprise about $10^3$ to $10^4$, $10^3$ to $10^5$, $10^4$ to $10^5$, $10^4$ to $10^6$, $10^5$ to $10^6$, $10^5$ to $10^7$ $10^6$ to $10^7$, $10^6$ to $10^8$, $10^7$ to $10^8$, $10^7$ to $10^9$, $10^8$ to $10^9$, $10^9$ to $10^{10}$, $10^{10}$ to $10^{11}$, or $10^{11}$ to $10^{12}$ dendritic cells loaded with brain cancer-associated peptide(s) per dose.

In certain embodiments, the dendritic cell-based IL-13Rα2 peptide-based vaccines are administered concurrently with a helper T cell epitope. In some embodiments, exemplary dendritic cell-based IL-13Rα2 peptide-based vaccines are administered concurrently with about 25, 50, 75, 100, 125, 150, 175, 200, 225, 250, 275, 300, 325, 350, 375, 400, 425, 450, 475, 500, 550, or 600 µg of a helper T cell epitope. In other embodiments, exemplary dendritic cell-based IL-13Rα2 peptide-based vaccines are administered concurrently with about 25 to 50, 25 to 75, 25 to 100, 50 to 100, 50 to 150, 50 to 200, 100 to 150, 100 to 200, 100 to 250, 100 to 300, 150 to 200, 150 to 250, 150 to 300, 200 to 250, 250 to 300, 250 to 350, 250 to 400, 300 to 350, 300 to 400, 300 to 450, 300 to 500, 350 to 400, 350 to 450, 400 to 500, 400 to 600, or 500 to 600 µg of a helper T cell epitope.

In certain embodiments, the dendritic cell-based IL-13Rα2 peptide-based vaccines are administered concurrently with an immune response modifier. In some embodiments, exemplary dendritic cell-based IL-13Rα2 peptide-based vaccines are administered concurrently with about 100, 200, 300, 400, 500, 600, 700, 800, 900, 1000, 1100, 1200, 1300, 1400, 1500, 1600, 1700, or 1800 µg of an immune response modifier. In other embodiments, exemplary dendritic cell-based IL-13Rα2 peptide-based vaccines are administered concurrently with about 100 to 300, 200 to 400, 400 to 800, 600 to 800, 800 to 1000, 800 to 1200, 1000 to 1200, 1000 to 1400, 1200 to 1400, 1200 to 1600, 1400 to 1600, 1400 to 1800, or 1600 to 1800 µg of an immune response modifier. In other embodiments, exemplary dendritic cell-based IL-13Rα2 peptide-based vaccines are administered concurrently with about 1, 5, 10, 15, 20, 25, 30, 35, 40, 45, 50, 55, of 60 µg of an immune response modifier per kilogram of the patient. In other embodiments, exemplary dendritic cell-based IL-13Rα2 peptide-based vaccines are administered concurrently with about 1 to 5, 1 to 10, 5 to 10, 5 to 15, 10 to 15, 10 to 20, 15 to 20, 15 to 25, 15 to 30, 20 to 25, 20 to 30, 20 to 35, 25 to 30, 25 to 35, 25 to 40, 30 to 35, 30 to 40, 35 to 40, 35 to 45, 40 to 45, 40 to 50, 45 to 50, 50 to 55, or 50 to 60 μg of an immune response modifier per kilogram of the patient.

In certain embodiments, the dendritic cell-based IL-13Rα2 peptide-based vaccines are administered concurrently with an adjuvant. In some embodiments, a composition comprising a dendritic cell-based IL-13Rα2 peptide-based vaccine is mixed 0.5 to 1, 1 to 0.5, 1 to 1, 1 to 2, 1 to 3, 2 to 1, or 3 to 1 with an adjuvant.

In certain embodiments, a composition described herein (e.g., a composition comprising an IL-13Rα2 peptide-based vaccine, a composition comprising an IL-13Rα2 peptide-based vaccine and a helper T cell epitope, an adjuvant, and/or an immune response modifier, or a composition comprising an immune response modifier) is administered to a subject once as a single dose. In some embodiments, a composition described herein (e.g., a composition comprising an IL-13Rα2 peptide-based vaccine, a composition comprising an IL-13Rα2 peptide-based vaccine and a helper T cell epitope, an adjuvant, and/or an immune response modifier, or a composition comprising an immune response modifier) is administered in multiple doses (e.g., 1, 2, 3, 4, 5, 6, 7, 8, 9, 10, or more than 10 doses), wherein the doses may be separated by at least 1 day, 2 days, 3 days, 4 days 5 days, 6 days, 7 days, 8 days, 9 days, 10 days, 15 days, or 30 days. In specific embodiments, the IL-13Rα2 peptide-based vaccine is administered intranodally or subcutaneously and the immune response modifier is administered intramuscularly.

In some embodiments, when a composition described herein comprises a cell-free IL-13Rα2 peptide-based vaccine, the composition may be administered over the course of 21 weeks, with administrations occurring on weeks 0, 3, 6, 9, 12, 15, 18 and 21. In certain embodiments, the composition comprising a cell-free IL-13Rα2 peptide-based vaccine is administered concurrently with a helper T cell epitope, an adjuvant, and/or an immune response modifier. In a specific embodiment, a composition described herein comprising a cell-free IL-13Rα2 peptide-based vaccine is administered over the course of 21 weeks, with administrations occurring on weeks 0, 3, 6, 9, 12, 15, 18 and 21, and the composition is administered concurrently with an immune response modifier, wherein the immune response modifier is administered on the day of each administration of the cell-free IL-13Rα2 peptide-based vaccine and on day 4 after each administration of the cell-free IL-13Rα2 peptide-based vaccine. In another specific embodiment, a composition described herein comprising a cell-free IL-13Rα2 peptide-based vaccine is administered over the course of 21 weeks, with administrations occurring on weeks 0, 3, 6, 9, 12, 15, 18 and 21, and the composition is administered concurrently with an immune response modifier, wherein the immune response modifier is administered on the day of each administration of the cell-free IL-13Rα2 peptide-based vaccine. In specific embodiments, the cell-free IL-13Rα2 peptide-based vaccine is administered subcutaneously and the immune response modifier is administered intramuscularly.

In some embodiments, when a composition described herein comprises a dendritic cell-based IL-13Rα2 peptide-based vaccine, the composition may be administered over the course of 6 weeks, with administrations occurring on weeks 0, 2, 4, and 6. In certain embodiments, the composition comprising a cell-free IL-13Rα2 peptide-based vaccine is administered concurrently with a helper T cell epitope, an adjuvant, and/or an immune response modifier. In a specific embodiment, a composition described herein comprising a dendritic cell-based IL-13Rα2 peptide-based vaccine is administered over the course of 6 weeks, with administrations occurring on weeks 0, 2, 4, and 6, and the composition is administered concurrently with an immune response modifier, wherein the immune response modifier is administered twice per week beginning on the first day of administration of the dendritic cell-based IL-13Rα2 peptide-based vaccine. In specific embodiments, the dendritic cell-based IL-13Rα2 peptide-based vaccine is administered intranodally and the immune response modifier is administered intramuscularly.

In some embodiments, when a composition described herein comprises a dendritic cell-based IL-13Rα2 peptide-based vaccine, the composition may be administered over the course of 26 weeks, with administrations occurring on weeks 0, 2, 4, 6, 10, 14, 18, 22, and 26. In certain embodiments, the composition comprising a cell-free IL-13Rα2 peptide-based vaccine is administered concurrently with a helper T cell epitope, an adjuvant, and/or an immune response modifier. In a specific embodiment, a composition described herein comprising a dendritic cell-based IL-13Rα2 peptide-based vaccine is administered over the course of 26 weeks, with administrations occurring on weeks 0, 2, 4, 6, 10, 14, 18, 22, and 26, and the composition is administered concurrently with an immune response modifier, wherein the immune response modifier is administered twice per week beginning on the first day of administration of the dendritic cell-based IL-13Rα2 peptide-based vaccine. In specific embodiments, the dendritic cell-based IL-13Rα2 peptide-based vaccine is administered intranodally and the immune response modifier is administered intramuscularly.

6.7.2 Brain Cancers

The IL-13Rα2 peptide-based vaccine described herein can be used in the prevention, treatment, and/or management of brain cancer. Any type of brain cancer can be treated with the IL-13Rα2 peptide-based vaccines described herein in accordance with the methods described herein. Exemplary brain cancers include, but are not limited to, gliomas (including astrocytoma (e.g., pilocytic astrocytoma, diffuse astrocytoma, and anaplastic astrocytoma), glioblastoma, oligodendroglioma, brain stem glioma, non-brain stem glioma, ependymoma, and mixed tumors comprising more than one glial cell types), acoustic schwannoma, cranialpharyngioma, meningioma, medulloblastoma, primary central nervous system lymphoma, and tumors of the pineal (e.g., pineal astrocytic tumors and pineal parenchymal tumors) and pituitary glands. Gliomas additionally include recurrent malignant gliomas, high-risk WHO Grade II Astrocytomas, Oligo Astrocytomas, recurrent WHO Grade II Gliomas, newly-diagnosed malignant or intrinsic brain stem gliomas, incompletely resected non-brainstem gliomas, and recurrent unresectable low-grade gliomas. Additional types of brain cancer that can be treated with the IL-13Rα2 peptide-based vaccines described herein in accordance with the methods described herein include adult low-grade infiltrative supratentorial astrocytoma/oligodendroglioma, adult low-grade infiltrative supratentorial astrocytoma, adult low-grade infiltrative supratentorial oligodendroglioma, adult low-grade infiltrative supratentorial astrocytoma/oligodendroglioma (excluding pilocytic astrocytoma), adult low-grade infiltrative supratentorial astrocytoma (excluding pilocytic astrocytoma), adult low-grade infiltrative supratentorial oligodendroglioma (excluding pilocytic astrocytoma), adult intracranial ependymoma, adult intracranial ependymoma (excluding subependymoma and myxopapillary), adult intracranial anaplastic ependymoma, anaplastic glioma, anaplastic glioblastoma, pilocytic astrocytoma, subependymoma, myxopapillary, 1 to 3 limited metastatic lesions (intraparenchymal), greater than 3 metastatic lesions (intraparenchymal), leptomeningeal metastases (neoplastic meningitis), primary CNS lymphoma, metastatic spine tumors, or meningiomas.

In one embodiment, the brain cancer treated with the IL-13Rα2 peptide-based vaccines described herein in accordance with the methods described herein is a glioma. In a specific embodiment, the brain cancer treated with the IL-13Rα2 peptide-based vaccines described herein in accordance with the methods described herein is recurrent malignant glioma. In another specific embodiment, the brain cancer treated with the IL-13Rα2 peptide-based vaccines described herein in accordance with the methods described herein is recurrent WHO Grade II Glioma. In another specific embodiment, the brain cancer treated with the IL-13Rα2 peptide-based vaccines described herein in accordance with the methods described herein is newly-diagnosed malignant or intrinsic brain stem glioma. In another specific embodiment, the brain cancer treated with the IL-13Rα2 peptide-based vaccines described herein in accordance with the methods described herein is incompletely resected non-brainstem glioma. In another specific embodiment, the brain cancer treated with the IL-13Rα2 peptide-based vaccines described herein in accordance with the methods described herein is recurrent unresectable low-grade glioma. In one embodiment, the patient is an adult with recurrent malignant glioma, recurrent glioblastoma, anaplastic astrocytoma, anaplastic oligodendroglioma, or anaplastic mixed oligoastrocytoma. In another specific embodiment, the patient is an adult with newly diagnosed high-risk low grade glioma. In another specific embodiment, the patient is an adult with newly diagnosed high-risk low grade astrocytoma. In another specific embodiment, the patient is an adult with newly diagnosed high-risk low grade oligoastrocytoma. In another specific embodiment, the patient is an adult with recurrent high-risk low grade astrocytoma. In another specific embodiment, the patient is an adult with recurrent high-risk low grade oligoastrocytoma. In another specific embodiment, the patient is an adult with recurrent high-risk low grade oligodendroglioma. In another specific embodiment, the patient is a child with newly diagnosed malignant glioma. In another specific embodiment, the patient is a child with intrinsic brain stem glioma. In another specific embodiment, the patient is a child with incompletely resected non-brainstem high-grade glioma. In another specific embodiment, the patient is a child with recurrent unresectable low-grade glioma. In another specific embodiment, the patient is a child with newly diagnosed diffuse intrinsic pontine glioma. In another specific embodiment, the patient is a child with any high-grade glioma involving the brainstem and treated with RT or without chemotherapy during RT. In another specific embodiment, the patient is a child with newly diagnosed non-brainstem high-grad glioma treated with RT with chemotherapy. In another specific embodiment, the patient is a child with newly diagnosed non-brainstem high-grad glioma treated with RT without chemotherapy. In another specific embodiment, the patient is a child with recurrent non-brainstem high-grade glioma that has recurred after treatment.

In another embodiment, the brain cancer treated with the IL-13Rα2 peptide-based vaccines described herein in accordance with the methods described herein is an astrocytoma. In a specific embodiment, the brain cancer treated with the IL-13Rα2 peptide-based vaccines described herein in accordance with the methods described herein is high-risk WHO Grade II Astrocytoma. In another specific embodiment, the brain cancer treated with the IL-13Rα2 peptide-based vaccines described herein in accordance with the methods described herein is Oligo Astrocytoma.

6.7.3 Patient Population

In certain an IL-13Rα2 peptide-based vaccine or composition described herein may be administered to a naïve subject, i.e., a subject that does not have brain cancer. In one embodiment, an IL-13Rα2 peptide-based vaccine or composition described herein is administered to a naïve subject that is at risk of acquiring brain cancer.

In certain embodiments, an IL-13Rα2 peptide-based vaccine or composition described herein is administered to a patient who has been diagnosed with brain cancer. In some embodiments, an IL-13Rα2 peptide-based vaccine or composition described herein is administered to a patient with brain cancer before symptoms manifest or symptoms become severe. In a preferred embodiment, the brain cancer is glioma.

In certain embodiments, an IL-13Rα2 peptide-based vaccine or composition described herein is administered to a patient who is in need of treatment, prevention, and/or management of brain cancer. Such subjects may or may not have been previously treated for cancer or may be in remission, relapsed, or may have failed treatment. Such patients may also have abnormal cytogenetics. The 13Rα2 peptide-based vaccines and compositions described herein may be used as any line of brain cancer therapy, e.g., a first line, second line, or third line of brain cancer therapy. In a specific embodiment, the subject to receive or receiving a vaccine or pharmaceutical composition described herein is receiving or has received other brain cancer therapies. In an alternative embodiment, the subject to receive or receiving a vaccine or pharmaceutical composition described herein has not received or is not receiving other brain cancer therapies.

In a specific embodiment, the subject has been diagnosed with brain cancer using techniques known to one of skill in the art including, but not limited to, neurological examination; imaging methods (e.g., computed tomography (CT), magnetic resonance imaging (MRI), ultrasound, X-ray imaging, fluid-attenuated inversion-recovery (FLAIR) sequences, T2 weighted imaging, and positron emission tomography (PET) scans); and biopsy (e.g., sterotactic biopsy). Tumor response to therapy may be evaluated by McDonald criteria or Response assessment in neuro-oncology (RANO) criteria. Tumor size or response to treatment can be evaluated by various magnetic resonance imaging techniques including diffusion-weighted imaging, perfusion-weighted imaging, dynamic contrast-enhanced T1 permeability imaging, dynamic susceptibility contrast, diffusion-tensor imaging, and magnetic resonance spectroscopy, anatomic MRI T2-weighted images, fluid attenuated inversion recovery (FLAIR) T2-weighted images, and gadolinium-enhanced T1-weighted images. These imagining techniques can be used to assess tumor cellularity, white matter invasion, metabolic derangement including hypoxia and necrosis, neovascular capillary blood volume, or permeability. Positron emission tomograph (PET) technology can also be used to image tumor response, such as 18F-fluoromisonidazole PET and 3'-deoxy-3'-18F-fluorothymidine PET.

In one embodiment, an IL-13Rα2 peptide-based vaccine or composition described herein is administered to a subject that is undergoing or has undergone radiation therapy to treat a brain cancer tumor. In a specific embodiment, an IL-13Rα2 peptide-based vaccine or composition described herein is administered to a subject concurrently or following radiation therapy to treat a brain cancer tumor. In another embodiment, an IL-13Rα2 peptide-based vaccine or composition described herein is administered to a subject before radiation therapy to treat a brain cancer tumor and, in some embodiments, during and/or after the radiation therapy. In some preferred embodiments, the radiation therapy is fractionated external beam radiotherapy, limited-field fractionated external beam radiotherapy, whole brain radiotherapy, stereotactic radiosurgery, or craniospinal radiotherapy In one embodiment, an IL-13Rα2 peptide-based vaccine or composition described herein is administered to a subject that is undergoing or has undergone chemotherapy to treat a brain cancer tumor. In a specific embodiment, an IL-13Rα2 peptide-based vaccine or composition described herein is administered to a subject concurrently or following chemotherapy to treat a brain cancer tumor. In another embodiment, an IL-13Rα2 peptide-based vaccine or composition described herein is administered to a subject before chemotherapy to treat a brain cancer tumor and, in some embodiments, during and/or after the chemotherapy. In some preferred embodiments, the chemotherapy is temozolomide (Temodar®), nitrosurea, platinum-based regimens, etoposide, cisplatin, bevacizumab (Avastin®), irinotecan, cyclophosphamide, BCNU (carmustine), capecitabine, high-dose methotrexate, topotecan, high-dose ARA-C, hydroxyurea, α-inteferon, somatostatin analogue, intra-CSF chemotherapy (liposomal cytarabine, methotrexate, cytarabine, thiotepa, or rituximab (Rituxan®)).

In one embodiment, an IL-13Rα2 peptide-based vaccine or composition described herein is administered to a subject that has failed, is undergoing or has undergone more than one therapeutic strategy, including chemotherapy, radiation therapy, or surgery to treat a brain cancer tumor. In a preferred embodiment, the brain cancer is glioma. For example, a patient may be failed, be undergoing, or have undergone both chemotherapy and surgery. Alternatively, a patient may have undergone or be undergoing both radiation and surgery. Moreover, a patient may have undergone or be undergoing chemotherapy and radiation. In some preferred embodiments, the combined therapies that the patient failed, is undergoing, or has undergone are resection and temozolomide (Temodar®) (150-200 mg/m$^2$) 5/28 schedule, resection and BCNU wafer (Gliadel®), bevacizumab (Avastin®) and chemotherapy, combination PCV (CCNU (lomustine) and procarbazine and vincristine), high-dose methotrexate and vincristine, procarbazine, cytaribine, or rituximab, high-dose chemotherapy with stem cell rescue, or rituximab (Rituxan®) and temozolomide (Temodar®).

In one embodiment, an IL-13Rα2 peptide-based vaccine or composition described herein is administered to a subject that is undergoing or has undergone surgery to remove a brain cancer tumor. In a specific embodiment, an IL-13Rα2 peptide-based vaccine or composition described herein is administered to a subject concurrently or following surgery to remove a brain cancer tumor. In another embodiment, an IL-13Rα2 peptide-based vaccine or composition described herein is administered to a subject before surgery to remove a brain cancer tumor and, in some embodiments, during and/or after surgery.

In certain embodiments, an IL-13Rα2 peptide-based vaccine or composition described herein is administered to a subject as an alternative to another therapy, e.g., chemotherapy, radiation therapy, hormonal therapy, surgery, small molecule therapy, anti-angiogenic therapy, and/or biological therapy including immunotherapy where the therapy has proven or may prove too toxic, i.e., results in unacceptable or unbearable side effects for the subject.

In a specific embodiment, an IL-13Rα2 peptide-based vaccine or composition described herein is administered to subjects that will have, are undergoing, or have had radiation therapy. Among these subjects are those that have received chemotherapy, hormonal therapy, small molecule therapy, anti-angiogenic therapy, and/or biological therapy, including immunotherapy as well as those who have undergone surgery.

In another embodiment, an IL-13Rα2 peptide-based vaccine or composition described herein is administered to subjects that will have, are undergoing, or have had hormonal therapy and/or biological therapy, including immunotherapy. Among these subjects are those that have received chemotherapy, small molecule therapy, anti-angiogenic therapy, and/or radiation therapy as well as those who have undergone surgery.

In certain embodiments, an IL-13Rα2 peptide-based vaccine or composition described herein is administered to a subject refractory to one or more therapies. In one embodiment, that a cancer is refractory to a therapy means that at least some significant portion of the cancer cells are not killed or their cell division is not arrested. The determination of whether the cancer cells are refractory can be made either in vivo or in vitro by any method known in the art for assaying the effectiveness of a therapy on cancer cells, using the art-accepted meanings of "refractory" in such a context. In various embodiments, a cancer is refractory where the amount of cancer cells has not been significantly reduced, or has increased.

In some embodiments, an IL-13Rα2 peptide-based vaccine or composition described herein is administered to a subject that is in remission from brain cancer. In a specific embodiment, the subject has no detectable brain cancer, i.e., no brain cancer is detectable using a conventional method described herein (e.g., MRI) or known to one of skill in the art.

In one embodiment, an IL-13Rα2 peptide-based vaccine or composition described herein is administered to a subject diagnosed with glioma. In a specific embodiment, an IL-13Rα2 peptide-based vaccine or composition described herein is administered to a subject diagnosed with astrocytoma (e.g., pilocytic astrocytoma, diffuse astrocytoma, and anaplastic astrocytoma). In another specific embodiment, an IL-13Rα2 peptide-based vaccine or composition described herein is administered to a subject diagnosed with glioblastoma. In another specific embodiment, an IL-13Rα2 peptide-based vaccine or composition described herein is administered to a subject diagnosed with oligodendroglioma. In another specific embodiment, an IL-13Rα2 peptide-based vaccine or composition described herein is administered to a subject diagnosed with brain stem glioma. In another specific embodiment, an IL-13Rα2 peptide-based vaccine or composition described herein is administered to a subject diagnosed with ependymoma. In another specific embodiment, an IL-13Rα2 peptide-based vaccine or composition described herein is administered to a subject diagnosed with a mixed tumor comprising more than one glial cell types.

In a specific embodiment, an IL-13Rα2 peptide-based vaccine or composition described herein is administered to a subject diagnosed with recurrent malignant glioma. In another specific embodiment, an IL-13Rα2 peptide-based vaccine or composition described herein is administered to a subject diagnosed with high-risk WHO Grade II Astrocytomas. In another specific embodiment, an IL-13Rα2 peptide-based vaccine or composition described herein is administered to a subject diagnosed with Oligo Astrocytoma. In another specific embodiment, an IL-13Rα2 peptide-based vaccine or composition described herein is administered to a subject diagnosed with recurrent WHO Grade II Glioma. In another specific embodiment, an IL-13Rα2 peptide-based vaccine or composition described herein is administered to a subject diagnosed with newly-diagnosed malignant or intrinsic brain stem glioma. In another specific embodiment, an IL-13Rα2 peptide-based vaccine or composition described herein is administered to a subject diagnosed with incompletely resected non-brainstem glioma. In another specific embodiment, an IL-13Rα2 peptide-based vaccine or composition described herein is administered to a subject diagnosed with recurrent unresectable low-grade glioma.

In a specific embodiment, an IL-13Rα2 peptide-based vaccine or composition described herein is administered to a subject diagnosed with acoustic schwannoma. In another specific embodiment, an IL-13Rα2 peptide-based vaccine or composition described herein is administered to a subject diagnosed with cranial pharyngioma. In another specific embodiment, an IL-13Rα2 peptide-based vaccine or composition described herein is administered to a subject diagnosed with meningioma. In another specific embodiment, an IL-13Rα2 peptide-based vaccine or composition described herein is administered to a subject diagnosed with medulloblastoma. In another specific embodiment, an IL-13Rα2 peptide-based vaccine or composition described herein is administered to a subject diagnosed with primary central nervous system lymphoma. In another specific embodiment, an IL-13Rα2 peptide-based vaccine or composition described herein is administered to a subject diagnosed with a tumor of the pineal gland (e.g., a pineal astrocytic tumor or a pineal parenchymal tumor). In another specific embodiment, an IL-13Rα2 peptide-based vaccine or composition described herein is administered to a subject diagnosed with a tumor of the pituitary gland.

In certain embodiments, a subject to be administered an IL-13Rα2 peptide-based vaccine or composition described herein is a human adult. In certain embodiments, a subject to be administered an IL-13Rα2 peptide-based vaccine or composition described herein is an elderly human subject. In certain embodiments, a subject to be administered an IL-13Rα2 peptide-based vaccine or composition described herein is a human child. In certain embodiments, a subject to be administered an IL-13Rα2 peptide-based vaccine or composition described herein is a human infant. In certain embodiments, a subject to be administered an IL-13Rα2 peptide-based vaccine or composition described herein is a human toddler.

In certain embodiments, a subject to be administered an IL-13Rα2 peptide-based vaccine or composition described herein is HLA-A2 positive as determined by, e.g., flow cytometry.

In certain embodiments, a subject to be administered an IL-13Rα2 peptide-based vaccine or composition described herein has a Karnofsky performance status (KPS) of >60. The KPS is used as a stratification and selection variable in randomized trials of chemotherapeutic agents and has a range of 0-100. Patients with a score >60 are unable to work, are able to live at home, and can care for most of their personal needs with varying degrees of required assistance. Patients with a score >70 carry on normal activity with effort and show some signs and symptoms of the disease. Patients with a score >80 are able to carry on normal activity and only show minor signs or symptoms of the disease. Patients with a score >90 are normal, have no health complaints, and show no signs or symptoms of the disease.

In certain embodiments, a subject to be administered an IL-13Rα2 peptide-based vaccine or composition described herein has a white blood count of about $1000/mm^3$, $1500/mm^3$, $2000/mm^3$, $2500/mm^3$, $3000/mm^3$, or $3500/mm^3$ or about $1000/mm^3$ to $1500/mm^3$, $1000/mm^3$ to $2000/mm^3$, $1500/mm^3$ to $2500/mm^3$, $1500/mm^3$ to $3000/mm^3$, $2000/mm^3$ to $3500/mm^3$, or $2500/mm^3$ to $3500/mm^3$. In a specific embodiment, a subject to be administered an IL-13Rα2 peptide-based vaccine or composition described herein has a white blood count greater than or equal to $2500/mm^3$.

In certain embodiments, a subject to be administered an IL-13Rα2 peptide-based vaccine or composition described herein has a lymphocyte count of about $100/mm^3$, $200/mm^3$, $300/mm^3$, $400/mm^3$, $500/mm^3$, or $600/mm^3$ or about $100/mm^3$ to $400/mm^3$, $200/mm^3$ to $400/mm^3$, $300/mm^3$ to $500/mm^3$, $300/mm^3$ to $600/mm^3$, $400/mm^3$ to $500/mm^3$, or $400/mm^3$ to $600/mm^3$. In a specific embodiment, a subject to be administered an IL-13Rα2 peptide-based vaccine or composition described herein has a lymphocyte count greater than or equal to $400/mm^3$.

In certain embodiments, a subject to be administered an IL-13Rα2 peptide-based vaccine or composition described herein has a platelet count of about $25,000/mm^3$, $50,000/mm^3$, $75,000/mm^3$, $100,000/mm^3$, $200,000/mm^3$, or $300,000/mm^3$ or about $25,000/mm^3$ to $100,000/mm^3$, $50,000/mm^3$ to $100,000/mm^3$, $75,000/mm^3$ to $100,000/mm^3$, $100,000/mm^3$ to $200,000/mm^3$, $100,000/mm^3$ to $300,000/mm^3$, or $200,000/mm^3$ to $300,000/mm^3$. In a specific embodiment, a subject to be administered an IL-13Rα2 peptide-based vaccine or composition described herein has a platelet count greater than or equal to $100,000/mm^3$.

In certain embodiments, a subject to be administered an IL-13Rα2 peptide-based vaccine or composition described herein has a hemoglobin count of about 5 g/dL, 10 g/dL, 15 g/dL, or 20 g/dL, or about 5 to 10 g/dL, 5 to 15 g/dL, 10 to 15 g/dL, or 10 to 20 g/dL. In a specific embodiment, a subject to be administered an IL-13Rα2 peptide-based vaccine or composition described herein has a hemoglobin count greater than or equal to 10 g/dL.

In certain embodiments, a subject to be administered an IL-13Rα2 peptide-based vaccine or composition described herein has AST, ALT, GGT, LDH, and alkaline phosphatase levels within 1, 1.5., 2, 2.5, or 3 times the upper normal limit. In a specific embodiment, a subject to be administered an IL-13Rα2 peptide-based vaccine or composition described herein has AST, ALT, GGT, LDH, and alkaline phosphatase levels within 2.5 times the upper normal limit.

In certain embodiments, a subject to be administered an IL-13Rα2 peptide-based vaccine or composition described herein has a total bilrubin of about 1 mg/dL, 1.5 mg/dL, 2 mg/dL, 2.5 mg/dL, or 3 mg/dL, or about 1.5 to 2.5 mg/dL, 1.5 to 3 mg/dL, 2 to 2.5 mg/dL, or 2 to 3 mg/dL. In a specific embodiment, a subject to be administered an IL-13Rα2 peptide-based vaccine or composition described herein has total bilrubin greater than or equal to 2 mg/dL.

In certain embodiments, a subject to be administered an IL-13Rα2 peptide-based vaccine or composition described herein has serum creatinine levels within 0.5, 1, 1.5., 2, 2.5, or 3 times the upper normal limit. In a specific embodiment, a subject to be administered an IL-13Rα2 peptide-based vaccine or composition described herein has serum creatinine levels within 1.5 times the upper normal limit.

In certain embodiments, a subject to be administered an IL-13Rα2 peptide-based vaccine or composition described herein has coagulation tests PT and PTT that are within 0.5, 1, 1.5., 2, 2.5, or 3 times the normal limits. In certain embodiments, a subject to be administered an IL-13Rα2 peptide-based vaccine or composition described herein has coagulation tests PT and PTT that are within normal limits.

In some embodiments, it may be advisable not to administer an IL-13Rα2 peptide-based vaccine or composition described herein to one or more of the following patient populations: elderly humans; infants younger than 6 months old; pregnant individuals; infants under the age of 1 years old; children under the age of 2 years old; children under the age of 3 years old; children under the age of 4 years old; children under the age of 5 years old; adults under the age of 20 years old; adults under the age of 25 years old; adults under the age of 30 years old; adults under the age of 35 years old; adults under the age of 40 years old; adults under the age of 45 years old; adults under the age of 50 years old; elderly humans over the age of 70 years old; elderly humans over the age of 75 years old; elderly humans over the age of 80 years old; elderly humans over the age of 85 years old; elderly humans over the age of 90 years old; elderly humans over the age of 95 years old; subjects undergoing chemotherapy; subjects undergoing radiation therapy; subjects undergoing biologic therapy; subjects undergoing interferon therapy; subjects that receive allergy desensitization injections; subjects that take illicit drugs; subjects receiving growth factor treatments (e.g. Procrit®, Aranesp®, Neulasta®); subjects receiving interleukin treatments (e.g. Proleukin®); subjects with metastatic disease; female subjects that are breast-feeding; subjects with active viral, bacterial, or fungal infection; subjects with a history of presence of autoimmune disease; subject with HIV; subjects being treated with investigational medicines that do not comprise a vaccine described herein; subjects with gliomatosis cerebri, cranial or spinal leptomeningeal metastatic disease; and/or subjects undergoing immunosuppressive treatment.

6.7.4 Combination Therapies

In certain embodiments, the methods provided herein for preventing, treating, and/or managing brain cancer comprise administering to a patient (e.g., a human patient) in need thereof a prophylactically and/or a therapeutically effective regimen, the regimen comprising administering to the patient an IL-13Rα2 peptide-based vaccine or composition described herein and one or more additional therapies, said additional therapy not being an IL-13Rα2 peptide-based vaccine or composition described herein. The an IL-13Rα2 peptide-based vaccine or composition described herein and the additional therapy can be administered separately, concurrently, or sequentially. The combination therapies can act additively or synergistically.

The combination therapies can be administered to a subject in the same pharmaceutical composition. Alternatively, the combination therapies can be administered concurrently to a subject in separate pharmaceutical compositions. The combination therapies may be administered to a subject by the same or different routes of administration.

Any therapy (e.g., therapeutic or prophylactic agent) which is useful, has been used, or is currently being used for the prevention, treatment, and/or management of cancer (e.g., brain cancer) can be used in combination with an IL-13Rα2 peptide-based vaccine or composition described herein in the methods described herein. Therapies include, but are not limited to, peptides, polypeptides, antibodies, conjugates, nucleic acid molecules, small molecules, mimetic agents, synthetic drugs, inorganic molecules, and organic molecules. Non-limiting examples of cancer therapies include chemotherapy, radiation therapy, hormonal therapy, surgery, small molecule therapy, anti-angiogenic therapy, differentiation therapy, epigenetic therapy, radioimmunotherapy, targeted therapy, and/or biological therapy including immunotherapy. In certain embodiments, a prophylactically and/or therapeutically effective regimen of the invention comprises the administration of a combination of therapies.

In one embodiment, the prior chemotherapy is temozolzimide. In embodiment, the prior therapy is radiation therapy. In another embodiment, the prior therapy is a combination of temozolomide and radiation therapy. In a preferred embodiment, the combination of temozolomide and radiation are administered using the Stupp regimen. In another embodiment, the prior therapy is surgery. In some embodiments, the patient undergoes surgery before the initiation of combination therapy. In some embodiments, the patient undergoes surgery before treatment with temozolomide. In some embodiments, the patient undergoes surgery before the initiation of radiation therapy. In each of these embodiments that describe the use of combination therapy, the IL-13Rα2 peptide-based vaccine may be administered before, during, or after the treatment of the patient with the therapy that is being combined.

Examples of cancer therapies which can be used in combination with an IL-13Rα2 peptide-based vaccine or composition described herein include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzoclepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; histone deacetylase inhibitors (HDACs) gemcitabine hydrochloride; hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies which can be used in combination with an IL-13Rα2 peptide-based vaccine or composition described herein include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine octfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; VITAXIN™ (see U.S. Patent Pub. No. US 2002/0168360 A1, dated Nov. 14, 2002, entitled "Methods of Preventing or Treating Inflammatory or Autoimmune Disorders by Administering Integrin αvβ3 Antagonists in Combination With Other Prophylactic or Therapeutic Agents"); vorozole; zanoterone; zeniplatin; zilascorb; and zinostatin stimalamer.

In some embodiments, the therapy(ies) used in combination with an IL-13Rα2 peptide-based vaccine or composition described herein is an immunomodulatory agent. Non-limiting examples of immunomodulatory agents which can be used in combination with an IL-13Rα2 peptide-based vaccine or composition described herein include proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, cytokine receptor modulators, and modulators mast cell modulators. Other examples of immunomodulatory agents can be found, e.g., in U.S. Publication No. 2005/0002934 A1 at paragraphs 259-275 which is incorporated herein by reference in its entirety. In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent.

In some embodiments, the therapy(ies) used in combination with a an IL-13Rα2 peptide-based vaccine or composition described herein is an anti-angiogenic agent. Non-limiting examples of anti-angiogenic agents which can be used in combination with an IL-13Rα2 peptide-based vaccine or composition described herein include proteins, polypeptides, peptides, conjugates, antibodies (e.g., human, humanized, chimeric, monoclonal, polyclonal, Fvs, ScFvs, Fab fragments, F(ab)2 fragments, and antigen-binding fragments thereof) such as antibodies that specifically bind to TNF-α, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In a preferred embodiment, the anti-angiogenic therapy is bevacizumab (Avastin®). In other embodiments, the therapy(ies) used in accordance with the invention is not an anti-angiogenic agent.

In some embodiments, the therapy(ies) used in combination with an IL-13Rα2 peptide-based vaccine or composition described herein is an anti-inflammatory agent. Non-limiting examples of anti-inflammatory agents which can be used in combination with an IL-13Rα2 peptide-based vaccine or composition described herein include any anti-inflammatory agent, including agents useful in therapies for inflammatory disorders, well-known to one of skill in the art. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), beta2-agonists (e.g., abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), and methylxanthines (e.g., theophylline (UNIPHYL™, THEO-DUR™, SLO-BID™, AND TEHO-42™)). Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), corticosteroids (e.g., methylprednisolone (MEDROL™)), cortisone, hydrocortisone, prednisone (PREDNISONE™ and DELTA-SONE™), prednisolone (PRELONE™ and PEDIAPRED™), triamcinolone, azulfidine, and inhibitors of eicosanoids (e.g., prostaglandins, thromboxanes, and leukotrienes. Other examples of anti-inflammatory agents can be found, e.g., in U.S. Publication No. 005/0002934 A1 at paragraphs 290-294, which is incorporated by reference in its entirety. In other embodiments, the therapy(ies) used in accordance with the invention is not an anti-inflammatory agent.

In certain embodiments, the therapy(ies) used in combination with an IL-13Rα2 peptide-based vaccine or composition described herein is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, cholormbucil, cyclophosphamide, ifosfamide, decarbazine, mechlorethamine, melphalan, and temozolomide.

Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the *vinca* alkaloids (vinblastine, vincristine, and vinorelbine).

Currently available cancer therapies and their dosages, routes of administration and recommended usage are known in the art and have been described in such literature as the Physician's Desk Reference (60th ed., 2006). In accordance with the present invention, the dosages and frequency of administration of chemotherapeutic agents are described supra.

6.7.5 Biological Assays

The IL-13Rα2 peptide-based vaccines and compositions described herein can be tested for their ability to treat, prevent, or manage brain cancer.

6.7.5.1 In Vivo Assays

The IL-13Rα2 peptide-based vaccines and compositions described herein can be tested in suitable animal model systems prior to use in humans. Such animal model systems include, but are not limited to, rats, mice, chicken, cows, monkeys, pigs, clogs, rabbits, etc. Any animal system well-known in the art may be used. Several aspects of the procedure may vary; said aspects include, but are not limited to, the temporal regime of administering the vaccine components, whether such vaccine components are administered separately or as an admixture, and the frequency of administration of the vaccine components.

Animal models for cancer can be used to assess the efficacy of an IL-13Rα2 peptide-based vaccine or composition described herein or a combination therapy described herein. Examples of animal models for brain cancer include, but are not limited to, xenograft studies using brain cancer cell lines that express IL-13Rα2, or primary human tumor cells that express IL-13Rα2. In these models, mice are immunized to induce an IL-13Rα2-specific T cell response, which is then evaluated for its ability to inhibit the growth of the tumor. In one embodiment, the tumor xenograft forms prior to the immunization to test the ability of the IL-13Rα2-specific T cell response to inhibit the growth of the preexisting tumor. In another embodiment, the IL-13Rα2-specific T cell response is induced prior to the injection of the tumor cells, to evaluate the ability of the immune response to prevent the formation of a tumor.

6.7.5.2 Cytotoxicity Assays

The toxicity and/or efficacy of the IL-13Rα2 peptide-based vaccines and compositions described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic regimens that exhibit large therapeutic indices are preferred. While therapeutic regimens that exhibit toxic side effects may be used, care should be taken to design a delivery system that targets such agents to the site of affected tissue in order to minimize potential damage to uninfected cells and, thereby, reduce side effects.

6.8 Articles of Manufacture

Also encompassed herein is a finished packaged and labeled pharmaceutical product. This article of manufacture includes the appropriate unit dosage form in an appropriate vessel or container such as a glass vial or other container that is hermetically sealed. The pharmaceutical product may contain, for example, the components of an IL-13Rα2 peptide-based vaccine described herein in a unit dosage form.

In a specific embodiment, the unit dosage form is suitable for parenteral, intravenous, intramuscular, intranasal, or subcutaneous delivery. Thus, encompassed herein are solutions, preferably sterile, suitable for each delivery route.

As with any pharmaceutical product, the packaging material and container are designed to protect the stability of the product during storage and shipment. Further, the products provided herein include instructions for use or other informational material that advise the physician, technician, or patient on how to appropriately prevent or treat brain cancer in question. In other words, the article of manufacture includes instruction means indicating or suggesting a dosing regimen including, but not limited to, actual doses, monitoring procedures, and other information.

Specifically, provided herein is an article of manufacture comprising packaging material, such as a box, bottle, tube, vial, container, sprayer, insufflator, intravenous (i.v.) bag, envelope and the like; and at least one unit dosage form of a vaccine or pharmaceutical composition described herein contained within said packaging material, wherein said vaccine or pharmaceutical composition described herein comprises an IL-13Rα2 peptide-based vaccine described herein, and wherein said packaging material includes instruction means which indicate that said IL-13Rα2 peptide-based vaccine described herein can be used to prevent, manage, and/or treat brain cancer or one or more symptoms thereof by administering specific doses and using specific dosing regimens as described herein.

7. EXAMPLES

The following examples further illustrate the invention but, of course, should not be construed as in any way limiting its scope.

7.1 Example 1

This example demonstrates the identification of modified peptides for IL-13Rα2$_{345-353}$ that enhance induction of the CTL response against native IL-13Rα2$_{345-353}$.

Three modified peptides were synthesized as listed in Table 1. The binding capability of these modified peptides was assessed using an HLA-A2 transfected T2 cell line. Aliquots of T2 cells were incubated with modified peptides or IL-13Rα2$_{345-353}$ at 1 nM overnight, and then examined for the surface expression levels of HLA-A2 on T2 cells by flow cytometry. Since stable binding of HLA-A2 with peptide epitopes further stabilizes the surface expression of HLA-A2 (Francini et al., 2002; Alves et al., 2003), quantitative expression levels of HLA-A2, which is indicated by Mean Fluorescence Intensity (MFI) in Table 1, correlate with the binding affinity of the peptide-epitopes that are co-incubated with the T2 cells. The modified peptides V9 and A1V9 possess higher hinging affinity to HLA-A2 than the native IL-13Rα2$_{345-353}$ (Table 1), suggesting the possibility that these modified peptides are more immunogenic than the IL-13Rα2$_{345-353}$.

TABLE 1

| Peptide | Amino Acid Sequence | Binding Index (MFI*) | Designation |
| --- | --- | --- | --- |
| Native IL-13Rα$_{345-353}$ | WLPFGFILI (SEQ ID NO: 1) | 237.4 | Native |
| V9: I was replaced with V at P9 | WLPFGFILV (SEQ ID NO: 2) | 375.6 | V9 |
| A1V9: W → A at P1, and I → V at P9 | ALPFGFILV (SEQ ID NO: 3) | 462.8 | A1V9 |
| A1V9: W → E at P1, and I → V at P9 | ELPFGFILV (SEQ ID NO: 4) | 241.6 | E1V9 |
| Control (Non-Peptide) | — | 121.8 | — |

*Mean Fluorescence Intensity at the peptide concentration of 1 nM

7.2 Example 2

This example demonstrates that CTL induced by the agonist analogue V9 recognized peptide IL-13Rα2$_{345-353}$ presented on HLA-A*0201 more efficiently than CTL induced by the wild type peptide.

Dendritic cells (DCs) derived from HLA-A*0201+ glioma patients were pulsed with either V9, A1V9, E1V9, a control influenza (flu), or the wild type peptide (10 µg/ml), and used to stimulate autologous CD8+ T cells. On day 7, the individual responder cell cultures were then restimulated once with autologous DCs loaded with the corresponding peptide used in the primary stimulation. Specific CTL activity of the induced T cell lines was first tested with T2 cells loaded with the wild type IL-13Rα2$_{345-353}$, or no peptide on day 10.

As depicted in FIG. 1, the T cells that had been stimulated with either wild type (IL-13R) or agonist analogues (V9, A1V9 and E1V9) efficiently lysed T2 target cells pulsed with 100 ng/ml wild type IL-13Rα2$_{345-353}$; whereas only low background lysis was observed in the absence of the peptide on T2 cells. T cells that had been stimulated with the control flu-peptide or no-peptide (control) did not demonstrate any lytic activity over background levels. These results demonstrated that the CTL lines induced by the wild type or agonist analogues recognized and lysed the cells presenting wild type IL-13Rα2$_{345-353}$ epitope specifically. In particular, the V9 peptide induced a significantly higher level of antigen-specific CTL response in comparison to the wild type IL-13Rα2$_{345-353}$ at each effector/target (E/T) ratio (p=0.018, 0.020 and 0.011 at an E/T ratio of 50, 25 and 12.5, respectively). The same set of experiments were repeated with at least three individual HLA-A2+ glioma patients, and the V9 peptide consistently demonstrated higher CTL activities than the native IL-13Rα2$_{345-353}$ in all four donors tested (data not shown).

Subsequently, the sensitivity of the CTL lines induced by agonist analogues or the wild type peptide was examined with T2 cells loaded with various concentrations (1-100 nM) of the IL-13Rα2$_{345-353}$ peptide by 4-Hr $^{51}$Cr-release assay (FIG. 2). All CTL lines demonstrated peptide-dose dependent lytic activities against peptide-loaded T2 cells. The CTL line induced by the agonist analogue V9 demonstrated higher CTL activities than the wild type IL-13Rα2$_{345-353}$ at all peptide-concentrations examined (P=0.029, 0.039 and 0.018 at 1, 10 and 100 nM, respectively). It is noteworthy that the average percent lysis value achieved by V9-induced CTL with 1 nM IL-13Rα2$_{345-353}$ was higher than that demonstrated with wild type peptide-induced CTL with 100 nM peptide, although this did not demonstrate a statistical significance due to a large standard variation. These results indicate that the V9 peptide is more efficient than the wild type peptide in inducing CTL that are capable of recognizing low concentrations of the target wild type IL-13Rα2$_{345-353}$ peptide. This ability is important because human tumor cells express low levels of target CTL epitopes on their HLA-molecules (Bakker et al., 1995; Lupetti et al., 1998).

7.3 Example 3

This example demonstrates that CTL induced by modified peptides lysed HLA-A2+ glioma cells that express IL-13Rα2 more efficiently than CTL induced by the native peptide.

The ability of modified peptides, such as IL-13Rα2-V9, to enhance the CTL activity against HLA-A2+ human glioma cells that endogenously expressed and presented IL-13Rα2-derived epitopes was examined. Human glioma cell lines U251 and SNB19 express HLA-A2 and IL-13Rα2, whereas human glioma cell line A172 expresses IL-13Rα2 but not HLA-A2 (Okano et al., 2002). Therefore, U251 and SNB19 were used as relevant target glioma cells, while A172 served as a negative control line to demonstrate HLA-A2-restriction of the response.

The lytic ability of the peptide-induced CTL lines against these glioma cells was examined using 4-hr $^{51}$Cr-release assays. As illustrated in FIG. 3, the U-251 and SNB19 cell lines were highly susceptible to cytotoxic activity of all the CTL lines that had been induced with IL-13Rα2$_{345-353}$ or each of its modified peptides. A172 cells, in contrast, were not lysed beyond the background level (<10%) by any of the CTL lines tested, suggesting that the IL-13Rα2$_{345-353}$ or modified peptide-induced CTL lines lysed SNB19 and U-251 glioma cells in an HLA-A2 restricted manner (data not shown). The T cells stimulated with a melanoma associated antigen epitope Mart-1$_{27-35}$ and T cells with no peptide stimulation showed only background level (<10%) lysis at all Effector/Target (E/T) ratios tested (data not shown). In this particular patient, both IL-13Rα2-V9 and -A1V9 induced higher levels of lysis of SNB19 and U-251 in each E/T ratio in comparison to the native IL-13Rα2$_{345-353}$ peptide.

To determine the specificity of the lytic activity, cold target competition experiments were performed by addition of non-radiolabeled (cold) T2 cells pulsed with IL-13Rα2$_{345-353}$ peptide in the 4-h $^{51}$Cr-release assay (FIG. 4). The anti-SNB19 glioma cell lytic activities by the CTL lines induced by the native IL-13Rα2$_{345-353}$ or IL-13Rα2-

V9 were almost completely inhibited by the addition of the cold T2 cells pulsed IL-13Rα2$_{345-353}$. The CTL activities, however, were not inhibited by the addition of non-peptide pulsed cold T2 cells, demonstrating that the lytic ability of the CTLs was specific for the epitope IL-13Rα2$_{345-353}$.

Furthermore, anti-HLA-A2 antibody (W6/32) was used to block the HLA-A2 mediated signaling in the CTL reactivity. As illustrated in FIG. 5, addition of this antibody inhibited the CTL-mediated lysis, confirming that the anti-glioma CTL reactivity induced by these peptides was HLA-A2 restricted.

7.4 Example 4

This example demonstrates the vaccination of HLA-A2 transgenic (HHD) mice with IL-13Rα2-derived CTL epitopes.

In order to examine whether immunization with IL-13Rα2$_{345-353}$ and/or its modified peptides can elicit CTL responses in vivo, and also to examine whether induced CTL responses can mediate therapeutic anti-tumor responses against IL-13Rα2$_{345-353}$-expressing brain tumors, the HHD mice were obtained from Dr. Francois A. Lemonnier (Pasteur Institute, Paris). HHD mice are D$^b$×β2 microglobulin (β2M) null, and transgenic for modified HLA-A2.1-β2 microglobulin single chain (HHD gene) (Pascolo et al., 1997). In vivo experiments showed that HHD mice exhibit HLA-A2-restricted responses to multiepitope proteins such as intact influenza virus (Pascolo et al., 1997) and novel cancer associated antigens, such as EphA2 (Alves et al., 2003), HER-2/neu and hTERT (Scardino et al., 2002), MAGE (Graff-Dubois et al., 2002) and a novel breast carcinoma associated BA46 (Carmon et al., 2002). Hence, these mice are a useful tool for the identification and characterization of potential tumor-derived, HLA-A2-restricted CTL epitopes.

To create an HHD mouse-syngeneic tumor cell line that expresses IL-13Rα2, HHD gene-transfected EL4 lymphoma cells (EL4-HHD) were obtained. EL4-HHD cells have been generated from EL4 by depletion of D$^b$×β2M and insertion of modified HLA-A2.1-132M single chain (Pascolo et al., 1997), thereby allowing syngeneic transplantation in HHD mice. EL4-HHD cells were stably transfected with an expression plasmid encoding IL-13Rα2. The cell line (EL4-HHD-IL-13Rα2) expressed IL-13Rα2 protein and formed tumors both in subcutaneous (s.c.) and intracranial (i.c.) space following injections to syngeneic HHD mice.

7.5 Example 5

This example demonstrates that in vivo immunization of HHD mice with the modified peptides induced higher magnitudes of CTL responses than the native peptide against the target cells expressing IL-13Rα2$_{345-353}$.

HHD mice received (on days 7 and 14) s.c. injections of 100 μg of peptide IL-13Rα2-V9, -A1V9, IL-13Rα2$_{345-353}$, or MART-1$_{27-35}$ emulsified in incomplete Freund's adjuvant (IFA) in the presence of 140 μg of the I-A$^b$-restricted HBVcore$_{128-140}$ (TPPAYRPPNAPIL) (SEQ ID NO:5) T-helper epitope, which stimulates a CD4+ helper T cell response, thereby promoting the stimulation of CD8+ CTLs. Control animals received IFA containing HBV helper-peptide only. Eleven days after the last immunization, the animals were sacrificed, and 5×10$^6$ spleen cells (SPCs) were stimulated in vitro with the same peptide that was used for in vivo stimulation (10 μM). On day 6 of culture, the bulk populations were tested for specific cytotoxicity against the EL4-HHD cells expressing IL-13Rα2 or EL4-HHD pulsed with IL-13 Rα2$_{345-353}$.

EL4-HHD-IL-13Rα2 and EL4-HHD were labeled with 100 μCi of $^{51}$Cr for 60 min, plated in 96-well V-bottomed plates (3×10$^3$ cell/well). Labeled EL4-HHD were pulsed with IL-13Rα2$_{345-353}$ (1 μM) at 37° C. for 2 h. Control target cells were pulsed with no peptides. Stimulated SPCs were then added as effector cells and incubated at 37° C. for 4 h. One hundred μl of supernatant were collected and radioactivity measured in a gamma counter.

FIG. 6 demonstrates that the CTL responses induced by the modified peptides were able to lyse T2 cells loaded with the native IL-13Rα2$_{345-353}$. Control non-pulsed EL4-HHD cells were not lysed by the CTLs beyond background levels (shown in FIG. 7). Furthermore, the immunization with IL-13Rα2-V9 displayed a trend toward higher levels of CTL reactivity against the EL4-HHD cells pulsed with the native IL-13Rα2$_{345-353}$ peptide than other peptides examined, although the difference was not statistically significant due to the variation within the triplicated samples. These data support the previous set of data with human HLA-A2+ patient derived T cells, in which the modified peptides induced higher levels of anti-IL-13Rα2$_{345-353}$ CTL response than the native peptide.

The ability of the same HHD mice-derived CTLs used in FIG. 6 to lyse EL4-HHD-IL-13Rα2 cells was examined in order to evaluate the ability of the CTLs to recognize the IL-13Rα2$_{345-353}$ peptide that is naturally processed by cells that endogenously express IL-13Rα2. FIG. 7 illustrates that immunization with the IL-13Rα2$_{345-353}$, IL-13Rα2-V9 or -A1V9 induced a specific CTL activity against EL4-HHD-IL-13Rα2 cells. The CTL activities were antigen-specific because control EL4-HHD were not lysed beyond the background level. Modified peptides IL-13Rα2-V9 and -A1V9 induced higher magnitude of CTL activities in comparison to native IL-13Rα2$_{345-353}$ against the EL4-HHD-IL-13Rα cells (p<0.05 at all effector/target ratios). The in vivo anti-tumor effect of vaccinations with the IL-13Rα2$_{345-353}$ or modified IL-13Rα2 peptides in HHD mice bearing EL4-HHD-IL-13Rα2 tumors is currently being evaluated.

7.6 Example 6

This example demonstrates that EphA2 has available HLA-A2-restricted CTL epitopes.

EphA2 is an attractive tumor-associated antigen and a target for tumor-vaccines, as 5 HLA-A2 and 3 DR4 T cell epitopes have been previously identified (Tatsumi et al., 2003). As shown in FIG. 8, 9 of 14 human glioblastoma multiforme (GBM) and 6 of 9 anaplastic astrocytoma (AA) cases express high levels of EphA2. In addition, anti-glioma CTL reactivity has been induced in CD8+ cells obtained from HLA-A2+ glioma patients by stimulation with the EphA2$_{883-891}$ epitope (FIG. 9). This response was specific for the EphA2$_{883-891}$ epitope because the parallel assay using T2 cells loaded with EphA2$_{883-891}$ demonstrated a peptide-specific response in comparison to the control unloaded T2 target (not shown). These data strongly suggest that EphA2$_{883-891}$ can serve as a CTL epitope.

7.7 Example 7

This Example describes a phase I/II trial performed to evaluate the safety and immunogenicity of a novel vaccination with α-type-1-polarized dendritic cells (αDC1) loaded with synthetic peptides for glioma associated antigen (GAA) epitopes and administration of poly-ICLC in human leukocyte antigen (HLA)-A2+ patients with recurrent malignant gliomas. GAAs for these peptides are EphA2, interleukin-13 receptor (IL-13R) α2, YKL-40 and gp100.

7.7.1 Patients and Methods

7.7.1.1 Patients

Patients with recurrent malignant glioma were enrolled with informed consent and approvals by the institutional review board (IRB) and US Food and Drug Administration (FDA) (BB-IND#12415). Clinical characteristics of patients are summarized in Tables 2 and 3A. Enrollment criteria included: histological diagnosis of glioblastoma multiforme (GBM) or anaplastic glioma (AG) including anaplastic astrocytoma (AA), anaplastic oligodendroglioma (AO) or anaplastic oligoastrocytoma (AOA); up to 2 previous recurrences; >18 years old; Karnofsky performance status >60; adequate liver and renal function and HLA-A2+. Minimum doses of corticosteroid (dexamethasone up to 4 mg/day) were permitted. Twenty-two patients were enrolled and received at least one vaccination. Nineteen of 22 patients completed the scheduled initial 4 immunizations; three patients (Patients 4, 11 and 13) were withdrawn from the protocol due to early tumor progression. Nine patients completed 5 additional booster vaccinations. Immunologic and safety data are presented on patients who had at least 4 vaccinations (n=19), and at least one vaccination (n=22), respectively.

TABLE 2

Demographics and Clinical Characteristics of Participating Patients

| | DC Dose Level (No. of DC/dose) | | Total (n = 22) | |
| --- | --- | --- | --- | --- |
| Characteristics | 1 (1 × 10$^7$) | 2 (3 × 10$^7$) | No. of Patients | % |
| Received at least one vaccine | 11 | 11 | 22 | |
| Completed at least 4 vaccines | 10 | 9 | 19 | 86 |
| Female (received at least 4 vaccines) | 5 | 4 | 9 | 47 |
| Median age, years | 52 | 46 | 48 | |
| Range | 37-71 | 28-63 | 28-71 | |
| Tumor Histology | | | | |
| AA | 3 | 2 | 5 | 23 |
| AO | 1 | 2 | 3 | 14 |
| AOA | 1 | 0 | 1 | 4 |
| GBM | 6 | 7 | 13 | 59 |
| No. of Previous Recurrences | | | | |
| 0 | 7 | 4 | 11 | 50 |
| 1 | 2 | 5 | 7 | 32 |
| 2 | 2 | 2 | 4 | 18 |

TABLE 3A

| | Pt ID | Age/Gender | Tumor Histol. | Location of Tumor | Prior Therapy | No. Prev. Rec. | DC IL-12 (pg) | ELISPOT (pos/neg) by Week 9 | | | | | Tetramer | | | RR at week 9 | TTP (Mo) | OS (Mo) |
| --- | --- | --- | --- | --- | --- | --- | --- | --- | --- | --- | --- | --- | --- | --- | --- | --- | --- | --- |
| | | | | | | | | I | E | Y | G | Pa | I | E | G | | | |
| Dose Level 1 (1 × 10$^7$ DC/dose) | 1 | 57/M | GBM | Rt. Temp/Pa | Res/RT/TMZ/Mol | 1 | 10 | N | N | N | N | N | P | P | P | PR | 7 | 14 |
| | 2 | 52/M | GBM | Rt. Temporal | Res/RT/TMZ | 1 | 25 | P | N | N | P | N | P | P | P | PD | <2 | 12 |
| | 3 | 37/M | AA | Rt. Parietal | Resx2/RT/TMZ/Mol | 2 | 25 | N | N | N | N | N | N | N | N | SD | 5 | 10 |
| | 4 | 68/F | AA | Rt. Frontal | SB/RT/TMZ | 0 | <10 | Not Tested | | | | | Not Tested | | | ND* | <2 | >37 |
| | 5 | 63/M | GBM | Rt. Parietal | SB/RT/TMZ | 0 | 26 | N | N | N | N | N | N | N | N | PD | <2 | 5 |
| | 6 | 56/M | AOA | Lt. Temporal | SB/RT/TMZ | 0 | 27 | N | P | N | P | P | P | P | P | SD | >30 | >30 |
| | 7 | 37/F | AA | Rt. Temporal | SB/RT/TMZ | 0 | 919 | N | N | N | N | N | P | P | P | SD | 25 | >33 |
| | 8 | 45/F | GBM | Rt. Frontal | SB/RT/TMZ/Mol | 0 | 480 | N | N | N | N | N | P§ | P§ | N | SD | 16 | >30 |
| | 9 | 43/F | AO | Rt. Frontal | Res/RT/TMZ/SR | 0 | 24 | P | N | N | P | P | N | N | N | PD | <2 | 23 |
| | 10 | 71/F | GBM | Lt. Parietal | Resx2/RT/TMZ/CE | 2 | <10 | P | N | N | P | P | N | N | N | SD | 5 | >27 |
| | 14 | 40/M | GBM | Lt. Front/Temp | Res/RT/TMZ | 0 | 551 | N | N | N | N | N | N | N | N | SD | 18 | >18 |
| Dose Level 2 (3 × 10$^7$ DC/dose) | 11 | 54/M | GBM | Rt. Temporal | Res/RT/TMZ/Mol | 2 | 38 | Not Tested | | | | | Not Tested | | | ND* | <2 | 3 |
| | 12 | 35/F | AO | Lt. Frontal | SB/TMZ | 0 | 111 | N | N | N | P | N | P§ | N | N | SD | 13 | >25 |
| | 13 | 46/M | AA | Rt. Parietal | Res/RT/TMZ | 1 | 151 | Not Tested | | | | | Not Tested | | | ND* | <2 | 4 |
| | 15 | 51/M | GBM | Multiple | Res/RT/TMZ | 0 | 35 | N | N | N | N | N | N | N | N | SD | 4 | 12 |
| | 16 | 33/M | AO | Rt. Frontal | Res/RT/TMZ/Mol | 2 | 985 | P | N | N | P | P | N | P§ | P§ | SD | >14 | >14 |
| | 17 | 30/F | GBM | Lt. Parietal | Resx2/RT/TMZ/CW | 1 | 123 | N | N | N | N | P | Not Tested | | | PD | <2 | 6 |
| | 18 | 61/F | GBM | Bil. Occipital | Res/RT/TMZ/BI | 1 | 125 | N | N | N | P | P | N | N | N | PD | <2 | 5 |
| | 19 | 63/M | GBM | Lt. Temporal | Res/RT/TMZ/SR | 1 | 199 | N | N | N | N | N | P§ | P§ | P | SD | >13 | >13 |
| | 20 | 62/M | GBM | Rt. Temporal | Res/RT/TMZ | 0 | 287 | N | N | N | N | N | P§ | P§ | P§ | PR | >13 | >13 |
| | 21 | 38/F | GBM | Rt. Hemi | Res/RT/TMZ/CPT-Bev | 1 | 27 | N | N | N | P | N | Not Tested | | | PD | <2 | 12 |
| | 22 | 28/M | AA | Brain Stem | SB/RT/TMZ/Res | 0 | 779 | N | N | N | N | P | N | N | N | SD | >12 | >12 |

Abbreviations: M, male; F, female; GBM, glioblastoma multiforme; AA, anaplastic astrocytoma; AO, anaplastic oligodendroglioma; AOA, anaplastic oligoastrocytoma; Temp, temporal; Pa, parietal; Bil, bilateral; Hemi, hemispheric; Res, resection; RT, radiation therapy; TMZ, temozolomide; Mol, molecularly targeted therapy; SB, stereotactic biopsy; SR, stereotactic radiosurgery; CE, carboplatin and etoposide; CW, carmustine-releasing wafer; BI, bevacizumab and irinotecan; No. Prev. Rec, number of previous recurrences; DC IL-12, production of IL-12 p70 by αDC1 (pg/10$^6$ cells/24 hours); I, IL- 13Rα2; E, EphA2; Y, YKL-40; G, gp100; Pa, PADRE; P, positive; N; negative; PR, partial response; SD, stable disease; PD; progressive disease; ND*, not determined due to early progression before Week 9; TTP, time to progression.

TABLE 3B

| | Pt ID | ELISPOT (best response) | | | | |
| --- | --- | --- | --- | --- | --- | --- |
| | | I | E | Y | G | Pa |
| Dose Level 1 ($1 \times 10^7$ DC/dose) | 1 | 25-49 | <25 | 25-49 | 25-49 | 100-199 @ |
| | 2 | 50-99 | 25-49 | 25-49 | >200 | 50-99 @ |
| | 3 | <25 | <25 | <25 | 25-49 | 25-49 |
| | 4 | | | Not Tested | | |
| | 5 | <25 | 25-49 | 25-49 | 25-49 | 25-49 |
| | 6 | 100-199 § | 100-199 | 50-99 § | 100-199 | >200 |
| | 7 | 50-99 § | <25 | <25 | 100-199 § | <25 |
| | 8 | 50-99 § | <25 | 50-99 § | 100-199 § | 25-49 |
| | 9 | 50-99 | <25 | 50-99 @ | 100-199 | 50-99 |
| | 10 | >200 | 100-199 @ | 50-99 @ | >200 | >200 |
| | 14 | <25 | 50-99 @ | 50-99 @ | 50-99 @ | <25 |
| Dose Level 2 ($3 \times 10^7$ DC/dose) | 11 | | | Not Tested | | |
| | 12 | 50-99 § | 50-99 § | 50-99 § | 50-99 | <25 |
| | 13 | | | Not Tested | | |
| | 15 | <25 | <25 | <25 | 100-199 @ | 25-49 |
| | 16 | 100-199 | 25-49 | <25 | >200 | >200 |
| | 17 | 50-99 @ | <25 | 50-99 @ | 25-49 | 50-99 |
| | 18 | 25-49 | <25 | 25-49 | >200 | 100-199 |
| | 19 | <25 | <25 | <25 | <25 | <25 |
| | 20 | <25 | <25 | <25 | 25-49 | <25 |
| | 21 | 25-49 | 25-49 | 50-99 @ | 50-99 | <25 |
| | 22 | 100-199 § | <25 | 25-49 | >200 § | 100-199 |

Abbreviations:
§, positive only after booster vaccines;
@, only a single point, but not two or more consecutive points demonstrated 50 or more spots/$10^5$ cells (thus not positive);
I, IL-13Rα2; E, EphA2; Y, YKL-40; G, gp100; Pa, PADRE.

7.7.1.2 Clinical Trial Design

This study was designed to assess toxicity and the induction of immune and preliminary clinical responses of vaccinations with GAA-loaded αDC1 and administration of poly-ICLC (Hiltonol®, Oncovir, Inc.). The first course of vaccines consisted of 4 ultrasound-guided intranodal (i.n.) administrations of 1 or $3 \times 10^7$ αDC1/injections every 2 weeks (FIG. 19) rotating each of inguinal and axillary lymph node clusters to minimize the potential effects of injection-induced trauma in the microenvironment of the lymph nodes by repeating injections in short periods. The first 10 evaluable patients received $1 \times 10^7$ αDC1/injection (Dose Level 1), then 9 received $3 \times 10^7$ αDC1/injection (Dose Level 2). All patients received intramuscular (i.m.) injections with poly-ICLC (20 μg/kg) twice/week for 8 weeks starting on day 1. Patients exhibiting stable disease or regression of disease without major adverse events (AE) after the 4$^{th}$ vaccination were eligible for additional vaccinations. Starting at Week 13, these patients were treated with the same dose of additional vaccinations every 4 weeks to a maximum of 5 vaccine injections and i.m. poly-ICLC starting on the day of the first additional vaccine and twice/week (1$^{st}$ booster phase). Patients not demonstrating major AE or tumor progression after the 1$^{st}$ booster phase were offered the same dose of additional vaccines (every 3 months) and poly-ICLC (every week) for up to three years from the first vaccination (2$^{nd}$ booster phase).

7.7.1.3 Toxicity Assessment and Stopping Rules

The trial was monitored continuously for treatment-related AE using National Cancer Institute Common Toxicity Criteria version 3.0. The following were considered to be dose-limiting toxicity (DLT) if they were judged possibly, probably or definitely associated with treatment: ≥Grade 2 hypersensitivity; ≥Grade 3 nonhematologic/metabolic toxicity; ≥Grade 3 hematological (except for lymphopenia) or metabolic toxicity that did not subside following 4 weeks temporary cessation of poly-ICLC. Stopping rules were implemented such that a dose level was considered to be excessively toxic, warranting that accrual be halted, if at any time the observed rate of DLT was ≥33% and at least 2 DLTs had been observed.

7.7.1.4 Peptides

HLA-A2-restricted peptides used in these studies included: ALPFGFILV (SEQ ID NO:3; IL-13Rα2$_{345\text{-}353:1A9V}$); TLADFDPRV (SEQ ID NO:6; EphA2$_{883\text{-}891}$); IMDQVPFSV (SEQ ID NO:11; GP100$_{209\text{-}217:M2}$); and SIMTYDFHGA (SEQ ID NO:10; YKL-40$_{201\text{-}210}$). αDC1 were also loaded with a pan-DR epitope (PADRE), which is a non-natural epitope optimized for helper T-cell response (see, e.g., Alexander et al, Immunity, 1:751-761, 1994). The peptides were synthesized by automated solid-phase peptide synthesis. Peptides were tested in multiple quality-assurance studies including purity, sterility, identity, potency, pyrogenicity and stability.

7.7.1.5 Vaccine Preparation

For the DC culture, monocytes were obtained from the leukapheresis product and purified by the Elutra™ System. The monocytes were cultured in CellGenix antibiotic-free culture medium supplemented with 1000 U/mL GM-CSF and 1000 U/mL IL-4 in sterile cartridges, using the Aastrom Replicell System. The immature (i) DC were harvested on day 6 and cryopreserved. Before each vaccination, aliquots of frozen iDCs were thawed, further matured and polarized with clinical grade IL-1β (10 ng/mL), TNF-α (10 ng/mL), IFN-α (3000 U/ml), IFN-γ (1000 U/ml) and poly-I:C (20 μg/ml) at 37° C. in 5% $CO_2$ for 48 hours and loaded with GAA peptides (10 μg/ml) for 4-6 hours. Two hours prior to harvest, the PADRE peptide was added to the cultures. Criteria for release of αDC1 included: Sterility by Gram stain and bacteriologic culture; negative Mycoplasma; endotoxin <5.0 E.U./kg of body weight; greater than 70% expression of both CD86 and HLA-DR on αDC1.

7.7.1.6 Collection of PBMCs

Peripheral blood (50-60 ml) was drawn at each visit for vaccine (before the vaccine) as well as Weeks 0, 9 and 33. Ficoll-isolated PBMC were cryopreserved in 10% dimethyl sulfoxide/90% FBS.

7.7.1.7 ELISPOT Assays

Enzyme-linked immunosorbent spot (ELISPOT) assays were performed as described previously (see, e.g., Kirkwood et al, Clin. Cancer Res., 15:1443-1451, 2009) with slight modifications. Briefly, batched PBMC samples were evaluated simultaneously following in vitro stimulation with autologous, irradiated PBMC loaded with wild-type IL-13R$\alpha_{345\text{-}353}$, EphA2$_{883\text{-}891}$, GP100$_{209\text{-}217}$ and YKL-40$_{202\text{-}211}$ for a week. A positive ELISPOT response was defined as a 2-fold increase in spot-forming T-cells over pre-vaccine level and at least 10 spots/20,000 cells for at least two consecutive post-vaccine time points against any antigen.

7.7.1.8 Tetramer Assays

Phycoerythrin (PE)-conjugated HLA-A*0201/ALPFGFILV (SEQ ID NO:3) (IL-13Rα2-tetramer), HLA-A*0201/IMDQVPFSV (SEQ ID NO:11) (gp100-tetramer) and HLA-A*0201/TLADFDPRV (SEQ ID NO:6) (EphA2-tetramer) were produced by the National Institute of Allergy and Infectious Disease tetramer facility within the Emory University Vaccine Center (Atlanta, Ga.) using the peptide synthesized by the University of Pittsburgh Peptide Production Facility. Fluorescein isothiocyanate (FITC)-conjugated anti-human CD8 was obtained from BD Biosciences. A single time-point positive response for a peptide was defined to be (0.1+B) % of all CD8$^+$ cells positive by tetramer assay (see, e.g., Weber et al, J Immunother., 31:215-23, 2008; and Celis, Cancer, 110:203-14, 2007), where B is the percent positive at baseline, which was less than 0.01% in all cases. A patient was considered to have responded if he/she had 2 consecutive single time-point responses for any peptide.

7.7.1.9 Cytokine and Chemokine Assays

Total RNA samples were obtained from PBMC using the PAXgene Blood RNA System (PreAnalytix, Switzerland). RT-PCR was performed in triplicate, and values were standardized to GAPDH and relative expression of mRNAs was calculated using the $\Delta\Delta C_T$ method (see, e.g., Livak and Schmittgen, Methods, 25:402-8, 2001). The Luminex-based assay was performed in serum samples as previously described (see, e.g., Zczepanski et al, Cancer Res., 69:3105-3113, 2009). Pre-tested, multiplex plates (Invitrogen) included standard curves and cytokine standards (R&D Systems). In situ hybridization with radiolabeled cRNA probe for CXCL10 was performed as described (see, e.g., Fallert and Reinhart, J Virol Methods, 99:23-32, 2002), with autoradiographic exposure times of 14 days.

7.7.1.10 Radiological Response Monitoring

Tumor size was assessed at Weeks 9, 17, 25, and 33, and every 3 months thereafter using MRI scans with contrast enhancement. Response was evaluated by McDonald criteria by gadolinium (Gd)-enhanced T1 weighted images, area of signal prolongation on T2 weighted images, or a combination of both, based on upon the appearance of the pre-treatment MRI.

7.7.1.11 Other Clinical Endpoints

Overall survival was defined by the interval from study entry to date of death. MRI scans were used to evaluate time to progression (TTP).

7.7.2 Results 7.7.2.1 Summary of Clinical Toxicities

Treatment-related AE are listed for all 22 patients in Table 4. There were no grade 3 or 4 toxicities, no deaths on study, and no DLT at any dose through the 1$^{st}$ booster phase. No incidences of autoimmunity were encountered. Toxicity profiles were comparable across dose levels. Grade 1 or 2 injection site reactions were the most common (82%). Grade 1 flu-like symptoms, including fatigue (73%), myalgia (32%), fever (23%), chills/rigors (18%) and headache (32%), were common and usually limited to 24 hours after each vaccine. Grade 2 lymphopenia was recorded in one patient (5%).

TABLE 4

| Adverse Event | Grade 1 No. | Grade 1 % | Grade 2 No. | Grade 2 % |
|---|---|---|---|---|
| Blood/Bone Marrow | | | | |
| Leukocytopenia | | | 1 | 5 |
| Injection site reactions | | | | |
| Redness, induration, pruritis, pain | 17 | 77 | 1 | 5 |
| Constitutional symptoms | | | | |
| Fatigue (lethargy, malaise, asthenia) | 16 | 73 | | |
| Fever | 5 | 23 | | |
| Chills/Rigors | 4 | 18 | | |
| Nausea | 7 | 32 | | |
| Vomiting | 1 | 5 | | |
| Headache | 5 | 23 | 2 | 9 |
| Insomnia | 1 | 5 | | |
| Light headed/dizziness | 2 | 9 | | |
| Myalgia | 7 | 32 | | |
| Body ache | 6 | 27 | | |
| Dermatological | | | | |
| Skin rash | 3 | 14 | | |
| Dry skin | 1 | 5 | | |
| Bruising | 2 | 9 | | |
| Urticaria | 1 | 5 | | |
| Pulmonary/Upper Respiratory | | | | |
| Rhinitis/Runny nose | 1 | 5 | | |

All AE listed were possibly, probably, or definitely related to the vaccine and/or poly ICLC administration. The numbers represent the number of patients (of 22) experiencing a particular event at any point during the treatment period, with the highest grade reported for any single individual. No grade 3 or grade 4 events observed related to treatment through the 1st booster phase. One patient (Patient 6) demonstrated grade 2 systemic urticaria following the 154th injection of poly-ICLC during the 2nd booster phase; this was considered to be DLT. However, because the relationship was unclear and the patient was progression-free for 22 months by that time, per IRB approval, the patient was re-treated with booster vaccines and poly-ICLC following pre-medication with oral diphenhydramine hydrochloride, and has never demonstrated similar reactions again.

7.7.2.2 IL-12 Production by αDC1

As shown in Tables 3A-3B, CD40L-induced IL-12 p70 production levels by αDC1 varied substantially between patients, and positively correlated with TTP (p=0.0255; FIG. 10) but not with IFN-γ ELISPOT response, patients' age or tumor types.

7.7.2.3 Induction of Epitope-Specific Immune Responses Against GAAs

All 19 patients who completed the initial course of 4 vaccinations had PBMCs available for immunological monitoring. Insufficient PBMC were obtained from Patients 17, 21 and 22 to perform both ELISPOT and tetramer assays; and functional ELISPOT assays were prioritized. The scheduled first 4 vaccines induced immune reactivity to at least one of the vaccine-targeted GAAs in 6 of 10 and 5 of 9 in Dose Levels 1 and 2, respectively, by either IFN-γ ELISPOT or tetramer assays (Tables 3A-3B). In patients 6, 7, 8, 16, 19, 20 and 22, some readouts reached the criteria for positive response following booster vaccines (indicated by § in Table 3B). In summary, 11 of 19 (58%) evaluable patients showed positive response after the initial 4 vaccinations, and 3 of 19 (Patients 8, 19 and 20; 16%) showed positive response only after booster vaccines.

Positive response rates (either by tetramer or ELISPOT) did not show significant differences across the two αDC1 doses per Fisher's exact test. Furthermore, the magnitudes of ELISPOT response, based on the summation of positive spots from Week 3 through 9, were comparable across the two αDC1 dose levels (Wilcoxon test). Therefore, the time course of IFN-γ ELISPOT responses is presented by combining results from both dose levels (FIG. 11). The gp100 epitope demonstrated the highest magnitude of response among the GAA peptides tested (p=0.0001, 0.0003 and 0.0005 against IL-13Rα2-, EphA2- and YKL-40-derived peptides, respectively, by Wilcoxon test). For the other epitopes, booster vaccines appeared to improve the induction of specific responses. A temporary decline of responses was typically observed at Week 13, which may reflect that some patients who demonstrated positive responses by Week 9 did not participate in the booster phase due to tumor progression (Patients 2, 9, 18 and 21) or lymphopenia (Patient 10), resulting in overall reduction of response when data are pooled for all patients. Patient 10 demonstrated the highest magnitude of IFN-γ ELISPOT responses against IL-13Rα2- and gp100-derived epitopes as well as PADRE (FIG. 12) but tetramer analyses on this patient yielded no responses (Table 3A). Patient 6, who demonstrates stable disease for longer than 30 months, developed durable and high level responses in tetramer (FIG. 13) and ELISPOT assays.

7.7.2.4 Induction of Type-1 Cytokine and Chemokine Responses

RT-PCR analyses of PBMC (FIGS. 14 and 15) revealed up-regulation of mRNA expression for several type-1 cytokines and chemokines, specifically IFN-α1, CXCL10 and TLR3, at both post-$1^{st}$ vaccine and post-$4^{th}$ vaccine. IFN-γ was found to be up-regulated after the $4^{th}$ vaccine, but not after the $1^{st}$ vaccine, suggesting that the IFN-γ up-regulation may be associated with the induction of adaptive, rather than innate, immune response. CCL22, which is known to attract regulatory T-cells (see, e.g., Muthuswamy et al., Cancer Res. 68:5972-5978, 2008), and CCL5 levels decreased in paired-analyses of post-$1^{st}$ vaccine samples. Perforin, Granzyme B, COX-2 and Foxp3 levels did not change significantly.

A panel of cytokines and chemokines was evaluated at protein levels in available pre-vaccine and post-vaccine serum samples from 5 patients (FIG. 16). Among them, IFN-α, CXCL10, IL-15, MCP-1 and MIP-1β were significantly up-regulated in post-vaccine sera. IL-17 was under detectable ranges in both RT-PCR and serum analyses.

In addition, three of five available tumors resected due to post-vaccine radiographic progression expressed mRNA for CXCL10, which is a critical chemokine for effective trafficking of CD8+ T-cells to brain tumor sites (see, e.g., Nishimura et al., Cancer Res 66:4478-4487, 2006; and Fujita et al., Cancer Res 69:1587-1595, 2009) (FIG. 17 for a representative case). These data suggest that the current regimen induces systemic, poly-functional immune responses in generally immunosuppressed patients with malignant glioma.

7.7.2.5 Immunohistochemistry Data

Immunohistochemistry data for 7 cases GAA cases are summarized in Table 5. These data suggest that expression of gp100 may be very low in primary high grade gliomas. For immunohistochemistry, the following polyclonal antibodies (Ab) and corresponding secondary Ab were used: anti-human(h)IL-13Rα2 (goat IgG; R&D Systems); anti-human EphA2 (H-77) (rabbit IgG; Santa Cruz Biotechnology); anti-human YKL-40 (rabbit IgG; Quidel) and anti-human gp100 (goat IgG; Santa Cruz Biotechnology).

TABLE 5

| Case # | Pre vs. Post vaccine | IL-13Rα2 | EphA2 | YKL-40 | gp100 |
|---|---|---|---|---|---|
| 1 (GBM) | Pre | 2* | 3* | 2 | 0* |
|  | Post | 2* | 1* | 2 | 0* |
| 2 (GBM) | Pre | 1* | 2* | 1 | 0* |
| 5 (GBM) | Post | 1 | 2 | 2 | 1 |
| 9 (AO) | Pre | 1* | 2 | 1 | 0* |
|  | Post | 1* | 1 | 1 | 0* |
| 10 (GBM) | Post | 2* | 1 | 2 | 0* |
| 12 (AO) | Pre | 2 | 2 | 1 | 1* |
| 14 (GBM) | Pre | 3 | 2 | 2 | 0 |

Expression of each GAA was graded as follows: grade 0, negative; 1, weakly positive; 2, moderately positive; 3, strongly positive. Numbers with asterisks indicate that the patient demonstrated positive ELISPOT or tetramer response against the antigen. Pre-vaccine does not mean that tumor tissues were obtained immediately before the vaccination, but obtained at variable time points before the vaccine, including the initial diagnostic biopsy or resection. Likewise, post-vaccine tissues were obtained at variable time points following the last vaccine because re-resection was not always indicated.

7.7.2.6 Clinical Outcomes

Two patients (Patient 1 and 20) experienced objective clinical tumor regressions (response rate=9%). Both patients were non-responders by ELISPOT, but tetramer responders. Patient 20 with recurrent GBM demonstrated complete response based on disappearance of the Gd-enhanced mass at Week 17 post-vaccine compared with the baseline MRI, which was durable and ongoing for at least 13 months since the initiation of the treatment (FIG. 18A-I). Patient 1 with recurrent GBM exhibited a partial response at Week 9. Following two booster vaccines, the Gd-enhanced lesion enlarged. Biopsy of the lesion, however, revealed intensive infiltration of CD8+ T-cells and CD68+ macrophages and no evidence of mitotically active tumor (FIG. 18J-L). Then, this patient received one additional vaccine before the recurrence at 7 months after the initial vaccine. Nine patients (41%; 4 and 5 with GBM and AG, respectively) were progression-free for at least 12 months. Five patients remained progression-free (Table 3A) and continued to receive booster vaccines. Median TTP are 4 and 13 months for GBM and AG, respectively (FIG. 20).

7.7.3 Conclusion

The study described in this Example evaluated αDC1-based vaccines loaded with novel GAA-derived peptides, in combination with poly-ICLC. The findings demonstrate safety and immunogenicity as well as preliminary efficacy of the approach.

7.8 Example 8

This example describes a study of the safety and efficacy of a therapeutic regimen for adults with recurrent WHO grade II gliomas that comprises vaccination with HLA-A2-restricted glioma antigen-peptides in combination with poly-ICLC.

7.8.1 Rationale

This Example describes a vaccination regime that is designed to efficiently induce anti-tumor T-cell responses in patients with recurrent WHO grade II glioma. The regime combines subcutaneous injections of glioma-associated antigen (GAA)-derived cytotoxic T-lymphocyte (CTL) epitope-peptides with simultaneous intramuscular (i.m.) administration of poly-ICLC.

Adults with supratentorial low-grade glioma (LGG) have a significant risk (24%) of tumor progression 2 years following treatment with surgery or surgery followed by radiation therapy (RT). The study described in this Example has both immunoprophylactic and immunotherapeutic potential to reduce the risk of tumor recurrence, which may translate into improved survival. Therapeutically, the immunotherapy approach may suppress the expansion of indolently growing neoplastic low grade II tumor cells. Prophylactically, the approach may prevent anaplastic transformation, which occurs in about one-half of recurrent LGG. The slower growth rate of LGG (in contrast to malignant gliomas) should allow sufficient time to repeat multiple immunizations, which may lead to the induction of high levels of GAA-specific immunity. In addition, poly-ICLC has been demonstrated to enhance the vaccine effects in preclinical brain tumor models (see, e.g., Zhu et al., J. Transl. Med., 5: 10, 2007), and to be safe in malignant glioma patients (see, e.g., Salazar et al., Neurosurgery, 38: 1096-1103, 1996). Therefore, we hypothesize that this form of vaccine in combination with poly-ICLC treatment will induce potent anti-glioma immune response, and will be safe.

7.8.2 Objectives

This Example describes a vaccine study in adults with recurrent WHO grade II glioma. The objectives of this Example include collection of immunological and safety data that may be used in additional studies. The patients in the study described in this Example may be followed for a minimum of 2 years, so that the actual 2-year overall survival (OS), 6-month and 2-year progression-free survival (PFS) rates may be determined in an exploratory manner.

7.8.2.1 Induction of GAA-Specific T-Cell Response

The response rate and magnitude of immune response in post-vaccine peripheral blood mononuclear cells (PBMC) against the GAA-peptides in response to this form of vaccine may be determined using IFN-γ-enzyme-linked immuno-spot (ELISPOT) and tetramer assays.

7.8.2.2 Safety

The incidence and severity of adverse events associated with the vaccine regime may be assessed, with an early stopping rule based on the frequency of Regimen Limiting Toxicity (RLT).

7.8.2.3 Clinical Response

Radiological response may be determined using the standard WHO response criteria. 6-month and 2-year progression-free survival (PFS) may be evaluated in an exploratory manner, based on serial magnetic resonance imaging (MRI) scans.

7.8.2.4 Tumor Tissues for Biological Correlates

For patients who develop progression, biopsy/resection may be encouraged. Whenever post-vaccine tumor tissues are available, they may be analyzed for GAA expression status and infiltration of GAA-specific T-cells.

7.8.3 Patient Selection

7.8.3.1 Eligibility Criteria

Pathological criteria—Patients have recurrent supratentorial WHO grade II astrocytoma, oligoastrocytoma or oligodendroglioma that is histologically confirmed either by the previous biopsy or resection, or at the time of re-operation (re-operation before entry to the current study is allowed; however post-surgery Decadron must be off for at least 4 weeks before administration of the first vaccine). Patients in this study should have received prior external beam radiotherapy and/or chemotherapy. With regard to the prior therapy, patients in this study should have had treatment for no more than 2 prior relapses. Relapse is defined as progression following initial therapy (i.e. radiation+/–chemo if that was used as initial therapy). The intent therefore is that patients in this study should have had 3 prior therapies (initial therapy and treatment for 2 relapses). If the patient had a surgical resection for relapsed disease, and no anti-cancer therapy was instituted for up to 12 weeks, and the patient undergoes another surgical resection, this is considered as 1 relapse.

Patients in this study should be HLA-A2 positive based on flow cytometry.

Patients in this study should have recovered from the toxic effects of prior therapy: 4 weeks from any investigational agent, 4 weeks from prior cytotoxic therapy and/or at least two weeks from vincristine, 4 weeks from nitrosoureas, 3 weeks from procarbazine administration, and 1 week for non-cytotoxic agents, e.g., interferon, tamoxifen, thalidomide, cis-retinoic acid, etc. (radiosensitizer does not count). With regard to previous radiation therapy (RT), there must be at least 6 months from the completion of RT (or radiosurgery).

Patients in this study should be >18 years old.

Patients in this study should have a Karnofsky performance status of >60 (Appendix I).

Female patients in this study of child-bearing age should have documented negative serum βHCG.

Patients in this study should be free of systemic infection. Patients with active infections (whether or not they require antibiotic therapy) may be eligible after complete resolution of the infection. Patients on antibiotic therapy should be off antibiotics for at least 7 days before beginning treatment.

Patients in this study should have adequate organ function as measured by white blood count ≥2500/mm$^3$; lymphocytes ≥400/mm$^3$; platelets ≥100,000/mm$^3$, hemoglobin ≥10.0 g/dL, AST, ALT, GGT, LDH, alkaline phosphatase within 2.5× upper normal limit, and total bilirubin ≤2.0 mg/dL, and serum creatinine within 1.5× upper limit of normal limit. Patients in this study should have coagulation tests and PT and PTT should be within normal limits.

7.8.3.2 Exclusion Criteria

Patients in this study should be excluded if they have presence of gliomatosis cerebri, cranial or spinal leptomeningeal metastatic disease.

Even if the initial diagnosis was WHO grade II glioma, if the pathological diagnosis for the recurrent disease demonstrate transformation to higher grade (i.e. WHO grade III or IV) gliomas, patients should be excluded from this study.

Patients in this study should be excluded if they are undergoing concurrent treatment or medications including: radiation therapy; chemotherapy; interferon (e.g. Intron-A®); allergy desensitization injections; growth factors (e.g. Procrit®, Aranesp®, Neulasta®); interleukins (e.g. Proleukin®); and/or any investigational therapeutic medication.

Patients in this study should not have had prior autoimmune disorders requiring cytotoxic or immunosuppressive therapy, or autoimmune disorders with visceral involvement. Patients in this study with an active autoimmune disorder requiring these therapies also should be excluded. Mild arthritis requiring NSAID medications should not be exclusionary.

Patients in this study should be excluded if they have used immunosuppressives within four weeks prior to entering the study or if they anticipate use of immunosuppressive agents. Dexamethasone, or other corticosteroid medications, if used peri-operative period and/or during radiotherapy, should be tapered by patients and discontinued at least four weeks before administration of the first vaccine in the study. Topical corticosteroids and Inhaled steroids (e.g.: Advair®, Flovent®, Azmacort®) should be acceptable.

Patients in this study should be excluded if they have another cancer diagnosis, except that the following diagnoses may be allowed: squamous cell cancer of the skin without known metastasis; basal cell cancer of the skin without known metastasis; carcinoma in situ of the breast (DCIS or LCIS); carcinoma in situ of the cervix; and/or any cancer without distant metastasis that has been treated successfully, without evidence of recurrence or metastasis for over 5 years.

Patients in this study should be excluded if they have known addiction to alcohol or illicit drugs.

Because patients with immune deficiency are not expected to respond to this therapy, HIV-positive patients should be excluded from the study.

7.8.4 Peptide Vaccine 7.8.4.1 Peptides

The following peptides may be included in the vaccine formulation: IL-13R$\alpha$2$_{345-353}$ 1A9V (ALPFGFILV; SEQ ID NO:3); EphA2$_{883-891}$ (TLADFDPRV; SEQ ID NO:6); Survivin$_{96-104}$:M2 (LMLGEFLKL; SEQ ID NO:7); WT1$_{126-134}$:Y1 (YMFPNAPYL; SEQ ID NO:8); and Tetanus Toxoid (TetA830) (AQYIKANSKFIGITEL; SEQ ID NO:9).

All peptides may be synthesized and the synthetic peptides may be purified by HPLC. The identity of the synthetic peptides may be confirmed by verifying their mass and amino acid sequences by mass spectrometry. Each lot of peptide may be evaluated as required by the FDA for identity, purity, sterility and pyrogenicity.

The peptides may be vialed under GMP conditions and saved at −70° C. Stability of lyophilized peptides may be tested annually by mass spectroscopy.

7.8.4.2 Other Agents

Montanide ISA-51 (SEPPIC Inc., Fairfield, N.J.) may be used as an additional agent in the peptide vaccines.

7.8.4.3 Dosage and Preparation

An aqueous solution (500 µL) containing each of four HLA-A2-restricted GAA peptides (300 µg/peptide) and the tetanus peptide (Peptide-tet; 200 µg) may be mixed 1/1 with Montanide ISA-51 to form one water-in-oil emulsion (i.e. the total volume/injection is 1 mL).

7.8.4.4 Administration

Patients in this study may be vaccinated subcutaneously in the right or left upper arms with intact draining axillary nodes. In case patients do not possess intact axillary lymph nodes as the draining nodes, the vaccines may be administered in the upper thigh on the same side with intact inguinal lymph nodes.

The vaccine may be administered on weeks on Weeks 0, 3, 6, 9, 12, 15, 18 and 7.8.5 Poly-ICLC Poly-ICLC may be prepared and packaged in the GMP facility of Bioserv, Corporation (San Diego, Calif.). Poly-ICLC may be supplied in vials containing 1 cc of translucent solution with a concentration of 2 mg per cc. Poly-ICLC is stable at room temperature for several days, but may be stored refrigerated at about 40° F.

7.8.5.1 Dosage and Administration

Poly-ICLC may be administered intramuscularly at doses of 20 µg/kg and up to 1640 µg/injection, with two injections on days 0 and 4 following each vaccination.

The first course of poly-ICLC administration (20 µg/kg i.m. and up to 1640 ng/injection) may be administered on the day of the first GAA/TT-vaccine and on day 4 after the vaccine. For each of the following repeated vaccinations (on Weeks 3, 6, 9, 12, 15, 18 and 21), poly-ICLC (20 µg/kg i.m. and up to 1640 µg/injection) may be administered on the day of the vaccine and on day 4 after the vaccine.

With regard to the injection sites, as poly-ICLC is expected to enhance the antigen-presentation process in the draining lymph nodes, poly-ICLC should be administered i.m. within the close vicinity to the previous peptide-injection site (e.g., less than 3 cm from the center of the previous peptide injection sites).

Poly-ICLC should be administered intramuscularly (i.m.) using sterile technique, as supplied from the vial, and in the amount prescribed for the patient's weight (up to 1640 µg/injection). Vital signs may be monitored before and for at least 20 minutes after the first treatment.

7.8.6 Treatment Plan

The study described in this Example may employ two cohorts of patients to assess the immunogenicity, safety and clinical efficacy of the GAA/TT-peptide vaccine and poly-ICLC in HLA-A2+ patients with recurrent WHO grade II gliomas. Because the peptide vaccine is sequestered locally, and the immune response occurs primarily locally and in the draining lymph nodes, the dose of the vaccine should not need to be scaled up proportionately to the size (by weight or body surface area) of the recipient, as might be done for a drug whose effect is related to its distribution in body fluid. With regard to the dose of poly-ICLC, a fixed dose (20 µg/kg/injection and up to 1640 µg/injection) may be employed, which has been demonstrated to be safe and to induce biological responses in patients with malignant glioma (see, e.g., Salazar et al., Neurosurgery, 38: 1096-1103, 1996).

7.8.6.1 Schedule

Patients may be treated with subcutaneous injections of GAA/TT-vaccines on Weeks 0, 3, 6, 9, 12, 15, 18 and 21. I.m. poly-ICLC may be administered (20 µg/kg i.m. and up to 1640 µg) on the day of and on day 4 after each vaccine (e.g. if the vaccine is administered on Thursday, poly-ICLC may be administered on the day of vaccine and the following Monday). Each vaccine may be administered within 2 hours before or after the i.m. poly-ICLC administration.

Patients may be evaluated for any possible adverse event, regimen limiting toxicity (RLT) as well as clinical/radiological responses by clinical visits and MRI scanning. MRI scans may be performed on Weeks 0, 12 and 24. If the scan on Week 12 demonstrates unequivocal tumor progression, the patient may be withdrawn.

Peripheral blood mononuclear cells (PBMC) obtained before the initial vaccine may be used as the base-line sample. If patients demonstrate any positive response in the two immunological assays (ELISPOT or Tetramer without RLT or tumor-progression, these patients may be offered additional GAA/TT-vaccines (see, e.g., Section 7.8.6.2) starting any time between on Week 34-40, and every 3 months thereafter until patients demonstrate tumor-progression, loss of immune response or RLT.

7.8.6.2 Additional Therapy

On Weeks 0 (baseline), 12, 15, 18, 21, and 24, patients' PBMC may be evaluated for the presence of GAA-specific T-cell responses against GAA peptides. If such a response is observed for any of the GAA peptides, the patient may undergo additional vaccinations with the GAA(s) that demonstrated the persisting response as well as poly-ICLC starting any time between on Week 34-40, and every 12 weeks thereafter up to 2 years from the initial vaccination. Additional PBMC samples may be obtained every 12 weeks (at the same visits for vaccine administrations) for immunological monitoring. Additional vaccines may be terminated in any of the following conditions: 1) tumor progression; 2) RLT; or 3) negative immunological response in two consecutive time points.

7.8.6.3 Dose Modification

7.8.6.3.1 Dose Modification for Poly-ICLC

For any Grade 2 or greater flu-like symptoms, including fever and fatigue, poly-ICLC may be discontinued until symptoms return to Grade 0. If Grade 2 or greater flu-like symptoms occur on the day of a vaccination, and if the symptoms do not return to Grade 0 by day 4 after the vaccination, the next poly-ICLC administration on day 4 after the vaccination may be skipped. If the patient is symptom-free on day 4 (Grade 0), poly-ICLC may be resumed at 50% of the original dose. If Grade 2 or greater flu-like symptoms occur following the poly-ICLC administration on day 4 after a vaccination, in the next vaccine cycle, two poly-ICLC administrations (on day 0 and 4 following the vaccines) may be given at 50% of the original dose. Pretreatment with acetaminophen 650-1000 mg or with any NSAID may be given. If further dosing is well tolerated, the original dose may be subsequently re-instituted.

In the case of hepatic enzyme elevation >4× baseline, or any other unforeseen intolerable side effects of grade 2 or greater, poly-ICLC may be discontinued until that toxicity has reduced to Grade 1 or less. Poly-ICLC may then be re-administered at one-half the original dose, and the patient may be closely observed. If the poly-ICLC cannot be re-initiated in the next vaccine cycle, the patient may be withdrawn for the RLT.

For patients who demonstrated grade 3 or lesser degree of lymphopenia at their study entry (our eligibility criterion requires 400 cells/µL), occurrence or continued presence of grade 3 lymphopenia during the study does not mandate the discontinuation of poly-ICLC. However, poly-ICLC may be suspended in case of grade 4 lymphopenia. Also, if the attribution of poly-ICLC is strongly suspected even for grade 3 lymphopenia, poly-ICLC administrations may be suspended. In these cases, re-administration at one-half the original dose may be allowed when absolute lymphocyte counts come back to at least 400/µL.

Patients may remain on the original dose for grade 1 toxicities. However, the dose may be reduced to 50% for grade 2 hematologic or non-hematologic toxicity (except for transient fever and fatigue as outlined earlier in this section). If at the 50% dose level there is no toxicity for a minimum of 2 weeks, the dose may be escalated back to the starting dose. Subsequent toxicities, should they occur, may require a dose reduction to 50%, and no further escalations may be allowed. If toxicity reoccurs at the reduced dose, the patient may be taken off treatment.

7.8.6.3.2 Dosing Delay for the Peptide Vaccines

In circumstances where poly-ICLC administration is suspended, if the event is not attributable to the peptides/ISA-51 vaccine, vaccine administrations may not be suspended. If the event is attributable to both poly-ICLC and peptide-vaccines, both may be suspended. If an adverse event is considered to be solely due to the peptides/ISA-51 vaccines, but not poly-ICLC, the vaccine and poly-ICLC administrations may be suspended. In circumstances where assessment of an adverse event is limited, such as by intercurrent illness, or when laboratory studies are required to assess for other causes of toxicity, the vaccine schedule may be interrupted for up to 4 weeks. Delay of one vaccine administration by up to 4 weeks will not be considered a protocol violation if due to an adverse event, regardless of attribution. If one or more vaccines is delayed by 4 weeks due to an adverse event, regardless of attribution, treatment should be discontinued.

Patients may be observed for regimen limiting toxicity (RLT) throughout the study. The following are considered to be RLTs if they are judged possibly, probably or definitely associated with treatment. Should they occur, individual patients may be taken off study and no further injections may be given.

≥Grade 2 or more bronchospasm or generalized uticaria (hypersensitivity).

≥Grade 2 or more allergic reaction, such as exfoliative erythroderma, anaphylaxis, or vascular collapse.

≥Grade 2 or more autoimmune disease (e.g. hypothyroidism, autoimmune encephalitis).

Any ≥Grade 3 toxicity possibly, probably, or definitely related to the vaccine with particular attention to the following events.

≥Grade 3 injection site reaction due to peptide-vaccine or poly-ICLC administration.

≥Grade 3 hematological or hepatic toxicity.

≥Grade 3 neurotoxicity: signs and symptoms that may indicate either tumor progression or an inflammatory immune response (i.e., pseudo-tumor progression) that requires a biopsy or resection with pathologic findings of inflammatory/lymphocytic infiltration.

≥Grade 3 nausea and vomiting without sufficient anti-emetic prophylaxis are not considered as RLTs.

Dosing delays >4 weeks for either poly-ICLC or peptide vaccines.

Therapy may be discontinued for the following reasons: (i) Regimen limiting toxicity—as defined above; (ii) disease progression—at least a 20% increase in the sum of the longest diameter of target lesion or the appearance of contrast enhancement in a previously non-enhancing tumor. However, if pseudo-tumor progression is suspected, then the patient may be placed on dexamethasone, up to 4 mg/day, and reimaged 4-8 weeks later. If they require >4 mg/day dexamethasone, or if their repeat imaging study continues to meet the criteria for disease progression, the patient may be taken off study and further study treatment may be discontinued. However, if their steroid dose is <4 mg/day and if their repeat imaging does not meet the criteria for disease progression, then the patient may continue in the study and receive study treatment as prescribed herein. Any cases of suspected tumor progression or pseudo-tumor progression should be reviewed to determine whether the subject should remain in the study. (iii) Intercurrent illness that prevents further administration of the vaccine or poly-ICLC administration. (iv) Pregnancy: Pregnant patients will continue to be followed for the duration of the pregnancy.

7.8.6.4 Treatment Duration

In the absence of treatment delays clue to adverse event(s), treatment may continue for 21 weeks (8 vaccinations) or until one of the following criteria applies: Regimen Limiting Toxicity (RLT); disease progression; and/or intercurrent illness that prevents further administration of treatment.

7.8.6.5 Concomitant Treatment

7.8.6.5.1 Acceptable

For fever, acetaminophen may be utilized (325 mg tabs, 1 or 2 p.o. every 4 hours). Pre-treatment of patients with acetaminophen may be instituted as warranted by side effects of poly-ICLC. Fevers lasting more than 8 hours after treatment may be evaluated in terms of potential infection.

For mild local pain, oral opiates may be planned (oxycodone, 5-10 mg p.o. every 3-4 hours). Pain that is of more than mild-moderate grade may be investigated for sources other than the therapy, and managed accordingly.

Dexamethasone (or similar corticosteroid medications) should not be used for at least 4 weeks prior the initiation of the vaccine/poly-ICLC therapy (Week 0). Dexamethasone (up to 4 mg/day) may be used in the setting of pseudo-tumor progression, and tapered/discontinued as soon as possible.

Anti-seizure medications should be used as indicated.

Antiemetics, if necessary, may be administered.

Other acceptable medications may include: Topical corticosteroids; nonsteroidal anti-inflammatory agents; antihistamines (e.g. Claritin®, Allegra®); chronic medications except those listed in Section 7.8.6.5.2; Influenza vaccines (these should be administered at least two weeks prior to the initiation of the study vaccines or at least two weeks after the 8$^{th}$ (last) vaccine); and/or corticosteroid medications administered parenterally or by inhalation (e.g.: Advair®, Flovent®, Azmacort®).

7.8.6.5.2 Unacceptable

Unacceptable medications may include interferon therapy (e.g. Intron-A®); chemotherapy; allergy desensitization injections; growth factors (e.g. Procrit®, Aranesp®, Neulasta®); interleukins (e.g. Proleukin®); other investigational medications; and/or illicit drugs.

7.8.7 Correlative/Special Studies

7.8.7.1 Immunological Monitoring

7.8.7.1.1 Enzyme Linked Immuno-SPOT (ELISPOT) Assays

Frequencies of glioma associated antigens (GAA)-responsive T-lymphocyte precursors in peripheral blood mononuclear cells (PBMC) prior to and after, administration of the GAA-peptide based vaccine may be measured by ELISPOT assay. The biological responses measured by ELISPOT may be done at the same time point at least for one individual patient to avoid inter-assay variability. Successful vaccination stimulates clonal populations of T cells that are capable of secreting cytokines in an antigen-specific, MHC-restricted fashion. The ELISPOT assay may be utilized to evaluate GAA-specific immune responses of CD8+ T-cell populations as well as CD4+ T cells that react against the helper TT peptide. IFN-γ production may then be evaluated to assess Type-1 T-cell response.

A subject may be considered to have responded, if at any of two consecutive post-vaccine time points against the same antigen[s] (Weeks 12, 15, 18, 21 and 24), the number of spots is double that at baseline, and there are at least 10 spots/20,000 cells, and if the number of the post-vaccine spots is at least three times the standard-deviation of the pre-vaccine value. Response can be to any one antigen.

7.8.7.1.2 Tetramer Analysis of GAA-Reactive T Cells in Patient's PBMC

Tetramer analyses allow for evaluation of the presence of GAA-specific CD8$^+$ T-cells in peripheral blood with a great sensitivity without in vitro re-stimulation of the cells. It is expected, based on previous data available from patients with malignant glioma, that significant (a log or more) increase in the frequency of peptide-responsive CD8$^+$ T cells may be observed in some, but not all, patients immunized with tumor-antigen based vaccines. In an exploratory manner, these PBMCs may be also evaluated for surface expression of an integrin receptor very late antigen (VLA)-4, which has been implicated to confer T-cell homing to CNS tumors (see, e.g., Zhu et al., J. Transl. Med., 5: 10, 2007) and chemokine receptors (e.g. CXCR3 and CCR5). Procedures for tetramer analysis are well established.

Tetramer assays may be done at baseline and at 5 time points after vaccinations (Weeks 12, 15, 18, 21 and 24). A single time-point positive response for a peptide to be (1+B) % of all CD8$^+$ cells positive by tetramer assay may be defined, where B is the percent positive at baseline, which is usually less than 0.1%. In analogy to the definition of ELISPOT response, a patient may be considered to have responded if he/she has two consecutive single time-point responses for any peptide.

7.8.7.1.3 Flow Cytometric Analyses of Lymphocyte Subsets

Numbers of CD4+ and CD8+ T cells as well as CD4+/Foxp3+ T regulatory cells at serial time points pre- and post-vaccines may be evaluated.

7.8.7.1.4 Analyses of Autoimmunity in Sera

Banked sera may be evaluated for presence of auto-antibodies.

7.8.7.2 Evaluation of Primary and Recurrent Tumor Tissues

GAA-expression in the patients' available tumor tissues may be evaluated (either pre-vaccine or after progression post-vaccines; or both) by immunohistochemistry (IHC) and reverse transcriptase-polymerase chain reaction (RT-PCR).

If tumors recur following vaccinations, it may be critical to evaluate how tumors escape the effects of vaccines. To this end, the following specific issues may be evaluated as much as the tissue-availability allows: (i) Antigen-loss: IHC and RT-PCR may be used to assess whether the recurrent tumors express the targeted GAAs, HLA-A2, and antigen processing machinery components, such as transporter associated with antigen processing; (ii) up-regulation of anti-apoptotic molecules: although Survivin may be targeted, other anti-apoptotic molecules may be up-regulated, e.g., cFLIP (cellular FLICE (Fas-associated death domain-like IL-1β-converting enzyme) inhibitory protein); and (iii) immune cell infiltration: one reason tumors may escape a vaccine-induced immune response is through the failure of reactive T cells to infiltrate the tumor. To examine this, whenever freshly resected tumor tissues (not fixed or frozen) are available, tumor infiltrating lymphocytes (TILs) may be isolated and their numbers, phenotype, and antigen-specificity may be characterized using HLA-A2 tetramers for each of GAAs. Using multi-color flow-cytometry, the function and viability of tetramer$^+$ TILs may be determined by staining for perforin/IFN-γ and Annexin-V, respectively. Control tissues may include pre-vaccine tumors (if available) and recurrent tumors from patients not in the study. These studies may allow for evaluation of whether vaccine-induced T-cells efficiently traffic to the brain tumor site and maintain their function and viability.

7.8.8 Study Parameters

This study may be conducted on an outpatient basis, with patients scheduled to be evaluated on weeks 0, 3, 6, 9, 12, 15, 18, 21 and 24. After this period, if patients do not receive additional vaccines, patients may be off study, and they may be clinically followed every 2-4 months thereafter as usually done for patients with the same tumor type. If patients are found to have progressing tumors, other therapies, such as chemotherapy or resection, may be offered. If patients receive additional vaccines, such additional vaccines may be administered every 12 weeks, and clinical, immunological and radiological (MRI) monitoring may be performed at every visit (q12 weeks) until the patients withdraw. Subjects with a complete response may be retreated with additional two vaccinations, with 12-week intervals, and then followed. Vaccinations may be halted for any patients with progressive disease or unacceptable toxicity at any time during the scheduled vaccinations.

7.8.8.1 Pre-Treatment (Screening and Baseline Data)

The following procedures may be undertaken before treatment proceeds: informed Consent should be obtained before initiation of screening; HLA typing (flow-cytometric evaluation for HLA-A2 positivity); documentation of diagnosis (pathological); complete history and physical examination (with vital signs and weight), including neurological examinations and performance status; vaccine sites are to be designated with confirmation of intact draining lymph nodes; demographic information should be recorded; CBC and platelets with differential should be evaluated; PT/PTT should be evaluated; Chemistry should be evaluated, including electrolytes, creatinine, blood urea nitrogen, glucose, AST, ALT, Alk phos, total bilirubin, LDH, calcium and albumin; GGT, phosphorus, and magnesium should be evaluated; Blood for in vitro assays should be taken; HGBA1C for patients with diabetes mellitus should be performed; ECG and echo cardiogram should be performed for patients with cardiac symptoms, history or current disease; urinalysis should be performed; MRI of the brain to evaluate the baseline status of disease should be performed; and/or women of child-bearing potential should be administered a serum beta-HCG pregnancy test.

7.8.8.2 Evaluation During Treatment

The following procedures may be undertaken as treatment proceeds. Pre-Administration (Weeks 0, 3, 6, 9, 12, 15, 18 and 21 before vaccine administration on the day of vaccination): history and physical including vital signs, weight, Karnofsky performance status and neurological function; blood for in vitro assays should be taken; Chemistry should be evaluated, including electrolytes, creatinine, blood urea nitrogen, glucose, AST, ALT, Alk phos, total bilirubin, LDH, calcium and albumin (Except for Week 0); AED levels should be evaluated if clinically indicated; patients should be screened for adverse events from previous doses, to include neurological evaluation and skin examination (injection sites); and/or MRI should be performed (only on Week 12 among these vaccine injection visits).

Following vaccine administration, all patients should be closely observed for adverse events for at least 20 minutes following each administration of GAA-peptide vaccine. On the same day, poly-ICLC (i.m. 20 mg/kg) may be administered within 2 hours before or after the vaccine, and monitored at least 20 minutes after the poly-ICLC injection.

7.8.8.3 Week 24 (Post 8 Vaccinations) Evaluation

After the vaccination cycle is complete, the following procedures may be undertaken: history and physical including vital signs, weight, Karnofsky performance status and neurological function; Blood for in vitro assays should be taken (Except for Week 3, 6 and 9); CBC and platelets with differential should be evaluated (Except for Week 0); Chemistry should be evaluated, including electrolytes, creatinine, blood urea nitrogen, glucose, AST, ALT, Alk phos, total bilirubin, LDH, calcium and albumin (Except for Week 0); AED levels should be evaluated if clinically indicated; patients should be screened for adverse events from previous doses, to include neurological evaluation and skin examination (injection sites); and/or MRI should be performed.

7.8.8.4 Evaluation with Additional Vaccines (Cases with Additional Vaccines)

Prior to administration with additional vaccines, the following procedures may be undertaken: history and physical including vital signs, weight, Karnofsky performance status and neurological function; Blood for in vitro assays should be taken (Except for Week 3, 6 and 9); CBC and platelets with differential should be evaluated (Except for Week 0); Chemistry should be evaluated, including electrolytes, creatinine, blood urea nitrogen, glucose, AST, ALT, Alk phos, total bilirubin, LDH, calcium and albumin (Except for Week 0); AED levels should be evaluated if clinically indicated; patients should be screened for adverse events from previous doses, to include neurological evaluation and skin examination (injection sites); and/or MRI should be performed.

Following administration with additional vaccines, all patients should be closely observed for adverse events for at least 20 minutes following each vaccination. Additional vaccines may be terminated in any of the following conditions: 1) tumor progression; 2) RLT; or 3) negative immunological response in two consecutive time points after initiation of additional vaccines.

TABLE 6

Study Calendar

| Management Table Studies & Tests | Pre-Vaccination Consent/ HLA-typing/ path | Within 4 Wks | Treatment (Week) | | | | | | | | every 12 Wks for additional vaccines * |
|---|---|---|---|---|---|---|---|---|---|---|---|
| | | | 0 | 3 | 6 | 9 | 12 | 15 | 18 | 21 | 24 | |
| Informed consent for HLA-typing | X | | | | | | | | | | | |
| HLA-typing | X | | | | | | | | | | | |
| Informed consent for treatment (if HLA-A2 is positive) | X-------------------X | | | | | | | | | | | |
| Pathology review | X | | | | | | | | | | | |
| Vaccination# | | | X | X | X | X | X | X | X | X | | X |
| CBC and Platelets with differential | | X | | X | X | X | X | X | X | X | X | X |
| Coagulation tests (PT and PTT) | | X | | | | | | | | | | |
| Chemistry## | | X | | X | X | X | X | X | X | X | X | X |
| GGT, Phosphorus, Magnesium | | X | | | | | | | | | | |
| AED if clinically indicated | | | X | X | X | X | X | X | X | X | | X |
| Demographics | | X | | | | | | | | | | |
| Concurrent Medications | | X | ←------------------------------→ | | | | | | | | | |

TABLE 6-continued

Study Calendar

| Management Table Studies & Tests | Pre-Vaccination | | Treatment (Week) | | | | | | | | every 12 Wks for additional vaccines * |
|---|---|---|---|---|---|---|---|---|---|---|---|
| | Consent/ HLA-typing/ path | Within 4 Wks | 0 | 3 | 6 | 9 | 12 | 15 | 18 | 21 | 24 | |
| Urinalysis | | X | | | | | | | | | | |
| β-HCG (women of childbearing potential) | | X | | | | | | | | | | |
| EKG or Echocardiogram<sup>###</sup> (if clinically indicated) | | X | | | | | | | | | | |
| Hgb A1c<sup>####</sup> | | X | | | | | | | | | | |
| Brain MRI | | X | | | | | X | | | X | | X** |
| History, Physical, and KPS | X (history only) | X | X | X | X | X | X | X | X | X | X | X |
| Research Blood Samples 8 × 10 cc green top tubes and one red top tube | | X | | | | | X | X | X | X | X | X** |
| Medication Diary | | | ←----------------------------------→ | | | | | | | | | |
| Adverse Event report | | | ←----------------------------------→ | | | | | | | | | |

<sup>#</sup>poly-ICLC (20 μg/kg i.m. and up to 1640 μg) may be administered on the day of the vaccine and on day 4 after each vaccine.
<sup>##</sup>Includes electrolytes, creatinine, blood urea nitrogen, glucose, AST, ALT, Alk phos, total bilirubin, LDH, calcium and albumin
<sup>###</sup>Testing required for patients with past or current cardiac disease, including symptoms
<sup>####</sup>Testing only required for patients with diabetes.
<* Additional Therapy> Subjects may undergo additional vaccinations for up to 2 years after administration of the first vaccine (See section 4.2.2), if progression free status based on the MRI, lack of RLT and anti-GAA immune response are observed following the initial 8 vaccinations. The additional vaccines (and poly-ICLC on the day of and on day 4 after each vaccine) may be given every 12 weeks, beginning any week between weeks 34-40. Additional vaccinations may be terminated if tumor-progression, RLT or negative GAA-response in two consecutive time points is observed. Physical and neurological exam, blood tests to check blood counts and blood chemistry and PBMC samples may be obtained every 12 weeks (at the same visits for vaccine administrations). An MRI scan may be done at Weeks 12 and 24 to check your tumor response (whether or not your tumor is responding to the vaccines and injections).
**For patients who undergo additional vaccines, head MRI and blood sample collection for immunological monitoring may be performed every 12 weeks starting at the first additional vaccination.

7.8.9 Measurement of Effect 7.8.9.1 Objectives 7.8.9.1.1 Immunogenicity

The response rate and magnitude of CD8+ T-cell responses against the GAA-peptides in post-vaccine PBMC may be assessed using IFN-γ-ELISPOT, and tetramer analysis by flow cytometry as the secondary assay.

ELISPOT assays indicate functional status of the antigen-specific T cells as cytokine-expression. Flow cytometric analyses using tetramers allow for a relatively accurate estimation of frequency of antigen-binding T-cells without a major in vitro manipulation of the patient-derived PBMC, and phenotype analyses, such as the homing receptor (integrins) expression on antigen-specific T cells.

The biological assays to measure the response in peripheral blood may be carried out at the same time point to avoid inter-assay variability.

Using flow-cytometry, the numbers of lymphocyte subsets such as CD4+ T cells, CD4+/Foxp3+ regulatory T cells also may be evaluated. In addition, in patients who undergo surgical debulking of the progressing tumor, if the tumor tissue is available, infiltration of antigen-specific CTLs may be evaluated by flow cytometry of tumor-infiltrating lymphocytes with epitope-specific MHC-tetramers.

7.8.9.1.2 Safety

The safety of the administration of the four HLA-A2-restricted glioma-associated antigen (GAA) epitope-peptides in conjunction with a class II MHC-restricted Tetanus Toxoid (TT)-derived helper T cell epitope and i.m. poly-ICLC in patients with recurrent grade II gliomas may be determined.

Endpoints may include incidence and severity of adverse events, using standard criteria as well as close clinical follow-up as would be performed normally in this group of patients following vaccinations. The regimen may be considered unacceptably toxic if >33% of patients in a given cohort develop RLT.

7.8.9.1.3 Response and Progression-Free Survival

Tumor recurrence may be assessed minimally at weeks 12 and 24, and every 3 months thereafter using MRI scans with contrast enhancement. Since low-grade gliomas are infiltrative tumors which typically do not enhance with contrast administration, for evaluation of response and progression-free survival, the tumor (i.e., target lesion) may be measured from the T2 or FLAIR MRI images. In case there is an enhancing lesion at the baseline, careful discussion may be made as to whether the pathology information as WHO grade II tumor truly represents the status of the tumor. If the enhancing tumor is still considered to be grade II, the size of the enhancing lesion may be used for evaluation. In addition, as noted below, emergence of enhancement in previously non-enhancing tumor is considered to be progressive disease (PD).

(A) Response (According to RECIST Criteria)

Complete Response (CR): Disappearance of all target lesions.

Partial Response (PR): At least a 30% decrease in the sum of the longest diameter (LD) of target lesions, taking as reference the baseline sum LD.

Progressive Disease (PD): At least a 20% increase in the sum of the LD of target lesions, taking as reference the smallest sum LD recorded since the treatment started or the appearance of contrast enhancement in a previously non-enhancing tumor. Because of the possibility of pseudo-tumor progression, patients may be placed on low-dose steroids and reimaged before being declared as having PD.

Stable Disease (SD): Neither sufficient shrinkage to qualify for PR nor sufficient increase to qualify for PD, taking as reference the smallest sum LD since the treatment started.

(B) Overall Survival (OS) and Progression-Free Survival (PFS)

PFS is defined as the duration of time from start of treatment to time of progression or death. All patients may be followed for a minimum of 2 years, so that their actual 2-year OS and PFS can be determined.

7.8.9.1.4 Analyses of Tumor Tissues Following Vaccinations

Tumor tissues may not be available from all patients in the study. However, the following aspects may be evaluated in an exploratory manner in all available tumor tissues obtained pre- and/or post-vaccines: (i) Antigen-loss; (ii) up-regulation of anti-apoptotic molecules; and (iii) immune cell infiltration.

7.8.10 Statistical Considerations 7.8.10.1 Assessment of Immunological Responses Evaluation of immune response may employ both IFN-γ ELISPOT and tetramer assays.

A responder may be defined as a patient who has responded in either IFN-γ ELISPOT or tetramer assays. A cohort may be considered worthy of further investigation if there are at least 4 responses in the 9 subjects. This criterion has the property that if the true response rate is <17%, there is <5% probability to observe 4 or more responses, and that if the true response rate is >66%, there is <5% probability to observe 3 or fewer responses.

7.8.10.2 Documentation and Evaluation of Safety

The NCI common terminology criteria for adverse events (AE) (CTCAE 3.0) may be used to evaluate toxicity; toxicity may be considered to be an adverse event that is possibly, probably or definitely related to treatment. The maximum grade of toxicity for each category of interest may be recorded for each patient and the summary results may be tabulated by category and grade.

For safety, the regimen may be considered to be excessively toxic if, at any time, the observed rate of regimen-limiting toxicity (RLT) ≥33% and at least 2 RLTs have been observed.

The study design has the following properties: if the true rate of RLT is ≥45%, there is at least 90% probability that accrual will stop; if the true RLT rate is ≤9%, there is 90% probability that the accrual will not stop, and that the regimen may be considered safe.

7.8.10.3 Assessment of Clinical Endpoints

All patients may be followed for a minimum of 2 years, so that their actual 2-year overall survival (OS), progression-free survival (PFS) and response rates can be tabulated as exploratory endpoints. PFS is defined as the time interval from the initiation of therapy to progression, based on serial MRI scans. If appropriate, exploratory analyses may investigate the relationship of immune response to imaging response and OS/PFS (using Fisher's exact test and the log rank test, respectively).

7.8.10.4 Demographic Data

Baseline descriptive statistics on all evaluable patients May be provided for demographic variables (age, sex, race/ethnicity), Karnofsky performance status, disease stage and status at the time of enrollment (stable disease, progressive disease), and/or treatment regimens previously used.

7.9 Example 9

This example describes a study to evaluate the effects of vaccinations with HLA-A2-restricted glioma antigen-peptides in combination with poly-ICLC administration for patients with high-risk WHO grade II astrocytomas and oligoastrocytomas.

7.9.1 Rationale

This Example describes a study of a vaccination regime that is designed to efficiently induce anti-tumor T-cell responses in patients with "high risk" WHO grade II astrocytoma and oligoastrocytoma; i.e., patients with a >50% likelihood of progression 5 years following surgery alone or surgery plus postoperative radiation therapy. The regime described in the study provided in this Example combines subcutaneous injections of glioma-associated antigen (GAA)-derived cytotoxic T-lymphocyte (CTL) epitope-peptides with simultaneous intramuscular (i.m.) administration of poly-ICLC.

Adults with supratentorial LGG have a significant risk (24%) of tumor progression 2 years following treatment with surgery or surgery followed by RT. For unfavorable subsets of these patients, the 2-year risk of progression is 40-50%. The study described in this Example has both immunoprophylactic and immunotherapeutic potential to reduce the risk of tumor recurrence, which may translate into improved survival. Therapeutically, the immunotherapy approach may suppress the expansion of indolently growing neoplastic low grade II tumor cells. Prophylactically, the approach may prevent anaplastic transformation, which occurs in about one-half of recurrent LGG. The slower growth rate of LGG (in contrast to malignant gliomas) should allow sufficient time to repeat multiple immunizations, which may lead to the induction of high levels of GAA-specific immunity. In addition, poly-ICLC has been demonstrated to enhance the vaccine effects in preclinical brain tumor models (see, e.g., Zhu et al., J. Transl. Med., 5: 10, 2007), and to be safe in malignant glioma patients (see, e.g., Salazar et al., Neurosurgery, 38: 1096-1103, 1996). Therefore, we hypothesize that this form of vaccine in combination with poly-ICLC treatment will induce potent anti-glioma immune response, and will be safe.

7.9.2 Objectives

This Example describes a vaccine study in adults with either WHO grade II astrocytoma or oligoastrocytoma. The objectives of this Example include collection of immunological and safety data that may be used in additional studies. The patients in the study described in this Example may be followed for a minimum of 2 years, so that the actual 2-year overall survival (OS), 6-month and 2-year progression-free survival (PFS) rates may be determined in an exploratory manner.

7.9.2.1 Induction of GAA-Specific T-Cell Response

The response rate and magnitude of immune response in post-vaccine peripheral blood mononuclear cells (PBMC) against the GAA-peptides in response to this form of vaccine may be determined using IFN-γ-enzyme-linked immuno-spot (ELISPOT) and tetramer assays.

7.9.2.2 Safety

The incidence and severity of adverse events associated with the vaccine regime may be assessed, with an early stopping rule based on the frequency of Regimen Limiting Toxicity (RLT).

7.9.2.3 Clinical Response

Radiological response may be determined using the standard WHO response criteria. 2-year progression-free survival (PFS) may be evaluated in an exploratory manner, based on serial magnetic resonance imaging (MRI) scans.

7.9.2.4 Tumor Tissues for Biological Correlates

For patients who develop progression, biopsy/resection may be encouraged. Whenever post-vaccine tumor tissues are available, they may be analyzed for GAA expression status and infiltration of GAA-specific T-cells.

7.9.2.5 Influence of RT on Induction of GAA-Specific Immune Response

The rate and magnitude of GAA-specific immune responses in the two cohorts may be compared using IFN-γ-ELISPOT assays and tetramer assays.

7.9.3 Patient Selection

7.9.3.1 Eligibility Criteria

Pathological criteria—Patients should have documented pathological diagnosis of a supratentorial WHO grade II astrocytoma or oligoastrocytoma.

Patients in this study should be HLA-A2 positive based on flow cytometry.

Patients in this study should have recovered from the toxic effects of prior therapy: 4 weeks from any investigational agent, 4 weeks from prior cytotoxic therapy and/or at least two weeks from vincristine, 4 weeks from nitrosoureas, 3 weeks from procarbazine administration, and 1 week for non-cytotoxic agents, e.g., interferon, tamoxifen, thalidomide, cis-retinoic acid, etc. (radiosensitizer does not count). With regard to previous radiation therapy (RT), there must be at least 6 months from the completion of RT (or radiosurgery).

Two cohorts of patients should be analyzed, based on whether patients have received prior RT. Cohort 1: Patients should have undergone surgery or biopsy alone (no postoperative radiation or chemotherapy) and have a baseline MRI scan (within 4 weeks of the first vaccine) that shows stable disease or regression (no progression from the initial surgery/biopsy). Cohort 2: Patients should have undergone surgery or biopsy and radiation therapy (RT) (including fractionated external beam radiation therapy and/or stereotactic radiosurgery), which was completed ≥6 months prior to enrollment, and have a baseline MRI scan within 4 weeks prior to the first vaccine that shows stable disease or regression.

Patients in this study should be (i) age ≥40 with any extent resection; (ii) age 18-39 with incomplete resection (post-op MRI showing >1 cm residual disease, based on the maximum dimension of residual T2 or FLAIR abnormality from the edge of the surgical cavity either laterally, anteroposteriorally, or supero-inferiorally) or (iii) age 18-39 with neurosurgeon-defined GTR but the tumor size is ≥4 cm (the maximum preoperative tumor diameter, based on the axial and/or coronal T2 or FLAIR MR images). All patients should be ≥18 years old.

Patients in this study should have a Karnofsky performance status of >60 (Appendix I).

Female patients in this study of child-bearing age should have documented negative serum βHCG.

Patients in this study should be free of systemic infection. Patients with active infections (whether or not they require antibiotic therapy) may be eligible after complete resolution of the infection. Patients on antibiotic therapy should be off antibiotics for at least 7 days before beginning treatment.

Patients in this study should have adequate organ function as measured by white blood count ≥2500/mm$^3$; lymphocytes ≥400/mm$^3$; platelets ≥100,000/mm$^3$, hemoglobin ≥10.0 g/dL, AST, ALT, GGT, LDH, alkaline phosphatase within 2.5× upper normal limit, and total bilirubin ≤2.0 mg/dL, and serum creatinine within 1.5× upper limit of normal limit. Patients in this study should have coagulation tests and PT and PTT should be within normal limits.

7.9.3.2 Exclusion Criteria

Patients in this study should be excluded if they have presence of gliomatosis cerebri, cranial or spinal leptomeningeal metastatic disease.

Patients in this study should be excluded if they have undergone prior chemotherapy or anti-glioma therapy of any type other than radiation therapy.

Patients in this study should be excluded if they are undergoing concurrent treatment or medications including: radiation therapy; chemotherapy; interferon (e.g. Intron-A®); allergy desensitization injections; growth factors (e.g. Procrit®, Aranesp®, Neulasta®); interleukins (e.g. Proleukin®); and/or any investigational therapeutic medication.

Patients in this study should not have had prior autoimmune disorders requiring cytotoxic or immunosuppressive therapy, or autoimmune disorders with visceral involvement. Patients in this study with an active autoimmune disorder requiring these therapies also should be excluded. Mild arthritis requiring NSAID medications should not be exclusionary.

Patients in this study should be excluded if they have used immunosuppressives within four weeks prior to entering the study or if they anticipate use of immunosuppressive agents. Dexamethasone, or other corticosteroid medications, if used peri-operative period and/or during radiotherapy, should be tapered by patients and discontinued at least four weeks before administration of the first vaccine in the study. Topical corticosteroids and Inhaled steroids (e.g.: Advair®, Flovent®, Azmacort®) should be acceptable.

Patients in this study should be excluded if they have another cancer diagnosis, except that the following diagnoses may be allowed: squamous cell cancer of the skin without known metastasis; basal cell cancer of the skin without known metastasis; carcinoma in situ of the breast (DCIS or LCIS); carcinoma in situ of the cervix; and/or any cancer without distant metastasis that has been treated successfully, without evidence of recurrence or metastasis for over 5 years.

Patients in this study should be excluded if they have known addiction to alcohol or illicit drugs.

Because patients with immune deficiency are not expected to respond to this therapy, HIV-positive patients should be excluded from the study.

7.9.4 Peptide Vaccine

7.9.4.1 Peptides

The following peptides may be included in the vaccine formulation: IL-13Rα2$_{345-353}$ IA9V (ALPFGFILV; SEQ ID NO:3); EphA2$_{883-891}$ (TLADFDPRV; SEQ ID NO:6); Survivin$_{96-104}$:M2 (LMLGEFLKL; SEQ ID NO:7); WT1$_{126-134}$:Y1 (YMFPNAPYL; SEQ ID NO:8); and Tetanus Toxoid (TetA830) (AQYIKANSKFIGITEL; SEQ ID NO:9).

All peptides may be synthesized and the synthetic peptides may be purified by HPLC. The identity of the synthetic peptides may be confirmed by verifying their mass and amino acid sequences by mass spectrometry. Each lot of peptide may be evaluated as required by the FDA for identity, purity, sterility and pyrogenicity.

The peptides may be vialed under GMP conditions and saved at −70° C. Stability of lyophilized peptides may be tested annually by mass spectroscopy.

7.9.4.2 Other Agents

Montanide ISA-51 (SEPPIC Inc., Fairfield, N.J.) may be used as an additional agent in the peptide vaccines.

7.9.4.3 Dosage and Preparation

An aqueous solution (500 µL) containing each of four HLA-A2-restricted GAA peptides (300 µg/peptide) and the tetanus peptide (Peptide-tet; 200 µg) may be mixed 1/1 with Montanide ISA-51 to form one water-in-oil emulsion (i.e. the total volume/injection is 1 mL).

7.9.4.4 Administration

Patients in this study may be vaccinated subcutaneously in the right or left upper arms with intact draining axillary nodes. In case patients do not possess intact axillary lymph nodes as the draining nodes, the vaccines may be administered in the upper thigh on the same side with intact inguinal lymph nodes.

The vaccine may be administered on weeks on Weeks 0, 3, 6, 9, 12, 15, 18 and 21.

7.9.5 Poly-ICLC

Poly-ICLC may be prepared and packaged in the GMP facility of Bioserv, Corporation (San Diego, Calif.). Poly-ICLC may be supplied in vials containing 1 cc of translucent solution with a concentration of 2 mg per cc. Poly-ICLC is stable at room temperature for several days, but may be stored refrigerated at about 40° F.

7.9.5.1 Dosage and Administration

Poly-ICLC may be administered intramuscularly at doses of 20 µg/kg and up to 1640 µg/injection, with two injections on days 0 and 4 following each vaccination.

The first course of poly-ICLC administration (20 µg/kg i.m. and up to 1640 µg/injection) may be administered on the day of the first GAA/TT-vaccine and on day 4 after the vaccine. For each of the following repeated vaccinations (on Weeks 3, 6, 9, 12, 15, 18 and 21), poly-ICLC (20 µg/kg i.m. and up to 1640 µg/injection) may be administered on the day of the vaccine and on day 4 after the vaccine.

With regard to the injection sites, as poly-ICLC is expected to enhance the antigen-presentation process in the draining lymph nodes, poly-ICLC should be administered i.m. within the close vicinity to the previous peptide-injection site (e.g., less than 3 cm from the center of the previous peptide injection sites).

Poly-ICLC should be administered intramuscularly (i.m.) using sterile technique, as supplied from the vial, and in the amount prescribed for the patient's weight (up to 1640 µg/injection). Vital signs may be monitored before and for at least 20 minutes after the first treatment.

7.9.6 Treatment Plan

The study described in this Example may employ two cohorts of patients to assess the immunogenicity, safety and clinical efficacy of the GAA/TT-peptide vaccine and poly-ICLC in HLA-A2+ patients with WHO grade II astrocytoma or oligo-astrocytoma with poor prognostic factors. Because the peptide vaccine is sequestered locally, and the immune response occurs primarily locally and in the draining lymph nodes, the dose of the vaccine should not need to be scaled up proportionately to the size (by weight or body surface area) of the recipient, as might be done for a drug whose effect is related to its distribution in body fluid. With regard to the dose of poly-ICLC, a fixed dose (20 µg/kg/injection and up to 1640 µg/injection) may be employed, which has been demonstrated to be safe and to induce biological responses in patients with malignant glioma (see, e.g., Salazar et al., Neurosurgery, 38: 1096-1103, 1996).

7.9.6.1 Schedule

Eligible patients in Cohort 1 should have undergone surgery or biopsy alone (no postoperative radiation or chemotherapy) and have a baseline MRI scan (within 4 weeks of the first vaccine) that shows stable disease or regression (no progression from the initial surgery/biopsy); patients in Cohort 2 should have completed RT ≥6 months prior to enrollment, and have a baseline MRI scan (within 4 weeks prior to the 1$^{st}$ vaccine) showing stable disease or regression. All patients must have discontinued dexamethasone or similar corticosteroid at least 4 weeks before the first vaccine.

Patients may be treated with subcutaneous injections of GAA/TT-vaccines on Weeks 0, 3, 6, 9, 12, 15, 18 and 21. I.m. poly-ICLC may be administered (20 µg/kg i.m. and up to 1640 µg) on the day of, and on day 4 after each vaccine (e.g. if the vaccine is administered on Thursday, poly-ICLC may be administered on the day of vaccine and the following Monday). Each vaccine may be administered within 2 hours before or after the i.m. poly-ICLC administration.

Patients may be evaluated for any possible adverse event, RLT as well as clinical/radiological responses by clinical visits and MRI scanning.

PBMC obtained before the initial vaccine may be used as the base-line sample. If patients demonstrate any positive response in the two immunological assays (ELISPOT or Tetramer without RLT or tumor-progression, these patients may be offered additional GAA/TT-vaccines (see, e.g., Section 7.9.6.2) starting any time between on Week 34-40, and every 3 months thereafter until patients demonstrate tumor-progression, loss of immune response or RLT.

7.9.6.2 Additional Therapy

On Weeks 0 (baseline), 12, 15, 18, 21, and 24, patients' PBMC may be evaluated for the presence of GAA-specific T-cell responses against GAA peptides. If such a response is observed for any of the GAA peptides, the patient may undergo additional vaccinations with the GAA(s) that demonstrated the persisting response as well as poly-ICLC starting any time between on Week 34-40, and every 12 weeks thereafter up to 2 years from the initial vaccination. Additional PBMC samples may be obtained every 12 weeks (at the same visits for vaccine administrations) for immunological monitoring. Additional vaccines may be terminated in any of the following conditions: 1) tumor progression; 2) RLT; or 3) negative immunological response in two consecutive time points.

7.9.6.3 Dose Modification

7.9.6.3.1 Dose modification for poly-ICLC

For any Grade 2 or greater flu-like symptoms, including fever and fatigue, poly-ICLC may be discontinued until symptoms return to Grade 0. If Grade 2 or greater flu-like symptoms occur on the day of a vaccination, and if the symptoms do not return to Grade 0 by day 4 after the vaccination, the next poly-ICLC administration on day 4 after the vaccination may be skipped. If the patient is symptom-free on day 4 (Grade 0), poly-ICLC may be resumed at 50% of the original dose. If Grade 2 or greater flu-like symptoms occur following the poly-ICLC administration on day 4 after a vaccination, in the next vaccine cycle, two poly-ICLC administrations (on day 0 and 4 following the vaccines) may be given at 50% of the original dose. Pretreatment with acetaminophen 650-1000 mg or with any NSAID may be given. If further dosing is well tolerated, the original dose may be subsequently re-instituted.

In the case of hepatic enzyme elevation >4× baseline, or any other unforeseen intolerable side effects of grade 2 or greater, poly-ICLC may be discontinued until that toxicity has reduced to Grade 1 or less. Poly-ICLC may then be re-administered at one-half the original dose, and the patient may be closely observed. If the poly-ICLC cannot be re-initiated in the next vaccine cycle, the patient may be withdrawn for the RLT.

Patients may remain on the original dose of poly-ICLC for grade 1 or 2 hematologic toxicity, or grade 1 non-hematologic toxicity. If at the 50% dose level there is no toxicity for a minimum of 2 weeks, the dose may be escalated back to the starting dose at the discretion of the investigator. Subsequent toxicities, should they occur, may require a dose reduction to 50%, and no further escalations may be allowed. If toxicity reoccurs at the reduced dose, the patient may be taken off treatment.

7.9.6.3.2 Dosing Delay for the Peptide Vaccines

In circumstances where poly-ICLC administration is suspended, if the event is not attributable to the peptides/ISA-51 vaccine, vaccine administrations may not be suspended. If the event is attributable to both poly-ICLC and peptide-vaccines, both may be suspended. If an adverse event is considered to be solely due to the peptides/ISA-51 vaccines, but not poly-ICLC, the vaccine and poly-ICLC administrations may be suspended. In circumstances where assessment of an adverse event is limited, such as by intercurrent illness, or when laboratory studies are required to assess for other causes of toxicity, the vaccine schedule may be interrupted for up to 4 weeks. Delay of one vaccine administration by up to 4 weeks will not be considered a protocol violation if due to an adverse event, regardless of attribution. If one or more vaccines is delayed by 4 weeks due to an adverse event, regardless of attribution, treatment should be discontinued.

Patients may be observed for regimen limiting toxicity (RLT) throughout the study. The following are considered to be RLTs if they are judged possibly, probably or definitely associated with treatment. Should they occur, individual patients may be taken off study and no further injections may be given.

≥Grade 2 or more bronchospasm or generalized uticaria (hypersensitivity).

≥Grade 2 or more allergic reaction, such as exfoliative erythroderma, anaphylaxis, or vascular collapse.

≥Grade 2 or more autoimmune disease (e.g. hypothyroidism, autoimmune encephalitis).

Any ≥Grade 3 toxicity possibly, probably, or definitely related to the vaccine with particular attention to the following events.

≥Grade 3 injection site reaction due to peptide-vaccine or poly-ICLC administration.

≥Grade 3 hematological or hepatic toxicity.

≥Grade 3 neurotoxicity: signs and symptoms that may indicate either tumor progression or an inflammatory immune response (i.e., pseudo-tumor progression) that requires a biopsy or resection with pathologic findings of inflammatory/lymphocytic infiltration.

≥Grade 3 nausea and vomiting without sufficient anti-emetic prophylaxis are not considered as RLTs.

Dosing delays >4 weeks for either poly-ICLC or peptide vaccines.

Therapy may be discontinued for the following reasons: (i) Regimen limiting toxicity—as defined above; (ii) disease progression—at least a 20% increase in the sum of the longest diameter of target lesion or the appearance of contrast enhancement in a previously non-enhancing tumor. However, if pseudo-tumor progression is suspected, then the patient may be placed on dexamethasone, up to 4 mg/day, and reimaged 4-8 weeks later. If they require >4 mg/day dexamethasone, or if their repeat imaging study continues to meet the criteria for disease progression, the patient may be taken off study and further study treatment may be discontinued. However, if their steroid dose is <4 mg/day and if their repeat imaging does not meet the criteria for disease progression, then the patient may continue in the study and receive study treatment as prescribed herein. Any cases of suspected tumor progression or pseudo-tumor progression should be reviewed to determine whether the subject should remain in the study. (iii) Intercurrent illness that prevents further administration of the vaccine or poly-ICLC administration. (iv) Pregnancy: Pregnant patients will continue to be followed for the duration of the pregnancy.

7.9.6.4 Treatment Duration

In the absence of treatment delays due to adverse event(s), treatment may continue for 21 weeks (8 vaccinations) or until one of the following criteria applies: Regimen Limiting Toxicity (RLT); disease progression; and/or intercurrent illness that prevents further administration of treatment.

7.9.6.5 Concomitant Treatment 7.9.6.5.1 Acceptable

For fever, acetaminophen may be utilized (325 mg tabs, 1 or 2 p.o. every 4 hours). Pre-treatment of patients with acetaminophen may be instituted as warranted by side effects of poly-ICLC. Fevers lasting more than 8 hours after treatment may be evaluated in terms of potential infection.

For mild local pain, oral opiates may be planned (oxycodone, 5-10 mg p.o. every 3-4 hours). Pain that is of more than mild-moderate grade may be investigated for sources other than the therapy, and managed accordingly.

Dexamethasone (or similar corticosteroid medications) should not be used for at least 4 weeks prior the initiation of the vaccine/poly-ICLC therapy (Week 0). Dexamethasone (up to 4 mg/day) may be used in the setting of pseudo-tumor progression, and tapered/discontinued as soon as possible.

Anti-seizure medications should be used as indicated.

Antiemetics, if necessary, may be administered.

Other acceptable medications may include: Topical corticosteroids; nonsteroidal anti-inflammatory agents; antihistamines (e.g. Claritin®, Allegra®); chronic medications except those listed in Section 7.8.6.5.2; Influenza vaccines (these should be administered at least two weeks prior to the initiation of the study vaccines or at least two weeks after the $8^{th}$ (last) vaccine); and/or corticosteroid medications administered parenterally or by inhalation (e.g.: Advair®, Flovent®, Azmacort®).

7.9.6.5.2 Unacceptable

Unacceptable medications may include interferon therapy (e.g. Intron-A®); chemotherapy; allergy desensitization injections; growth factors (e.g. Procrit®, Aranesp®, Neulasta®); interleukins (e.g. Proleukin®); other investigational medications; and/or illicit drugs.

7.9.7 Correlative/Special Studies 7.9.7.1 Immunological Monitoring 7.9.7.1.1 ELISPOT Assays Frequencies of glioma associated antigens (GAA)-responsive T-lymphocyte precursors in peripheral blood mononuclear cells (PBMC) prior to and after, administration of the GAA-peptide based vaccine may be measured by ELISPOT assay. The biological responses measured by ELISPOT may be done at the same time point at least for one individual patient to avoid inter-assay variability. Successful vaccination stimulates clonal populations of T cells that are capable of secreting cytokines in an antigen-specific, MHC-restricted fashion. The ELISPOT assay may be utilized to evaluate GAA-specific immune responses of CD8+ T-cell populations as well as CD4+ T cells that react against the helper TT peptide. IFN-γ production may then be evaluated to assess Type-1 T-cell response.

A subject may be considered to have responded, if at any of two consecutive post-vaccine time points against the same antigen[s] (Weeks 12, 15, 18, 21 and 24), the number of spots is double that at baseline, and there are at least 10 spots/20,000 cells, and if the number of the post-vaccine spots is at least three times the standard-deviation of the pre-vaccine value. Response can be to any one antigen.

7.9.7.1.2 Tetramer Analysis of GAA-Reactive T Cells in Patient's PBMC

Tetramer analyses allow for evaluation of the presence of GAA-specific $CD8^+$ T-cells in peripheral blood with a great sensitivity without in vitro re-stimulation of the cells. It is expected, based on previous data available from patients with malignant glioma, that significant (a log or more) increase in the frequency of peptide-responsive $CD8^+$ T cells may be observed in some, but not all, patients immunized with tumor-antigen based vaccines. In an exploratory manner, these PBMCs may be also evaluated for surface expression of an integrin receptor very late antigen (VLA)-4, which has been implicated to confer T-cell homing to CNS tumors (see, e.g., Zhu et al., J. Transl. Med., 5: 10, 2007) and chemokine receptors (e.g. CXCR3 and CCR5). Procedures for tetramer analysis are well established.

Tetramer assays may be done at baseline and at 5 time points after vaccinations (Weeks 12, 15, 18, 21 and 24). A single time-point positive response for a peptide to be (1+B) % of all $CD8^+$ cells positive by tetramer assay may be defined, where B is the percent positive at baseline, which is usually less than 0.1%. In analogy to the definition of ELISPOT response, a patient may be considered to have responded if he/she has two consecutive single time-point responses for any peptide.

7.9.7.1.3 Flow Cytometric Analyses of Lymphocyte Subsets

Numbers of CD4+ and CD8+ T cells as well as CD4+/Foxp3+ T regulatory cells at serial time points pre- and post-vaccines may be evaluated.

7.9.7.1.4 Analyses of Autoimmunity in Sera

Banked sera may be evaluated for presence of auto-antibodies.

7.9.7.2 Evaluation of Primary and Recurrent Tumor Tissues

GAA-expression in the patients' available tumor tissues may be evaluated (either pre-vaccine or after progression post-vaccines; or both) by immunohistochemistry (IHC) and reverse transcriptase-polymerase chain reaction (RT-PCR).

If tumors recur following vaccinations, it may be critical to evaluate how tumors escape the effects of vaccines. To this end, the following specific issues may be evaluated as much as the tissue-availability allows: (i) Antigen-loss: IHC and RT-PCR may be used to assess whether the recurrent tumors express the targeted GAAs, HLA-A2, and antigen processing machinery components, such as transporter associated with antigen processing; (ii) up-regulation of anti-apoptotic molecules: although Survivin may be targeted, other anti-apoptotic molecules may be up-regulated, e.g., cFLIP (cellular FLICE (Fas-associated death domain—like IL-1β-converting enzyme) inhibitory protein); and (iii) immune cell infiltration: one reason tumors may escape a vaccine-induced immune response is through the failure of reactive T cells to infiltrate the tumor. To examine this, whenever freshly resected tumor tissues (not fixed or frozen) are available, tumor infiltrating lymphocytes (TILs) may be isolated and their numbers, phenotype, and antigen-specificity may be characterized using HLA-A2 tetramers for each of GAAs. Using multi-color flow-cytometry, the function and viability of tetramer+ TILs may be determined by staining for perforin/IFN-γ and Annexin-V, respectively. Control tissues may include pre-vaccine tumors (if available) and recurrent tumors from patients not in the study. These studies may allow for evaluation of whether vaccine-induced T-cells efficiently traffic to the brain tumor site and maintain their function and viability.

7.9.8 Study Parameters

This study may be conducted on an outpatient basis, with patients scheduled to be evaluated on weeks 0, 3, 6, 9, 12, 15, 18, 21 and 24. After this period, if patients do not receive additional vaccines, patients may be off study, and they may be clinically followed every 2-4 months thereafter as usually done for patients with the same tumor type. If patients are found to have progressing tumors, other therapies, such as chemotherapy or resection, may be offered. If patients receive additional vaccines, such additional vaccines may be administered every 12 weeks, and clinical, immunological and radiological (MRI) monitoring may be performed at every visit (q12 weeks) until the patients withdraw. Subjects with a complete response may be retreated with additional two vaccinations, with 12-week intervals, and then followed. Vaccinations may be halted for any patients with progressive disease or unacceptable toxicity at any time during the scheduled vaccinations.

7.9.8.1 Pre-Treatment (Screening and Baseline Data)

The following procedures may be undertaken before treatment proceeds: informed Consent should be obtained before initiation of screening; HLA typing (flow-cytometric evaluation for HLA-A2 positivity); documentation of diagnosis (pathological); complete history and physical examination (with vital signs and weight), including neurological examinations and performance status; vaccine sites are to be designated with confirmation of intact draining lymph nodes; demographic information should be recorded; CBC and platelets with differential should be evaluated; PT/PTT should be evaluated; Chemistry should be evaluated, including electrolytes, creatinine, blood urea nitrogen, glucose, AST, ALT, Alk phos, total bilirubin, LDH, calcium and albumin; GGT, phosphorus, and magnesium should be evaluated; Blood for in vitro assays should be taken; HGBA1C for patients with diabetes mellitus should be performed; ECG and echo cardiogram should be performed for patients with cardiac symptoms, history or current disease; urinalysis should be performed; MRI of the brain to evaluate the baseline status of disease should be performed; and/or women of child-bearing potential should be administered a serum beta-HCG pregnancy test.

7.9.8.2 Evaluation During Treatment

The following procedures may be undertaken as treatment proceeds. Pre-Administration (Weeks 0, 3, 6, 9, 12, 15, 18 and 21 before vaccine administration on the day of vaccination): history and physical including vital signs, weight, Karnofsky performance status and neurological function; blood for in vitro assays should be taken; Chemistry should be evaluated, including electrolytes, creatinine, blood urea nitrogen, glucose, AST, ALT, Alk phos, total bilirubin, LDH, calcium and albumin (Except for Week 0); AED levels should be evaluated if clinically indicated; patients should be screened for adverse events from previous doses, to include neurological evaluation and skin examination (injection sites); and/or MRI should be performed (only on Week 12 among these vaccine injection visits).

Following vaccine administration, all patients should be closely observed for adverse events for at least 20 minutes following each administration of GAA-peptide vaccine. On the same day, poly-ICLC (i.m. 20 mg/kg) may be administered within 2 hours before or after the vaccine, and monitored at least 20 minutes after the poly-ICLC injection.

7.9.8.3 Week 24 (Post 8 Vaccinations) Evaluation

After the vaccination cycle is complete, the following procedures may be undertaken: history and physical including vital signs, weight, Karnofsky performance status and neurological function; Blood for in vitro assays should be taken (Except for Week 3, 6 and 9); CBC and platelets with differential should be evaluated (Except for Week 0); Chemistry should be evaluated, including electrolytes, creatinine, blood urea nitrogen, glucose, AST, ALT, Alk phos, total bilirubin, LDH, calcium and albumin (Except for Week 0); AED levels should be evaluated if clinically indicated; patients should be screened for adverse events from previous doses, to include neurological evaluation and skin examination (injection sites); and/or MRI should be performed.

7.9.8.4 Evaluation with Additional Vaccines (Cases with Additional Vaccines)

Prior to administration with additional vaccines, the following procedures may be undertaken: history and physical including vital signs, weight, Karnofsky performance status and neurological function; Blood for in vitro assays should be taken (Except for Week 3, 6 and 9); CBC and platelets with differential should be evaluated (Except for Week 0); Chemistry should be evaluated, including electrolytes, creatinine, blood urea nitrogen, glucose, AST, ALT, Alk phos, total bilirubin, LDH, calcium and albumin (Except for Week 0); AED levels should be evaluated if clinically indicated; patients should be screened for adverse events from previous doses, to include neurological evaluation and skin examination (injection sites); and/or MRI should be performed.

Following administration with additional vaccines, all patients should be closely observed for adverse events for at least 20 minutes following each vaccination. Additional vaccines may be terminated in any of the following conditions: 1) tumor progression; 2) RLT; or 3) negative immunological response in two consecutive time points after initiation of additional vaccines.

TABLE 7

Study Calendar

| Management Table Studies & Tests | Pre-Vaccination Consent/ HLA-typing/ pathology | Within 4 Wks | Treatment (Week) 0 | 3 | 6 | 9 | 12 | 15 | 18 | 21 | 24 | Every 12 Wks for additional vaccines* |
|---|---|---|---|---|---|---|---|---|---|---|---|---|
| Informed consent for HLA-typing | X | | | | | | | | | | | |
| HLA-typing | X | | | | | | | | | | | |
| Informed consent for treatment (if HLA-A2 is positive) | X--------------------X | | | | | | | | | | | |
| Pathology review | X | | | | | | | | | | | |
| Vaccination# | | | X | X | X | X | X | X | X | X | | X |
| CBC and Platelets with differential | | X | X | X | X | X | X | X | X | X | | X |
| Coagulation tests (PT and PTT) | | X | | | | | | | | | | |
| Chemistry## | | X | X | X | X | X | X | X | X | X | | X |
| GGT, Phosphorus, Magnesium | | X | | | | | | | | | | |
| AED if clinically indicated | | | X | X | X | X | X | X | X | X | | X |
| Demographics | | X | | | | | | | | | | |
| Concurrent Medications | | X | ←---------------------------→ | | | | | | | | | |
| Urinalysis | | X | | | | | | | | | | |
| β-HCG (women of childbearing potential) | | X | | | | | | | | | | |
| EKG or Echocardiogram### (if clinically indicated) | | X | | | | | | | | | | |
| Hgb A1c#### | | X | | | | | | | | | | |
| Brain MRI | | X | | | | | X | | | X | | X** |
| History, Physical and KPS | X (history only) | X | X | X | X | X | X | X | X | X | X | X |
| Research Blood Samples 8 × 10 cc green top tubes and one red top tube | | X | | | | X | X | X | X | X | | X** |
| Medication Diary | | | ←---------------------------→ | | | | | | | | | |
| Adverse Event report | | | ←---------------------------→ | | | | | | | | | |

Poly-ICLC (20 μg/kg i.m. and up to 1640 μg) may be administered on the day of the vaccine and on day 4 after each vaccine.

Includes electrolytes, creatinine, blood urea nitrogen, glucose, AST, ALT, Alk phos, total bilirubin, LDH, calcium and albumin

Testing required for participants with past or current cardiac disease, including symptoms.

Testing only required for participants with diabetes.

*Additional Therapy> Subjects may undergo additional vaccinations for up to 2 years after administration of the first vaccine (See section 4.2.2), if progression free status based on the MRI, lack of RLT and anti-GAA immune response are observed following the initial 8 vaccinations. The additional vaccines (and poly-ICLC on the day of and on day 4 after each vaccine) may be given every 12 weeks, beginning any week between weeks 34-40. Additional vaccinations may be terminated if tumor-progression, RLT or negative GAA-response in two consecutive time points is observed. Physical and neurological exam, blood tests to check blood counts and blood chemistry and PBMC samples may be obtained every 12 weeks (at the same visits for vaccine administrations). A MRI scan may be done at Weeks 12 and 24 to check your tumor response (whether or not your tumor is responding to the vaccines and injections).

**For participants who undergo additional vaccines, head MRI and blood sample collection for immunological monitoring may be performed every 12 weeks starting at the first additional vaccination.

7.9.9 Measurement of Effect

7.9.9.1 Objectives

7.9.9.1.1 Immunogenicity

The response rate and magnitude of CD8+ T-cell responses against the GAA-peptides in post-vaccine PBMC may be assessed using IFN-γ-ELISPOT, and tetramer analysis by flow cytometry as the secondary assay.

ELISPOT assays indicate functional status of the antigen-specific T cells as cytokine-expression. Flow cytometric analyses using tetramers allow for a relatively accurate estimation of frequency of antigen-binding T-cells without a major in vitro manipulation of the patient-derived PBMC, and phenotype analyses, such as the homing receptor (integrins) expression on antigen-specific T cells.

The biological assays to measure the response in peripheral blood may be carried out at the same time point to avoid inter-assay variability.

Using flow-cytometry, the numbers of lymphocyte subsets such as CD4+ T cells, CD4+/Foxp3+ regulatory T cells also may be evaluated. In addition, in patients who undergo surgical debulking of the progressing tumor, if the tumor tissue is available, infiltration of antigen-specific CTLs may be evaluated by flow cytometry of tumor-infiltrating lymphocytes with epitope-specific MHC-tetramers.

7.9.9.1.2 Safety

The safety of the administration of the four HLA-A2-restricted glioma-associated antigen (GAA) epitope-peptides in conjunction with a class II MHC-restricted Tetanus Toxoid (TT)-derived helper T cell epitope and i.m. poly-ICLC in patients with grade II astrocytoma and oligoastrocytoma may be determined.

Endpoints may include incidence and severity of adverse events, using standard criteria as well as close clinical follow-up as would be performed normally in this group of patients following vaccinations. The regimen may be considered unacceptably toxic if >33% of patients in a given cohort develop RLT.

7.9.9.1.3 Response and Progression-Free Survival

Tumor recurrence may be assessed minimally at weeks 12 and 24, and every 3 months thereafter using MRI scans with contrast enhancement. Since low-grade gliomas are infiltrative tumors which typically do not enhance with contrast administration, for evaluation of response and progression-free survival, the tumor (i.e., target lesion) may be measured from the T2 or FLAIR MRI images. In case there is an enhancing lesion at the baseline, careful discussion may be made as to whether the pathology information as WHO grade II tumor truly represents the status of the tumor. If the enhancing tumor is still considered to be grade II, the size of the enhancing lesion may be used for evaluation. In addition, as noted below, emergence of enhancement in previously non-enhancing tumor is considered to be progressive disease (PD).

(A) Response (According to RECIST Criteria)

Complete Response (CR): Disappearance of all target lesions.

Partial Response (PR): At least a 30% decrease in the sum of the longest diameter (LD) of target lesions, taking as reference the baseline sum LD.

Progressive Disease (PD): At least a 20% increase in the sum of the LD of target lesions, taking as reference the smallest sum LD recorded since the treatment started or the appearance of contrast enhancement in a previously non-enhancing tumor. Because of the possibility of pseudo-tumor progression, patients may be placed on low-dose steroids and reimaged before being declared as having PD.

Stable Disease (SD): Neither sufficient shrinkage to qualify for PR nor sufficient increase to qualify for PD, taking as reference the smallest sum LD since the treatment started.

(B) Overall Survival (OS) and Progression-Free Survival (PFS)

PFS is defined as the duration of time from start of treatment to time of progression or death. All patients may be followed for a minimum of 2 years, so that their actual 2-year OS and PFS can be determined.

7.9.9.1.4 Analyses of Tumor Tissues Following Vaccinations

Tumor tissues may not be available from all patients in the study. However, the following aspects may be evaluated in an exploratory manner in all available tumor tissues obtained pre- and/or post-vaccines: (i) Antigen-loss; (ii) up-regulation of anti-apoptotic molecules; and (iii) immune cell infiltration.

7.9.10 Statistical Considerations

7.9.10.1 Assessment of Immunological Responses

Evaluation of immune response may employ both IFN-γ ELISPOT and tetramer assays.

A responder may be defined as a patient who has responded in either IFN-γ ELISPOT or tetramer assays. A cohort may be considered worthy of further investigation if there are at least 4 responses in the 9 subjects. This criterion has the property that if the true response rate is <17%, there is <5% probability to observe 4 or more responses, and that if the true response rate is >66%, there is <5% probability to observe 3 or fewer responses.

7.9.10.2 Documentation and Evaluation of Safety

The NCI common terminology criteria for adverse events (AE) (CTCAE 3.0) may be used to evaluate toxicity; toxicity may be considered to be an adverse event that is possibly, probably or definitely related to treatment. The maximum grade of toxicity for each category of interest may be recorded for each patient and the summary results may be tabulated by category and grade.

For safety, the regimen may be considered to be excessively toxic if, at any time, the observed rate of regimen-limiting toxicity (RLT) ≥33% and at least 2 RLTs have been observed.

The study design has the following properties: if the true rate of RLT is ≥45%, there is at least 90% probability that accrual will stop; if the true RLT rate is <9%, there is 90% probability that the accrual will not stop, and that the regimen may be considered safe.

7.9.10.3 Assessment of Clinical Endpoints

All patients may be followed for a minimum of 2 years, so that their actual 2-year overall survival (OS), progression-free survival (PFS) and response rates can be tabulated as exploratory endpoints. PFS is defined as the time interval from a patient's pathological diagnosis of WHO grade II astrocytoma or oligoastrocytoma to progression, based on serial MRI scans. If appropriate, exploratory analyses may investigate the relationship of immune response to imaging response and OS/PFS (using Fisher's exact test and the log rank test, respectively).

7.9.10.4 Demographic Data

Baseline descriptive statistics on all evaluable patients may be provided for demographic variables (age, sex, race/ethnicity), Karnofsky performance status, disease stage and status at the time of enrollment (stable disease, progressive disease), and/or treatment regimens previously used.

7.10 Example 10

This example describes a study to Evaluate the Effects of vaccinations with HLA-A2-restricted glioma antigen-peptides in combination with poly-ICLC for children with newly diagnosed malignant or intrinsic brain stem gliomas (BSG) or incompletely resected non-brainstem high-grade gliomas (HGG) or recurrent unresectable low-grade gliomas (LGG).

7.10.1 Rationale

Currently, there are no effective therapeutic modalities for pediatric malignant gliomas. Immunotherapy, particularly active vaccinations, has the potential to develop as an effective and safe modality. Vaccines using GAA-specific peptides, in comparison to whole glioma-derived antigens, may be more feasible because these vaccines may induce glioma-specific immune responses without theoretical concerns of auto-immune encephalitis. Evidence from recent studies suggests that pediatric gliomas and intrinsic brain stem gliomas have a similar pattern of expression of glioma-associated antigens (GAAs), which can be targeted by vaccine-based therapy. In view of the dismal prognosis for children with intrinsic brainstem gliomas, incompletely resected malignant gliomas, it is appropriate to evaluate the activity and safety of immunization following radiation therapy in these tumors. Likewise, deep-seated low-grade gliomas also express a similar spectrum of GAAs. Because these lesions commonly become refractory to conventional therapy, with increasing morbidity and mortality, it is appropriate to evaluate the potential efficacy of vaccine therapy in those patients who have had disease progression following at least two chemotherapy or biological therapy regimens or irradiation.

Administration of poly-ICLC along with the GAA peptides remarkably enhance the induction of anti-GAA CTL responses and trafficking of antigen-specific T cells to the brain tumor sites. In the study described in this example, pediatric patients with newly diagnosed malignant glioma or treatment-refractory low-grade gliomas may be vaccinated with multiple novel GAA-derived HLA-A2 restricted CTL epitopes in combination with intramuscular administration of poly-ICLC.

7.10.2 Objectives

This Example describes a vaccine study in children with newly diagnosed malignant or intrinsic brain stem gliomas (BSG) or incompletely resected non-brainstem high-grade gliomas (HGG) or recurrent unresectable low-grade gliomas (LGG).

7.10.2.1 Induction of GAA-Specific T-Cell Response

The response rate and magnitude of immune response in post-vaccine peripheral blood mononuclear cells (PBMC) against the GAA-peptides in response to this form of vaccine may be determined using IFN-γ-enzyme-linked immuno-spot (ELISPOT) and tetramer assays.

7.10.2.2 Safety

The incidence and severity of adverse events associated with the vaccine regime may be assessed, with an early stopping rule based on the frequency of Regimen Limiting Toxicity (RLT) in children with newly diagnosed malignant brain stem gliomas (BSG), and in children with newly diagnosed incompletely resected non-brain stem malignant gliomas (HGG). The incidence and severity of adverse events associated with the vaccine regimen may also be assessed in patients with treatment-refractory, unresectable low-grade gliomas that have progressed after two chemotherapy or biological therapy regimens or irradiation.

7.10.2.3 Clinical Response

Radiological response may be determined using the standard WHO response criteria. 2-year progression-free survival (PFS) may be evaluated in an exploratory manner, based on serial magnetic resonance imaging (MRI) scans.

7.10.2.4 Tumor Tissues for Biological Correlates

For patients with non-brainstem tumors who develop progression, biopsy/tumor debulking may be encouraged. Whenever post-vaccine tumor tissues are available, they may be analyzed for GAA expression status and infiltration of GAA-specific T-cells.

7.10.3 Patient Selection 7.10.3.1 Eligibility Criteria

Pathological criteria—Patients will have glioma. In some embodiments, the glioma patient is in one of the following strata: (i) Stratum A: Newly diagnosed diffuse intrinsic pontine gliomas or any biopsy proven high-grade glioma involving the brainstem; (ii) Stratum B: newly diagnosed, incompletely resected, non-brainstem high-grade glioma (i.e. definite residual tumor visible on imaging); or (iii) Stratum C: Unresectable, progressive low-grade glioma of any subtype that has recurred despite two prior chemotherapy or biological therapy regimens and/or radiation therapy; (iv) Stratum D: Newly diagnosed diffuse intrinsic pontine gliomas (DIPG) OR any biopsy proven high-grade glioma* involving the brainstem treated with radiation therapy with or without chemotherapy during irradiation; (v) Stratum E: Newly diagnosed non-brainstem high-grade gliomas* (HGG) treated with radiation therapy with or without chemotherapy during irradiation; (vi) Stratum F: Recurrent non-brainstem high-grade gliomas* that have recurred following treatment. Patients must have recovered from the toxic effects of prior therapy. Eligible histologies for high-grade glioma include glioblastoma (GBM), anaplastic astrocytoma (AA) or gliosarcoma. Patients with any oligodendroglioma component may not be eligible for the particular protocol described in this example.

Patients in this study should be HLA-A2 positive based on flow cytometry.

Patients in Stratum A and B should have received standard involved field RT defined as fractionated external beam radiotherapy with total doses between 5000-6000 cGy. Patients in these strata should be registered within 4-12 weeks of completing RT.

Patients in this study should be clinically stable and off or on low-dose (no more than 0.1 mg/kg/day, max 4 mg/day Dexamethasone) corticosteroid for at least one week prior to study registration.

Patients in this study should be 3 and <21 years of age at the time of study.

Patients in this study should have a performance status of 50; (Karnofsky if >16 years and Lansky if <16 years of age).

Female patients in this study who are post-menarchal should have documented negative serum βHCG.

Patients in this study should be free of systemic infection. Patients on antibiotic therapy should be off antibiotics for at least 7 days before beginning treatment.

Patients in this study should have adequate organ function as measured by: (i) Bone marrow: ANC >1,000/µl; Platelets >100,000/µl (transfusion independent); Hemoglobin >8 g/dl (may be transfused); (ii) Hepatic: bilirubin ≤1.5× institutional normal for age; SGPT (ALT)<3× institutional normal and albumin ≥2 g/dl; (iii) Renal: Serum creatinine based on age or Creatinine clearance or radioisotope GFR ≥70 ml/min/1.73 m² Patients in this study should have coagulation tests and PT and PTT within normal limits for their age.

Patients in this study should have no overt cardiac, gastrointestinal, pulmonary or psychiatric disease.

For patients in stratum C, recovery from the effects of prior chemotherapy may be required.

7.10.3.2 Exclusion Criteria

Patients in Stratum A and Stratum B of this study should be excluded if they have presence of leptomeningeal metastatic disease.

Patients in this study should be excluded if they have gross totally resected tumors, i.e. no definite visible residual disease on MRI scan at the time of study.

Patients in Stratum A and Stratum B of this study should be excluded if they have received any prior chemotherapy or anti-glioma therapy of any type other than radiation therapy. (Patients in stratum C of this study should have received at least two prior chemotherapy or biologic therapy regimens and/or radiation therapy.)

Patients in this study should be excluded if they are undergoing concurrent treatment or medications including: radiation therapy; interferon (e.g. Intron-A®); allergy desensitization injections; inhaled steroids (e.g.: Advair®, Flovent®, Azmacort®); growth factors (e.g. Procrit®, Aranesp®, Neulasta®); interleukins (e.g. Proleukin®); and/or any investigational therapeutic medication.

Patients in this study should not have had prior autoimmune disorders requiring cytotoxic or immunosuppressive therapy, or autoimmune disorders with visceral involvement. Mild arthritis requiring NSAID medications should not be exclusionary.

Patients in this study should be excluded if they have used immunosuppressives within four weeks prior to entering the study or if they anticipate use of immunosuppressive agents. Dexamethasone, or other corticosteroid medications, if used peri-operative period and/or during radiotherapy, should be tapered by patients (no more than 0.1 mg/kg/day, max 4 mg/day dexamethasone) for at least one week before study registration. Topical corticosteroids should be acceptable.

Patients in this study should be excluded if they have known addiction to alcohol or illicit drugs.

Because patients with immune deficiency are not expected to respond to this therapy, HIV-positive patients should be excluded from the study.

7.10.4 Peptide Vaccine

7.10.4.1 Peptides

The following peptides may be included in the vaccine formulation: IL-13R$\alpha$2$_{345-353}$ 1A9V (ALPFGFILV; SEQ ID NO:3); EphA2$_{883-891}$ (TLADFDPRV; SEQ ID NO:6); Survivin$_{96-104}$:M2 (LMLGEFLKL; SEQ ID NO:7); and Tetanus Toxoid (TetA830) (AQYIKANSKFIGITEL; SEQ ID NO:9).

All peptides may be synthesized and the synthetic peptides may be purified by HPLC. The identity of the synthetic peptides may be confirmed by verifying their mass and amino acid sequences by mass spectrometry. Each lot of peptide may be evaluated as required by the FDA for identity, purity, sterility and pyrogenicity.

The peptides may be vialed under GMP conditions and saved at $-70°$ C. Stability of lyophilized peptides may be tested annually by mass spectroscopy.

7.10.4.2 Other Agents

Montanide ISA-51 (SEPPIC Inc., Fairfield, N.J.) may be used as an additional agent in the peptide vaccines.

7.10.4.3 Dosage and Preparation

An aqueous solution (400 µL) containing each of four HLA-A2-restricted GAA peptides (300 µg/peptide) and the tetanus peptide (Peptide-tet; 200 µg) may be mixed 1/1 with Montanide ISA-51 to form one water-in-oil emulsion (i.e. the total volume/injection is 800 µL).

7.10.4.4 Administration

Patients in this study may be vaccinated subcutaneously in the upper arm or thigh.

The vaccine may be administered Q3Wk starting 4-12 wks following the completion of RT (Wk 1).

7.10.5 Poly-ICLC

Poly-ICLC may be prepared and packaged in the GMP facility of Bioserv, Corporation (San Diego, Calif.). Poly-ICLC may be supplied in vials containing 1 cc of translucent solution with a concentration of 2 mg per cc. Poly-ICLC is stable at room temperature for several days, but may be stored refrigerated at about 40° F.

7.10.5.1 Dosage and Administration

The first course of poly-ICLC administration (30 µg/kg i.m.) may be administered on the day of the first GAA/TT-vaccine. For each of the following repeated vaccinations (Q3W), poly-ICLC (30 µg/kg i.m.) may be administered on the day of the vaccine.

With regard to the injection sites, as poly-ICLC is expected to enhance the antigen-presentation process in the draining lymph nodes, poly-ICLC should be administered i.m. within the close vicinity to the previous peptide-injection site (e.g., less than 3 cm from the center of the previous peptide injection sites).

Poly-ICLC should be administered intramuscularly (i.m.) using sterile technique, as supplied from the vial, and in the amount prescribed for the patient's weight. The poly-ICLC treatments may be administered on the same day as the vaccine. Vital signs may be monitored before and for at least 20 minutes after the first treatment.

7.10.6 Treatment Plan

The study described in this Example may employ three strata to assess the immunogenicity, safety and preliminary clinical efficacy of the GAA/TT-peptide vaccine and poly-ICLC in HLA-A2+ children with newly diagnosed intrinsic brain stem gliomas (BSG) or biopsy proven GBM, AA or gliosarcoma involving the brainstem (Stratum A); or incompletely resected non-brainstem GBM, AA or gliosarcoma (Stratum B); or recurrent progressive low grade gliomas (Stratum C).

7.10.6.1 Schedule

Following diagnosis (for Stratum A and B) or after disease progression (for stratum C), treatment according to the study described in this Example may be discussed with potentially eligible patients. All patients in Stratum A and B may receive fractionated external beam radiation therapy (FEBRT). Patients may be assessed for HLA-A2 status. Eligibility screening and the baseline MRI scan and laboratory studies should be completed within 2 weeks of registering to participate in the study and within 3 weeks of receiving the first vaccine. Patients in Stratum A and B should be registered to participate in the study within 4-12 weeks following the completion of FEBRT. The timing of study registration for these patients will depend on whether the post-RT MRI (typically done at week 4) shows evidence of increased enhancement or mass effect and the patient is clinically symptomatic/worse. If so, study registration will occur when the patient has been clinically stable/improved and on low dose (0.1 mg/kg/day max 4 mg decadron) or off steroids x one week.

Patients may be treated with subcutaneous injections of GAA/TT-vaccines starting on Week 1 and every 3 weeks thereafter for up to 8 cycles. I.m. poly-ICLC may be administered (30 µg/kg i.m.) on the same day as the vaccine. Each vaccine may be administered just prior to the i.m. poly-ICLC administration. Poly-ICLC should be administered i.m. within close vicinity to the previous peptide-injection site (e.g., less than 3 cm from the center of the previous peptide injection sites).

Patients may be evaluated for any possible adverse event, RLT as well as clinical/radiological responses by clinical visits and MRI scanning. Follow-up MRIs may be performed every 9 weeks starting at Week 7 (Weeks 7, 16 and 25).

PBMC obtained before the initial vaccine may be used as the base-line sample. On weeks, 7, 16 and 25, PBMC may be obtained as post-vaccine samples. Immunological assays may be performed for all PBMC samples obtained from at least one participant at one time, so that inter-assay variability will be avoided.

7.10.6.2 Additional "Continuation" Therapy

After the scheduled $8^{th}$ vaccination, if the patient demonstrates radiological response (i.e. complete or partial response) or stable disease without RLT, the patient may receive additional peptide vaccinations in conjunction with poly-ICLC starting 6 weeks after the $8^{th}$ vaccination, and every 6 weeks thereafter up to 2 years from the initial vaccination as long as there is no tumor progression and no RLT. Additional PBMC samples may be obtained at the same visits for vaccine administrations for immunological monitoring. Additional vaccines may be terminated in any of the following conditions: 1) tumor progression; 2) RLT; or 3) patient withdrawal.

7.10.6.3 Dose Modification 7.10.6.3.1 Dose Modification for Poly-ICLC

Pretreatment with acetaminophen or with any NSAID should be given before each poly-ICLC dose. For Grade 2 or greater constitutional symptoms that persist for greater than 48 hours after the injection, the next poly-ICLC dose should be given at 67% of the original dose (i.e. 20 µg/kg). If further dosing is well tolerated, the original dose may be subsequently re-instituted. If grade 2 or greater symptoms again occur despite one dose reduction and last >48 hours, the patient may be withdrawn for RLT.

In the case of hepatic enzyme elevation >5× baseline (Grade 3), or any intolerable grade 2 non-hematologic toxicity that lasts for ≥7 days, poly-ICLC may be held until that toxicity has reduced to Grade 1 or less. Poly-ICLC may then be re-administered at two-thirds of the original dose (i.e. 20 µg/kg), and the participant may be closely observed. If the same dose-limiting toxicity again recurs despite the dose reduction, the participant may be withdrawn for RLT.

For grade 3 or greater hematologic toxicity, the next dose should be reduced to 67% (i.e. 20 µg/kg) as long as the toxicity has resolved to grade 1 or less by the time the next dose is due. If the toxicity has not resolved by the time the next dose is due, the patient is off treatment. If the same dose-limiting hematologic toxicities again occur despite the reduced dose, the patient may be taken off treatment for RLT.

7.10.6.3.2 Dosing Delay for the Peptide Vaccines

In circumstances where poly-ICLC administration is suspended, if the event is not attributable to the peptides/ISA-51 vaccine, vaccine administration should continue on schedule. In circumstances where assessment of an adverse event is limited, such as by intercurrent illness, or when laboratory studies are required to assess for other causes of toxicity, the vaccine schedule may be interrupted for up to 6 weeks. If vaccine administration is delayed by longer than 6 weeks due to an adverse event other than for pseudo-tumor progression, regardless of attribution, treatment should be discontinued.

Patients may be observed for regimen limiting toxicity (RLT) throughout the study. The following are considered to be RLTs if they are judged possibly, probably or definitely associated with treatment. Should they occur, individual patients may be taken off study and no further injections may be given.

≥Grade 2 or more bronchospasm or generalized uticaria (hypersensitivity).

≥Grade 2 or more allergic reaction, such as exfoliative erythroderma, anaphylaxis, or vascular collapse.

Any ≥Grade 3 non-hematologic toxicity (excluding hepatic toxicity) possibly, probably, or definitely related to the therapy regimen including ≥Grade 3 injection site reaction due to peptide-vaccine or poly-ICLC administration.

≥Grade 3 hematologic or hepatic toxicity that recurs despite a 33% dose reduction or does not resolve to grade 1 or less by the time the next dose is due.

Intolerable grade 2 non-hematologic toxicity lasting ≥7 days that recurs despite a 33% dose reduction or does not resolve to grade 1 or less by the time the next dose is due.

Grade 2 or greater constitutional symptoms that persist for >48 hours despite a dose reduction.

≥Grade 3 neurotoxicity due to a regimen-related inflammatory immune response (i.e., pseudo-tumor progression that does not respond to a 7 day trial of 0.3 mg/kg day decadron (max 12 mg/day) and/or requires debulking surgery, if feasible.

≥Grade 3 nausea and vomiting despite sufficient antiemetic prophylaxis.

Dosing delays >6 weeks for either poly-ICLC or peptide vaccines due to toxicity other than PTP.

Therapy may be discontinued for the following reasons: (i) Regimen limiting toxicity other than PTP—as defined above; (ii) disease progression—at least a 25% increase in the product of the longest tumor diameter and its perpendicular diameter on MRI scan. (iii) Intercurrent illness that prevents further administration of the vaccine or poly-ICLC administration for longer than 6 weeks. (iv) Pregnancy: Pregnant patients will continue to be followed for the duration of the pregnancy.

7.10.6.4 Treatment Duration

In the absence of treatment delays due to adverse event(s), treatment may continue for 25 weeks (8 vaccinations and the follow-up visit at Week 25) or until one of the Off-Treatment criteria in Section 7.10.6.3.2 occurs.

7.10.6.5 Concomitant Treatment 7.10.6.5.1 Acceptable

Patients should receive a dose of acetaminophen (15 mg/kg up to a max of 1000 mg) 30-60 minutes before each poly-ICLC administration. For fever following the injection, acetaminophen (15 mg/kg up to a max of 1000 mg q 4-6 hours prn, not to exceed 4 g/day) may be given. Patients with fevers lasting longer than 48 hours should be evaluated for potential infection.

For mild local pain, oral opiates may be used (tylenol and codeine 0.5 mg/kg p.o. every 4 hours). Pain that is of more than mild-moderate grade will be investigated for non-therapy related causes, and managed accordingly.

Dexamethasone—no more than 0.1 mg/kg/day, max 4 mg/day for at least one week prior to the initiation of the vaccine/poly-ICLC therapy (Week 0). Dexamethasone dose may be increased in the setting of pseudo-tumor progression and tapered/discontinued as soon as possible.

Anti-seizure medications should be used as indicated.

Antiemetics, if necessary, may be administered.

Other acceptable medications may include: Topical corticosteroids; nonsteroidal anti-inflammatory agents; antihistamines (e.g. Claritin®, Allegra®); chronic medications except those listed in Section 7.10.6.5.2; and/or Influenza vaccines (these should be administered at least two weeks prior to the initiation of the study vaccines or at least two weeks after the 8$^{r1}$ (last) vaccine).

7.10.6.5.2 Unacceptable

Unacceptable medications may include interferon therapy (e.g. Intron-A®); chemotherapy; allergy desensitization injections; corticosteroid medications administered parenterally or by inhalation (e.g.: Advair®, Flovent®, Azmacort®); growth factors (e.g. Procrit®, Aranesp®, Neulasta®); interleukins (e.g. Proleukin®); other investigational medications; and/or illicit drugs.

7.10.7 Correlative/Special Studies

7.10.7.1 Immunological Monitoring

7.10.7.1.1 ELISPOT Assays

Frequencies of glioma associated antigens (GAA)-responsive T-lymphocyte precursors in peripheral blood mononuclear cells (PBMC) prior to and after, administration of the GAA-peptide based vaccine may be measured by ELISPOT assay. The biological responses measured by ELISPOT may be done at the same time point at least for one individual patient to avoid inter-assay variability. Successful vaccination stimulates clonal populations of T cells that are capable of secreting cytokines in an antigen-specific, MHC-restricted fashion. The ELISPOT assay may be utilized to evaluate GAA-specific immune responses of CD8+ T-cell populations as well as CD4+ T cells that react against the helper TT peptide. IFN-γ production may then be evaluated to assess Type-1 T-cell response.

A subject may be considered to have responded, if at any of two consecutive post-vaccine time points against the same antigen[s] (Weeks 12, 15, 18, 21 and 24), the number of spots is double that at baseline, and there are at least 10 spots/20,000 cells, and if the number of the post-vaccine spots is at least three times the standard-deviation of the pre-vaccine value. Response can be to any one antigen.

7.10.7.1.2 Tetramer Analysis of GAA-Reactive T Cells in Patient's PBMC

Tetramer analyses allow for evaluation of the presence of GAA-specific CD8$^+$ T-cells in peripheral blood with a great sensitivity without in vitro re-stimulation of the cells. It is expected, based on previous data available from patients with malignant glioma, that significant (a log or more) increase in the frequency of peptide-responsive CD8$^+$ T cells may be observed in some, but not all, patients immunized with tumor-antigen based vaccines. In an exploratory manner, these PBMCs may be also evaluated for surface expression of an integrin receptor very late antigen (VLA)-4, which has been implicated to confer T-cell homing to CNS tumors (see, e.g., Zhu et al., J. Transl. Med., 5: 10, 2007) and chemokine receptors (e.g. CXCR3 and CCR5). Procedures for tetramer analysis are well established.

Tetramer assays may be done at baseline and at 5 time points after vaccinations (Weeks 12, 15, 18, 21 and 24). A single time-point positive response for a peptide to be (1+B) % of all CD8$^+$ cells positive by tetramer assay may be defined, where B is the percent positive at baseline, which is usually less than 0.1%. In analogy to the definition of ELISPOT response, a patient may be considered to have responded if he/she has two consecutive single time-point responses for any peptide.

7.10.7.1.3 Flow Cytometric Analyses of Lymphocyte Subsets

Numbers of CD4+ and CD8+ T cells as well as CD4+/Foxp3+ T regulatory cells at serial time points pre- and post-vaccines may be evaluated.

7.10.7.2 Evaluation of Primary and Recurrent Tumor Tissues

GAA-expression in the patients' available tumor tissues may be evaluated (either pre-vaccine or after progression post-vaccines; or both) by immunohistochemistry (IHC) and reverse transcriptase-polymerase chain reaction (RT-PCR).

If tumors recur following vaccinations, it may be critical to evaluate how tumors escape the effects of vaccines. To this end, the following specific issues may be evaluated as much as the tissue-availability allows: (i) Antigen-loss: IHC and RT-PCR may be used to assess whether the recurrent tumors express the targeted GAAs, HLA-A2, and antigen processing machinery components, such as transporter associated with antigen processing; (ii) up-regulation of anti-apoptotic molecules: although Survivin may be targeted, other anti-apoptotic molecules may be up-regulated, e.g., cFLIP (cellular FLICE (Fas-associated death domain-like IL-1β-converting enzyme) inhibitory protein); and (iii) immune cell infiltration: one reason tumors may escape a vaccine-induced immune response is through the failure of reactive T cells to infiltrate the tumor. To examine this, whenever freshly resected tumor tissues (not fixed or frozen) are available, tumor infiltrating lymphocytes (TILs) may be isolated and their numbers, phenotype, and antigen-specificity may be characterized using HLA-A2 tetramers for each of GAAs. Using multi-color flow-cytometry, the function and viability of tetramer$^+$ TILs may be determined by staining for perforin/IFN-γ and Annexin-V, respectively. Control tissues may include pre-vaccine tumors (if available) and recurrent tumors from patients not in the study. These studies may allow for evaluation of whether vaccine-induced T-cells efficiently traffic to the brain tumor site and maintain their function and viability.

7.10.8 Study Parameters

This study may be conducted on an outpatient basis, with patients scheduled to be evaluated every 3 weeks for up to 8 vaccinations. If patients receive additional vaccines, administered every 6 weeks as part of the continuation phase, clinical, immunological and radiological (MRI) monitoring may be performed at every visit (Q6Wk) until one of the criteria for ending treatment are met. Vaccinations may be halted for any patients with progressive disease or unacceptable toxicity at any time during the scheduled vaccinations.

7.10.8.1 Pre-Treatment (Screening and Baseline Data)

The following procedures may be undertaken before treatment proceeds: informed Consent should be obtained before initiation of screening; HLA typing (flow-cytometric evaluation for HLA-A2 positivity); and documentation of diagnosis (histological for non-brainstem primaries (i.e., Stratum B); pathological or imaging for brainstem primaries); complete history and physical examination (with vital signs and weight), including neurological examinations and performance status; concurrent medication demographic information should be recorded; CBC and platelets with differential should be evaluated; PT/PTT should be evaluated; comprehensive metabolic panel should be evaluated, including electrolytes, creatinine, blood urea nitrogen, glucose, AST, ALT, Alk phos, total bilirubin, LDH, calcium and albumin; GGT, phosphorus, and magnesium should be evaluated; Blood for in vitro assays should be taken; urinalysis should be performed; MRI of the brain should be performed; and/or women of child-bearing potential should be administered a serum beta-HCG pregnancy test.

7.10.8.2 Evaluation During Treatment

The following procedures may be undertaken as treatment proceeds. Pre-Administration: history and physical including vital signs, weight, performance status, concurrent medication, and neurological function; blood for in vitro assays should be taken; Chemistry should be evaluated, including electrolytes, creatinine, blood urea nitrogen, glucose, AST, ALT, Alk phos, total bilirubin, LDH, calcium and albumin; patients should be screened for adverse events from previous doses, to include neurological evaluation and skin examination (injection sites); and/or MRI should be performed (every 9 weeks starting Week 6; i.e. Weeks 6, 15 and 24).

Following vaccine administration, all patients should be closely observed for adverse events for at least 20 minutes following each administration of GAA-peptide vaccine. On the same day, poly-ICLC (i.m. 30 mg/kg) will be administered after each vaccine, and patients will be monitored for at least 20 minutes after the poly-ICLC injection.

7.10.8.3 Week 24 (Post 8 Vaccinations) Evaluation

After the vaccination cycle is complete, the following procedures may be undertaken: history and physical including vital signs, weight, performance status, concurrent medication, and neurological function; Blood for in vitro assays should be taken; CBC and platelets with differential should be evaluated; Chemistry should be evaluated, including electrolytes, creatinine, blood urea nitrogen, glucose, AST, ALT, Alk phos, total bilirubin, LDH, calcium and albumin (Except for Week 0); and/or patients should be screened for adverse events from previous doses, to include neurological evaluation and skin examination (injection sites).

7.10.8.4 Evaluation with Additional "Continuation" Vaccines

Prior to administration with additional vaccines, the following procedures may be undertaken: history and physical including vital signs, weight, performance status, concurrent medication, and neurological function; Blood for in vitro assays should be taken; CBC and platelets with differential should be evaluated; Chemistry should be evaluated, including electrolytes, creatinine, blood urea nitrogen, glucose, AST, ALT, Alk phos, total bilirubin, LDH, calcium and albumin (Except for Week 0); patients should be screened for adverse events from previous doses, to include neurological evaluation and skin examination (injection sites); and/or MRI should be performed.

Following administration with additional vaccines, all patients should be closely observed for adverse events for at least 20 minutes following each vaccination. Additional vaccines may be terminated in any of the following conditions: 1) tumor progression; 2) RLT; or 3) negative immunological response in two consecutive time points after initiation of additional vaccines.

TABLE 8

Study Calendar

| Management Table Studies & Tests | Pre-vac@ | 0 | 3 | 6 | 9 | 12 | 15 | 18 | 21 | 24 | every 12 Wks for additional vaccines * |
|---|---|---|---|---|---|---|---|---|---|---|---|
| Informed consent | X | | | | | | | | | | |
| HLA-typing | X | | | | | | | | | | |
| Pathology review | X | | | | | | | | | | |
| Vaccination # | | X | X | X | X | X | X | X | X | | X (Q6 Wks) |
| CBC with differential | X | X | X | X | X | X | X | X | X | X | X (Q6 Wks) |
| Comprehensive chemistry including LDH, ALT and AST | X | X | X | X | X | X | X | X | X | X | X (Q6 Wks) |
| Demographics | X | | | | | | | | | | |
| Concurrent Medications | X | | ←--------------------------------------------→ | | | | | | | | |
| Urinalysis | X | | | | | | | | | | |
| β-HCG (women of childbearing potential) | X | | | | | | | | | | |
| Brain MRI | X | | | X | | X | | X | | X | X** |
| History, Physical, and KPS | X | X | X | X | X | X | X | X | X | X | X (Q6 Wks) |
| 35 cc green top tubes (7 tubes) | X | | | X | | X | | X | | X | X** |

@Within 2 weeks of registration (Wk −2 to 0) for H&P, MRI and laboratory tests. HLA-typing is done any time after signing Part 1 of the consent form.
poly-ICLC (30 μg/kg i.m.) may be administered after each vaccine.
<* Additional Therapy> Subjects may undergo additional vaccinations, if progression free status based on the MRI and lack of RLT are observed following the initial 8 vaccinations. The additional vaccines and poly-ICLC may be given every 6 weeks, starting 6 weeks after the 8th vaccination, and up to 2 years from the initial vaccination.. Additional vaccinations may be terminated if Off-Treatment criteria are met.
**For patients who undergo additional vaccines, brain MRI and blood sample collection for immunological monitoring may be performed every 6 weeks.

7.10.9 Measurement of Effect 7.10.9.1 Objectives 7.10.9.1.1 Immunogenicity

The response rate and magnitude of CD8+ T-cell responses against the GAA-peptides in post-vaccine PBMC may be assessed using IFN-γ-ELISPOT, and tetramer analysis by flow cytometry as the secondary assay.

ELISPOT assays indicate functional status of the antigen-specific T cells as cytokine-expression. Flow cytometric analyses using tetramers allow for a relatively accurate estimation of frequency of antigen-binding T-cells without a major in vitro manipulation of the patient-derived PBMC, and phenotype analyses, such as the homing receptor (integrins) expression on antigen-specific T cells.

The biological assays to measure the response in peripheral blood may be carried out at the same time point to avoid inter-assay variability.

Using flow-cytometry, the numbers of lymphocyte subsets such as CD4+ T cells, CD4+/Foxp3+ regulatory T cells also may be evaluated. In addition, in patients who undergo surgical debulking of the progressing tumor, if the tumor tissue is available, infiltration of antigen-specific CTLs may be evaluated by flow cytometry of tumor-infiltrating lymphocytes with epitope-specific MHC-tetramers.

7.10.9.1.2 Safety

The safety of the administration of the four HLA-A2-restricted glioma-associated antigen (GAA) epitope-peptides in conjunction with a class II MHC-restricted Tetanus Toxoid (TT)-derived helper T cell epitope and i.m. poly-ICLC in patients with newly diagnosed brainstem and non-brainstem malignant gliomas immediately following irradiation (Stratum A and B, respectively) and in patients with treatment-refractory, unresectable, low-grade glioma (Stratum C) may be determined.

Endpoints may include incidence and severity of adverse events, using standard criteria as well as close clinical follow-up as would be performed normally in this group of patients following vaccinations. The regimen may be considered unacceptably toxic if >33% of patients in a given cohort develop RLT.

7.10.9.1.3 Response and Progression-Free Survival

For evaluation of response and progression-free survival, the tumor (i.e., target lesion) may be measured from gadolinium (Gd)-enhanced T1 MRI images or, for tumors with non-enhancing components, from T2-weighted images.

(A) Response (According to RECIST Criteria)

Complete Response (CR): Complete disappearance on MRI of all visible tumor and mass effect, on a stable or decreasing dose of corticosteroids (or only adrenal replacement doses), accompanied by a stable or improving neurologic examination, and maintained for at least 6 weeks.

Partial Response (PR): Greater than or equal to 50% reduction in tumor size by bi-dimensional measurement on a stable or decreasing dose of corticosteroids, accompanied by a stable or improving neurologic examination, and maintained for at least 6 weeks.

Progressive Disease (PD): neurologic abnormalities or worsening neurologic status not explained by causes unrelated to tumor progression (e.g., anticonvulsant or corticosteroid toxicity, electrolyte disturbances, sepsis, hyperglycemia, etc.), or a greater than 25% increase in the bi-dimensional measurement, or increasing doses of corticosteroids required to maintain stable neurologic status or imaging.

Stable Disease (SD): Neurologic exam is at least stable and maintenance corticosteroid dose not increased, and MR imaging meets neither the criteria for PR or the criteria for Progressive Disease. If this category is to be reported as of possible clinical benefit, Stable Disease status must be maintained for at least 12 weeks.

Pseudo-Progressive Disease (Pseudo-PD) Patients with pseudo-progression, who remain on study and ultimately experience SD, PR, or CR may be classified as both pseudo-PD and either SD, PR, or CR, respectively, for response determinations.

(B) Overall Survival (OS) and Progression-Free Survival (PFS)

PFS is defined as the duration of time from start of treatment to time of progression or death. All patients will be followed to determine OS and PFS.

7.10.9.1.4 Analyses of Tumor Tissues Following Vaccinations

Tumor tissues may not be available from all patients in the study. However, the following aspects may be evaluated in an exploratory manner in all available tumor tissues obtained pre- and/or post-vaccines: (i) Antigen-loss; (ii) up-regulation of anti-apoptotic molecules; and (iii) immune cell infiltration.

7.10.10 Statistical Considerations

7.10.10.1 Assessment of Immunological Responses

Evaluation of immune response may employ both IFN-γ ELISPOT and tetramer assays.

A responder may be defined as a patient who has responded in either IFN-γ ELISPOT or tetramer assays. Each of the three strata should be evaluated independently. A stratum will be considered worthy of further investigation if there are at least 5 responses in the 12 subjects. This criterion has the property that if the true response rate is <18%, there is <5% probability to observe 5 or more responses, and that if the true response rate is >68%, there is <5% probability to observe 4 or fewer responses.

7.10.10.2 Documentation and Evaluation of Safety

The NCI common terminology criteria for adverse events (AE) (CTCAE 3.0) may be used to evaluate toxicity; toxicity may be considered to be an adverse event that is possibly, probably or definitely related to treatment. The maximum grade of toxicity for each category of interest may be recorded for each patient and the summary results may be tabulated by category and grade.

For safety, the regimen may be considered to be excessively toxic if, at any time, the observed rate of regimen-limiting toxicity (RLT) ≥33% and at least 2 RLTs have been observed.

The study design has the following properties: if the true rate of RLT in this patient population is ≥42%, there is at least 90% probability that accrual will stop; if the true RLT rate is ≤8.7%, there is 90% probability that the accrual will not stop, and that the regimen will be considered safe.

7.10.10.3 Assessment of Clinical Endpoints

Clinical responses may be documented, and the response rate and its 95% confidence bounds computed. All patients may be followed for assessment of overall survival (OS) and progression-free survival (PFS). PFS is defined for Stratum A and B as the time interval from a patient's diagnosis to death or progression, and for Stratum C from the time of study registration to death or progression, based on serial MRI scans. If appropriate, exploratory analyses may investigate the relationship of immune response to clinical response and OS/PFS (using Fisher's exact test and the log rank test, respectively).

7.10.10.4 Demographic Data

Baseline descriptive statistics on all evaluable patients may be provided for demographic variables (age, sex, race/ethnicity), Karnofsky or Lansky performance status, disease stage and status at the time of enrollment (stable disease, progressive disease), and treatment regimens previously used (for Stratum C).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it may be readily apparent to those of ordinary skill in the art in light of the teachings of this invention that certain changes and modifications may be made thereto without departing from the spirit or scope of the appended claims.

Alexander J, Sidney J, Southwood S, et al. Development of high potency universal DR-restricted helper epitopes by modification of high affinity DR-blocking peptides. Immunity. 1: 751-761, 1994.

Alves P M, Faure O, Graff-Dubois S, Gross D A, Cornet S, Chouaib S, Miconnet I, Lemonnier F A, Kosmatopoulos K. (2003). EphA2 as target of anticancer immunotherapy: identification of HLA-A*0201-restricted epitopes. Cancer Res 63: 8476-8480, 2003.

Bakker A B, Marland G, de Boer A J, Huijbens R J, Danen E H, Adema G I, Figdor C G. Generation of antimelanoma cytotoxic T lymphocytes from healthy donors after presentation of melanoma-associated antigen-derived epitopes by dendritic cells in vitro. Cancer Res. 55: 5330-5334, 1995.

Bedrosian I, Mick R, Xu S, et al. Intranodal administration of peptide-pulsed mature dendritic cell vaccines results in superior CD8+ T-cell function in melanoma patients. J. Clin. Oncol. 21: 3826-3835, 2003.

Bigg H F, Wait R, Rowan A D, Cawston T E. The mammalian chitinase-like lectin, YKL-40, binds specifically to type I collagen and modulates the rate of type I fibril formation. J Biol Chem. 281: 21082-95, 2006.

Bigner D D, Pitts O M, Wikstrand C J. Induction of lethal experimental allergic encephalomyelitis in non-human primates and guinea pigs with human glioblastoma multiforme tissue. J Neurosurg 55: 32-42, 1981.

Blanc-Brude O P, Yu J, Simosa H, Sessa W C, Altieri D C. Inhibitor of apoptosis protein survivin regulates vascular injury. Nat. Medicine 8: 987-994, 2002.

Bownds S, Tong-On P, Rosenberg S A, Parkhurst, M. Induction of tumor-reactive cytotoxic T-lymphocytes using a peptide from NY-ESO-1 modified at the carboxy-terminus to enhance HLA-A2.1 binding affinity and stability in solution. J. Immunother. 24: 1-9, 2001.

Butowski N, Chang S M, Junck L, et al. A phase II clinical trial of poly-ICLC with radiation for adult patients with newly diagnosed supratentorial glioblastoma: a North American Brain Tumor Consortium (NABTC01-05). J Neurooncol. 91: 175-182, 2009.

Butowski N, Lamborn K R, Lee B L, et al. A North American brain tumor consortium phase II study of poly-ICLC for adult patients with recurrent anaplastic gliomas. J Neurooncol 91: 183-189, 2009.

Cannon L, Bobilev-Priel I, Brenner B, Bobilev D, Paz A, Bar-Haim E, Tirosh B, Klein T, Fridkin M, Lemonnier F, Tzehoval E, Eisenbach L. Characterization of novel breast carcinoma-associated BA46-derived peptides in HLA-A2.1/D(b)-beta2m transgenic mice. J. Clin. Invest 110: 453-462, 2002.

Chen J L, Dunbar P R, Gileadi U, Jager E, Gnjatic S, Nagata Y, Stockert E, Panicali D L, Chen Y T, Knuth A, Old L J, Cerundolo V. Identification of N Y-ESO-1 peptide analogues capable of improved stimulation of tumor-reactive CTL. J Immunol 165: 948-955, 2000.

Chianese-Bullock K A, Pressley J, Garbee C, et al. MAGE-A1-, MAGE-A10-, and gp100-derived peptides are immunogenic when combined with granulocyte-macrophage colony-stimulating factor and montanide ISA-51 adjuvant and administered as part of a multipeptide vaccine for melanoma. J. Immunol. 174: 3080-3086, 2005.

Cohen M H, Shen Y L, Keegan P, et al. FDA Drug Approval Summary: Bevacizumab (Avastin(R)) as Treatment of Recurrent Glioblastoma Multiforme. Oncologist 14: 1131-1138, 2009.

De Vleeschouwer S, Fieuws S, Rutkowski S, et al. Postoperative adjuvant dendritic cell-based immunotherapy in patients with relapsed glioblastoma multiforme. Clin. Cancer. Res. 14: 3098-3104, 2008.

Debinski W, Gibo D M, Hulet S W, et al. Receptor for interleukin 13 is a marker and therapeutic target for human high-grade gliomas. Clin. Cancer Res. 5: 985-990, 1999.

Debinski W, Gibo D M, Slagle B, Powers S K, Gillespie G Y. (1999). Receptor for interleukin 13 is abundantly and specifically over-expressed in patients with glioblastoma multiforme. Int. J. Oncol. 75: 481-486, 1999.

Debinski W, Gibo D M. (2000). Molecular expression analysis of restrictive receptor for interleukin 13, a brain tumor-associated cancer/testis antigen. Mol. Med. 6: 440-449, 2000.

Debinski W, Gibo D M. Molecular expression analysis of restrictive receptor for interleukin 13, a brain tumor-associated cancer/testis antigen. Mol Med 6: 440-449, 2000.

Debinski W, Slagle B, Gibo D M, Powers S K, Gillespie G Y. (2000). Expression of a restrictive receptor for interleukin 13 is associated with glial transformation. J. Neurooncol. 48: 103-111, 2000.

Eguchi 0.1, Hatano M, Nishimura F, et al. Identification of interleukin-13 receptor alpha2 peptide analogues capable of inducing improved antiglioma CTL responses. Cancer Res 66: 5883-5891, 2006.

Fallert B A, Reinhart T A. Improved detection of simian immunodeficiency virus RNA by in situ hybridization in fixed tissue sections: combined effects of temperatures for tissue fixation and probe hybridization. J Virol Methods 99: 23-32, 2002.

Fichtner-Feigl S, Strober W, Kawakami K, Puri R K, Kitani A: IL-13 signaling through the IL-13a2 receptor is involved in induction of TGF-b1 production and fibrosis. Nat. Medicine 12: 99-106, 2006.

Francini G, Scardino A, Kosmatopoulos K, Lemonnier F A, Campoccia G, Sabatino M, Pozzessere D, Petrioli R, Lozzi L, Neri P, Fanetti G, Cusi M G, Correale P. (2002). High-affinity HLA-A(*)02.01 peptides from parathyroid hormone-related protein generate in vitro and in vivo antitumor CTL response without autoimmune side effects. J. Immunol. 169: 4840-4849, 2002.

Fujita M, Zhu X, Ueda R, et al Effective Immunotherapy against Murine Gliomas Using Type 1 Polarizing Dendritic Cells—Significant Roles of CXCL10. Cancer Res 69: 1587-1595, 2009.

Gilliet M, Kleinhans M, Lantelme E, et al. Intranodal injection of semimature monocyte-derived dendritic cells induces T helper type 1 responses to protein neoantigen. Blood 102: 36-42, 2003.

Graff-Dubois S, Faure O, Gross D A, Alves P, Scardino A, Chouaib S, Lemonnier F A, Kosmatopoulos K. Generation of CTL recognizing an HLA-A*0201-restricted epitope shared by MAGE-A1, -A2, -A3, -A4, -A6, -A10, and -A12 tumor antigens: implication in a broad-spectrum tumor immunotherapy. Immunol. 169: 575-580, 2002.

Greten T F, Korangy F, Neumann G, Wedemeyer H, Schlote K, Heller A, Scheffer S, Pardoll D M, Garbe A I, Schneck J P, Manns M P. Peptide-beta2-microglobulin-MHC fusion molecules bind antigen-specific T cells and can be used for multivalent MHC-Ig complexes. J. Immunol. Methods 277: 125-135, 2002.

Gross D A, Graff-Dubois S, Opolon P, Cornet S, Alves P, Naceur-Griscelli O, Faure O, Guillaume P, Firat H, Chouaib S, et al. (2004). High vaccination efficiency of low-affinity epitopes in antitumor immunotherapy. J Clin Invest 113: 425-433, 2004.

Hatano M, Eguchi J, Tatsumi T, et al. EphA2 as a Glioma-Associated Antigen: A Novel Target for Glioma Vaccines. Neoplasia 7: 717-722, 2005.

Hatano M, Kuwashima N, Tatsumi T, Dusak J E, Nishimura F, Reilly K M, Storkus W J, Okada H. Vaccination with EphA2-derived T cell-epitopes promotes immunity against both EphA2-expressing and EphA2-negative tumors. J Transl Med 2: 40, 2004.

Hatano M, Kuwashima N, Tatsumi T, et al. Vaccination with EphA2-derived T cell-epitopes promotes immunity against both EphA2-expressing and EphA2-negative tumors. J Transl Med. 2: 40, 2004.

Herrem C J, Tatsumi T, Olson K S, Shirai K, Finke J H, Bukowski R M, Zhou M, Richmond A L, Derweesh I, Kinch M S, et al. Expression of EphA2 is prognostic of disease-free interval and overall survival in surgically treated patients with renal cell carcinoma. Clin Cancer Res 11: 226-231, 2005.

Izumoto S, Tsuboi A, Oka Y, et al. Phase II clinical trial of Wilms tumor 1 peptide vaccination for patients with recurrent glioblastoma multiforme. J. Neurosurg. 108: 963-971, 2008.

Kalinski P, Hilkens C M, Snijders A, et al. IL-12-deficient dendritic cells, generated in the presence of prostaglandin E2, promote type 2 cytokine production in maturing human naive T helper cells. J Immunol. 159: 28-35, 1997.

Kalinski P, Okada H. Polarized dendritic cells as cancer vaccines: Directing effector-type T cells to tumors. Semin. Immunol. In Press, 2010.

Kalinski P, Schuitemaker J H, Hilkens C M, et al. Final maturation of dendritic cells is associated with impaired responsiveness to IFN-gamma and to bacterial IL-12 inducers: decreased ability of mature dendritic cells to produce IL-12 during the interaction with Th cells. J. Immunol. 162: 3231-3236, 1999.

Kikuchi T, Akasaki Y, Abe T, et al. Vaccination of glioma patients with fusions of dendritic and glioma cells and recombinant human interleukin 12. J. Immunother. 27: 452-459, 2004.

Kinch M S, Carles-Kinch K. Overexpression and functional alterations of the EphA2 tyrosine kinase in cancer. Clin Exp Metastasis 20: 59-68, 2003.

Kirkwood J M, Lee S, Moschos S J, et al. Immunogenicity and antitumor effects of vaccination with peptide vaccine+/−granulocyte-monocyte colony-stimulating factor and/or IFN-alpha2b in advanced metastatic melanoma: Eastern Cooperative Oncology Group Phase II Trial E1696. Clin Cancer Res. 15: 1443-1451, 2009.

Koch G L E, Smith M J, Mortara R A. An abundant ubiquitous glycoprotein (GP100) in nucleated mammalian cells. FEBS Lett. 179: 294-298, 1985.

Liau L M, Prins R M, Kiertscher S M, et al. Dendritic cell vaccination in glioblastoma patients induces systemic and intracranial T-cell responses modulated by the local central nervous system tumor microenvironment. Clin Cancer Res. 11: 5515-5525, 2005.

Liu F, Park P J, Lai W, et al. A genome-wide screen reveals functional gene clusters in the cancer genome and identifies EphA2 as a mitogen in glioblastoma. Cancer Res 66: 10815-10823, 2006.

Liu G, Ying H, Zeng G, et al. HER-2, gp100, and MAGE-1 are expressed in human glioblastoma and recognized by cytotoxic T cells. Cancer Res. 64: 4980-4986, 2004.

Livak K J, Schmittgen T D. Analysis of relative gene expression data using real-time quantitative PCR and the 2(-Delta Delta C(T)) Method Methods 25: 402-8, 2001.

Lupetti R, Pisarra P, Verrecchia A, Farina C, Nicolini G, Anichini A, Bordignon C, Sensi M, Parmiani G, Traversari C. Translation of a retained intron in tyrosinase-related protein (TRP) 2 mRNA generates a new cytotoxic T lymphocyte (CTL)-defined and shared human melanoma antigen not expressed in normal cells of the melanocytic lineage. J. Exp. Med. 188, 1005-1016, 1998.

Mailliard R B, Wankowicz-Kalinska A, Cai Q, et al. Alpha-type-1 polarized dendritic cells: a novel immunization tool with optimized CTL-inducing activity. Cancer Res. 64: 5934-5937, 2004.

Melanoma Study Group of the Mayo Clinic Cancer C, Celis E. Overlapping human leukocyte antigen class I/II binding peptide vaccine for the treatment of patients with stage IV melanoma: evidence of systemic immune dysfunction. Cancer 110: 203-14, 2007.

Monsurro V, Nagorsen D, Wang E, et al. Functional heterogeneity of vaccine-induced CD8(+) T cells. J. Immunol 168: 5933-5942, 2002.

Muthuswamy R, Urban J, Lee J J, et al. Ability of mature dendritic cells to interact with regulatory T cells is imprinted during maturation. Cancer Res. 68: 5972-5978, 2008.

Naruse-Nakajimaa C, Asanoa M, Iwakura Y. Involvement of EphA2 in the formation of the tail notochord via interaction with ephrinA1. Mech. Develop. 102: 95-105, 2001.

Nishimura F, Dusak J E, Eguchi J, et al. Adoptive transfer of Type 1 CTL mediates effective anti-central nervous system tumor response: critical roles of IFN-inducible protein-10. Cancer Res 66: 4478-4487, 2006.

Nutt C L, Betensky R A, Brower M A, et al. YKL-40 is a differential diagnostic marker for histologic subtypes of high-grade gliomas. Clin Cancer Res. 11: 2258-2264, 2005.

O'Connell K A, Bailey J R, Blankson J N. Elucidating the elite: mechanisms of control in HIV-1 infection. Trends in Pharmacological Sciences 30: 631-637, 2009.

Ogawa K, Pasqualini R, Lindberg R A, Kain R, Freeman A L, Pasquale E B. The ephrin-A1 ligand and its receptor, EphA2, are expressed during tumor neovascularization. Oncogene 19: 6043-6052, 2000.

Ogden A T, Horgan D, Waziri A, et al. Defective receptor expression and dendritic cell differentiation of monocytes in glioblastomas. Neurosurgery 59: 902-909, 2006.

Okada H, Kohanbash G, Zhu X, et al. Immunotherapeutic approaches for glioma. Crit Rev Immunol. 29: 1-42, 2009.

Okada H, Lieberman F S, Edington H D, et al. Autologous glioma cell vaccine admixed with interleukin-4 gene transfected fibroblasts in the treatment of recurrent glioblastoma: preliminary observations in a patient with a favorable response to therapy. J. Neurooncol. 64: 13-20, 2003.

Okada H, Lieberman F S, Edington H D, Witham T F, Wargo M J, Cai Q, Elder E H, Whiteside T L, Schold S C Jr, Pollack I F. Autologous glioma cell vaccine admixed with interleukin-4 gene transfected fibroblasts in the treatment of recurrent glioblastoma: preliminary observations in a patient with a favorable response to therapy. J Neuro-Oncol 64: 13-20, 2003.

Okada H, Lieberman F S, Walter K A, et al. Autologous glioma cell vaccine admixed with interleukin-4 gene transfected fibroblasts in the treatment of patients with malignant gliomas. J. Transl. Med. 5: 67, 2007.

Okada H, Pollack I F, Lieberman F, Lunsford L D, Kondziolka D, Schiff D Attanucci J, Edington H, Chambers W, Kalinski P, et al. Gene therapy of malignant gliomas: a pilot study of vaccination with irradiated autologous glioma and dendritic cells admixed with IL-4 transduced fibroblasts to elicit an immune response. Hum Gene Ther 12: 575-595, 2001.

Okada H, Tahara H, Shurin M R, Attanucci J, Giezeman-Smits K M, Fellows K W, Lotze M T, Chambers W H, Bozik M E. Bone marrow derived dendritic cells pulsed with a tumor specific peptide elicit effective anti-tumor immunity against intracranial neoplasms. Int. J. Cancer 78: 196-201, 1998.

Okada H, Villa L A, Attanucci J, Erff M, Fellows W K, Lotze M T, Pollack I F, and Chambers W H. Cytokine Gene Therapy of Gliomas: Effective Induction of Therapeutic Immunity to Intracranial Tumors by Peripheral Immunization with Interleukin-4 Transduced Glioma Cells. Gene Ther. 8: 1157-1166, 2001.

Okano F, Storkus W J, Chambers W H, et al. Identification of a novel HLA-A*0201 restricted cytotoxic T lymphocyte epitope in a human glioma associated antigen, interleukin-13 receptor 2 chain. Clin Cancer Res. 8: 2851-2855, 2002.

Okano F, Storkus W J, Chambers W H, Pollack I F, Okada H. Identification of a novel HLA-A*0201 restricted cytotoxic T lymphocyte epitope in a human glioma associated antigen, interleukin-13 receptor 2 chain. Clin. Cancer Res. 8: 2851-2855, 2002.

Pascolo S, Bervas N, Ure J M, Smith A G, Lemonnier F A, Perarnau B. HLA-A2.1-restricted education and cytolytic activity of CD8(+) T lymphocytes from beta2 microglobulin (beta2m) HLA-A2.1 monochain transgenic H-2 Db beta2m double knockout mice. J Exp Med 185: 2043-2051, 1997.

Pelloski C E, Mahajan A, Maor M, et al. YKL-40 expression is associated with poorer response to radiation and shorter overall survival in glioblastoma. Clin Cancer Res. 11: 3326-3334, 2005.

Pollack I F, Finkelstein S D, Woods J, et al. Expression of p53 and prognosis in children with malignant gliomas. N. Engl. J Med. 346: 420-427, 2002.

Riker A, Cormier J, Panelli M, Kammula U, Wang E, Abati A, Fetsch P, Lee K H, Steinberg S, Rosenberg S, et al. Immune selection after antigen-specific immunotherapy of melanoma. Surgery 126: 112-120, 1999.

Rodrigues J C, Gonzalez G C, Zhang L, et al. Normal human monocytes exposed to glioma cells acquire myeloid-derived suppressor cell-like properties. Neuro Oncol 12: 351-365, 2010.

Saikali S, Avril T, Collet B, et al. Expression of nine tumour antigens in a series of human glioblastoma multiforme: interest of EGFRvIII, IL-13Ralpha2, gp100 and TRP-2 for immunotherapy. J. Neurooncol. 81: 139-148, 2007.

Sainio K, Hellstedt P, Kriedberg J A, Saxen L, Sariola H. Differential regulation of two sets of mesonephric tubles by WT-1. Development 124: 1293-1299, 1997.

Salazar A M, Levy H B, Ondra S, et al. Long-term treatment of malignant gliomas with intramuscularly administered polyinosinic-polycytidylic acid stabilized with polylysine and carboxymethylcellulose: an open pilot study. Neurosurgery 38: 1096-1103, 1996.

Salgaller M L, Marincola F M, Cormier J N, et al. Immunization against epitopes in the human melanoma antigen gp100 following patient immunization with synthetic peptides. Cancer Res. 56: 4749-4757, 1996.

Sampson J H, Archer G E, Mitchell D A, et al. An epidermal growth factor receptor variant III-targeted vaccine is safe and immunogenic in patients with glioblastoma multiforme. Molecular Cancer Therapeutics 8: 2773-2779, 2009.

Sasaki K, Zhu X, Vasquez C, et al. Preferential expression of very late antigen-4 on type 1 CTL cells plays a critical role in trafficking into central nervous system tumors. Cancer Res 67: 6451-6458, 2007.

Scardino A, Gross D A, Alves P, Schultze J L, Graff-Dubois S, Faure 0, Tourdot S, Chouaib S, Nadler L M, Lemonnier F A, Vonderheide R H, Cardoso A A, Kosmatopoulos K. HER-2/neu and hTERT cryptic epitopes as novel targets for broad spectrum tumor immunotherapy. J. Immunol. 168: 5900-5906, 2002.

Slingluff C L, Jr., Petroni G R, Olson W, et al. Helper T-cell responses and clinical activity of a melanoma vaccine with multiple peptides from MAGE and melanocytic differentiation antigens. J Clin Oncol 26: 4973-80, 2008.

Smith J S, Tachibana I, Passe S M, et al. PTEN Mutation, EGFR Amplification, and Outcome in Patients With Anaplastic Astrocytoma and Glioblastoma Multiforme. J. Natl. Cancer Inst. 93: 1246-1256, 2001.

Szczepanski M J, Czystowska M, Szajnik M, et al. Triggering of Toll-like Receptor 4 Expressed on Human Head and Neck Squamous Cell Carcinoma Promotes Tumor Development and Protects the Tumor from Immune Attack. Cancer Res 69: 3105-3113, 2009.

Tatsumi T, Herrem C J, Olson W C, Finke J H, Bukowski R M, Kinch M S, Ranieri E, Storkus W J. Disease stage variation in CD4+ and CD8+ T-cell reactivity to the receptor tyrosine kinase EphA2 in patients with renal cell carcinoma. Cancer Res 63: 4481-4489, 2003.

Vredenburgh J J, Desjardins A, Herndon J E, et al. Bevacizumab plus irinotecan in recurrent glioblastoma multiforme. J. Clin. Oncol. 25: 4722-4729, 2007.

Vredenburgh J J, Desjardins A, Herndon J E, et al. Phase II Trial of Bevacizumab and irinotecan in Recurrent Malignant Glioma. Clinical Cancer Research 13: 1253-1259, 2007.

Watchmaker P B, Berk E, Muthuswamy R, et al. Independent Regulation of Chemokine Responsiveness and Cytolytic Function versus CD8+ T Cell Expansion by Dendritic Cells. J Immunol 184: 591-597, 2010.

Weber J, Boswell W, Smith J, et al. Phase 1 trial of intranodal injection of a Melan-A/MART-1 DNA plasmid vaccine in patients with stage IV melanoma. J Immunother 31: 215-23, 2008.

Wen P Y, Kesari S. Malignant gliomas. Curr Neurol Neurosci Rep 4: 218-227, 2004. Wheeler C J, Black K L, Liu G, et al. Vaccination elicits correlated immune and clinical responses in glioblastoma multiforme patients. Cancer Res. 68: 5955-5964, 2008.

Yamanaka R, Homma J, Yajima N, et al. Clinical evaluation of dendritic cell vaccination for patients with recurrent glioma: results of a clinical phase I/II trial. Clin. Cancer Res. 11: 4160-4167, 2005.

Yu J S, Liu G, Ying H, Yong W H, Black K L, Wheeler C J. Vaccination with tumor lysate-pulsed dendritic cells elicits antigen-specific, cytotoxic T-cells in patients with malignant glioma. Cancer Res 64: 4973-4979, 2004.

Zelinski D P, Zantek N D, Stewart J C, Irizarry A R, Kinch M S. EphA2 overexpression causes tumorigenesis of mammary epithelial cells. Cancer Res 61: 2301-2306, 2001.

Zhu X, Fallert-Junecko B, Fujita M, et al. Poly-ICLC promotes the infiltration of effector T cells into intracranial gliomas via induction of CXCL10 in IFN-α and IFN-γ dependent manners. Cancer Immunology, Immunotherapy 59: 1401-1409, 2010.

Zhu X, Fallert-Junecko B A, Fujita M, et al. Poly-ICLC promotes the infiltration of vaccine-induced T cells into intracranial gliomas via induction of CXCL10 in IFN-α and IFN-γ dependent manners. Cancer Immunol. Immunother. In Press, 2010.

Zhu X, Nishimura F, Sasaki K, et al. Toll like receptor-3 ligand poly-ICLC promotes the efficacy of peripheral vaccinations with tumor antigen-derived peptide epitopes in murine CNS tumor models. J. Transl. Med. 5: 10, 2007.

SEQUENCE LISTING

<160> NUMBER OF SEQ ID NOS: 11

<210> SEQ ID NO 1
<211> LENGTH: 9
<212> TYPE: PRT
<213> ORGANISM: Artificial Sequence
<220> FEATURE:
<223> OTHER INFORMATION: Amino acid residues 345-353 of Interleukin-13
      Receptor alpha

<400> SEQUENCE: 1

Trp Leu Pro Phe Gly Phe Ile Leu Ile
1               5

<210> SEQ ID NO 2
<211> LENGTH: 9
<212> TYPE: PRT
<213> ORGANISM: Artificial Sequence
<220> FEATURE:
<223> OTHER INFORMATION: Amino acid residues 345-353 of Interleukin-13
      Receptor alpha 2 with mutation of I to V at position 353

<400> SEQUENCE: 2

Trp Leu Pro Phe Gly Phe Ile Leu Val
1               5

<210> SEQ ID NO 3
<211> LENGTH: 9
<212> TYPE: PRT
<213> ORGANISM: Artificial Sequence
<220> FEATURE:
<223> OTHER INFORMATION: Amino acid residues 345-353 of Interleukin-13
      Receptor alpha with mutation of W to A at position 345 and I to V
      at position 353

<400> SEQUENCE: 3

Ala Leu Pro Phe Gly Phe Ile Leu Val
1               5

<210> SEQ ID NO 4
<211> LENGTH: 9
<212> TYPE: PRT
<213> ORGANISM: Artificial Sequence
<220> FEATURE:
<223> OTHER INFORMATION: Amino acid residues 345-353 of Interleukin-13
      Receptor alpha with mutation of W to E at position 345 and I to V
      at position 353

<400> SEQUENCE: 4

Glu Leu Pro Phe Gly Phe Ile Leu Val
1               5

<210> SEQ ID NO 5
<211> LENGTH: 13
<212> TYPE: PRT
<213> ORGANISM: Artificial Sequence
<220> FEATURE:
<223> OTHER INFORMATION: Amino acid residues 128-140 of HBV

<400> SEQUENCE: 5

Thr Pro Pro Ala Tyr Arg Pro Pro Asn Ala Pro Ile Leu
1               5                   10

<210> SEQ ID NO 6
<211> LENGTH: 9
<212> TYPE: PRT
<213> ORGANISM: Artificial Sequence
<220> FEATURE:

```
<223> OTHER INFORMATION: Amino acid residues 883-891 of EphA2

<400> SEQUENCE: 6

Thr Leu Ala Asp Phe Asp Pro Arg Val
1               5

<210> SEQ ID NO 7
<211> LENGTH: 9
<212> TYPE: PRT
<213> ORGANISM: Artificial Sequence
<220> FEATURE:
<223> OTHER INFORMATION: Amino acid residues 96-104 of Survivin

<400> SEQUENCE: 7

Leu Met Leu Gly Glu Phe Leu Lys Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Amino acid residues 126-134 of WT1

<400> SEQUENCE: 8

Tyr Met Phe Pro Asn Ala Pro Tyr Leu
1               5

<210> SEQ ID NO 9
<211> LENGTH: 16
<212> TYPE: PRT
<213> ORGANISM: Artificial Sequence
<220> FEATURE:
<223> OTHER INFORMATION: Tetanus Toxoid peptide

<400> SEQUENCE: 9

Ala Gln Tyr Ile Lys Ala Asn Ser Lys Phe Ile Gly Ile Thr Glu Leu
1               5                   10                  15

<210> SEQ ID NO 10
<211> LENGTH: 10
<212> TYPE: PRT
<213> ORGANISM: Artificial Sequence
<220> FEATURE:
<223> OTHER INFORMATION: Amino acid residues 201-210 of YKL-40

<400> SEQUENCE: 10

Ser Ile Met Thr Tyr Asp Phe His Gly Ala
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Amino acid residues 209-217 of GP100 with
      mutation of T to M at position 210

<400> SEQUENCE: 11

Ile Met Asp Gln Val Pro Phe Ser Val
1               5
```

I claim:

1. A method for treating glioblastoma in a subject in need thereof, wherein the subject has failed prior therapy with temozolomide, radiation therapy, and surgery, the method comprising administering to the subject (a) bevacizumab and (b) a pharmaceutical composition, wherein the pharmaceutical composition is cell-free and comprises 250 to 400 µg of an IL-13Rα2 peptide, 250 to 400 µg of an EphA2 peptide, 250 to 400 µg of a survivin peptide, and 250 to 400 µg of a WT1 peptide; wherein the IL-13Rα2 peptide comprises the amino acid sequence of any one of SEQ ID NOs:1-4, the EphA2 peptide comprises the amino acid sequence of SEQ ID NO:6, the survivin peptide comprises the amino acid sequence of SEQ ID NO:7, and the WT1 peptide comprises the amino acid sequence of SEQ ID NO:8.

2. The method of claim 1, wherein the pharmaceutical composition further comprises an adjuvant.

3. The method of claim 2, wherein the adjuvant is Montanide ISA-51.

4. The method of claim 1, further comprising administering to the subject a helper T cell epitope, wherein the helper T cell epitope is a PADRE peptide, a Tetanus toxoid peptide, or the $HBV_{128-140}$ core peptide.

5. The method of claim 1, further comprising administering to the subject an immune response modifier, wherein the immune response modifier is poly-ICLC or imiquimod.

6. The method of claim 1, wherein the pharmaceutical composition is administered to the subject subcutaneously or intranodally.

7. The method of claim 1, wherein the subject is human.

8. A method for treating glioblastoma in a subject in need thereof, wherein the subject has failed prior therapy with temozolomide, radiation therapy, and surgery, the method comprising administering to a subject (a) bevacizumab and (b) a pharmaceutical composition, wherein the pharmaceutical composition is cell-free and comprises 250 to 400 µg of an IL-13Rα2 peptide, 250 to 400 µg of an EphA2 peptide, and 250 to 400 µg of a survivin peptide, wherein the IL-13Rα2 peptide comprises the amino acid sequence of any one of SEQ ID NOs:1-4, the EphA2 peptide comprises the amino acid sequence of SEQ ID NO:6, and the survivin peptide comprises the amino acid sequence of SEQ ID NO:7.

9. The method of claim 8, wherein the pharmaceutical composition further comprises an adjuvant.

10. The method of claim 9, wherein the adjuvant is Montanide ISA-51.

11. The method of claim 8, further comprising administering to the subject a helper T cell epitope, wherein the helper T cell epitope is a PADRE peptide, a Tetanus toxoid peptide, or the $HBV_{128-140}$ core peptide.

12. The method of claim 8, further comprising administering to the subject an immune response modifier, wherein the immune response modifier is poly-ICLC or imiquimod.

13. The method of claim 8, wherein the pharmaceutical composition is administered to the subject subcutaneously or intranodally.

14. The method of claim 8, wherein the subject is human.

* * * * *